(12) United States Patent
Cotta-Ramusino et al.

(10) Patent No.: US 11,236,313 B2
(45) Date of Patent: Feb. 1, 2022

(54) CAS9 FUSION MOLECULES, GENE EDITING SYSTEMS, AND METHODS OF USE THEREOF

(71) Applicant: Editas Medicine, Inc., Cambridge, MA (US)

(72) Inventors: Cecilia Cotta-Ramusino, Cambridge, MA (US); Hariharan Jayaram, San Mateo, CA (US); John Anthony Zuris, Cambridge, MA (US)

(73) Assignee: Editas Medicine, Inc., Cambridge, MA (US)

(*) Notice: Subject to any disclaimer, the term of this patent is extended or adjusted under 35 U.S.C. 154(b) by 230 days.

(21) Appl. No.: 16/093,336

(22) PCT Filed: Apr. 12, 2017

(86) PCT No.: PCT/US2017/027126
§ 371 (c)(1),
(2) Date: Oct. 12, 2018

(87) PCT Pub. No.: WO2017/180694
PCT Pub. Date: Oct. 19, 2017

(65) Prior Publication Data
US 2019/0136210 A1    May 9, 2019

Related U.S. Application Data

(60) Provisional application No. 62/322,026, filed on Apr. 13, 2016.

(51) Int. Cl.
| | | |
|---|---|---|
| C12N 9/22 | (2006.01) | |
| C12N 15/63 | (2006.01) | |
| C07K 19/00 | (2006.01) | |
| C12N 15/10 | (2006.01) | |
| C12N 15/11 | (2006.01) | |
| C12N 15/90 | (2006.01) | |

(52) U.S. Cl.
CPC ............ *C12N 9/22* (2013.01); *C07K 19/00* (2013.01); *C12N 15/10* (2013.01); *C12N 15/102* (2013.01); *C12N 15/11* (2013.01); *C12N 15/63* (2013.01); *C12N 15/907* (2013.01); *C12Y 301/00* (2013.01); *C07K 2319/80* (2013.01); *C12N 2310/20* (2017.05); *C12N 2800/80* (2013.01)

(58) Field of Classification Search
CPC .......... C12N 9/22; C12N 15/63; C12N 15/10; C12N 15/11; C12N 15/907; C12N 15/102; C12N 2800/80; C12N 2310/20; C12Y 301/00; C07K 19/00; C07K 2319/80
See application file for complete search history.

(56) References Cited

U.S. PATENT DOCUMENTS

| | | |
|---|---|---|
| 8,546,553 B2 | 10/2013 | Terns et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,199 B1 | 7/2015 | Chavez et al. |
| 9,228,208 B2 | 1/2016 | Frendewey et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |
| 9,476,065 B2 | 10/2016 | Horwitz et al. |
| 9,493,844 B2 | 11/2016 | Sastry-Dent et al. |
| 9,512,444 B2 | 12/2016 | Chen et al. |
| 9,512,446 B1 | 12/2016 | Joung et al. |
| 9,528,124 B2 | 12/2016 | Fahrenkrug et al. |
| 9,546,384 B2 | 1/2017 | Frendewey et al. |
| 9,567,603 B2 | 2/2017 | Joung et al. |

(Continued)

FOREIGN PATENT DOCUMENTS

| | | |
|---|---|---|
| WO | WO-2007/025097 A2 | 3/2007 |
| WO | WO-2010/011961 A2 | 1/2010 |

(Continued)

OTHER PUBLICATIONS

US 10,077,445 B2, 09/2018, Doudna et al. (withdrawn)

(Continued)

*Primary Examiner* — Delia M Ramirez

(74) *Attorney, Agent, or Firm* — McCarter & English, LLP; Maria Laccotripe Zacharakis; Marcie B. Clarke

(57) ABSTRACT

Disclosed herein are enzymatically active Cas9 (eaCas9) fusion molecules, comprising an eaCas9 molecule linked, e.g., covalently or non-covalently, to a template nucleic acid; gene editing systems comprising the eaCas9 fusion molecules, and methods of use thereof.

14 Claims, 8 Drawing Sheets

Specification includes a Sequence Listing.

(56) References Cited

U.S. PATENT DOCUMENTS

| | | |
|---|---|---|
| 9,567,604 B2 | 2/2017 | Joung et al. |
| 9,587,252 B2 | 3/2017 | Church et al. |
| 9,637,739 B2 | 5/2017 | Šikšnys et al. |
| 9,663,782 B2 | 5/2017 | Yu et al. |
| 9,688,971 B2 | 6/2017 | Doudna et al. |
| 9,725,714 B2 | 8/2017 | May et al. |
| 9,738,908 B2 | 8/2017 | Wu |
| 9,752,132 B2 | 9/2017 | Joung et al. |
| 9,790,490 B2 | 10/2017 | Zhang et al. |
| 9,803,194 B2 | 10/2017 | May et al. |
| 9,809,814 B1 | 11/2017 | May et al. |
| 9,822,370 B2 | 11/2017 | Musunuru et al. |
| 9,822,372 B2 | 11/2017 | Zhang et al. |
| 9,840,713 B2 | 12/2017 | Zhang |
| 9,873,894 B2 | 1/2018 | Conway et al. |
| 9,879,269 B2 | 1/2018 | Sarrangou et al. |
| 9,885,026 B2 | 2/2018 | Brouns et al. |
| 9,902,974 B2 | 2/2018 | Conway et al. |
| 9,909,122 B2 | 3/2018 | May et al. |
| 9,926,545 B2 | 3/2018 | Joung et al. |
| 9,926,546 B2 | 3/2018 | Joung et al. |
| 9,944,912 B2 | 4/2018 | Joung et al. |
| 9,963,689 B2 | 5/2018 | Doudna et al. |
| 9,970,001 B2 | 5/2018 | Miller |
| 9,970,024 B2 | 5/2018 | Church et al. |
| 9,970,028 B2 | 5/2018 | Cost et al. |
| 10,041,092 B2 | 8/2018 | Horwitz et al. |
| 10,066,233 B2 | 9/2018 | Barrangou et al. |
| 10,077,453 B2 | 9/2018 | Liu et al. |
| 10,093,910 B2 | 10/2018 | Joung et al. |
| 10,100,291 B2 | 10/2018 | Chavez et al. |
| 10,113,167 B2 | 10/2018 | Doudna et al. |
| 10,113,179 B2 | 10/2018 | Begemann et al. |
| 10,113,207 B2 | 10/2018 | Wang |
| 10,119,133 B2 | 11/2018 | Joung et al. |
| 10,125,361 B2 | 11/2018 | May et al. |
| 2010/0076057 A1 | 3/2010 | Sontheimer et al. |
| 2010/0093617 A1 | 4/2010 | Barrangou et al. |
| 2013/0011828 A1 | 1/2013 | Barrangou et al. |
| 2014/0068797 A1 | 3/2014 | Doudna et al. |
| 2014/0093941 A1 | 4/2014 | Terns et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0242664 A1 | 8/2014 | Zhang et al. |
| 2014/0242699 A1 | 8/2014 | Zhang |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356956 A1 | 12/2014 | Church et al. |
| 2014/0357523 A1 | 12/2014 | Zeiner et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0079680 A1 | 3/2015 | Bradley et al. |
| 2015/0079681 A1 | 3/2015 | Zhang |
| 2015/0128300 A1 | 5/2015 | Warming et al. |
| 2015/0140664 A1 | 5/2015 | Byrne et al. |
| 2015/0159174 A1 | 6/2015 | Frendewey et al. |
| 2015/0159175 A1 | 6/2015 | Frendewey et al. |
| 2015/0176013 A1 | 6/2015 | Musunuru et al. |
| 2015/0184139 A1 | 7/2015 | Zhang et al. |
| 2015/0184199 A1 | 7/2015 | Horwitz et al. |
| 2015/0203872 A1 | 7/2015 | Zhang |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0240263 A1 | 8/2015 | Holmes et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0353917 A1 | 12/2015 | Miller |
| 2015/0356239 A1 | 12/2015 | Zhang et al. |
| 2015/0376645 A1 | 12/2015 | Zechiedrich et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0024529 A1 | 1/2016 | Carstens |
| 2016/0029604 A1 | 2/2016 | Fahrenkrug et al. |
| 2016/0032274 A1 | 2/2016 | Church et al. |
| 2016/0032292 A1 | 2/2016 | Storici et al. |
| 2016/0040155 A1 | 2/2016 | Maizels et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0060657 A1 | 3/2016 | Frendewey et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0102324 A1 | 4/2016 | Duchateau et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145644 A1 | 5/2016 | Cost et al. |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0160291 A1 | 6/2016 | Scully et al. |
| 2016/0168592 A1 | 6/2016 | Church et al. |
| 2016/0175462 A1 | 6/2016 | Zhang et al. |
| 2016/0177340 A1 | 6/2016 | Bradley et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201089 A1 | 7/2016 | Gersbach et al. |
| 2016/0207983 A1 | 7/2016 | Bradley et al. |

(56) References Cited

U.S. PATENT DOCUMENTS

| | | |
|---|---|---|
| 2016/0208243 A1 | 7/2016 | Zhang et al. |
| 2016/0215276 A1 | 7/2016 | Liu et al. |
| 2016/0222416 A1 | 8/2016 | Church et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0257948 A1 | 9/2016 | Bradley et al. |
| 2016/0257974 A1 | 9/2016 | Bradley et al. |
| 2016/0264995 A1 | 9/2016 | Yamamoto et al. |
| 2016/0272965 A1 | 9/2016 | Zhang et al. |
| 2016/0281072 A1 | 9/2016 | Zhang |
| 2016/0281111 A1 | 9/2016 | Cotta-Ramusino et al. |
| 2016/0298097 A1 | 10/2016 | Chavez et al. |
| 2016/0298125 A1 | 10/2016 | Chen et al. |
| 2016/0298132 A1 | 10/2016 | Chen et al. |
| 2016/0298133 A1 | 10/2016 | Chen et al. |
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304855 A1 | 10/2016 | Stark et al. |
| 2016/0304907 A1 | 10/2016 | Mali et al. |
| 2016/0312198 A1 | 10/2016 | Joung et al. |
| 2016/0312199 A1 | 10/2016 | Joung et al. |
| 2016/0312280 A1 | 10/2016 | May et al. |
| 2016/0319260 A1 | 11/2016 | Joung et al. |
| 2016/0319261 A1 | 11/2016 | Joung et al. |
| 2016/0319281 A1 | 11/2016 | Tsai et al. |
| 2016/0319349 A1 | 11/2016 | May et al. |
| 2016/0340662 A1 | 11/2016 | Zhang et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2016/0369258 A1 | 12/2016 | Maizels et al. |
| 2016/0376610 A1 | 12/2016 | Davis et al. |
| 2017/0002380 A1 | 1/2017 | Buerckstuemmer |
| 2017/0009256 A1 | 1/2017 | Buerckstuemmer |
| 2017/0016027 A1 | 1/2017 | Lee et al. |
| 2017/0029805 A1 | 2/2017 | Li et al. |
| 2017/0037416 A1 | 2/2017 | Barrangou et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0058299 A1 | 3/2017 | Horwitz et al. |
| 2017/0067078 A1 | 3/2017 | Frendewey et al. |
| 2017/0073705 A1 | 3/2017 | Chen et al. |
| 2017/0081650 A1 | 3/2017 | Joung et al. |
| 2017/0107536 A1 | 4/2017 | Zhang et al. |
| 2017/0152508 A1 | 6/2017 | Joung et al. |
| 2017/0152528 A1 | 6/2017 | Zhang |
| 2017/0166875 A1 | 6/2017 | Maizels et al. |
| 2017/0166893 A1 | 6/2017 | Doudna et al. |
| 2017/0166903 A1 | 6/2017 | Zhang et al. |
| 2017/0175140 A1 | 6/2017 | Hummel et al. |
| 2017/0175142 A1 | 6/2017 | Zhang et al. |
| 2017/0175144 A1 | 6/2017 | Zhang et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0211142 A1 | 7/2017 | Smargon et al. |
| 2017/0233703 A1 | 8/2017 | Xie et al. |
| 2017/0251647 A1 | 9/2017 | Mashimo et al. |
| 2017/0260547 A1 | 9/2017 | Dombrowski et al. |
| 2017/0268022 A1 | 9/2017 | Liu et al. |
| 2017/0273284 A1 | 9/2017 | Shen |
| 2017/0275611 A1 | 9/2017 | Bradley et al. |
| 2017/0298330 A1 | 10/2017 | Sato et al. |
| 2017/0306306 A1 | 10/2017 | Potter et al. |
| 2017/0306307 A1 | 10/2017 | Zhang et al. |
| 2017/0306335 A1 | 10/2017 | Zhang et al. |
| 2017/0327805 A1 | 11/2017 | Joung et al. |
| 2017/0327806 A1 | 11/2017 | Joung et al. |
| 2017/0327820 A1 | 11/2017 | May et al. |
| 2017/0349915 A1 | 12/2017 | May et al. |
| 2017/0362611 A1 | 12/2017 | Tsai |
| 2018/0002682 A1 | 1/2018 | Sternberg et al. |
| 2018/0016601 A1 | 1/2018 | Qi et al. |
| 2018/0030425 A1 | 2/2018 | Joung et al. |
| 2018/0044700 A1 | 2/2018 | Doudna et al. |
| 2018/0049412 A1 | 2/2018 | Shen |
| 2018/0051298 A1 | 2/2018 | Fahrenkrug et al. |
| 2018/0066242 A1 | 3/2018 | Zhang et al. |
| 2018/0073002 A1 | 3/2018 | Deiters et al. |
| 2018/0073039 A1 | 3/2018 | Durocher et al. |
| 2018/0080051 A1 | 3/2018 | Sheikh et al. |
| 2018/0100148 A1 | 4/2018 | Vakulskas et al. |
| 2018/0105564 A1 | 4/2018 | Davis et al. |
| 2018/0112235 A1 | 4/2018 | Li et al. |
| 2018/0119121 A1 | 5/2018 | Brouns et al. |
| 2018/0119175 A1 | 5/2018 | Conway et al. |
| 2018/0127780 A1 | 5/2018 | Liu et al. |
| 2018/0127785 A1 | 5/2018 | Junge et al. |
| 2018/0127787 A1 | 5/2018 | Gurumurthy et al. |
| 2018/0135073 A1 | 5/2018 | Chen et al. |
| 2018/0142262 A1 | 5/2018 | Webber et al. |
| 2018/0148735 A1 | 5/2018 | Begemann et al. |
| 2018/0155708 A1 | 6/2018 | Church et al. |
| 2018/0155716 A1 | 6/2018 | Zhang et al. |
| 2018/0163188 A1 | 6/2018 | Xie et al. |
| 2018/0163213 A1 | 6/2018 | Aneja et al. |
| 2018/0187176 A1 | 7/2018 | Behlke et al. |
| 2018/0187195 A1 | 7/2018 | Siksnys et al. |
| 2018/0208931 A1 | 7/2018 | Doudna et al. |
| 2018/0216088 A1 | 8/2018 | Joung et al. |
| 2018/0216135 A1 | 8/2018 | Tsai et al. |
| 2018/0230494 A1 | 8/2018 | Joung et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0235194 A1 | 8/2018 | Fahrenkrug et al. |
| 2018/0237801 A1 | 8/2018 | Doudna et al. |
| 2018/0245100 A1 | 8/2018 | Doudna et al. |
| 2018/0245101 A1 | 8/2018 | Doudna et al. |
| 2018/0250424 A1 | 9/2018 | Cotta-Ramusino |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0265864 A1 | 9/2018 | Li et al. |
| 2018/0273932 A1 | 9/2018 | Bothmer et al. |
| 2018/0273981 A1 | 9/2018 | Doudna et al. |
| 2018/0282713 A1 | 10/2018 | Van Der Oost |
| 2018/0282714 A1 | 10/2018 | Joung et al. |
| 2018/0282764 A1 | 10/2018 | Jinek et al. |
| 2018/0291383 A1 | 10/2018 | Musunuru et al. |
| 2018/0298360 A1 | 10/2018 | Sternberg et al. |
| 2018/0298392 A1 | 10/2018 | Cotta-Ramusino |
| 2018/0298406 A1 | 10/2018 | Doudna et al. |
| 2018/0298407 A1 | 10/2018 | Doudna et al. |
| 2018/0305697 A1 | 10/2018 | Sfeir et al. |
| 2018/0305718 A1 | 10/2018 | Nelson et al. |
| 2018/0305719 A1 | 10/2018 | Perez-Pinera et al. |
| 2018/0312824 A1 | 11/2018 | Zhang et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0320163 A1 | 11/2018 | Koonin et al. |
| 2018/0320197 A1 | 11/2018 | Gersbach et al. |
| 2018/0320201 A1 | 11/2018 | Vakulskas et al. |
| 2018/0327761 A1 | 11/2018 | Duchateau et al. |

FOREIGN PATENT DOCUMENTS

| | | |
|---|---|---|
| WO | WO-2013/098244 A1 | 7/2013 |
| WO | WO-2013/141680 A1 | 9/2013 |
| WO | WO-2013/142578 A1 | 9/2013 |
| WO | WO-2013/176772 A1 | 11/2013 |

(56) References Cited

FOREIGN PATENT DOCUMENTS

| | | |
|---|---|---|
| WO | WO-2013/188522 A2 | 12/2013 |
| WO | WO-2014/018423 A2 | 1/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/127287 A1 | 8/2014 |
| WO | WO-2014/143381 A1 | 9/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO-2014/165825 A2 | 10/2014 |
| WO | WO-2014/172458 A1 | 10/2014 |
| WO | WO-2014/186585 A2 | 11/2014 |
| WO | WO-2014/191518 A1 | 12/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006290 A1 | 1/2015 |
| WO | WO-2015/010114 A1 | 1/2015 |
| WO | WO-2015/013583 A2 | 1/2015 |
| WO | WO-2015/021426 A1 | 2/2015 |
| WO | WO-2015/035162 A2 | 3/2015 |
| WO | WO-2015/040402 A1 | 3/2015 |
| WO | WO-2015/048577 A2 | 4/2015 |
| WO | WO-2015/077290 A2 | 5/2015 |
| WO | WO-2015/077318 A1 | 5/2015 |
| WO | WO-2015/079056 A1 | 6/2015 |
| WO | WO-2015/088643 A1 | 6/2015 |
| WO | WO 2015/089277 * | 6/2015 |
| WO | WO-2015/089351 A1 | 6/2015 |
| WO | WO-2015/089354 A1 | 6/2015 |
| WO | WO-2015/089427 A1 | 6/2015 |
| WO | WO-2015/089486 A2 | 6/2015 |
| WO | WO-2015/095804 A1 | 6/2015 |
| WO | WO-2015/127439 A1 | 8/2015 |
| WO | WO-2015/138620 A1 | 9/2015 |
| WO | WO-2015/160683 A1 | 10/2015 |
| WO | WO-2015/168125 A1 | 11/2015 |
| WO | WO-2015/188056 A1 | 12/2015 |
| WO | WO-2015/188065 A1 | 12/2015 |
| WO | WO-2016/022363 A2 | 2/2016 |
| WO | WO-2016/025759 A1 | 2/2016 |
| WO | WO-2016/028682 A1 | 2/2016 |
| WO | WO-2016/036754 A1 | 3/2016 |
| WO | WO-2016/054326 A1 | 4/2016 |
| WO | WO-2016/057821 A2 | 4/2016 |
| WO | WO-2016/057961 A1 | 4/2016 |
| WO | WO-2016/065364 A1 | 4/2016 |
| WO | WO-2016/073990 A2 | 5/2016 |
| WO | WO-2016/081923 A2 | 5/2016 |
| WO | WO-2016/090385 A1 | 6/2016 |
| WO | WO-2016/100819 A1 | 6/2016 |
| WO | WO-2016/106236 A1 | 6/2016 |
| WO | WO-2016/106244 A1 | 6/2016 |
| WO | WO-2016/112242 A1 | 7/2016 |
| WO | WO-2016/114972 A1 | 7/2016 |
| WO | WO-2016/115326 A1 | 7/2016 |
| WO | WO-2016/138574 A1 | 9/2016 |
| WO | WO-2016/141224 A1 | 9/2016 |
| WO | WO-2016/142719 A1 | 9/2016 |
| WO | WO-2016/154579 A2 | 9/2016 |
| WO | WO-2016/161207 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/183448 A1 | 11/2016 |
| WO | WO-2016/195598 A1 | 12/2016 |
| WO | WO-2016/196655 A1 | 12/2016 |
| WO | WO-2016/196887 A1 | 12/2016 |
| WO | WO-2016/205613 A1 | 12/2016 |
| WO | WO-2016/205711 A1 | 12/2016 |
| WO | WO-2016/205749 A1 | 12/2016 |
| WO | WO-2016/205759 A1 | 12/2016 |
| WO | WO-2016/210271 A1 | 12/2016 |
| WO | WO-2017/011519 A1 | 1/2017 |
| WO | WO-2017/015015 A1 | 1/2017 |
| WO | WO-2017/015101 A1 | 1/2017 |
| WO | WO-2017/031483 A1 | 2/2017 |
| WO | WO-2017/040348 A1 | 3/2017 |
| WO | WO-2017/040511 A1 | 3/2017 |
| WO | WO-2017/040709 A1 | 3/2017 |
| WO | WO-2017/048969 A1 | 3/2017 |
| WO | WO-2017/053729 A1 | 3/2017 |
| WO | WO-2017/053879 A1 | 3/2017 |
| WO | WO-2017/062754 A1 | 4/2017 |
| WO | WO-2017/064546 A1 | 4/2017 |
| WO | WO-2017/066588 A2 | 4/2017 |
| WO | WO-2017/070633 A2 | 4/2017 |
| WO | WO-2017/074962 A1 | 5/2017 |
| WO | WO-2017/096041 A1 | 6/2017 |
| WO | WO-2017/099494 A1 | 6/2017 |
| WO | WO-2017/123609 A1 | 7/2017 |
| WO | WO-2017/127807 A1 | 7/2017 |
| WO | WO-2017/129811 A1 | 8/2017 |
| WO | WO-2017/136335 A1 | 8/2017 |
| WO | WO-2017/142923 A1 | 8/2017 |
| WO | WO-2017/147056 A1 | 8/2017 |
| WO | WO-2017/160752 A1 | 9/2017 |
| WO | WO-2017/161068 A1 | 9/2017 |
| WO | WO-2017/165655 A1 | 9/2017 |
| WO | WO-2017/165826 A1 | 9/2017 |
| WO | WO-2017/172775 A1 | 10/2017 |
| WO | WO-2017/180694 A1 | 10/2017 |
| WO | WO-2017/180711 A1 | 10/2017 |
| WO | WO-2017/181107 A2 | 10/2017 |
| WO | WO-2017/184768 A1 | 10/2017 |
| WO | WO-2017/186550 A1 | 11/2017 |
| WO | WO-2017/186718 A1 | 11/2017 |
| WO | WO-2017/189308 A1 | 11/2017 |
| WO | WO-2017/189336 A1 | 11/2017 |
| WO | WO-2017/197238 A1 | 11/2017 |
| WO | WO-2017/201311 A2 | 11/2017 |
| WO | WO-2017/205650 A1 | 11/2017 |
| WO | WO-2017/207589 A1 | 12/2017 |
| WO | WO-2017/212264 A1 | 12/2017 |
| WO | WO-2017/215648 A1 | 12/2017 |
| WO | WO-2017/216771 A2 | 12/2017 |
| WO | WO-2017/219027 A1 | 12/2017 |
| WO | WO-2017/219033 A1 | 12/2017 |
| WO | WO-2017/220527 A1 | 12/2017 |
| WO | WO-2017/222773 A1 | 12/2017 |
| WO | WO-2018/013840 A1 | 1/2018 |
| WO | WO-2018/013932 A1 | 1/2018 |
| WO | WO-2018/015936 A2 | 1/2018 |
| WO | WO-2018/022634 A1 | 2/2018 |
| WO | WO-2018/025206 A1 | 2/2018 |
| WO | WO-2018/030208 A1 | 2/2018 |
| WO | WO-2018/030457 A1 | 2/2018 |
| WO | WO-2018/033110 A1 | 2/2018 |
| WO | WO-2018/035387 A1 | 2/2018 |
| WO | WO-2018/035388 A1 | 2/2018 |
| WO | WO-2018/035423 A1 | 2/2018 |

(56) References Cited

FOREIGN PATENT DOCUMENTS

| | | |
|---|---|---|
| WO | WO-2018/049073 A1 | 3/2018 |
| WO | WO-2018/049077 A1 | 3/2018 |
| WO | WO-2018/049079 A1 | 3/2018 |
| WO | WO-2018/049168 A1 | 3/2018 |
| WO | WO-2018/052247 A1 | 3/2018 |
| WO | WO-2018/053053 A1 | 3/2018 |
| WO | WO-2018/064352 A1 | 4/2018 |
| WO | WO-2018/064371 A1 | 4/2018 |
| WO | WO-2018/068053 A2 | 4/2018 |
| WO | WO-2018/069474 A1 | 4/2018 |
| WO | WO-2018/071663 A1 | 4/2018 |
| WO | WO-2018/071868 A1 | 4/2018 |
| WO | WO-2018/071892 A1 | 4/2018 |
| WO | WO-2018/074979 A1 | 4/2018 |
| WO | WO-2018/081470 A1 | 5/2018 |
| WO | WO-2018/081476 A2 | 5/2018 |
| WO | WO-2018/089437 A1 | 5/2018 |
| WO | WO-2018/089664 A1 | 5/2018 |
| WO | WO-2018/096356 A1 | 5/2018 |
| WO | WO-2018/097257 A1 | 5/2018 |
| WO | WO-2018/098383 A1 | 5/2018 |
| WO | WO-2018/108272 A1 | 6/2018 |
| WO | WO-2018/108338 A1 | 6/2018 |
| WO | WO-2018/108339 A1 | 6/2018 |
| WO | WO-2018/109101 A1 | 6/2018 |
| WO | WO-2018/112451 A1 | 6/2018 |
| WO | WO-2018/119060 A1 | 6/2018 |
| WO | WO-2018/138385 A1 | 8/2018 |
| WO | WO-2018/144546 A1 | 8/2018 |
| WO | WO-2018/149888 A1 | 8/2018 |
| WO | WO-2018/152325 A1 | 8/2018 |
| WO | WO-2018/162702 A1 | 9/2018 |
| WO | WO-2018/170015 A1 | 9/2018 |
| WO | WO-2018/172556 A1 | 9/2018 |
| WO | WO-2018/175872 A1 | 9/2018 |
| WO | WO-2018/188571 A1 | 10/2018 |
| WO | WO-2018/191715 A2 | 10/2018 |
| WO | WO-2018/195313 A1 | 10/2018 |
| WO | WO-2018/195418 A1 | 10/2018 |
| WO | WO-2018/195540 A1 | 10/2018 |
| WO | WO-2018/195545 A2 | 10/2018 |
| WO | WO-2018/195555 A1 | 10/2018 |
| WO | WO-2018/197020 A1 | 11/2018 |
| WO | WO-2018/197495 A1 | 11/2018 |
| WO | WO-2018/209712 A1 | 11/2018 |
| WO | WO-2018/213351 A1 | 11/2018 |

OTHER PUBLICATIONS

Schaeffer et al., Aust. J. Chem. 62:1328-1332, 2009.*
Stein et al., ChemBioChem 8:2191-2194, 2007.*
Gianneschi et al., Angew. Chem. Int. Ed. 46:3955-3958, 2007.*
Niemeyer, C., Trends in Biotechnology 20(9):395-401, 2002.*
Bolukbasi et al., DNA-binding-domain fusions enhance the targeting range and precision of Cas9. Nat Methods. Dec. 2015;12(12):1150-6.
Kuscu et al., Genome-wide analysis reveals characteristics of off-target sites bound by the Cas9 endonuclease. Nat Biotechnol. Jul. 2014;32(7):677-83.
Lovendahl et al., Sequence-Directed Covalent Protein-DNA Linkages in a Single Step Using HUH-Tags. J Am Chern Soc. May 24, 2017;139(20):7030-7035.
International Search Report and Written Opinion for Application No. PCT/US2017/027126, dated Jul. 4, 2017, 11 pages.
International Preliminary Report on Patentability for Application No. PCT/US2017/027126, dated Oct. 25, 2018, 8 pages.

* cited by examiner

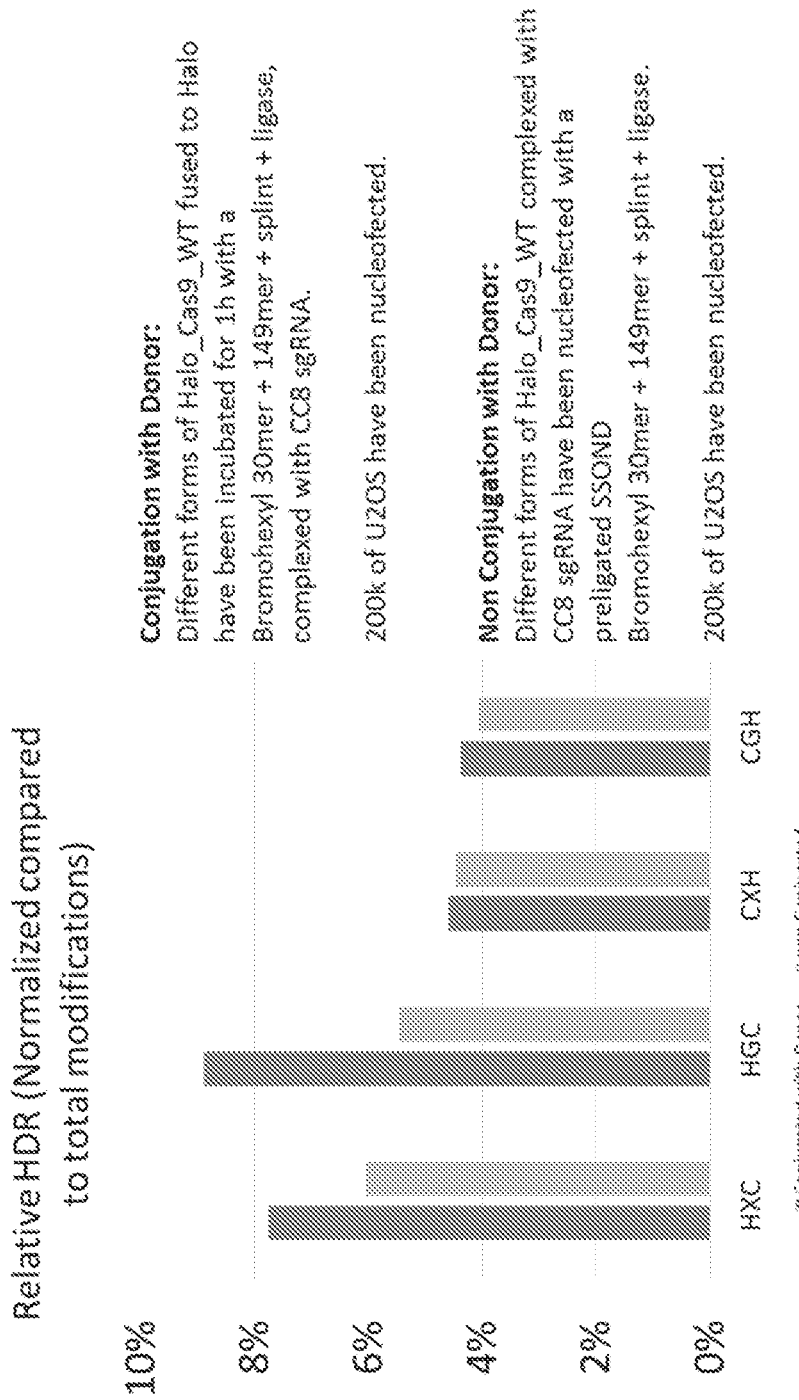

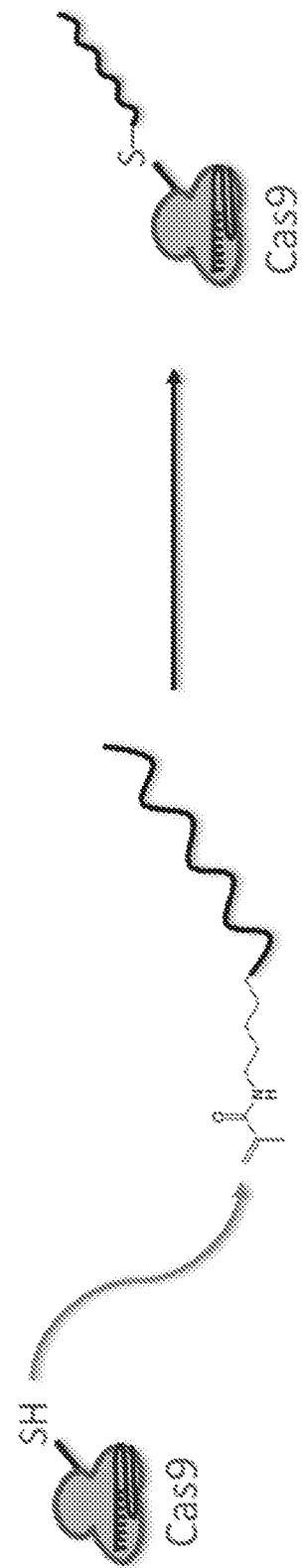

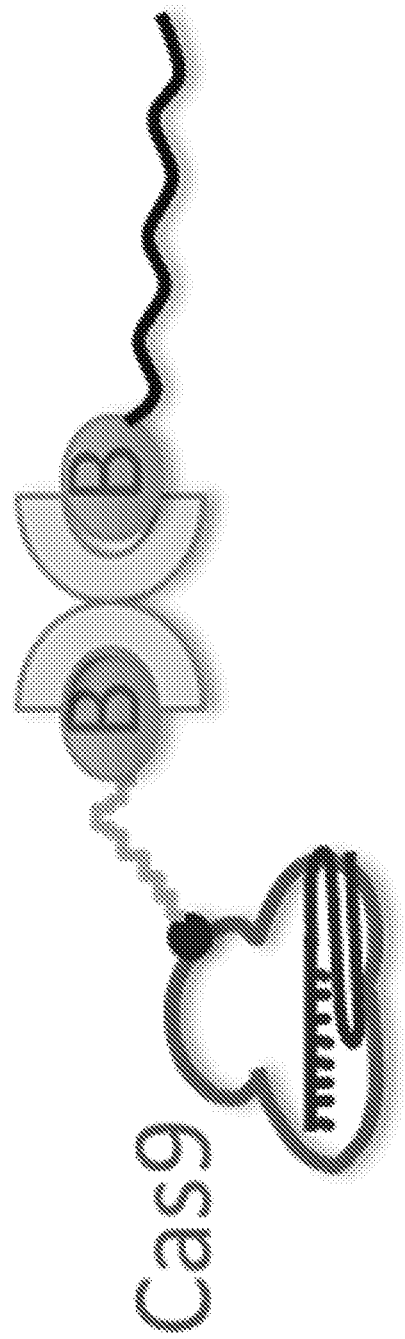

SEQUENCE LISTING

```
<160> NUMBER OF SEQ ID NOS: 219

<210> SEQ ID NO 1
<211> LENGTH: 1345
<212> TYPE: PRT
<213> ORGANISM: Streptococcus mutans
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 1

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Val Lys Tyr
        115                 120                 125

His Glu Asn Phe Pro Thr Ile Tyr His Leu Arg Gln Tyr Leu Ala Asp
    130                 135                 140
```

```
Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
        275                 280                 285

Leu Phe Leu Ser Ala Lys Lys Leu Tyr Asp Ser Ile Leu Leu Ser Gly
290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350

Asp Val Ser Lys Asp Gly Tyr Ala Gly Tyr Ile Asp Gly Lys Thr Asn
        355                 360                 365

Gln Glu Ala Phe Tyr Lys Tyr Leu Lys Gly Leu Leu Asn Lys Ile Glu
370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
        435                 440                 445

Pro Tyr Tyr Val Gly Pro Leu Ala Arg Gly Lys Ser Asp Phe Ala Trp
450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
        515                 520                 525

Tyr Lys Thr Glu Gln Gly Lys Thr Ala Phe Phe Asp Ala Asn Met Lys
530                 535                 540

Gln Glu Ile Phe Asp Gly Val Phe Lys Val Tyr Arg Lys Val Thr Lys
545                 550                 555                 560
```

```
Asp Lys Leu Met Asp Phe Leu Glu Lys Glu Phe Asp Glu Phe Arg Ile
            565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
            595                 600                 605

Asp Asn Ser Lys Asn Glu Lys Ile Leu Glu Asp Ile Val Leu Thr Leu
            610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
            645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
            675                 680                 685

Asn Ser Asn Arg Asn Phe Met Gln Leu Ile Asn Asp Asp Ala Leu Ser
            690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
            725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
            755                 760                 765

Phe Thr Asn Gln Gly Arg Arg Asn Ser Gln Gln Arg Leu Lys Gly Leu
            770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
            805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
            835                 840                 845

Asp Asn Ser Ile Asp Asn Arg Val Leu Thr Ser Ser Lys Glu Asn Arg
            850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
            885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
            915                 920                 925

Lys His Val Ala Arg Ile Leu Asp Glu Arg Phe Asn Thr Glu Thr Asp
            930                 935                 940

Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
            965                 970                 975

Glu Ile Asn Asp Tyr His His Ala His Asp Ala Tyr Leu Asn Ala Val
```

```
                    980             985                 990
Ile Gly Lys Ala Leu Leu Gly Val Tyr Pro Gln Leu Glu Pro Glu Phe
            995                1000                 1005

Val Tyr Gly Asp Tyr Pro His Phe His Gly His Lys Glu Asn Lys
1010                1015                1020

Ala Thr Ala Lys Lys Phe Phe Tyr Ser Asn Ile Met Asn Phe Phe
1025                1030                1035

Lys Lys Asp Asp Val Arg Thr Asp Lys Asn Gly Glu Ile Ile Trp
1040                1045                1050

Lys Lys Asp Glu His Ile Ser Asn Ile Lys Lys Val Leu Ser Tyr
1055                1060                1065

Pro Gln Val Asn Ile Val Lys Lys Val Glu Glu Gln Thr Gly Gly
1070                1075                1080

Phe Ser Lys Glu Ser Ile Leu Pro Lys Gly Asn Ser Asp Lys Leu
1085                1090                1095

Ile Pro Arg Lys Thr Lys Lys Phe Tyr Trp Asp Thr Lys Lys Tyr
1100                1105                1110

Gly Gly Phe Asp Ser Pro Ile Val Ala Tyr Ser Ile Leu Val Ile
1115                1120                1125

Ala Asp Ile Glu Lys Gly Lys Ser Lys Lys Leu Lys Thr Val Lys
1130                1135                1140

Ala Leu Val Gly Val Thr Ile Met Glu Lys Met Thr Phe Glu Arg
1145                1150                1155

Asp Pro Val Ala Phe Leu Glu Arg Lys Gly Tyr Arg Asn Val Gln
1160                1165                1170

Glu Glu Asn Ile Ile Lys Leu Pro Lys Tyr Ser Leu Phe Lys Leu
1175                1180                1185

Glu Asn Gly Arg Lys Arg Leu Leu Ala Ser Ala Arg Glu Leu Gln
1190                1195                1200

Lys Gly Asn Glu Ile Val Leu Pro Asn His Leu Gly Thr Leu Leu
1205                1210                1215

Tyr His Ala Lys Asn Ile His Lys Val Asp Glu Pro Lys His Leu
1220                1225                1230

Asp Tyr Val Asp Lys His Lys Asp Glu Phe Lys Glu Leu Leu Asp
1235                1240                1245

Val Val Ser Asn Phe Ser Lys Lys Tyr Thr Leu Ala Glu Gly Asn
1250                1255                1260

Leu Glu Lys Ile Lys Glu Leu Tyr Ala Gln Asn Asn Gly Glu Asp
1265                1270                1275

Leu Lys Glu Leu Ala Ser Ser Phe Ile Asn Leu Leu Thr Phe Thr
1280                1285                1290

Ala Ile Gly Ala Pro Ala Thr Phe Lys Phe Phe Asp Lys Asn Ile
1295                1300                1305

Asp Arg Lys Arg Tyr Thr Ser Thr Thr Glu Ile Leu Asn Ala Thr
1310                1315                1320

Leu Ile His Gln Ser Ile Thr Gly Leu Tyr Glu Thr Arg Ile Asp
1325                1330                1335

Leu Asn Lys Leu Gly Gly Asp
1340                1345

<210> SEQ ID NO 2
<211> LENGTH: 1368
<212> TYPE: PRT
<213> ORGANISM: Streptococcus pyogenes
```

```
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320
```

```
Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
    435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
    515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
    595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
    675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
```

```
              740             745             750
Arg His Lys Pro Glu Asn Ile Val Ile Glu Met Ala Arg Glu Asn Gln
            755             760             765

Thr Thr Gln Lys Gly Gln Lys Asn Ser Arg Glu Arg Met Lys Arg Ile
770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
            820             825             830

Leu Ser Asp Tyr Asp Val Asp His Ile Val Pro Gln Ser Phe Leu Lys
            835             840             845

Asp Asp Ser Ile Asp Asn Lys Val Leu Thr Arg Ser Asp Lys Asn Arg
            850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
            915             920             925

Lys His Val Ala Gln Ile Leu Asp Ser Arg Met Asn Thr Lys Tyr Asp
            930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
            995             1000            1005

Val Tyr Gly Asp Tyr Lys Val Tyr Asp Val Arg Lys Met Ile Ala
            1010            1015            1020

Lys Ser Glu Gln Glu Ile Gly Lys Ala Thr Ala Lys Tyr Phe Phe
            1025            1030            1035

Tyr Ser Asn Ile Met Asn Phe Phe Lys Thr Glu Ile Thr Leu Ala
            1040            1045            1050

Asn Gly Glu Ile Arg Lys Arg Pro Leu Ile Glu Thr Asn Gly Glu
            1055            1060            1065

Thr Gly Glu Ile Val Trp Asp Lys Gly Arg Asp Phe Ala Thr Val
            1070            1075            1080

Arg Lys Val Leu Ser Met Pro Gln Val Asn Ile Val Lys Lys Thr
            1085            1090            1095

Glu Val Gln Thr Gly Gly Phe Ser Lys Glu Ser Ile Leu Pro Lys
            1100            1105            1110

Arg Asn Ser Asp Lys Leu Ile Ala Arg Lys Lys Asp Trp Asp Pro
            1115            1120            1125

Lys Lys Tyr Gly Gly Phe Asp Ser Pro Thr Val Ala Tyr Ser Val
            1130            1135            1140

Leu Val Val Ala Lys Val Glu Lys Gly Lys Ser Lys Lys Leu Lys
            1145            1150            1155
```

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 3
<211> LENGTH: 4107
<212> TYPE: DNA
<213> ORGANISM: Streptococcus pyogenes

<400> SEQUENCE: 3
atggataaaa agtacagcat cgggctggac atcggtacaa actcagtggg gtgggccgtg     60
attacggacg agtacaaggt acccctccaaa aaatttaaag tgctgggtaa cacgacagaa    120
cactctataa agaaaaatct tattggagcc ttgctgttcg actcaggcga gacagccgaa    180
gccacaaggt tgaagcggac cgccaggagg cggtatacca ggagaaagaa ccgcatatgc    240
tacctgcaag aaatcttcag taacgagatg gcaaggttg acgatagctt tttccatcgc    300
ctggaagaat cctttcttgt tgaggaagac aagaagcacg aacggcaccc catctttggc    360
aatattgtcg acgaagtggc atatcacgaa agtacccga ctatctacca cctcaggaag    420
aagctggtgg actctaccga taaggcggac ctcagactta tttatttggc actcgcccac    480
atgattaaat ttagaggaca tttcttgatc gagggcgacc tgaacccgga caacagtgac    540
gtcgataagc tgttcatcca acttgtgcag acctacaatc aactgttcga agaaaaccct    600
ataaatgctt caggagtcga cgctaaagca atcctgtccg cgcgcctctc aaaatctaga    660
agacttgaga atctgattgc tcagttgccc ggggaaaaga aaatggatt gtttggcaac    720 ctgatcgccc tcagtctcgg actgaccca aatttcaaaa gtaacttcga cctggccgaa    780
gacgctaagc tccagctgtc caaggacaca tacgatgacg acctcgacaa tctgctggcc    840

```
cagattgggg atcagtacgc cgatctcttt ttggcagcaa agaacctgtc cgacgccatc    900
ctgttgagcg atatcttgag agtgaacacc gaaattacta aagcacccct tagcgcatct    960
atgatcaagc ggtacgacga gcatcatcag gatctgaccc tgctgaaggc tcttgtgagg   1020
caacagctcc ccgaaaaata caaggaaatc ttctttgacc agagcaaaaa cggctacgct   1080
ggctatatag atggtggggc cagtcaggag gaattctata aattcatcaa gcccattctc   1140
gagaaaatgg acggcacaga ggagttgctg gtcaaactta acaggaggga cctgctgcgg   1200
aagcagcgga cctttgacaa cgggtctatc ccccaccaga ttcatctggg cgaactgcac   1260
gcaatcctga ggaggcagga ggatttttat ccttttctta aagataaccg cgagaaaata   1320
gaaaagattc ttacattcag gatcccgtac tacgtgggac ctctcgcccg gggcaattca   1380
cggtttgcct ggatgacaag gaagtcagag gagactatta cacctggaa cttcgaagaa   1440 gtggtggaca agggtgcatc tgcccagtct ttcatcgagc ggatgacaaa ttttgacaag   1500
aacctcccta tgagaaggt gctgcccaaa cattctctgc tctacgagta ctttaccgtc   1560
tacaatgaac tgactaaagt caagtacgtc accgagggaa tgaggaagcc ggcattcctt   1620
agtggagaac agaagaaggc gattgtagac ctgttgttca agaccaacag gaaggtgact   1680
gtgaagcaac ttaaagaaga ctactttaag aagatcgaat gttttgacag tgtggaaatt   1740
tcaggggttg aagaccgctt caatgcgtca ttggggactt accatgatct tctcaagatc   1800
ataaaggaca aagacttcct ggacaacgaa gaaaatgagg atattctcga agacatcgtc   1860
ctcaccctga ccctgttcga agacagggaa atgatagaag agcgcttgaa aacctatgcc   1920
cacctcttcg acgataaagt tatgaagcag ctgaagcgca ggagatacac aggatgggga   1980
agattgtcaa ggaagctgat caatggaatt agggataaac agagtggcaa gaccatactg   2040
gatttcctca aatctgatgg cttcgccaat aggaacttca tgcaactgat tcacgatgac   2100
tctcttacct tcaaggagga cattcaaaag gctcaggtga gcgggcaggg agactccctt   2160
catgaacaca tcgcgaattt ggcaggttcc cccgctatta aaaagggcat ccttcaaact   2220
gtcaaggtgg tggatgaatt ggtcaaggta atgggcagac ataagccaga aaatattgtg   2280
atcgagatgc cccgcgaaaa ccagaccaca cagaagggcc agaaaaatag tagagagcgg   2340
atgaagagga tcgaggaggg catcaaagag ctgggatctc agattctcaa agaaccccc    2400 gtagaaaaca cacagctgca gaacgaaaaa ttgtacttgt actatctgca gaacggcaga   2460
gacatgtacg tcgaccaaga acttgatatt aatagactgt ccgactatga cgtagaccat   2520
atcgtgcccc agtccttcct gaaggacgac tccattgata caaagtctt gacaagaagc   2580 gacaagaaca ggggtaaaag tgataatgtg cctagcgagg aggtggtgaa aaaaatgaag   2640
aactactggc gacagctgct taatgcaaag ctcattacac aacggaagtt cgataatctg   2700
acgaaagcag agagaggtgg cttgtctgag ttggacaagg cagggtttat taagcggcag   2760
ctggtggaaa ctaggcagat cacaaagcac gtggcgcaga ttttggacag ccggatgaac   2820
acaaaatacg acgaaaatga taaactgata cgagaggtca agttatcac gctgaaaagc   2880 aagctggtgt ccgattttcg gaaagacttc cagttctaca agttcgcga gattaataac   2940 taccatcatg ctcacgatgc gtacctgaac gctgttgtcg ggaccgcctt gataaagaag   3000
tacccaaagc tggaatccga gttcgtatac ggggattaca agtgtacga tgtgaggaaa   3060 atgatagcca gtccgagca ggagattgga aaggccacag ctaagtactt ctttttattct   3120 aacatcatga attttttaa gacgaaatt accctggcca acggagagat cagaaagcgg   3180
ccccttatag agacaaatgg tgaaacaggt gaaatcgtct gggataaggg cagggatttc   3240
```

-continued

```
gctactgtga ggaaggtgct gagtatgcca caggtaaata tcgtgaaaaa aaccgaagta    3300
cagaccggag gattttccaa ggaaagcatt ttgcctaaaa gaaactcaga caagctcatc    3360
gcccgcaaga aagattggga ccctaagaaa tacgggggat ttgactcacc caccgtagcc    3420
tattctgtgc tggtggtagc taaggtggaa aaaggaaagt ctaagaagct gaagtccgtg    3480
aaggaactct tgggaatcac tatcatggaa agatcatcct ttgaaaagaa ccctatcgat    3540
ttcctggagg ctaagggtta caaggaggtc aagaaagacc tcatcattaa actgccaaaa    3600
tactctctct tcgagctgga aaatggcagg aagagaatgt tggccagcgc cggagagctg    3660
caaaagggaa acgagcttgc tctgccctcc aaatatgtta attttctcta tctcgcttcc    3720
cactatgaaa agctgaaagg gtctcccgaa gataacgagc agaagcagct gttcgtcgaa    3780
cagcacaagc actatctgga tgaaataatc gaacaaataa gcgagttcag caaaagggtt    3840
atcctggcgg atgctaattt ggacaaagta ctgtctgctt ataacaagca ccgggataag    3900
cctattaggg aacaagccga gaatataatt cacctcttta cactcacgaa tctcggagcc    3960
cccgccgcct tcaaatactt tgatacgact atcgaccgga aacggtatac cagtaccaaa    4020
gaggtcctcg atgccaccct catccaccag tcaattactg gcctgtacga aacacggatc    4080
gacctctctc aactgggcgg cgactag                                        4107
```

<210> SEQ ID NO 4
<211> LENGTH: 1388
<212> TYPE: PRT
<213> ORGANISM: Streptococcus thermophilus
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (760)..(767)
<223> OTHER INFORMATION: RuvC-like domain
<220> FEATURE:
<221> NAME/KEY: misc_feature
<222> LOCATION: (844)..(870)
<223> OTHER INFORMATION: HNH-like domain
<220> FEATURE:
<221> NAME/KEY: misc_feature
<222> LOCATION: (989)..(996)
<223> OTHER INFORMATION: RuvC-like domain

<400> SEQUENCE: 4

```
Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125
```

```
His Asp Glu Phe Pro Thr Ile Tyr His Leu Arg Lys Tyr Leu Ala Asp
    130                 135                 140
Ser Thr Lys Lys Ala Asp Leu Arg Leu Val Tyr Leu Ala Leu Ala His
145                 150                 155                 160
Met Ile Lys Tyr Arg Gly His Phe Leu Ile Glu Gly Glu Phe Asn Ser
                165                 170                 175
Lys Asn Asn Asp Ile Gln Lys Asn Phe Gln Asp Phe Leu Asp Thr Tyr
            180                 185                 190
Asn Ala Ile Phe Glu Ser Asp Leu Ser Leu Glu Asn Ser Lys Gln Leu
        195                 200                 205
Glu Glu Ile Val Lys Asp Lys Ile Ser Lys Leu Glu Lys Lys Asp Arg
    210                 215                 220
Ile Leu Lys Leu Phe Pro Gly Glu Lys Asn Ser Gly Ile Phe Ser Glu
225                 230                 235                 240
Phe Leu Lys Leu Ile Val Gly Asn Gln Ala Asp Phe Arg Lys Cys Phe
                245                 250                 255
Asn Leu Asp Glu Lys Ala Ser Leu His Phe Ser Lys Glu Ser Tyr Asp
            260                 265                 270
Glu Asp Leu Glu Thr Leu Leu Gly Tyr Ile Gly Asp Asp Tyr Ser Asp
        275                 280                 285
Val Phe Leu Lys Ala Lys Lys Leu Tyr Asp Ala Ile Leu Leu Ser Gly
    290                 295                 300
Phe Leu Thr Val Thr Asp Asn Glu Thr Glu Ala Pro Leu Ser Ser Ala
305                 310                 315                 320
Met Ile Lys Arg Tyr Asn Glu His Lys Glu Asp Leu Ala Leu Leu Lys
                325                 330                 335
Glu Tyr Ile Arg Asn Ile Ser Leu Lys Thr Tyr Asn Glu Val Phe Lys
            340                 345                 350
Asp Asp Thr Lys Asn Gly Tyr Ala Gly Tyr Ile Asp Gly Lys Thr Asn
        355                 360                 365
Gln Glu Asp Phe Tyr Val Tyr Leu Lys Lys Leu Leu Ala Glu Phe Glu
    370                 375                 380
Gly Ala Asp Tyr Phe Leu Glu Lys Ile Asp Arg Glu Asp Phe Leu Arg
385                 390                 395                 400
Lys Gln Arg Thr Phe Asp Asn Gly Ser Ile Pro Tyr Gln Ile His Leu
                405                 410                 415
Gln Glu Met Arg Ala Ile Leu Asp Lys Gln Ala Lys Phe Tyr Pro Phe
            420                 425                 430
Leu Ala Lys Asn Lys Glu Arg Ile Glu Lys Ile Leu Thr Phe Arg Ile
        435                 440                 445
Pro Tyr Tyr Val Gly Pro Leu Ala Arg Gly Asn Ser Asp Phe Ala Trp
    450                 455                 460
Ser Ile Arg Lys Arg Asn Glu Lys Ile Thr Pro Trp Asn Phe Glu Asp
465                 470                 475                 480
Val Ile Asp Lys Glu Ser Ser Ala Glu Ala Phe Ile Asn Arg Met Thr
                485                 490                 495
Ser Phe Asp Leu Tyr Leu Pro Glu Glu Lys Val Leu Pro Lys His Ser
            500                 505                 510
Leu Leu Tyr Glu Thr Phe Asn Val Tyr Asn Glu Leu Thr Lys Val Arg
        515                 520                 525
Phe Ile Ala Glu Ser Met Arg Asp Tyr Gln Phe Leu Asp Ser Lys Gln
    530                 535                 540
Lys Lys Asp Ile Val Arg Leu Tyr Phe Lys Asp Lys Arg Lys Val Thr
```

```
            545                 550                 555                 560
        Asp Lys Asp Ile Ile Glu Tyr Leu His Ala Ile Tyr Gly Tyr Asp Gly
                        565                 570                 575

Ile Glu Leu Lys Gly Ile Glu Lys Gln Phe Asn Ser Ser Leu Ser Thr
                        580                 585                 590

Tyr His Asp Leu Leu Asn Ile Asn Asp Lys Glu Phe Leu Asp Asp
                        595                 600                 605

Ser Ser Asn Glu Ala Ile Ile Glu Glu Ile Ile His Thr Leu Thr Ile
                610                 615                 620

Phe Glu Asp Arg Glu Met Ile Lys Gln Arg Leu Ser Lys Phe Glu Asn
        625                 630                 635                 640

Ile Phe Asp Lys Ser Val Leu Lys Lys Leu Ser Arg Arg His Tyr Thr
                        645                 650                 655

Gly Trp Gly Lys Leu Ser Ala Lys Leu Ile Asn Gly Ile Arg Asp Glu
                        660                 665                 670

Lys Ser Gly Asn Thr Ile Leu Asp Tyr Leu Ile Asp Asp Gly Ile Ser
                        675                 680                 685

Asn Arg Asn Phe Met Gln Leu Ile His Asp Asp Ala Leu Ser Phe Lys
                        690                 695                 700

Lys Lys Ile Gln Lys Ala Gln Ile Ile Gly Asp Glu Asp Lys Gly Asn
        705                 710                 715                 720

Ile Lys Glu Val Val Lys Ser Leu Pro Gly Ser Pro Ala Ile Lys Lys
                        725                 730                 735

Gly Ile Leu Gln Ser Ile Lys Ile Val Asp Glu Leu Val Lys Val Met
                        740                 745                 750

Gly Gly Arg Lys Pro Glu Ser Ile Val Val Glu Met Ala Arg Glu Asn
                        755                 760                 765

Gln Tyr Thr Asn Gln Gly Lys Ser Asn Ser Gln Arg Leu Lys Arg
                        770                 775                 780

Leu Glu Lys Ser Leu Lys Glu Leu Gly Ser Lys Ile Leu Lys Glu Asn
        785                 790                 795                 800

Ile Pro Ala Lys Leu Ser Lys Ile Asp Asn Asn Ala Leu Gln Asn Asp
                        805                 810                 815

Arg Leu Tyr Leu Tyr Leu Gln Asn Gly Lys Asp Met Tyr Thr Gly
                        820                 825                 830

Asp Asp Leu Asp Ile Asp Arg Leu Ser Asn Tyr Asp Ile Asp His Ile
                        835                 840                 845

Ile Pro Gln Ala Phe Leu Lys Asp Asn Ser Ile Asp Asn Lys Val Leu
                        850                 855                 860

Val Ser Ser Ala Ser Asn Arg Gly Lys Ser Asp Asp Val Pro Ser Leu
        865                 870                 875                 880

Glu Val Val Lys Lys Arg Lys Thr Phe Trp Tyr Gln Leu Leu Lys Ser
                        885                 890                 895

Lys Leu Ile Ser Gln Arg Lys Phe Asp Asn Leu Thr Lys Ala Glu Arg
                        900                 905                 910

Gly Gly Leu Ser Pro Glu Asp Lys Ala Gly Phe Ile Gln Arg Gln Leu
                        915                 920                 925

Val Glu Thr Arg Gln Ile Thr Lys His Val Ala Arg Leu Leu Asp Glu
                        930                 935                 940

Lys Phe Asn Asn Lys Lys Asp Glu Asn Asn Arg Ala Val Arg Thr Val
        945                 950                 955                 960

Lys Ile Ile Thr Leu Lys Ser Thr Leu Val Ser Gln Phe Arg Lys Asp
                        965                 970                 975
```

```
Phe Glu Leu Tyr Lys Val Arg Glu Ile Asn Asp Phe His His Ala His
            980                 985                 990
Asp Ala Tyr Leu Asn Ala Val Val Ala Ser Ala Leu Leu Lys Lys Tyr
            995                 1000                1005
Pro Lys Leu Glu Pro Glu Phe Val Tyr Gly Asp Tyr Pro Lys Tyr
    1010                1015                1020
Asn Ser Phe Arg Glu Arg Lys Ser Ala Thr Glu Lys Val Tyr Phe
    1025                1030                1035
Tyr Ser Asn Ile Met Asn Ile Phe Lys Lys Ser Ile Ser Leu Ala
    1040                1045                1050
Asp Gly Arg Val Ile Glu Arg Pro Leu Ile Glu Val Asn Glu Glu
    1055                1060                1065
Thr Gly Glu Ser Val Trp Asn Lys Glu Ser Asp Leu Ala Thr Val
    1070                1075                1080
Arg Arg Val Leu Ser Tyr Pro Gln Val Asn Val Val Lys Lys Val
    1085                1090                1095
Glu Glu Gln Asn His Gly Leu Asp Arg Gly Lys Pro Lys Gly Leu
    1100                1105                1110
Phe Asn Ala Asn Leu Ser Ser Lys Pro Lys Pro Asn Ser Asn Glu
    1115                1120                1125
Asn Leu Val Gly Ala Lys Glu Tyr Leu Asp Pro Lys Lys Tyr Gly
    1130                1135                1140
Gly Tyr Ala Gly Ile Ser Asn Ser Phe Thr Val Leu Val Lys Gly
    1145                1150                1155
Thr Ile Glu Lys Gly Ala Lys Lys Lys Ile Thr Asn Val Leu Glu
    1160                1165                1170
Phe Gln Gly Ile Ser Ile Leu Asp Arg Ile Asn Tyr Arg Lys Asp
    1175                1180                1185
Lys Leu Asn Phe Leu Leu Glu Lys Gly Tyr Lys Asp Ile Glu Leu
    1190                1195                1200
Ile Ile Glu Leu Pro Lys Tyr Ser Leu Phe Glu Leu Ser Asp Gly
    1205                1210                1215
Ser Arg Arg Met Leu Ala Ser Ile Leu Ser Thr Asn Asn Lys Arg
    1220                1225                1230
Gly Glu Ile His Lys Gly Asn Gln Ile Phe Leu Ser Gln Lys Phe
    1235                1240                1245
Val Lys Leu Leu Tyr His Ala Lys Arg Ile Ser Asn Thr Ile Asn
    1250                1255                1260
Glu Asn His Arg Lys Tyr Val Glu Asn His Lys Lys Glu Phe Glu
    1265                1270                1275
Glu Leu Phe Tyr Tyr Ile Leu Glu Phe Asn Glu Asn Tyr Val Gly
    1280                1285                1290
Ala Lys Lys Asn Gly Lys Leu Leu Asn Ser Ala Phe Gln Ser Trp
    1295                1300                1305
Gln Asn His Ser Ile Asp Glu Leu Cys Ser Ser Phe Ile Gly Pro
    1310                1315                1320
Thr Gly Ser Glu Arg Lys Gly Leu Phe Glu Leu Thr Ser Arg Gly
    1325                1330                1335
Ser Ala Ala Asp Phe Glu Phe Leu Gly Val Lys Ile Pro Arg Tyr
    1340                1345                1350
Arg Asp Tyr Thr Pro Ser Ser Leu Leu Lys Asp Ala Thr Leu Ile
    1355                1360                1365
```

-continued

```
His Gln Ser Val Thr Gly Leu Tyr Glu Thr Arg Ile Asp Leu Ala
    1370                1375                1380

Lys Leu Gly Glu Gly
    1385

<210> SEQ ID NO 5
<211> LENGTH: 1334
<212> TYPE: PRT
<213> ORGANISM: Listeria innocua
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (762)..(769)
<223> OTHER INFORMATION: RuvC-like domain
<220> FEATURE:
<221> NAME/KEY: misc_feature
<222> LOCATION: (840)..(866)
<223> OTHER INFORMATION: HNH-like domain
<220> FEATURE:
<221> NAME/KEY: misc_feature
<222> LOCATION: (985)..(992)
<223> OTHER INFORMATION: RuvC-like domain

<400> SEQUENCE: 5

Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Lys Gln Ile Lys Lys Asn Phe Trp
        35                  40                  45

Gly Val Arg Leu Phe Asp Glu Gly Gln Thr Ala Ala Asp Arg Arg Met
    50                  55                  60

Ala Arg Thr Ala Arg Arg Arg Ile Glu Arg Arg Arg Asn Arg Ile Ser
65                  70                  75                  80

Tyr Leu Gln Gly Ile Phe Ala Glu Glu Met Ser Lys Thr Asp Ala Asn
                85                  90                  95

Phe Phe Cys Arg Leu Ser Asp Ser Phe Tyr Val Asp Asn Glu Lys Arg
            100                 105                 110

Asn Ser Arg His Pro Phe Phe Ala Thr Ile Glu Glu Val Glu Tyr
        115                 120                 125

His Lys Asn Tyr Pro Thr Ile Tyr His Leu Arg Glu Glu Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
            180                 185                 190

Asn Gln Val Phe Ala Ser Gly Ile Glu Asp Gly Ser Leu Lys Lys Leu
        195                 200                 205

Glu Asp Asn Lys Asp Val Ala Lys Ile Leu Val Glu Lys Val Thr Arg
    210                 215                 220

Lys Glu Lys Leu Glu Arg Ile Leu Lys Leu Tyr Pro Gly Glu Lys Ser
225                 230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
```

```
            260                 265                 270
Ala Lys Asp Ser Tyr Glu Glu Asp Leu Glu Ser Leu Leu Ala Leu Ile
            275                 280                 285

Gly Asp Glu Tyr Ala Glu Leu Phe Val Ala Ala Lys Asn Ala Tyr Ser
290                 295                 300

Ala Val Val Leu Ser Ser Ile Ile Thr Val Ala Glu Thr Glu Thr Asn
305                 310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
            340                 345                 350

Tyr Glu Glu Ile Phe Ser Asn Thr Glu Lys His Gly Tyr Ala Gly Tyr
            355                 360                 365

Ile Asp Gly Lys Thr Lys Gln Ala Asp Phe Tyr Lys Tyr Met Lys Met
        370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile
                405                 410                 415

Pro His Gln Leu His Leu Glu Glu Leu Glu Ala Ile Leu His Gln Gln
            420                 425                 430

Ala Lys Tyr Tyr Pro Phe Leu Lys Glu Asn Tyr Asp Lys Ile Lys Ser
            435                 440                 445

Leu Val Thr Phe Arg Ile Pro Tyr Phe Val Gly Pro Leu Ala Asn Gly
        450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
            500                 505                 510

Val Leu Pro Lys His Ser Leu Cys Tyr Gln Lys Tyr Leu Val Tyr Asn
            515                 520                 525

Glu Leu Thr Lys Val Arg Tyr Ile Asn Asp Gln Gly Lys Thr Ser Tyr
        530                 535                 540

Phe Ser Gly Gln Glu Lys Glu Gln Ile Phe Asn Asp Leu Phe Lys Gln
545                 550                 555                 560

Lys Arg Lys Val Lys Lys Lys Asp Leu Glu Leu Phe Leu Arg Asn Met
                565                 570                 575

Ser His Val Glu Ser Pro Thr Ile Glu Gly Leu Glu Asp Ser Phe Asn
            580                 585                 590

Ser Ser Tyr Ser Thr Tyr His Asp Leu Leu Lys Val Gly Ile Lys Gln
            595                 600                 605

Glu Ile Leu Asp Asn Pro Val Asn Thr Glu Met Leu Glu Asn Ile Val
        610                 615                 620

Lys Ile Leu Thr Val Phe Glu Asp Lys Arg Met Ile Lys Glu Gln Leu
625                 630                 635                 640

Gln Gln Phe Ser Asp Val Leu Asp Gly Val Val Leu Lys Lys Leu Glu
                645                 650                 655

Arg Arg His Tyr Thr Gly Trp Gly Arg Leu Ser Ala Lys Leu Leu Met
            660                 665                 670

Gly Ile Arg Asp Lys Gln Ser His Leu Thr Ile Leu Asp Tyr Leu Met
            675                 680                 685
```

```
Asn Asp Asp Gly Leu Asn Arg Asn Leu Met Gln Leu Ile Asn Asp Ser
    690                 695                 700

Asn Leu Ser Phe Lys Ser Ile Ile Glu Lys Glu Gln Val Thr Thr Ala
705                 710                 715                 720

Asp Lys Asp Ile Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
            740                 745                 750

Ser Val Met Gly Tyr Pro Pro Gln Thr Ile Val Glu Met Ala Arg
        755                 760                 765

Glu Asn Gln Thr Thr Gly Lys Gly Lys Asn Asn Ser Arg Pro Arg Tyr
770                 775                 780

Lys Ser Leu Glu Lys Ala Ile Lys Glu Phe Gly Ser Gln Ile Leu Lys
785                 790                 795                 800

Glu His Pro Thr Asp Asn Gln Glu Leu Arg Asn Asn Arg Leu Tyr Leu
                805                 810                 815

Tyr Tyr Leu Gln Asn Gly Lys Asp Met Tyr Thr Gly Gln Asp Leu Asp
            820                 825                 830

Ile His Asn Leu Ser Asn Tyr Asp Ile Asp His Ile Val Pro Gln Ser
        835                 840                 845

Phe Ile Thr Asp Asn Ser Ile Asp Asn Leu Val Leu Thr Ser Ser Ala
850                 855                 860

Gly Asn Arg Glu Lys Gly Asp Asp Val Pro Pro Leu Glu Ile Val Arg
865                 870                 875                 880

Lys Arg Lys Val Phe Trp Glu Lys Leu Tyr Gln Gly Asn Leu Met Ser
                885                 890                 895

Lys Arg Lys Phe Asp Tyr Leu Thr Lys Ala Glu Arg Gly Gly Leu Thr
            900                 905                 910

Glu Ala Asp Lys Ala Arg Phe Ile His Arg Gln Leu Val Glu Thr Arg
        915                 920                 925

Gln Ile Thr Lys Asn Val Ala Asn Ile Leu His Gln Arg Phe Asn Tyr
930                 935                 940

Glu Lys Asp Asp His Gly Asn Thr Met Lys Gln Val Arg Ile Val Thr
945                 950                 955                 960

Leu Lys Ser Ala Leu Val Ser Gln Phe Arg Lys Gln Phe Gln Leu Tyr
                965                 970                 975

Lys Val Arg Asp Val Asn Asp Tyr His His Ala His Asp Ala Tyr Leu
            980                 985                 990

Asn Gly Val Val Ala Asn Thr Leu Leu Lys Val Tyr Pro Gln Leu Glu
        995                 1000                1005

Pro Glu Phe Val Tyr Gly Asp Tyr His Gln Phe Asp Trp Phe Lys
    1010                1015                1020

Ala Asn Lys Ala Thr Ala Lys Lys Gln Phe Tyr Thr Asn Ile Met
    1025                1030                1035

Leu Phe Phe Ala Gln Lys Asp Arg Ile Ile Asp Glu Asn Gly Glu
    1040                1045                1050

Ile Leu Trp Asp Lys Lys Tyr Leu Asp Thr Val Lys Lys Val Met
    1055                1060                1065

Ser Tyr Arg Gln Met Asn Ile Val Lys Lys Thr Glu Ile Gln Lys
    1070                1075                1080

Gly Glu Phe Ser Lys Ala Thr Ile Lys Pro Lys Gly Asn Ser Ser
    1085                1090                1095
```

-continued

Lys Leu Ile Pro Arg Lys Thr Asn Trp Asp Pro Met Lys Tyr Gly
    1100                1105                1110

Gly Leu Asp Ser Pro Asn Met Ala Tyr Ala Val Val Ile Glu Tyr
    1115                1120                1125

Ala Lys Gly Lys Asn Lys Leu Val Phe Glu Lys Lys Ile Ile Arg
    1130                1135                1140

Val Thr Ile Met Glu Arg Lys Ala Phe Glu Lys Asp Glu Lys Ala
    1145                1150                1155

Phe Leu Glu Glu Gln Gly Tyr Arg Gln Pro Lys Val Leu Ala Lys
    1160                1165                1170

Leu Pro Lys Tyr Thr Leu Tyr Glu Cys Glu Glu Gly Arg Arg Arg
    1175                1180                1185

Met Leu Ala Ser Ala Asn Glu Ala Gln Lys Gly Asn Gln Gln Val
    1190                1195                1200

Leu Pro Asn His Leu Val Thr Leu Leu His His Ala Ala Asn Cys
    1205                1210                1215

Glu Val Ser Asp Gly Lys Ser Leu Asp Tyr Ile Glu Ser Asn Arg
    1220                1225                1230

Glu Met Phe Ala Glu Leu Leu Ala His Val Ser Glu Phe Ala Lys
    1235                1240                1245

Arg Tyr Thr Leu Ala Glu Ala Asn Leu Asn Lys Ile Asn Gln Leu
    1250                1255                1260

Phe Glu Gln Asn Lys Glu Gly Asp Ile Lys Ala Ile Ala Gln Ser
    1265                1270                1275

Phe Val Asp Leu Met Ala Phe Asn Ala Met Gly Ala Pro Ala Ser
    1280                1285                1290

Phe Lys Phe Phe Glu Thr Thr Ile Glu Arg Lys Arg Tyr Asn Asn
    1295                1300                1305

Leu Lys Glu Leu Leu Asn Ser Thr Ile Ile Tyr Gln Ser Ile Thr
    1310                1315                1320

Gly Leu Tyr Glu Ser Arg Lys Arg Leu Asp Asp
    1325                1330

<210> SEQ ID NO 6
<211> LENGTH: 1053
<212> TYPE: PRT
<213> ORGANISM: Staphylococcus aureus

<400> SEQUENCE: 6

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

```
Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540
```

```
Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
```

```
                965                 970                 975
Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
        1010                1015                1020

Thr Gln Ser Ile Lys Lys Tyr Ser Thr Asp Ile Leu Gly Asn Leu
        1025                1030                1035

Tyr Glu Val Lys Ser Lys Lys His Pro Gln Ile Ile Lys Lys Gly
        1040                1045                1050

<210> SEQ ID NO 7
<211> LENGTH: 3159
<212> TYPE: DNA
<213> ORGANISM: Staphylococcus aureus

<400> SEQUENCE: 7
```

| | |
|---|---:|
| atgaaaagga actacattct ggggctggac atcgggatta caagcgtggg gtatgggatt | 60 |
| attgactatg aaacaaggga cgtgatcgac gcaggcgtca gactgttcaa ggaggccaac | 120 |
| gtggaaaaca atgagggacg gagaagcaag aggggagcca ggcgcctgaa acgacggaga | 180 |
| aggcacagaa tccagagggt gaagaaactg ctgttcgatt acaacctgct gaccgaccat | 240 |
| tctgagctga gtggaattaa tccttatgaa gccagggtga aaggcctgag tcagaagctg | 300 |
| tcagaggaag agttttccgc agctctgctg cacctggcta agcgccgagg agtgcataac | 360 |
| gtcaatgagg tggaagagga caccggcaac gagctgtcta caaggaaca gatctcacgc | 420 |
| aatagcaaag ctctggaaga aagtatgtc gcagagctgc agctggaacg gctgaagaaa | 480 |
| gatggcgagg tgagagggtc aattaatagg ttcaagacaa gcgactacgt caaagaagcc | 540 |
| aagcagctgc tgaaagtgca gaaggcttac caccagctgg atcagagctt catcgatact | 600 |
| tatatcgacc tgctggagac tcggagaacc tactatgagg gaccaggaga agggagcccc | 660 |
| ttcggatgga agacatcaa ggaatggtac gagatgctga tgggacattg cacctatttt | 720 |
| ccagaagagc tgagaagcgt caagtacgct tataacgcag atctgtacaa cgccctgaat | 780 |
| gacctgaaca acctggtcat caccagggat gaaaacgaga actggaata ctatgagaag | 840 |
| ttccagatca tcgaaaacgt gtttaagcag aagaaaagc ctacactgaa acagattgct | 900 |
| aaggagatcc tggtcaacga gaggacatc aagggctacc gggtgacaag cactggaaaa | 960 |
| ccagagttca ccaatctgaa agtgtatcac gatattaagg acatcacagc acggaaagaa | 1020 |
| atcattgaga cgccgaact gctggatcag attgctaaga tcctgactat ctaccagagc | 1080 |
| tccgaggaca tccaggaaga gctgactaac ctgaacagcg agctgaccca ggaagagatc | 1140 |
| gaacagatta gtaatctgaa ggggtacacc ggaacacaca acctgtccct gaaagctatc | 1200 |
| aatctgattc tggatgagct gtggcataca acgacaatc agattgcaat ctttaaccgg | 1260 |
| ctgaagctgg tcccaaaaaa ggtggacctg agtcagcaga agagatccc aaccacactg | 1320 |
| gtggacgatt tcattctgtc acccgtggtc aagcggagct tcatccagag catcaaagtg | 1380 |
| atcaacgcca tcatcaagaa gtacggcctg cccaatgata tcattatcga gctggctagg | 1440 |
| gagaagaaca gcaaggacgc acagaagatg atcaatgaga tgcagaaacg aaaccggcag | 1500 |
| accaatgaac gcattgaaga gattatccga actaccggga agagaacgc aaagtacctg | 1560 |
| attgaaaaaa tcaagctgca cgatatgcag gagggaaagt gtctgtattc tctggaggcc | 1620 |

| | |
|---|---:|
| atcccctgg aggacctgct gaacaatcca ttcaactacg aggtcgatca tattatcccc | 1680 |
| agaagcgtgt ccttcgacaa ttcctttaac aacaaggtgc tggtcaagca ggaagagaac | 1740 |
| tctaaaaagg gcaataggac tcctttccag tacctgtcta gttcagattc caagatctct | 1800 |
| tacgaaacct ttaaaaagca cattctgaat ctggccaaag gaaagggccg catcagcaag | 1860 |
| accaaaaagg agtacctgct ggaagagcgg gacatcaaca gattctccgt ccagaaggat | 1920 |
| tttattaacc ggaatctggt ggacacaaga tacgctactc gcggcctgat gaatctgctg | 1980 |
| cgatcctatt tccgggtgaa caatctggat gtgaaagtca agtccatcaa cggcgggttc | 2040 |
| acatcttttc tgaggcgcaa atggaagttt aaaaaggagc gcaacaaagg gtacaagcac | 2100 |
| catgccgaag atgctctgat tatcgcaaat gccgacttca tctttaagga gtggaaaaag | 2160 |
| ctggacaaag ccaagaaagt gatggagaac cagatgttcg aagagaagca ggccgaatct | 2220 |
| atgcccgaaa tcgagacaga acaggagtac aaggagattt tcatcactcc tcaccagatc | 2280 |
| aagcatatca aggatttcaa ggactacaag tactctcacc gggtggataa aaagcccaac | 2340 |
| agagagctga tcaatgacac cctgtatagt acaagaaaag acgataaggg gaatacgctg | 2400 |
| attgtgaaca atctgaacgg actgtacgac aaagataatg acaagctgaa aaagctgatc | 2460 |
| aacaaaagtc ccgagaagct gctgatgtac caccatgatc ctcagacata tcagaaactg | 2520 |
| aagctgatta tggagcagta cggcgacgag aagaacccac tgtataagta ctatgaagag | 2580 |
| actgggaact acctgaccaa gtatagcaaa aaggataatg ccccgtgat caagaagatc | 2640 |
| aagtactatg gaacaagct gaatgcccat ctggacatca cagacgatta ccctaacagt | 2700 |
| cgcaacaagg tggtcaagct gtcactgaag ccatacagat cgatgtcta tctggacaac | 2760 |
| ggcgtgtata aatttgtgac tgtcaagaat ctggatgtca tcaaaaagga gaactactat | 2820 |
| gaagtgaata gcaagtgcta cgaagaggct aaaaagctga aaaagattag caaccaggca | 2880 |
| gagttcatcg cctccttta caacaacgac ctgattaaga tcaatggcga actgtatagg | 2940 |
| gtcatcgggg tgaacaatga tctgctgaac cgcattgaag tgaatatgat tgacatcact | 3000 |
| taccgagagt atctggaaaa catgaatgat aagcgccccc tcgaattat caaaacaatt | 3060 |
| gcctctaaga ctcagagtat caaaaagtac tcaaccgaca ttctgggaaa cctgtatgag | 3120 |
| gtgaagagca aaaagcaccc tcagattatc aaaaagggc | 3159 |

<210> SEQ ID NO 8
<211> LENGTH: 3159
<212> TYPE: DNA
<213> ORGANISM: Staphylococcus aureus

<400> SEQUENCE: 8

| | |
|---|---:|
| atgaagcgga actacatcct gggcctggac atcggcatca ccagcgtggg ctacggcatc | 60 |
| atcgactacg agacacggga cgtgatcgat gccggcgtgc ggctgttcaa agaggccaac | 120 |
| gtggaaaaca acgagggcag gcggagcaag agaggcgcca aaggctgaa gcggcggagg | 180 |
| cggcatagaa tccagagagt gaagaagctg ctgttcgact acaacctgct gaccgaccac | 240 |
| agcgagctga gcggcatcaa ccctacgag gccagagtga agggcctgag ccagaagctg | 300 |
| agcgaggaag agttctctgc cgccctgctg cacctggcca agagaagagg cgtgcacaac | 360 |
| gtgaacgagg tggaagagga caccggcaac gagctgtcca ccaaagagca gatcagccgg | 420 |
| aacagcaagg ccctggaaga gaaatacgtg gccgaactgc agctggaacg gctgaagaaa | 480 |
| gacggcgaag tgcggggcag catcaacaga ttcaagacca gcgactacgt gaagaagcc | 540 |
| aaacagctgc tgaaggtgca gaaggcctac caccagctgg accagagctt catcgacacc | 600 |

```
tacatcgacc tgctggaaac ccggcggacc tactatgagg gacctggcga gggcagcccc    660
ttcggctgga aggacatcaa agaatggtac gagatgctga tgggccactg cacctacttc    720
cccgaggaac tgcggagcgt gaagtacgcc tacaacgccg acctgtacaa cgccctgaac    780
gacctgaaca atctcgtgat caccagggac gagaacgaga gctggaata ttacgagaag     840
ttccagatca tcgagaacgt gttcaagcag aagaagaagc ccaccctgaa gcagatcgcc    900
aaagaaatcc tcgtgaacga agaggatatt aagggctaca gagtgaccag caccggcaag    960
cccgagttca ccaacctgaa ggtgtaccac gacatcaagg acattaccgc ccggaaagag   1020
attattgaga cgccgagct gctggatcag attgccaaga tcctgaccat ctaccagagc    1080
agcgaggaca tccaggaaga actgaccaat ctgaactccg agctgaccca ggaagagatc   1140
gagcagatct ctaatctgaa gggctatacc ggcacccaca acctgagcct gaaggccatc   1200
aacctgatcc tggacgagct gtggcacacc aacgacaacc agatcgctat cttcaaccgg   1260
ctgaagctgg tgcccaagaa ggtggacctg tcccagcaga agagatccc caccaccctg   1320
gtggacgact tcatcctgag ccccgtcgtg aagagaagct tcatccagag catcaaagtg   1380
atcaacgcca tcatcaagaa gtacggcctg cccaacgaca tcattatcga gctggcccgc   1440
gagaagaact ccaaggacgc ccagaaaatg atcaacgaga tgcagaagcg gaaccggcag   1500
accaacgagc ggatcgagga aatcatccgg accaccggca agagaacgc caagtacctg   1560
atcgagaaga tcaagctgca cgacatgcag gaaggcaagt gcctgtacag cctggaagcc   1620
atccctctgg aagatctgct gaacaacccc ttcaactatg aggtggacca catcatcccc   1680
agaagcgtgt ccttcgacaa cagcttcaac aacaaggtgc tcgtgaagca ggaagaaaac   1740
agcaagaagg gcaaccggac cccattccag tacctgagca gcagcgacag caagatcagc   1800
tacgaaacct tcaagaagca catcctgaat ctggccaagg gcaagggcag aatcagcaag   1860
accaagaaag agtatctgct ggaagaacgg gacatcaaca ggttctccgt gcagaaagac   1920
ttcatcaacc ggaacctggt ggataccaga tacgccacca gaggcctgat gaacctgctg   1980
cggagctact tcagagtgaa caacctggac gtgaaagtga agtccatcaa tggcggcttc   2040
accagctttc tgcggcggaa gtggaagttt aagaaagagc ggaacaaggg gtacaagcac   2100
cacgccgagg acgccctgat cattgccaac gccgatttca tcttcaaaga gtggaagaaa   2160
ctggacaagg ccaaaaaagt gatggaaaac cagatgttcg aggaaaagca ggccgagagc   2220
atgcccgaga tcgaaaccga gcaggagtac aaagagatct tcatcacccc ccaccagatc   2280
aagcacatta aggacttcaa ggactacaag tacagccacc gggtggacaa gaagcctaat   2340
agagagctga ttaacgacac cctgtactcc acccggaagg acgacaaggg caacaccctg   2400
atcgtgaaca atctgaacgg cctgtacgac aaggacaatg acaagctgaa aaagctgatc   2460
aacaagagcc ccgaaaagct gctgatgtac caccacgacc cccagaccta ccagaaactg   2520
aagctgatta tggaacagta cggcgacgag aagaatcccc tgtacaagta ctacgaggaa   2580
accgggaact acctgaccaa gtactccaaa aaggacaacg gccccgtgat caagaagatt   2640
aagtattacg gcaacaaact gaacgcccat ctggacatca ccgacgacta ccccaacagc   2700
agaaacaagg tcgtgaagct gtccctgaag ccctacagat cgacgtgta cctggacaat   2760
ggcgtgtaca agttcgtgac cgtgaagaat ctggatgtga tcaaaaaaga aaactactac   2820
gaagtgaata gcaagtgcta tgaggaagct aagaagctga aagaagatcag caaccaggcc   2880
gagtttatcg cctccttcta caacaacgat ctgatcaaga tcaacggcga gctgtataga   2940
```

```
gtgatcggcg tgaacaacga cctgctgaac cggatcgaag tgaacatgat cgacatcacc   3000
taccgcgagt acctggaaaa catgaacgac aagaggcccc ccaggatcat taagacaatc   3060
gcctccaaga cccagagcat taagaagtac agcacagaca ttctgggcaa cctgtatgaa   3120
gtgaaatcta agaagcaccc tcagatcatc aaaaagggc                          3159
```

<210> SEQ ID NO 9
<211> LENGTH: 3159
<212> TYPE: DNA
<213> ORGANISM: Staphylococcus aureus

<400> SEQUENCE: 9

```
atgaagcgca actacatcct cggactggac atcggcatta cctccgtggg atacggcatc     60
atcgattacg aaactaggga tgtgatcgac gctggagtca ggctgttcaa agaggcgaac    120
gtggagaaca acgaggggcg cgctcaaag aggggggccc ccggctgaa gcgccgccgc      180 agacatagaa tccagcgcgt gaagaagctg ctgttcgact acaaccttct gaccgaccac    240
tccgaacttt ccggcatcaa cccatatgag ctagagtgaa agggattgtc ccaaaagctg    300
tccgaggaag agttctccgc cgcgttgctc cacctcgcca agcgcagggg agtgcacaat    360
gtgaacgaag tggaagaaga taccggaaac gagctgtcca ccaaggagca gatcagccgg    420
aactccaagg ccctggaaga gaaatacgtg gcggaactgc aactggagcg gctgaagaaa    480
gacggagaag tgcgcggctc gatcaaccgc ttcaagacct cggactacgt gaaggaggcc    540
aagcagctcc tgaaagtgca aaaggcctat caccaacttg accagtcctt tatcgatacc    600
tacatcgatc tgctcgagac tcggcggact tactacgagg gtccagggga gggctcccca    660
tttggttgga aggatattaa ggagtggtac gaaatgctga tgggacactg cacatacttc    720
cctgaggagc tgcggagcgt gaaatacgca tacaacgcag acctgtacaa cgcgctgaac    780
gacctgaaca atctcgtgat cacccgggac gagaacgaaa agctcgagta ttacgaaaag    840
ttccagatta ttgagaacgt gttcaaacag aagaagaagc cgacactgaa gcagattgcc    900
aaggaaatcc tcgtgaacga gaggacatca agggctatc gagtgacctc aacgggaaag    960
ccggagttca ccaatctgaa ggtctaccac gacatcaaag acattaccgc ccggaaggag   1020
atcattgaga cgcggagct gttggaccag attgcgaaga ttctgaccat ctaccaatcc   1080
tccgaggata ttcaggaaga actcaccaac ctcaacagcg aactgaccca ggaggagata   1140
gagcaaatct ccaacctgaa gggctacacc ggaactcata acctgagcct gaaggccatc   1200
aacttgatcc tggacgagct gtggcacacc aacgataacc agatcgctat tttcaatcgg   1260
ctgaagctgg tccccaagaa agtggacctc tcacaacaaa aggagatccc tactacccTT   1320
gtggacgatt tcattctgtc ccccgtggtc aagagaagct tcatacagtc aatcaaagtg   1380
atcaatgcca ttatcaagaa atacggtctg cccaacgaca ttatcattga gctcgcccgc   1440
gagaagaact cgaaggacgc ccagaagatg attaacgaaa tgcagaagag gaaccgacag   1500
actaacgaac ggatcgaaga aatcatccgg accaccggga aggaaaacgc gaagtacctg   1560
atcgaaaaga tcaagctcca tgacatgcag gaaggaaagt gtctgtactc gctggaggcc   1620
attccgctgg aggacttgct gaacaaccct tttaactacg aagtggatca tatcattccg   1680
aggagcgtgt cattcgacaa ttccttcaac aacaaggtcc tcgtgaagca ggaggaaaac   1740
tcgaagaagg gaaaccgcac gccgttccag tacctgagca gcagcgactc caagatttcc   1800
tacgaaacct tcaagaagca catcctcaac ctggcaaagg ggaagggtcg catctccaag   1860
accaagaagg aatatctgct ggaagaaaga gacatcaaca gattctccgt gcaaaaggac   1920
```

-continued

| | |
|---|---|
| ttcatcaacc gcaacctcgt ggatactaga tacgctactc ggggtctgat gaacctcctg | 1980 |
| agaagctact ttagagtgaa caatctggac gtgaaggtca agtcgattaa cggaggtttc | 2040 |
| acctccttcc tgcggcgcaa gtggaagttc aagaaggaac ggaacaaggg ctacaagcac | 2100 |
| cacgccgagg acgccctgat cattgccaac gccgacttca tcttcaaaga atggaagaaa | 2160 |
| cttgacaagg ctaagaaggt catggaaaac cagatgttcg aagaaaagca ggccgagtct | 2220 |
| atgcctgaaa tcgagactga acaggagtac aaggaaatct ttattacgcc acaccagatc | 2280 |
| aaacacatca aggatttcaa ggattacaag tactcacatc gcgtggacaa aaagccgaac | 2340 |
| agggaactga tcaacgacac cctctactcc acccggaagg atgacaaagg gaatacctc | 2400 |
| atcgtcaaca accttaacgg cctgtacgac aaggacaacg ataagctgaa gaagctcatt | 2460 |
| aacaagtcgc ccgaaaagtt gctgatgtac caccacgacc ctcagactta ccagaagctc | 2520 |
| aagctgatca tggagcagta tggggacgag aaaaacccgt tgtacaagta ctacgaagaa | 2580 |
| actgggaatt atctgactaa gtactccaag aaagataacg ccccgtgat taagaagatt | 2640 |
| aagtactacg gcaacaagct gaacgcccat ctggacatca ccgatgacta ccctaattcc | 2700 |
| cgcaacaagg tcgtcaagct gagcctcaag ccctaccggt ttgatgtgta ccttgacaat | 2760 |
| ggagtgtaca agttcgtgac tgtgaagaac cttgacgtga tcaagaagga gaactactac | 2820 |
| gaagtcaact ccaagtgcta cgaggaagca aagaagttga agaagatctc gaaccaggcc | 2880 |
| gagttcattg cctccttcta taacaacgac ctgattaaga tcaacggcga actgtaccgc | 2940 |
| gtcattggcg tgaacaacga tctcctgaac cgcatcgaag tgaacatgat cgacatcact | 3000 |
| taccgggaat acctggagaa tatgaacgac aagcgcccgc cccggatcat taagactatc | 3060 |
| gcctcaaaga cccagtcgat caagaagtac agcaccgaca tcctgggcaa cctgtacgag | 3120 |
| gtcaaatcga agaagcaccc ccagatcatc aagaaggga | 3159 |

<210> SEQ ID NO 10
<211> LENGTH: 3159
<212> TYPE: DNA
<213> ORGANISM: Staphylococcus aureus

<400> SEQUENCE: 10

| | |
|---|---|
| atgaaaagga actacattct ggggctggcc atcgggatta caagcgtggg gtatgggatt | 60 |
| attgactatg aaacaaggga cgtgatcgac gcaggcgtca gactgttcaa ggaggccaac | 120 |
| gtggaaaaca atgagggacg gagaagcaag aggggagcca ggcgcctgaa acgacggaga | 180 |
| aggcacagaa tccagagggt gaagaaactg ctgttcgatt acaacctgct gaccgaccat | 240 |
| tctgagctga gtggaattaa tccttatgaa gccagggtga aaggcctgag tcagaagctg | 300 |
| tcagaggaag agttttccgc agctctgctg cacctggcta agcgccgagg agtgcataac | 360 |
| gtcaatgagg tggaagagga caccggcaac gagctgtcta caaaggaaca gatctcacgc | 420 |
| aatagcaaag ctctggaaga agagtatgtc gcagagctgc agctggaacg gctgaagaaa | 480 |
| gatggcgagg tgagagggtc aattaatagg ttcaagacaa gcgactacgt caaagaagcc | 540 |
| aagcagctgc tgaaagtgca gaaggcttac caccagctgg atcagagctt catcgatact | 600 |
| tatatcgacc tgctggagac tcggagaacc tactatgagg accaggagag gggagcccc | 660 |
| ttcggatgga aagacatcaa ggaatggtac gagatgctga tgggacattg cacctatttt | 720 |
| ccagaagagc tgagaagcgt caagtacgct ataacgcag atctgtacaa cgccctgaat | 780 |
| gacctgaaca acctggtcat caccaggat gaaaacgaga aactggaata ctatgagaag | 840 |

```
ttccagatca tcgaaaacgt gtttaagcag aagaaaaagc ctacactgaa acagattgct      900
aaggagatcc tggtcaacga agaggacatc aagggctacc gggtgacaag cactggaaaa      960
ccagagttca ccaatctgaa agtgtatcac gatattaagg acatcacagc acggaaagaa     1020
atcattgaga acgccgaact gctggatcag attgctaaga tcctgactat ctaccagagc     1080
tccgaggaca tccaggaaga gctgactaac ctgaacagcg agctgaccca ggaagagatc     1140
gaacagatta gtaatctgaa ggggtacacc ggaacacaca acctgtccct gaaagctatc     1200
aatctgattc tggatgagct gtggcataca aacgacaatc agattgcaat ctttaaccgg     1260
ctgaagctgg tcccaaaaaa ggtggacctg agtcagcaga aagagatccc aaccacactg     1320
gtggacgatt tcattctgtc acccgtggtc aagcggagct tcatccagag catcaaagtg     1380
atcaacgcca tcatcaagaa gtacggcctg cccaatgata tcattatcga gctggctagg     1440
gagaagaaca gcaaggacgc acagaagatg atcaatgaga tgcagaaacg aaaccggcag     1500
accaatgaac gcattgaaga gattatccga actaccggga agagaacgc aaagtacctg     1560 attgaaaaaa tcaagctgca cgatatgcag gagggaaagt gtctgtattc tctggaggcc     1620 atcccctgg aggacctgct gaacaatcca ttcaactacg aggtcgatca tattatcccc     1680
agaagcgtgt ccttcgacaa ttcctttaac aacaaggtgc tggtcaagca ggaagagaac     1740
tctaaaaagg gcaataggac tccttttccag tacctgtcta gttcagattc caagatctct     1800
tacgaaacct ttaaaagca cattctgaat ctggccaaag aaagggccg catcagcaag     1860 accaaaaagg agtacctgct ggaagagcgg gacatcaaca gattctccgt ccagaaggat     1920
tttattaacc ggaatctggt ggacacaaga tacgctactc gcggcctgat gaatctgctg     1980
cgatcctatt tccgggtgaa caatctggat gtgaaagtca agtccatcaa cggcgggttc     2040 acatctttc tgaggcgcaa atggaagttt aaaaaggagc gcaacaaagg gtacaagcac     2100
catgccgaag atgctctgat tatcgcaaat gccgacttca tctttaagga gtggaaaaag     2160
ctggacaaag ccaagaaagt gatggagaac cagatgttcg aagagaagca ggccgaatct     2220
atgcccgaaa tcgagacaga acaggagtac aaggagattt tcatcactcc tcaccagatc     2280
aagcatatca aggatttcaa ggactacaag tactctcacc gggtggataa aaagcccaac     2340
agagagctga tcaatgacac cctgtatagt acaagaaaag acgataaggg gaatacccctg     2400 attgtgaaca atctgaacgg actgtacgac aaagataatg acaagctgaa aaagctgatc     2460
aacaaaagtc ccgagaagct gctgatgtac caccatgatc ctcagacata tcagaaactg     2520
aagctgatta tggagcagta cggcgacgag aagaacccac tgtataagta ctatgaagag     2580
actgggaact acctgaccaa gtatagcaaa aaggataatg cccccgtgat caagaagatc     2640
aagtactatg gaacaagct gaatgcccat ctggacatca cagacgatta ccctaacagt     2700
cgcaacaagg tggtcaagct gtcactgaag ccatacagat tcgatgtcta tctggacaac     2760
ggcgtgtata aatttgtgac tgtcaagaat ctggatgtca tcaaaaagga gaactactat     2820
gaagtgaata gcaagtgcta cgaagaggct aaaaagctga aaaagattag caaccaggca     2880
gagttcatcg cctccttta caacaacgac ctgattaaga tcaatggcga actgtatagg     2940
gtcatcgggg tgaacaatga tctgctgaac cgcattgaag tgaatatgat tgacatcact     3000
taccgagagt atctggaaaa catgaatgat aagcgccccc tcgaattat caaaacaatt     3060 gcctctaaga ctcagagtat caaaaagtac tcaaccgaca ttctgggaaa cctgtatgag     3120
gtgaagagca aaaagcaccc tcagattatc aaaaagggc                           3159
```

<210> SEQ ID NO 11
<211> LENGTH: 3159
<212> TYPE: DNA
<213> ORGANISM: Staphylococcus aureus

<400> SEQUENCE: 11

| | | | | | |
|---|---|---|---|---|---|
| atgaaaagga | actacattct | ggggctggac | atcgggatta | caagcgtggg gtatgggatt | 60 |
| attgactatg | aaacaaggga | cgtgatcgac | gcaggcgtca | gactgttcaa ggaggccaac | 120 |
| gtggaaaaca | atgagggacg | gagaagcaag | agggagccca | ggcgcctgaa acgacggaga | 180 |
| aggcacagaa | tccagagggt | gaagaaactg | ctgttcgatt | acaacctgct gaccgaccat | 240 |
| tctgagctga | gtggaattaa | tccttatgaa | gccagggtga | aaggcctgag tcagaagctg | 300 |
| tcagaggaag | agttttccgc | agctctgctg | cacctggcta | agcgccgagg agtgcataac | 360 |
| gtcaatgagg | tggaagagga | caccggcaac | gagctgtcta | caaaggaaca gatctcacgc | 420 |
| aatagcaaag | ctctggaaga | gaagtatgtc | gcagagctgc | agctggaacg gctgaagaaa | 480 |
| gatggcgagg | tgagagggtc | aattaatagg | ttcaagacaa | gcgactacgt caaagaagcc | 540 |
| aagcagctgc | tgaaagtgca | gaaggcttac | caccagctgg | atcagagctt catcgatact | 600 |
| tatatcgacc | tgctggagac | tcggagaacc | tactatgagg | gaccaggaga agggagcccc | 660 |
| ttcggatgga | aagacatcaa | ggaatggtac | gagatgctga | tgggacattg cacctatttt | 720 |
| ccagaagagc | tgagaagcgt | caagtacgct | tataacgcag | atctgtacaa cgccctgaat | 780 |
| gacctgaaca | acctggtcat | caccagggat | gaaaacgaga | aactggaata ctatgagaag | 840 |
| ttccagatca | tcgaaaacgt | gtttaagcag | aagaaaaagc | ctacactgaa acagattgct | 900 |
| aaggagatcc | tggtcaacga | gaggacatc | aagggctacc | gggtgacaag cactggaaaa | 960 |
| ccagagttca | ccaatctgaa | agtgtatcac | gatattaagg | acatcacagc acggaaagaa | 1020 |
| atcattgaga | acgccgaact | gctggatcag | attgctaaga | tcctgactat ctaccagagc | 1080 |
| tccgaggaca | tccaggaaga | gctgactaac | ctgaacagcg | agctgaccca ggaagagatc | 1140 |
| gaacagatta | gtaatctgaa | ggggtacacc | ggaacacaca | acctgtccct gaaagctatc | 1200 |
| aatctgattc | tggatgagct | gtggcataca | acgacaatc | agattgcaat ctttaaccgg | 1260 |
| ctgaagctgg | tcccaaaaaa | ggtggacctg | agtcagcaga | aagagatccc aaccacactg | 1320 |
| gtggacgatt | tcattctgtc | acccgtggtc | aagcggagct | tcatccagag catcaaagtg | 1380 |
| atcaacgcca | tcatcaagaa | gtacggcctg | cccaatgata | tcattatcga gctggctagg | 1440 |
| gagaagaaca | gcaaggacgc | acagaagatg | atcaatgaga | tgcagaaacg aaaccggcag | 1500 |
| accaatgaac | gcattgaaga | gattatccga | actaccggga | aagagaacgc aaagtacctg | 1560 |
| attgaaaaaa | tcaagctgca | cgatatgcag | gagggaaagt | gtctgtattc tctggaggcc | 1620 |
| atccccctgg | aggacctgct | gaacaatcca | ttcaactacg | aggtcgatca tattatcccc | 1680 |
| agaagcgtgt | ccttcgacaa | ttcctttaac | aacaaggtgc | tggtcaagca ggaagaggcc | 1740 |
| tctaaaaagg | gcaataggac | tccttttcag | tacctgtcta | gttcagattc caagatctct | 1800 |
| tacgaaacct | ttaaaaagca | cattctgaat | ctggccaaag | gaaagggccg catcagcaag | 1860 |
| accaaaaagg | agtacctgct | ggaagagcgg | gacatcaaca | gattctccgt ccagaaggat | 1920 |
| tttattaacc | ggaatctggt | ggacacaaga | tacgctactc | gcggcctgat gaatctgctg | 1980 |
| cgatcctatt | tccgggtgaa | caatctggat | gtgaaagtca | agtccatcaa cggcgggttc | 2040 |
| acatcttttc | tgaggcgcaa | atggaagttt | aaaaaggagc | gcaacaaagg gtacaagcac | 2100 |
| catgccgaag | atgctctgat | tatcgcaaat | gccgacttca | tctttaagga gtggaaaaag | 2160 |

-continued

```
ctggacaaag ccaagaaagt gatggagaac cagatgttcg aagagaagca ggccgaatct      2220
atgcccgaaa tcgagacaga acaggagtac aaggagattt tcatcactcc tcaccagatc      2280
aagcatatca aggatttcaa ggactacaag tactctcacc gggtggataa aaagcccaac      2340
agagagctga tcaatgacac cctgtatagt acaagaaaag acgataaggg gaatacccgt      2400
attgtgaaca atctgaacgg actgtacgac aaagataatg acaagctgaa aaagctgatc      2460
aacaaaagtc ccgagaagct gctgatgtac caccatgatc ctcagacata tcagaaactg      2520
aagctgatta tggagcagta cggcgacgag aagaacccac tgtataagta ctatgaagag      2580
actgggaact acctgaccaa gtatagcaaa aaggataatg ccccgtgat caagaagatc       2640 aagtactatg ggaacaagct gaatgcccat ctggacatca cagacgatta ccctaacagt      2700
cgcaacaagg tggtcaagct gtcactgaag ccatacagat cgatgtcta tctggacaac       2760 ggcgtgtata aatttgtgac tgtcaagaat ctggatgtca tcaaaaagga gaactactat      2820
gaagtgaata gcaagtgcta cgaagaggct aaaaagctga aaaagattag caaccaggca      2880
gagttcatcg cctccttta caacaacgac ctgattaaga tcaatggcga actgtatagg       2940
gtcatcgggg tgaacaatga tctgctgaac cgcattgaag tgaatatgat tgacatcact      3000
taccgagagt atctggaaaa catgaatgat aagcgcccc ctcgaattat caaaacaatt       3060
gcctctaaga ctcagagtat caaaaagtac tcaaccgaca ttctgggaaa cctgtatgag      3120
gtgaagagca aaaagcaccc tcagattatc aaaaagggc                             3159
```

<210> SEQ ID NO 12
<211> LENGTH: 1082
<212> TYPE: PRT
<213> ORGANISM: Neisseria meningitidis

<400> SEQUENCE: 12

```
Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
```

-continued

```
            195                 200                 205
Gln Ala Glu Leu Ile Leu Leu Phe Glu Lys Gln Lys Glu Phe Gly Asn
    210                 215                 220
Pro His Val Ser Gly Gly Leu Lys Glu Gly Ile Glu Thr Leu Leu Met
225                 230                 235                 240
Thr Gln Arg Pro Ala Leu Ser Gly Asp Ala Val Gln Lys Met Leu Gly
                245                 250                 255
His Cys Thr Phe Glu Pro Ala Glu Pro Lys Ala Ala Lys Asn Thr Tyr
                260                 265                 270
Thr Ala Glu Arg Phe Ile Trp Leu Thr Lys Leu Asn Asn Leu Arg Ile
            275                 280                 285
Leu Glu Gln Gly Ser Glu Arg Pro Leu Thr Asp Thr Glu Arg Ala Thr
            290                 295                 300
Leu Met Asp Glu Pro Tyr Arg Lys Ser Lys Leu Thr Tyr Ala Gln Ala
305                 310                 315                 320
Arg Lys Leu Leu Gly Leu Glu Asp Thr Ala Phe Phe Lys Gly Leu Arg
                325                 330                 335
Tyr Gly Lys Asp Asn Ala Glu Ala Ser Thr Leu Met Glu Met Lys Ala
                340                 345                 350
Tyr His Ala Ile Ser Arg Ala Leu Glu Lys Glu Gly Leu Lys Asp Lys
            355                 360                 365
Lys Ser Pro Leu Asn Leu Ser Pro Glu Leu Gln Asp Glu Ile Gly Thr
    370                 375                 380
Ala Phe Ser Leu Phe Lys Thr Asp Glu Asp Ile Thr Gly Arg Leu Lys
385                 390                 395                 400
Asp Arg Ile Gln Pro Glu Ile Leu Glu Ala Leu Leu Lys His Ile Ser
                405                 410                 415
Phe Asp Lys Phe Val Gln Ile Ser Leu Lys Ala Leu Arg Arg Ile Val
                420                 425                 430
Pro Leu Met Glu Gln Gly Lys Arg Tyr Asp Glu Ala Cys Ala Glu Ile
            435                 440                 445
Tyr Gly Asp His Tyr Gly Lys Lys Asn Thr Glu Glu Lys Ile Tyr Leu
            450                 455                 460
Pro Pro Ile Pro Ala Asp Glu Ile Arg Asn Pro Val Val Leu Arg Ala
465                 470                 475                 480
Leu Ser Gln Ala Arg Lys Val Ile Asn Gly Val Val Arg Arg Tyr Gly
                485                 490                 495
Ser Pro Ala Arg Ile His Ile Glu Thr Ala Arg Glu Val Gly Lys Ser
                500                 505                 510
Phe Lys Asp Arg Lys Glu Ile Glu Lys Arg Gln Glu Glu Asn Arg Lys
            515                 520                 525
Asp Arg Glu Lys Ala Ala Lys Phe Arg Glu Tyr Phe Pro Asn Phe
            530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
                580                 585                 590
Ser Arg Thr Trp Asp Asp Ser Phe Asn Asn Lys Val Leu Val Leu Gly
            595                 600                 605
Ser Glu Asn Gln Asn Lys Gly Asn Gln Thr Pro Tyr Glu Tyr Phe Asn
    610                 615                 620
```

-continued

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
            645                 650                 655

Phe Asp Glu Asp Gly Phe Lys Glu Arg Asn Leu Asn Asp Thr Arg Tyr
        660                 665                 670

Val Asn Arg Phe Leu Cys Gln Phe Val Ala Asp Arg Met Arg Leu Thr
            675                 680                 685

Gly Lys Gly Lys Lys Arg Val Phe Ala Ser Asn Gly Gln Ile Thr Asn
        690                 695                 700

Leu Leu Arg Gly Phe Trp Gly Leu Arg Lys Val Arg Ala Glu Asn Asp
705                 710                 715                 720

Arg His His Ala Leu Asp Ala Val Val Ala Cys Ser Thr Val Ala
                725                 730                 735

Met Gln Gln Lys Ile Thr Arg Phe Val Arg Tyr Lys Glu Met Asn Ala
                740                 745                 750

Phe Asp Gly Lys Thr Ile Asp Lys Glu Thr Gly Glu Val Leu His Gln
            755                 760                 765

Lys Thr His Phe Pro Gln Pro Trp Glu Phe Phe Ala Gln Glu Val Met
770                 775                 780

Ile Arg Val Phe Gly Lys Pro Asp Gly Lys Pro Glu Phe Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
                820                 825                 830

Ala Pro Asn Arg Lys Met Ser Gly Gln Gly His Met Glu Thr Val Lys
            835                 840                 845

Ser Ala Lys Arg Leu Asp Glu Gly Val Ser Val Leu Arg Val Pro Leu
850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
            885                 890                 895

Asp Asp Pro Ala Lys Ala Phe Ala Glu Pro Phe Tyr Lys Tyr Asp Lys
        900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
            965                 970                 975

Arg Ala Val Val Gln Gly Lys Asp Glu Asp Trp Gln Leu Ile Asp
                980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys
        1010                1015                1020

His Arg Gly Thr Gly Asn Ile Asn Ile Arg Ile His Asp Leu Asp
        1025                1030                1035

```
His Lys Ile Gly Lys Asn Gly Ile Leu Glu Gly Ile Gly Val Lys
    1040            1045                1050

Thr Ala Leu Ser Phe Gln Lys Tyr Gln Ile Asp Glu Leu Gly Lys
    1055            1060                1065

Glu Ile Arg Pro Cys Arg Leu Lys Lys Arg Pro Pro Val Arg
    1070            1075                1080

<210> SEQ ID NO 13
<211> LENGTH: 3249
<212> TYPE: DNA
<213> ORGANISM: Neisseria meningitidis
<220> FEATURE:
<221> NAME/KEY: misc_feature
<222> LOCATION: (1)..(3249)
<223> OTHER INFORMATION: Exemplary codon optimized Cas9

<400> SEQUENCE: 13
atggccgcct tcaagcccaa ccccatcaac tacatcctgg gcctggacat cggcatcgcc      60
agcgtgggct gggccatggt ggagatcgac gaggacgaga cccccatctg cctgatcgac     120
ctgggtgtgc gcgtgttcga gcgcgctgag gtgcccaaga ctggtgacag tctggctatg     180
gctcgccggc ttgctcgctc tgttcggcgc cttactcgcc ggcgcgctca ccgccttctg     240
cgcgctcgcc gcctgctgaa gcgcgagggt gtgctgcagg ctgccgactt cgacgagaac     300
ggcctgatca gagcctgcc caacactcct tggcagctgc gcgctgccgc tctggaccgc     360
aagctgactc ctctggagtg gagcgccgtg ctgctgcacc tgatcaagca ccgcggctac     420
ctgagccagc gcaagaacga gggcgagacc gccgacaagg agctgggtgc tctgctgaag     480
ggcgtggccg acaacgccca cgccctgcag actggtgact ccgcactcc tgctgagctg     540 gccctgaaca gttcgagaa ggagagcggc cacatccgca accagcgcgg cgactacagc     600
cacaccttca gccgcaagga cctgcaggcc gagctgatcc tgctgttcga aagcagaag     660 gagttcggca cccccacgt gagcggcggc ctgaaggagg catcgagac cctgctgatg     720 acccagcgcc ccgccctgag cggcgacgcc gtgcagaaga tgctgggcca ctgcaccttc     780
gagccagccg agcccaaggc cgccaagaac acctacaccc gcgagcgctt catcctggctg     840 accaagctga caacctgcg catcctggag cagggcagca gcgccccct gaccgacacc     900 gagcgcgcca ccctgatgga cgagccctac cgcaagagca gctgaccta cgcccaggcc     960 cgcaagctgc tgggtctgga ggacaccgcc ttcttcaagg gcctgcgcta cggcaaggac    1020
aacgccgagg ccagcaccct gatggagatg aaggcctacc acgccatcag ccgcgccctg    1080
gagaaggagg cctgaagga caagaagagt cctctgaacc tgagccccga gctgcaggac    1140
gagatcggca ccgccttcag cctgttcaag accgacgagg acatcaccgg ccgcctgaag    1200
gaccgcatcc agcccgagat cctggaggcc tgctgaagc acatcagctt cgacaagttc    1260
gtgcagatca gcctgaaggc cctgcgccgc atcgtgcccc tgatggagca gggcaagcgc    1320
tacgacgagg cctgcgccga gatctacggc gaccactacg gcaagaagaa caccgaggag    1380
aagatctacc tgcctcctat ccccgccgac gagatccgca accccgtggt gctgcgcgcc    1440
ctgagccagg cccgcaaggt gatcaacggc gtggtgcgcc gctacggcag ccccgcccgc    1500
atccacatcg agaccgcccg cgaggtgggc aagagcttca aggaccgcaa ggagatcgag    1560
aagcgccagg aggagaaccg caaggaccgc gagaaggccg ccgccaagtt ccgcgagtac    1620
ttccccaact tcgtgggcga gcccaagagc aaggacatcc tgaagctgcg cctgtacgag    1680
cagcagcacg gcaagtgcct gtacagcggc aaggagatca acctgggccg cctgaacgag    1740
```

```
aagggctacg tggagatcga ccacgccctg cccttcagcc gcacctggga cgacagcttc    1800
aacaacaagg tgctggtgct gggcagcgag aaccagaaca agggcaacca gacccctac     1860 gagtacttca acggcaagga caacagccgc gagtggcagg agttcaaggc ccgcgtggag    1920
accagccgct tcccccgcag caagaagcag cgcatcctgc tgcagaagtt cgacgaggac    1980
ggcttcaagg agcgcaacct gaacgacacc cgctacgtga accgcttcct gtgccagttc    2040
gtggccgacc gcatgcgcct gaccggcaag ggcaagaagc gcgtgttcgc cagcaacggc    2100
cagatcacca acctgctgcg cggcttctgg ggcctgcgca aggtgcgcgc cgagaacgac    2160
cgccaccacg ccctggacgc cgtggtggtg gcctgcagca ccgtggccat gcagcagaag    2220
atcacccgct tcgtgcgcta caaggagatg aacgccttcg acggtaaaac catcgacaag    2280
gagaccggcg aggtgctgca ccagaagacc cacttccccc agccctggga gttcttcgcc    2340
caggaggtga tgatccgcgt gttcggcaag cccgacggca gcccgagtt cgaggaggcc     2400 gacaccccg agaagctgcg cacccctgctg gccgagaagc tgagcagccg ccctgaggcc    2460
gtgcacgagt acgtgactcc tctgttcgtg agccgcgccc caaccgcaa gatgagcggt     2520 cagggtcaca tggagaccgt gaagagcgcc aagcgcctgg acgagggcgt gagcgtgctg    2580
cgcgtgcccc tgacccagct gaagctgaag gacctggaga agatggtgaa ccgcgagcgc    2640
gagcccaagc tgtacgaggc cctgaaggcc cgcctggagg cccacaagga cgacccgcc     2700 aaggccttcg ccgagccctt ctacaagtac gacaaggccg gcaaccgcac ccagcaggtg    2760
aaggccgtgc gcgtggagca ggtgcagaag accggcgtgt gggtgcgcaa ccacaacggc    2820
atcgccgaca cgccaccat ggtgcgcgtg gacgtgttcg agaagggcga caagtactac     2880
ctggtgccca tctacagctg gcaggtggcc aagggcatcc tgcccgaccg cgccgtggtg    2940
cagggcaagg acgaggagga ctggcagctg atcgacgaca gcttcaactt caagttcagc    3000
ctgcacccca cgacctggt ggaggtgatc accaagaagg cccgcatgtt cggctacttc      3060
gccagctgcc accgcggcac cggcaacatc aacatccgca tccacgacct ggaccacaag    3120
atcggcaaga acggcatcct ggagggcatc ggcgtgaaga ccgccctgag cttccagaag    3180
taccagatcg acgagctggg caaggagatc cgcccctgcc gcctgaagaa gcgccctcct    3240
gtgcgctaa                                                            3249
```

<210> SEQ ID NO 14
<211> LENGTH: 859
<212> TYPE: PRT
<213> ORGANISM: Artificial Sequence
<220> FEATURE:
<223> OTHER INFORMATION: Synthetic Cas9 consensus sequence derived from
      Sm, Sp, St, and Li Cas9 sequences
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(18)
<223> OTHER INFORMATION: N-terminal RuvC-like domain
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)

```
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: Each Xaa can independently be any naturally
      occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Each Xaa can independently be any naturally
      occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
```

```
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (128)..(133)
<223> OTHER INFORMATION: Each Xaa can independently be any naturally
      occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(147)
<223> OTHER INFORMATION: Each Xaa can independently be any naturally
      occurring amino acid
<220> FEATURE:
<221> NAME/KEY: misc_feature
<222> LOCATION: (153)..(155)
<223> OTHER INFORMATION: Each Xaa can independently be any naturally
      occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(168)
<223> OTHER INFORMATION: Each Xaa can independently be any naturally
      occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (173)..(175)
<223> OTHER INFORMATION: Each Xaa can independently be any naturally
      occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
```

```
<222> LOCATION: (183)..(183)
<223> OTHER INFORMATION: Xaa can be any naturally occurring amino acid
<220> FEATURE:
<221> NAME/KEY: misc_feature
<222> LOCATION: (185)..(187)
<223> OTHER INFORMATION: Each Xaa can independently be any naturally
      occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (192)..(195)
<223> OTHER INFORMATION: Each Xaa can independently be any naturally
      occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (241)..(241)
```

```
<223> OTHER INFORMATION: Xaa can be any naturally occurring amino acid
<220> FEATURE:
<221> NAME/KEY: misc_feature
<222> LOCATION: (244)..(246)
<223> OTHER INFORMATION: Each Xaa can independently be any naturally
      occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (252)..(254)
<223> OTHER INFORMATION: Each Xaa can independently be any naturally
      occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (292)..(294)
<223> OTHER INFORMATION: Each Xaa can independently be any naturally
      occurring amino acid
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (308)..(308)
```

```
<223> OTHER INFORMATION: Xaa can be any naturally occurring amino acid
<220> FEATURE:
<221> NAME/KEY: misc_feature
<222> LOCATION: (319)..(322)
<223> OTHER INFORMATION: Each Xaa can independently be any naturally
      occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (335)..(337)
<223> OTHER INFORMATION: Each Xaa can independently be any naturally
      occurring amino acid
<220> FEATURE:
<221> NAME/KEY: misc_feature
<222> LOCATION: (346)..(346)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (356)..(361)
<223> OTHER INFORMATION: Each Xaa can independently be any naturally
      occurring amino acid
<220> FEATURE:
<221> NAME/KEY: misc_feature
<222> LOCATION: (363)..(363)
<223> OTHER INFORMATION: Xaa can be any naturally occurring amino acid
<220> FEATURE:
<221> NAME/KEY: misc_feature
<222> LOCATION: (370)..(373)
<223> OTHER INFORMATION: Each Xaa can independently be any naturally
      occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (376)..(376)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (386)..(390)
<223> OTHER INFORMATION: Each Xaa can independently be any naturally
      occurring amino acid
<220> FEATURE:
<221> NAME/KEY: misc_feature
<222> LOCATION: (393)..(393)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid
<220> FEATURE:
```

```
-continued

<221> NAME/KEY: misc_feature
<222> LOCATION: (403)..(403)
<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (413)..(416)
<223> OTHER INFORMATION: Each Xaa can independently be any naturally
      occurring amino acid
<220> FEATURE:
<221> NAME/KEY: misc_feature
<222> LOCATION: (418)..(418)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (433)..(433)
<223> OTHER INFORMATION: Xaa can be any naturally occurring amino acid
<220> FEATURE:
<221> NAME/KEY: misc_feature
<222> LOCATION: (437)..(439)
<223> OTHER INFORMATION: Each Xaa can independently be any naturally
      occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (465)..(469)
<223> OTHER INFORMATION: Each Xaa can independently be any naturally
      occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
```

```
<221> NAME/KEY: misc_feature
<222> LOCATION: (490)..(490)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (495)..(502)
<223> OTHER INFORMATION: RuvC-like domain
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (513)..(513)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (517)..(517)
<223> OTHER INFORMATION: Xaa can be any naturally occurring amino acid
<220> FEATURE:
<221> NAME/KEY: misc_feature
<222> LOCATION: (520)..(520)
<223> OTHER INFORMATION: Xaa can be any naturally occurring amino acid
<220> FEATURE:
<221> NAME/KEY: misc_feature
<222> LOCATION: (525)..(525)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (529)..(529)
<223> OTHER INFORMATION: Xaa can be any naturally occurring amino acid
<220> FEATURE:
<221> NAME/KEY: misc_feature
<222> LOCATION: (531)..(531)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (546)..(546)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
```

```
<220> FEATURE:
<221> NAME/KEY: misc_feature
<222> LOCATION: (555)..(575)
<223> OTHER INFORMATION: HNH-like domain
<220> FEATURE:
<221> NAME/KEY: misc_feature
<222> LOCATION: (556)..(556)
<223> OTHER INFORMATION: Xaa can be any naturally occurring amino acid
<220> FEATURE:
<221> NAME/KEY: misc_feature
<222> LOCATION: (560)..(560)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (565)..(565)
<223> OTHER INFORMATION: Xaa can be any naturally occurring amino acid
<220> FEATURE:
<221> NAME/KEY: misc_feature
<222> LOCATION: (567)..(567)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (582)..(582)
<223> OTHER INFORMATION: Xaa can be any naturally occurring amino acid
<220> FEATURE:
<221> NAME/KEY: misc_feature
<222> LOCATION: (583)..(583)
<223> OTHER INFORMATION: Xaa can be any naturally occurring amino acid
<220> FEATURE:
<221> NAME/KEY: misc_feature
<222> LOCATION: (585)..(585)
<223> OTHER INFORMATION: Xaa can be any naturally occurring amino acid
<220> FEATURE:
<221> NAME/KEY: misc_feature
<222> LOCATION: (588)..(588)
<223> OTHER INFORMATION: Xaa can be any naturally occurring amino acid
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (594)..(596)
<223> OTHER INFORMATION: Each Xaa can independently be any naturally
      occurring amino acid
<220> FEATURE:
<221> NAME/KEY: misc_feature
<222> LOCATION: (610)..(610)
<223> OTHER INFORMATION: Xaa can be any naturally occurring amino acid
<220> FEATURE:
<221> NAME/KEY: misc_feature
<222> LOCATION: (616)..(616)
<223> OTHER INFORMATION: Xaa can be any naturally occurring amino acid
<220> FEATURE:
<221> NAME/KEY: misc_feature
<222> LOCATION: (628)..(628)
<223> OTHER INFORMATION: Xaa can be any naturally occurring amino acid
<220> FEATURE:
<221> NAME/KEY: misc_feature
<222> LOCATION: (631)..(631)
<223> OTHER INFORMATION: Xaa can be any naturally occurring amino acid
<220> FEATURE:
<221> NAME/KEY: misc_feature
<222> LOCATION: (633)..(633)
<223> OTHER INFORMATION: Xaa can be any naturally occurring amino acid
<220> FEATURE:
<221> NAME/KEY: misc_feature
```

```
<222> LOCATION: (634)..(634)
<223> OTHER INFORMATION: Xaa can be any naturally occurring amino acid
<220> FEATURE:
<221> NAME/KEY: misc_feature
<222> LOCATION: (636)..(636)
<223> OTHER INFORMATION: Xaa can be any naturally occurring amino acid
<220> FEATURE:
<221> NAME/KEY: misc_feature
<222> LOCATION: (638)..(641)
<223> OTHER INFORMATION: Each Xaa can independently be any naturally
      occurring amino acid
<220> FEATURE:
<221> NAME/KEY: misc_feature
<222> LOCATION: (643)..(645)
<223> OTHER INFORMATION: Each Xaa can independently be any naturally
      occurring amino acid
<220> FEATURE:
<221> NAME/KEY: misc_feature
<222> LOCATION: (653)..(653)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (659)..(659)
<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (665)..(665)
<223> OTHER INFORMATION: Xaa can be any naturally occurring amino acid
<220> FEATURE:
<221> NAME/KEY: misc_feature
<222> LOCATION: (666)..(666)
<223> OTHER INFORMATION: Xaa can be any naturally occurring amino acid
<220> FEATURE:
<221> NAME/KEY: misc_feature
<222> LOCATION: (668)..(668)
<223> OTHER INFORMATION: Xaa can be any naturally occurring amino acid
<220> FEATURE:
<221> NAME/KEY: misc_feature
<222> LOCATION: (669)..(669)
<223> OTHER INFORMATION: Xaa can be any naturally occurring amino acid
<220> FEATURE:
<221> NAME/KEY: misc_feature
<222> LOCATION: (670)..(677)
<223> OTHER INFORMATION: RuvC-like domain
<220> FEATURE:
<221> NAME/KEY: misc_feature
<222> LOCATION: (680)..(680)
<223> OTHER INFORMATION: Xaa can be any naturally occurring amino acid
<220> FEATURE:
<221> NAME/KEY: misc_feature
<222> LOCATION: (681)..(681)
<223> OTHER INFORMATION: Xaa can be any naturally occurring amino acid
<220> FEATURE:
<221> NAME/KEY: misc_feature
<222> LOCATION: (683)..(683)
<223> OTHER INFORMATION: Xaa can be any naturally occurring amino acid
<220> FEATURE:
<221> NAME/KEY: misc_feature
<222> LOCATION: (686)..(686)
<223> OTHER INFORMATION: Xaa can be any naturally occurring amino acid
<220> FEATURE:
<221> NAME/KEY: misc_feature
<222> LOCATION: (696)..(696)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (704)..(704)
```

```
<223> OTHER INFORMATION: Xaa can be any naturally occurring amino acid
<220> FEATURE:
<221> NAME/KEY: misc_feature
<222> LOCATION: (708)..(708)
<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
<221> NAME/KEY: misc_feature
<222> LOCATION: (711)..(711)
<223> OTHER INFORMATION: Xaa can be any naturally occurring amino acid
<220> FEATURE:
<221> NAME/KEY: misc_feature
<222> LOCATION: (714)..(714)
<223> OTHER INFORMATION: Xaa can be any naturally occurring amino acid
<220> FEATURE:
<221> NAME/KEY: misc_feature
<222> LOCATION: (717)..(720)
<223> OTHER INFORMATION: Each Xaa can independently be any naturally
      occurring amino acid
<220> FEATURE:
<221> NAME/KEY: misc_feature
<222> LOCATION: (722)..(722)
<223> OTHER INFORMATION: Xaa can be any naturally occurring amino acid
<220> FEATURE:
<221> NAME/KEY: misc_feature
<222> LOCATION: (725)..(725)
<223> OTHER INFORMATION: Xaa can be any naturally occurring amino acid
<220> FEATURE:
<221> NAME/KEY: misc_feature
<222> LOCATION: (727)..(727)
<223> OTHER INFORMATION: Xaa can be any naturally occurring amino acid
<220> FEATURE:
<221> NAME/KEY: misc_feature
<222> LOCATION: (733)..(735)
<223> OTHER INFORMATION: Each Xaa can independently be any naturally
      occurring amino acid
<220> FEATURE:
<221> NAME/KEY: misc_feature
<222> LOCATION: (740)..(740)
<223> OTHER INFORMATION: Xaa can be any naturally occurring amino acid
<220> FEATURE:
<221> NAME/KEY: misc_feature
<222> LOCATION: (742)..(742)
<223> OTHER INFORMATION: Xaa can be any naturally occurring amino acid
<220> FEATURE:
<221> NAME/KEY: misc_feature
<222> LOCATION: (749)..(754)
<223> OTHER INFORMATION: Each Xaa can independently be any naturally
      occurring amino acid
<220> FEATURE:
<221> NAME/KEY: misc_feature
<222> LOCATION: (758)..(761)
<223> OTHER INFORMATION: Each Xaa can independently be any naturally
      occurring amino acid
<220> FEATURE:
<221> NAME/KEY: misc_feature
<222> LOCATION: (763)..(768)
<223> OTHER INFORMATION: Each Xaa can independently be any naturally
      occurring amino acid
<220> FEATURE:
<221> NAME/KEY: misc_feature
<222> LOCATION: (771)..(771)
<223> OTHER INFORMATION: Xaa can be any naturally occurring amino acid
<220> FEATURE:
<221> NAME/KEY: misc_feature
<222> LOCATION: (774)..(777)
<223> OTHER INFORMATION: Each Xaa can independently be any naturally
      occurring amino acid
<220> FEATURE:
<221> NAME/KEY: misc_feature
<222> LOCATION: (782)..(782)
<223> OTHER INFORMATION: Xaa can be any naturally occurring amino acid
<220> FEATURE:
<221> NAME/KEY: misc_feature
<222> LOCATION: (784)..(786)
<223> OTHER INFORMATION: Each Xaa can independently be any naturally
```

```
      occurring amino acid
<220> FEATURE:
<221> NAME/KEY: misc_feature
<222> LOCATION: (788)..(788)
<223> OTHER INFORMATION: Xaa can be any naturally occurring amino acid
<220> FEATURE:
<221> NAME/KEY: misc_feature
<222> LOCATION: (790)..(790)
<223> OTHER INFORMATION: Xaa can be any naturally occurring amino acid
<220> FEATURE:
<221> NAME/KEY: misc_feature
<222> LOCATION: (795)..(795)
<223> OTHER INFORMATION: Xaa can be any naturally occurring amino acid
<220> FEATURE:
<221> NAME/KEY: misc_feature
<222> LOCATION: (799)..(799)
<223> OTHER INFORMATION: Xaa can be any naturally occurring amino acid
<220> FEATURE:
<221> NAME/KEY: misc_feature
<222> LOCATION: (801)..(801)
<223> OTHER INFORMATION: Xaa can be any naturally occurring amino acid
<220> FEATURE:
<221> NAME/KEY: misc_feature
<222> LOCATION: (802)..(802)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (806)..(813)
<223> OTHER INFORMATION: Each Xaa can independently be any naturally
      occurring amino acid
<220> FEATURE:
<221> NAME/KEY: misc_feature
<222> LOCATION: (815)..(818)
<223> OTHER INFORMATION: Each Xaa can independently be any naturally
      occurring amino acid
<220> FEATURE:
<221> NAME/KEY: misc_feature
<222> LOCATION: (820)..(820)
<223> OTHER INFORMATION: Xaa can be any naturally occurring amino acid
<220> FEATURE:
<221> NAME/KEY: misc_feature
<222> LOCATION: (823)..(827)
<223> OTHER INFORMATION: Each Xaa can independently be any naturally
      occurring amino acid
<220> FEATURE:
<221> NAME/KEY: misc_feature
<222> LOCATION: (829)..(829)
<223> OTHER INFORMATION: Xaa can be any naturally occurring amino acid
<220> FEATURE:
<221> NAME/KEY: misc_feature
<222> LOCATION: (830)..(830)
<223> OTHER INFORMATION: Xaa can be any naturally occurring amino acid
<220> FEATURE:
<221> NAME/KEY: misc_feature
<222> LOCATION: (832)..(832)
<223> OTHER INFORMATION: Xaa can be any naturally occurring amino acid
<220> FEATURE:
<221> NAME/KEY: misc_feature
<222> LOCATION: (835)..(837)
<223> OTHER INFORMATION: Each Xaa can independently be any naturally
      occurring amino acid
<220> FEATURE:
<221> NAME/KEY: misc_feature
<222> LOCATION: (842)..(844)
<223> OTHER INFORMATION: Each Xaa can independently be any naturally
      occurring amino acid
<220> FEATURE:
<221> NAME/KEY: misc_feature
<222> LOCATION: (846)..(846)
<223> OTHER INFORMATION: Xaa can be any naturally occurring amino acid
<220> FEATURE:
<221> NAME/KEY: misc_feature
<222> LOCATION: (848)..(848)
<223> OTHER INFORMATION: Xaa can be any naturally occurring amino acid
<220> FEATURE:
```

```
<221> NAME/KEY: misc_feature
<222> LOCATION: (851)..(851)
<223> OTHER INFORMATION: Xaa can be any naturally occurring amino acid
<220> FEATURE:
<221> NAME/KEY: misc_feature
<222> LOCATION: (857)..(857)
<223> OTHER INFORMATION: Xaa can be any naturally occurring amino acid
<220> FEATURE:
<221> NAME/KEY: misc_feature
<222> LOCATION: (857)..(857)
<223> OTHER INFORMATION: Xaa can be any naturally occurring amino acid

<400> SEQUENCE: 14

Met Lys Tyr Xaa Ile Gly Leu Asp Ile Gly Thr Asn Ser Val Gly Trp
1               5                   10                  15

Ala Val Thr Asp Xaa Tyr Xaa Lys Xaa Lys Gly Xaa Xaa Xaa Ile
            20              25                  30

Xaa Lys Asn Xaa Gly Leu Phe Asp Gly Thr Ala Arg Xaa Arg Thr Ala
                35                  40                  45

Arg Arg Arg Arg Arg Xaa Asn Arg Ile Tyr Leu Gln Ile Phe Xaa Glu
50                  55                  60

Met Asp Phe Phe Arg Leu Xaa Ser Phe Val Xaa Xaa Lys Xaa Xaa Xaa
65                  70                  75                  80

Pro Xaa Phe Xaa Xaa Glu Tyr His Xaa Xaa Pro Thr Ile Tyr His Leu
                85                  90                  95

Arg Xaa Leu Xaa Lys Asp Leu Arg Leu Xaa Tyr Leu Ala Leu Ala His
            100                 105                 110

Xaa Ile Lys Xaa Arg Gly Asn Phe Leu Ile Glu Gly Xaa Xaa Asn Xaa
        115                 120                 125

Xaa Xaa Xaa Xaa Xaa Tyr Xaa Phe Xaa Ile Xaa Xaa Xaa Xaa Xaa Xaa
130                 135                 140

Xaa Xaa Xaa Pro Glu Lys Gly Phe Xaa Xaa Xaa Leu Xaa Gly Xaa Phe
145                 150                 155                 160

Xaa Phe Xaa Leu Glu Xaa Xaa Xaa Lys Xaa Xaa Tyr Xaa Xaa Xaa Leu
                165                 170                 175

Xaa Leu Leu Ile Gly Asp Xaa Tyr Xaa Xaa Xaa Phe Xaa Ala Lys Xaa
            180                 185                 190

Xaa Xaa Xaa Leu Ser Xaa Xaa Val Thr Xaa Ala Leu Ser Xaa Xaa Met
        195                 200                 205

Ile Xaa Arg Xaa Xaa His Asp Leu Leu Lys Xaa Xaa Tyr Xaa Glu Xaa
    210                 215                 220

Phe Xaa Lys Gly Tyr Ala Gly Tyr Ile Asp Gly Xaa Gln Phe Tyr Xaa
225                 230                 235                 240

Xaa Lys Leu Xaa Xaa Xaa Gly Xaa Xaa Xaa Lys Xaa Xaa Xaa Glu Xaa
                245                 250                 255

Xaa Leu Arg Lys Gln Arg Thr Phe Asp Asn Gly Xaa Ile Pro Xaa Gln
            260                 265                 270

Xaa His Leu Glu Xaa Ala Ile Xaa Xaa Gln Xaa Tyr Pro Phe Leu Asn
        275                 280                 285

Xaa Xaa Ile Xaa Xaa Xaa Thr Phe Arg Ile Pro Tyr Xaa Val Gly Pro
290                 295                 300

Leu Ala Gly Xaa Ser Phe Ala Trp Arg Lys Ile Pro Trp Asn Xaa Xaa
305                 310                 315                 320

Xaa Xaa Asp Ser Ala Phe Ile Xaa Xaa Met Thr Asp Leu Pro Xaa Xaa
            325                 330                 335

Xaa Val Leu Pro Lys His Ser Leu Tyr Xaa Xaa Val Tyr Asn Glu Leu
        340                 345                 350
```

```
Thr Lys Val Xaa Xaa Xaa Xaa Xaa Lys Xaa Ile Phe Lys Arg Lys
        355                 360                 365

Val Xaa Xaa Xaa Gly Xaa Xaa Phe Asn Xaa Ser Thr Tyr His Asp
    370                 375                 380

Leu Xaa Xaa Xaa Xaa Leu Asp Xaa Asn Xaa Xaa Glu Xaa Ile Xaa
385                 390                 395                 400

Leu Thr Xaa Phe Glu Asp Xaa Met Ile Xaa Xaa Leu Xaa Xaa Xaa Xaa
            405                 410                     415

Lys Xaa Leu Arg Arg Xaa Tyr Thr Gly Trp Gly Xaa Leu Ser Xaa Leu
            420                 425                 430

Xaa Gly Ile Arg Xaa Xaa Xaa Ser Thr Ile Leu Asp Xaa Leu Asp Asn
        435                 440                 445

Arg Asn Xaa Met Gln Leu Ile Xaa Asp Leu Xaa Phe Lys Ile Lys Gln
        450                 455                 460

Xaa Xaa Xaa Xaa Xaa Gly Ser Pro Ala Ile Lys Lys Gly Ile Leu Gln
465                 470                 475                 480

Xaa Xaa Lys Xaa Val Asp Glu Leu Val Xaa Met Gly Pro Xaa Ile Val
            485                 490                 495

Xaa Glu Met Ala Arg Glu Asn Gln Thr Xaa Gly Asn Ser Xaa Arg Lys
        500                 505                 510

Xaa Xaa Lys Glu Xaa Gly Ser Xaa Ile Leu Lys Glu Xaa Xaa Asn Leu
        515                 520                 525

Xaa Asn Xaa Xaa Leu Xaa Leu Tyr Tyr Leu Gln Asn Gly Xaa Asp Met
        530                 535                 540

Tyr Xaa Xaa Leu Asp Ile Leu Ser Xaa Tyr Asp Xaa Asp His Ile Xaa
545                 550                 555                 560

Pro Gln Xaa Phe Xaa Asp Xaa Ser Ile Asp Asn Val Leu Ser Asn Arg
            565                 570                 575

Lys Asp Xaa Val Pro Xaa Xaa Val Xaa Lys Lys Xaa Trp Xaa Leu Xaa
            580                 585                 590

Leu Xaa Xaa Xaa Arg Lys Phe Asp Leu Thr Lys Ala Glu Arg Gly Gly
        595                 600                 605

Leu Xaa Asp Lys Ala Phe Ile Xaa Arg Gln Leu Val Glu Thr Arg Gln
        610                 615                 620

Ile Thr Lys Xaa Val Ala Xaa Leu Xaa Xaa Asn Xaa Asp Xaa Xaa Xaa
625                 630                 635                 640

Xaa Val Xaa Xaa Xaa Thr Leu Lys Ser Leu Val Ser Xaa Phe Arg Lys
            645                 650                 655

Xaa Phe Xaa Xaa Leu Tyr Lys Val Xaa Xaa Asn Xaa Xaa His His Ala
            660                 665                 670

His Asp Ala Tyr Leu Asn Val Xaa Xaa Leu Xaa Tyr Pro Xaa Leu Glu
        675                 680                 685

Glu Phe Val Tyr Gly Asp Tyr Xaa Xaa Lys Ala Thr Lys Phe Tyr Xaa
        690                 695                 700

Asn Ile Met Xaa Phe Xaa Xaa Gly Glu Xaa Trp Lys Xaa Xaa Xaa Xaa
705                 710                 715                 720

Val Xaa Met Gln Xaa Asn Xaa Val Lys Lys Glu Gln Xaa Xaa Xaa Pro
        725                 730                 735

Lys Asn Ser Xaa Leu Xaa Lys Asp Lys Tyr Gly Gly Xaa Xaa Xaa Xaa
            740                 745                 750

Xaa Xaa Lys Gly Lys Xaa Xaa Xaa Ile Xaa Xaa Xaa Xaa Xaa
        755                 760                 765
```

```
Phe Leu Xaa Gly Tyr Xaa Xaa Xaa Xaa Leu Pro Lys Tyr Xaa Leu Xaa
    770                 775                 780

Xaa Xaa Gly Xaa Arg Xaa Leu Ala Ser Glu Xaa Lys Gly Asn Xaa Leu
785                 790                 795                 800

Xaa Xaa Leu Xaa Ala Xaa Xaa Xaa Xaa Xaa Xaa Xaa Glu Xaa Xaa
            805                 810                 815

Xaa Xaa Phe Xaa Ala Asn Xaa Xaa Xaa Xaa Leu Xaa Xaa Gly Xaa
            820                 825                 830

Ala Phe Xaa Xaa Xaa Ile Arg Arg Tyr Xaa Xaa Xaa Thr Xaa Ile Xaa
        835                 840                 845

Gln Ser Xaa Thr Gly Leu Tyr Glu Xaa Arg Leu
    850                 855
```

<210> SEQ ID NO 15
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (2)..(2)
<223> OTHER INFORMATION: Xaa is Val or His
<220> FEATURE:
<221> NAME/KEY: VARIANT
<222> LOCATION: (3)..(3)
<223> OTHER INFORMATION: Xaa is Ile, Leu, or Val
<220> FEATURE:
<221> NAME/KEY: VARIANT
<222> LOCATION: (5)..(5)
<223> OTHER INFORMATION: Xaa is Met or Thr

<400> SEQUENCE: 15

```
Ile Xaa Xaa Glu Xaa Ala Arg Glu
1               5
```

<210> SEQ ID NO 16
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (3)..(3)
<223> OTHER INFORMATION: Xaa is Ile, Leu, or Val

<400> SEQUENCE: 16

```
Ile Val Xaa Glu Met Ala Arg Glu
1               5
```

<210> SEQ ID NO 17
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (4)..(4)
<223> OTHER INFORMATION: Xaa is His or Leu
<220> FEATURE:
<221> NAME/KEY: VARIANT
<222> LOCATION: (7)..(7)
<223> OTHER INFORMATION: Xaa is Arg or Val
<220> FEATURE:
<221> NAME/KEY: VARIANT
<222> LOCATION: (8)..(8)
<223> OTHER INFORMATION: Xaa is Glu or Val

<400> SEQUENCE: 17

His His Ala Xaa Asp Ala Xaa Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: RuvC-like domain

<400> SEQUENCE: 18

His His Ala His Asp Ala Tyr Leu
1               5

<210> SEQ ID NO 19
<211> LENGTH: 30
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Lys or Pro
<220> FEATURE:
<221> NAME/KEY: VARIANT
<222> LOCATION: (4)..(4)
<223> OTHER INFORMATION: Xaa is Val, Leu, Ile, or Phe
<220> FEATURE:
<221> NAME/KEY: VARIANT
<222> LOCATION: (5)..(5)
<223> OTHER INFORMATION: Xaa is Gly, Ala, or Ser
<220> FEATURE:
<221> NAME/KEY: VARIANT
<222> LOCATION: (6)..(6)
<223> OTHER INFORMATION: Xaa is Leu, Ile, Val, or Phe
<220> FEATURE:
<221> NAME/KEY: MOD_RES
<222> LOCATION: (7)..(26)
<223> OTHER INFORMATION: N-terminal RuvC-like domain, each Xaa can be
      any amino acid or absent, region may encompass 5-20 residues
<220> FEATURE:
<221> NAME/KEY: VARIANT
<222> LOCATION: (29)..(29)
<223> OTHER INFORMATION: Xaa is Asp, Glu, Asn, or Gln

<400> SEQUENCE: 19

Lys Xaa Tyr Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Thr Asp Xaa Tyr
            20                  25                  30

<210> SEQ ID NO 20
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or
      Leu
<220> FEATURE:
<221> NAME/KEY: VARIANT
<222> LOCATION: (5)..(5)

```
<223> OTHER INFORMATION: Xaa is Asn, Ser, Gly, Ala, Asp, Thr, Arg, Met,
      or Phe
<220> FEATURE:
<221> NAME/KEY: VARIANT
<222> LOCATION: (6)..(6)
<223> OTHER INFORMATION: Xaa is Ser, Tyr, Asn, or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 20

Asp Xaa Gly Xaa Xaa Xaa Xaa Gly Xaa Xaa Xaa Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or
      Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met,
      or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 21

Asp Xaa Gly Xaa Xaa Ser Xaa Gly Xaa Xaa Xaa Xaa
1               5                   10
```

```
<210> SEQ ID NO 22
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or
      Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met,
      or Phe
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 22

Asp Ile Gly Xaa Xaa Ser Val Gly Trp Ala Xaa Xaa
1               5                   10

<210> SEQ ID NO 23
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: MOD_RES
<222> LOCATION: (12)..(12)
<223> OTHER INFORMATION: Any non-polar alkyl amino acid or a hydroxyl
      amino acid

<400> SEQUENCE: 23

Asp Ile Gly Thr Asn Ser Val Gly Trp Ala Val Xaa
1               5                   10

<210> SEQ ID NO 24
<211> LENGTH: 73
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (8)..(8)
<223> OTHER INFORMATION: Xaa is Lys or Arg
<220> FEATURE:
<221> NAME/KEY: VARIANT
<222> LOCATION: (12)..(12)
<223> OTHER INFORMATION: Xaa is Val or Thr
<220> FEATURE:
<221> NAME/KEY: VARIANT
<222> LOCATION: (13)..(13)
<223> OTHER INFORMATION: Xaa is Gly or Asp
<220> FEATURE:
<221> NAME/KEY: VARIANT
<222> LOCATION: (14)..(14)
<223> OTHER INFORMATION: Xaa is Glu, Gln, or Asp
<220> FEATURE:
<221> NAME/KEY: VARIANT
<222> LOCATION: (15)..(15)
<223> OTHER INFORMATION: Xaa is Glu or Asp
<220> FEATURE:
<221> NAME/KEY: VARIANT
<222> LOCATION: (19)..(19)
```

```
<223> OTHER INFORMATION: Xaa is Asp, Asn, or His
<220> FEATURE:
<221> NAME/KEY: VARIANT
<222> LOCATION: (20)..(20)
<223> OTHER INFORMATION: Xaa is Tyr, Arg, or Asn
<220> FEATURE:
<221> NAME/KEY: VARIANT
<222> LOCATION: (23)..(23)
<223> OTHER INFORMATION: Xaa is Gln, Asp, or Asn
<220> FEATURE:
<221> NAME/KEY: MOD_RES
<222> LOCATION: (25)..(64)
<223> OTHER INFORMATION: HNH-like domain, each Xaa can be any amino acid
      or absent, region may encompass 15-40 residues
<220> FEATURE:
<221> NAME/KEY: VARIANT
<222> LOCATION: (67)..(67)
<223> OTHER INFORMATION: Xaa is Gly or Glu
<220> FEATURE:
<221> NAME/KEY: VARIANT
<222> LOCATION: (69)..(69)
<223> OTHER INFORMATION: Xaa is Ser or Gly
<220> FEATURE:
<221> NAME/KEY: VARIANT
<222> LOCATION: (71)..(71)
<223> OTHER INFORMATION: Xaa is Asp or Asn

<400> SEQUENCE: 24

Leu Tyr Tyr Leu Gln Asn Gly Xaa Asp Met Tyr Xaa Xaa Xaa Xaa Leu
1               5                   10                  15

Asp Ile Xaa Xaa Leu Ser Xaa Tyr Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Asn Arg Xaa Lys Xaa Asp Xaa Val Pro
65                  70

<210> SEQ ID NO 25
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp, Glu, Gln, or Asn
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, Phe,
      or Trp
<220> FEATURE:
<221> NAME/KEY: VARIANT
<222> LOCATION: (9)..(9)
```

```
<223> OTHER INFORMATION: Xaa is Ser, Ala, Asp, Thr, or Lys
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg,
      Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr,
      Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met,
      Ala, Glu, Gly, or Ser
<220> FEATURE:
<221> NAME/KEY: VARIANT
<222> LOCATION: (13)..(13)
<223> OTHER INFORMATION: Xaa is Asp, Ser, Asn, Arg, Leu, or Thr
<220> FEATURE:
<221> NAME/KEY: VARIANT
<222> LOCATION: (14)..(14)
<223> OTHER INFORMATION: Xaa is Asp, Asn, or Ser
<220> FEATURE:
<221> NAME/KEY: VARIANT
<222> LOCATION: (15)..(15)
<223> OTHER INFORMATION: Xaa is Ser, Ala, Thr, Gly, or Arg
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
      Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
      Leu, Gln, Met, Gly, Tyr, or Val
<220> FEATURE:
<221> NAME/KEY: VARIANT
<222> LOCATION: (19)..(19)
<223> OTHER INFORMATION: Xaa is Lys, Leu, Arg, Met, Thr, or Phe
<220> FEATURE:
<221> NAME/KEY: VARIANT
<222> LOCATION: (20)..(20)
<223> OTHER INFORMATION: Xaa is Val, Leu, Ile, Ala, or Thr
<220> FEATURE:
<221> NAME/KEY: VARIANT
<222> LOCATION: (21)..(21)
<223> OTHER INFORMATION: Xaa is Leu, Ile, Val, or Ala
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
      Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln,
      Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile,
      Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu,
      Ser, Thr, Gly, Lys, Met, Asp, or Phe

<400> SEQUENCE: 25

Xaa Xaa Xaa His Xaa Xaa Pro Xaa Xaa Xaa Xaa Xaa Xaa Xaa Xaa Xaa
1               5                   10                  15
```

Xaa Asn Xaa Xaa Xaa Xaa Xaa Xaa Xaa Xaa Asn
            20                  25

<210> SEQ ID NO 26
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, Phe,
     or Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg,
     Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr,
     Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met,
     Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
     Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
     Leu, Gln, Met, Gly, Tyr, or Val
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
     Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln,
     Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile, Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu,
       Ser, Thr, Gly, Lys, Met, Asp, or Phe

<400> SEQUENCE: 26

Xaa Xaa Xaa His Xaa Xaa Pro Xaa Ser Xaa Xaa Xaa Asp Asp Ser Xaa
1               5                   10                  15

Xaa Asn Lys Val Leu Xaa Xaa Xaa Xaa Xaa Asn
            20                  25

<210> SEQ ID NO 27
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, or
       Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg,
       Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr,
       Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met,
       Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
       Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
       Leu, Gln, Met, Gly, Tyr, or Val
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
       Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln,
       Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile,
       Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu, Ser, Thr, Gly, Lys, Met, Asp, or Phe

<400> SEQUENCE: 27

Xaa Val Xaa His Ile Val Pro Xaa Ser Xaa Xaa Xaa Asp Asp Ser Xaa
1               5                   10                  15

Xaa Asn Lys Val Leu Thr Xaa Xaa Xaa Xaa Asn
            20                  25

<210> SEQ ID NO 28
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (2)..(2)
<223> OTHER INFORMATION: Xaa is Ile or Val
<220> FEATURE:
<221> NAME/KEY: VARIANT
<222> LOCATION: (6)..(6)
<223> OTHER INFORMATION: Xaa is Ile or Val
<220> FEATURE:
<221> NAME/KEY: VARIANT
<222> LOCATION: (9)..(9)
<223> OTHER INFORMATION: Xaa is Ala or Ser
<220> FEATURE:
<221> NAME/KEY: VARIANT
<222> LOCATION: (11)..(11)
<223> OTHER INFORMATION: Xaa is Ile or Leu
<220> FEATURE:
<221> NAME/KEY: VARIANT
<222> LOCATION: (12)..(12)
<223> OTHER INFORMATION: Xaa is Lys or Thr
<220> FEATURE:
<221> NAME/KEY: VARIANT
<222> LOCATION: (14)..(14)
<223> OTHER INFORMATION: Xaa is Asp or Asn
<220> FEATURE:
<221> NAME/KEY: VARIANT
<222> LOCATION: (19)..(19)
<223> OTHER INFORMATION: Xaa is Arg, Lys, or Leu
<220> FEATURE:
<221> NAME/KEY: VARIANT
<222> LOCATION: (22)..(22)
<223> OTHER INFORMATION: Xaa is Thr or Val
<220> FEATURE:
<221> NAME/KEY: VARIANT
<222> LOCATION: (23)..(23)
<223> OTHER INFORMATION: Xaa is Ser or Arg
<220> FEATURE:
<221> NAME/KEY: VARIANT
<222> LOCATION: (25)..(25)
<223> OTHER INFORMATION: Xaa is Lys, Asp, or Ala
<220> FEATURE:
<221> NAME/KEY: VARIANT
<222> LOCATION: (26)..(26)
<223> OTHER INFORMATION: Xaa is Glu, Lys, Gly, or Asn

<400> SEQUENCE: 28

Asp Xaa Asp His Ile Xaa Pro Gln Xaa Phe Xaa Xaa Asp Xaa Ser Ile
1               5                   10                  15

Asp Asn Xaa Val Leu Xaa Xaa Ser Xaa Xaa Asn
            20                  25

<210> SEQ ID NO 29
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature

```
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 29
nnnnnnnnnn nnnnnnnnnn guuuuagagc uaugcuguuu uggaaacaaa acagcauagc      60
aaguuaaaau aaggcuaguc cguuaucaac uugaaaaagu ggcaccgagu cggugc         116

<210> SEQ ID NO 30
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 30
nnnnnnnnnn nnnnnnnnnn guauuagagc uaugcuguau uggaaacaau acagcauagc      60
aaguuaauau aaggcuaguc cguuaucaac uugaaaaagu ggcaccgagu cggugc         116

<210> SEQ ID NO 31
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting domain
<220> FEATURE:
<221> NAME/KEY: misc_feature
<222> LOCATION: (21)..(32)
<223> OTHER INFORMATION: first complementarity domain
<220> FEATURE:
```

```
<221> NAME/KEY: misc_feature
<222> LOCATION: (33)..(36)
<223> OTHER INFORMATION: linking domain
<220> FEATURE:
<221> NAME/KEY: misc_feature
<222> LOCATION: (37)..(50)
<223> OTHER INFORMATION: second complementarity domain
<220> FEATURE:
<221> NAME/KEY: misc_feature
<222> LOCATION: (51)..(62)
<223> OTHER INFORMATION: proximal domain

<400> SEQUENCE: 31
nnnnnnnnnn nnnnnnnnnn guuuaagagc uagaaauagc aaguuuaaau aaggcuaguc    60
cguuaucaac uugaaaaagu ggcaccgagu cggugc                              96

<210> SEQ ID NO 32
<211> LENGTH: 47
<212> TYPE: RNA
<213> ORGANISM: Artificial Sequence
<220> FEATURE:
<223> OTHER INFORMATION: gRNA proximal and tail domains derived from S.
      pyogenes

<400> SEQUENCE: 32
aaggcuaguc cguuaucaac uugaaaaagu ggcaccgagu cggugcu                  47

<210> SEQ ID NO 33
<211> LENGTH: 49
<212> TYPE: RNA
<213> ORGANISM: Artificial Sequence
<220> FEATURE:
<223> OTHER INFORMATION: gRNA proximal and tail domains

<400> SEQUENCE: 33
aaggcuaguc cguuaucaac uugaaaaagu ggcaccgagu cggugguge                49

<210> SEQ ID NO 34
<211> LENGTH: 51
<212> TYPE: RNA
<213> ORGANISM: Artificial Sequence
<220> FEATURE:
<223> OTHER INFORMATION: gRNA proximal and tail domains

<400> SEQUENCE: 34
aaggcuaguc cguuaucaac uugaaaaagu ggcaccgagu cggugcggau c             51

<210> SEQ ID NO 35
<211> LENGTH: 31
<212> TYPE: RNA
<213> ORGANISM: Artificial Sequence
<220> FEATURE:
<223> OTHER INFORMATION: gRNA proximal and tail domains

<400> SEQUENCE: 35
aaggcuaguc cguuaucaac uugaaaaagu g                                   31

<210> SEQ ID NO 36
<211> LENGTH: 18
<212> TYPE: RNA
<213> ORGANISM: Artificial Sequence
<220> FEATURE:
<223> OTHER INFORMATION: gRNA proximal and tail domains

<400> SEQUENCE: 36
aaggcuaguc cguuauca                                                  18
```

```
<210> SEQ ID NO 37
<211> LENGTH: 12
<212> TYPE: RNA
<213> ORGANISM: Artificial Sequence
<220> FEATURE:
<223> OTHER INFORMATION: gRNA proximal and tail domains

<400> SEQUENCE: 37
aaggcuaguc cg                                                              12

<210> SEQ ID NO 38
<211> LENGTH: 102
<212> TYPE: RNA
<213> ORGANISM: Artificial Sequence
<220> FEATURE:
<223> OTHER INFORMATION: Unimolecular gRNA derived from S. aureus
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 38
nnnnnnnnnn nnnnnnnnnn guuuuaguac ucuggaaaca gaaucuacua aaacaaggca          60
aaaugccgug uuuaucucgu caacuuguug gcgagauuuu uu                            102

<210> SEQ ID NO 39
<211> LENGTH: 42
<212> TYPE: RNA
<213> ORGANISM: Artificial
<220> FEATURE:
<223> OTHER INFORMATION: Modular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 39
nnnnnnnnnn nnnnnnnnnn guuuuagagc uaugcuguuu ug                             42

<210> SEQ ID NO 40
<211> LENGTH: 85
<212> TYPE: RNA
<213> ORGANISM: Artificial Sequence
<220> FEATURE:
<223> OTHER INFORMATION: Modular gRNA derived from S. pyogenes
<220> FEATURE:
<221> NAME/KEY: misc_feature
<222> LOCATION: (1)..(9)
<223> OTHER INFORMATION: 5' extension domain
<220> FEATURE:
<221> NAME/KEY: misc_feature
<222> LOCATION: (10)..(33)
<223> OTHER INFORMATION: Second complementarity domain
<220> FEATURE:
<221> NAME/KEY: misc_feature
<222> LOCATION: (34)..(45)
<223> OTHER INFORMATION: Proximal domain
<220> FEATURE:
<221> NAME/KEY: misc_feature
```

```
<222> LOCATION: (46)..(85)
<223> OTHER INFORMATION: Tail domain

<400> SEQUENCE: 40
ggaaccauuc aaaacagcau agcaaguuaa aauaaggcua guccguuauc aacuugaaaa    60
aguggcaccg agucggugcu uuuuu                                         85

<210> SEQ ID NO 41
<211> LENGTH: 62
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 41
nnnnnnnnnn nnnnnnnnnn guuuuagagc uagaaauagc aaguuaaaau aaggcuaguc    60
cg                                                                  62

<210> SEQ ID NO 42
<211> LENGTH: 102
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain
<220> FEATURE:
```

```
<221> NAME/KEY: misc_feature
<222> LOCATION: (63)..(102)
<223> OTHER INFORMATION: Tail domain

<400> SEQUENCE: 42
nnnnnnnnnn nnnnnnnnnn guuuuagagc uagaaauagc aaguuaaaau aaggcuaguc    60
cguuaucaac uugaaaaagu ggcaccgagu cggugcuuuu uu                      102

<210> SEQ ID NO 43
<211> LENGTH: 75
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain
<220> FEATURE:
<221> NAME/KEY: misc_feature
<222> LOCATION: (59)..(70)
<223> OTHER INFORMATION: Proximal domain
<220> FEATURE:
<221> NAME/KEY: misc_feature
<222> LOCATION: (71)..(75)
<223> OTHER INFORMATION: Tail domain

<400> SEQUENCE: 43
nnnnnnnnnn nnnnnnnnnn guuuuagagc uaugcugaaa agcauagcaa guuaaaauaa    60
ggcuaguccg uuauc                                                    75

<210> SEQ ID NO 44
<211> LENGTH: 87
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (43)..(46)
<223> OTHER INFORMATION: Linking domain
<220> FEATURE:
<221> NAME/KEY: misc_feature
<222> LOCATION: (57)..(70)
<223> OTHER INFORMATION: Second complementarity domain
```

```
<220> FEATURE:
<221> NAME/KEY: misc_feature
<222> LOCATION: (71)..(82)
<223> OTHER INFORMATION: Proximal domain
<220> FEATURE:
<221> NAME/KEY: misc_feature
<222> LOCATION: (83)..(87)
<223> OTHER INFORMATION: Tail domain

<400> SEQUENCE: 44
nnnnnnnnnn nnnnnnnnnn guuuuagagc uaugcuguuu uggaaacaaa acagcauagc    60
aaguuaaaau aaggcuaguc cguuauc                                       87

<210> SEQ ID NO 45
<211> LENGTH: 42
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 45
nnnnnnnnnn nnnnnnnnnn guuuuagagc uguuuguuu cg                       42

<210> SEQ ID NO 46
<211> LENGTH: 78
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(3)
<223> OTHER INFORMATION: 5' extension domain
<220> FEATURE:
<221> NAME/KEY: misc_feature
<222> LOCATION: (4)..(27)
<223> OTHER INFORMATION: Second complementarity domain
<220> FEATURE:
<221> NAME/KEY: misc_feature
<222> LOCATION: (28)..(40)
<223> OTHER INFORMATION: Proximal domain
<220> FEATURE:
<221> NAME/KEY: misc_feature
<222> LOCATION: (41)..(78)
<223> OTHER INFORMATION: Tail domain

<400> SEQUENCE: 46
gggcgaaaca acacagcgag uuaaaauaag gcuuaguccg uacucaacuu gaaaaggugg    60
caccgauucg guguuuuu                                                 78

<210> SEQ ID NO 47
<211> LENGTH: 85
<212> TYPE: RNA
<213> ORGANISM: Artificial Sequence
<220> FEATURE:
<223> OTHER INFORMATION: Modular gRNA derived from S. pyogenes

<400> SEQUENCE: 47
```

```
gaaccauuca aaacagcaua gcaaguuaaa auaaggcuag uccguuauca acuugaaaaa      60
guggcaccga gucggugcuu uuuuu                                            85

<210> SEQ ID NO 48
<211> LENGTH: 96
<212> TYPE: RNA
<213> ORGANISM: Artificial Sequence
<220> FEATURE:
<223> OTHER INFORMATION: gRNA from S. pyogenes
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 48
nnnnnnnnnn nnnnnnnnnn guuuuagagc uagaaauagc aaguuaaaau aaggcuaguc      60
cguuaucaac uugaaaaagu ggcaccgagu cggugc                                96

<210> SEQ ID NO 49
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 49
nnnnnnnnnn nnnnnnnnnn guauuagagc uagaaauagc aaguuaauau aaggcuaguc      60
cguuaucaac uugaaaaagu ggcaccgagu cggugc                                96

<210> SEQ ID NO 50
<211> LENGTH: 104
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
```

```
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain

<400> SEQUENCE: 50
nnnnnnnnnn nnnnnnnnnn guuuuagagc uaugcugaaa agcauagcaa guuaaaauaa    60
ggcuaguccg uuaucaacuu gaaaaagugg caccgagucg gugc                     104

<210> SEQ ID NO 51
<211> LENGTH: 106
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(37)
<223> OTHER INFORMATION: First complementarity domain
<220> FEATURE:
<221> NAME/KEY: misc_feature
<222> LOCATION: (38)..(41)
<223> OTHER INFORMATION: Linking domain
<220> FEATURE:
<221> NAME/KEY: misc_feature
<222> LOCATION: (42)..(60)
<223> OTHER INFORMATION: Second complementarity domain

<400> SEQUENCE: 51
nnnnnnnnnn nnnnnnnnnn guuuuagagc uaugcuggaa acagcauagc aaguuaaaau    60
aaggcuaguc cguuaucaac uugaaaaagu ggcaccgagu cggugc                   106

<210> SEQ ID NO 52
<211> LENGTH: 12
<212> TYPE: PRT
<213> ORGANISM: Peptoniphilus duerdenii

<400> SEQUENCE: 52

Asp Ile Gly Thr Ala Ser Val Gly Trp Ala Val Thr
1               5                   10

<210> SEQ ID NO 53
<211> LENGTH: 12
<212> TYPE: PRT
<213> ORGANISM: Treponema denticola

<400> SEQUENCE: 53

Asp Val Gly Thr Gly Ser Val Gly Trp Ala Val Thr
1               5                   10

<210> SEQ ID NO 54
<211> LENGTH: 12
<212> TYPE: PRT
```

```
<213> ORGANISM: S. mutans

<400> SEQUENCE: 54

Asp Ile Gly Thr Asn Ser Val Gly Trp Ala Val Val
1               5                   10

<210> SEQ ID NO 55
<211> LENGTH: 12
<212> TYPE: PRT
<213> ORGANISM: S. pyogenes

<400> SEQUENCE: 55

Asp Ile Gly Thr Asn Ser Val Gly Trp Ala Val Ile
1               5                   10

<210> SEQ ID NO 56
<211> LENGTH: 12
<212> TYPE: PRT
<213> ORGANISM: L. innocua

<400> SEQUENCE: 56

Asp Ile Gly Thr Asn Ser Val Gly Trp Ala Val Leu
1               5                   10

<210> SEQ ID NO 57
<211> LENGTH: 12
<212> TYPE: PRT
<213> ORGANISM: Flavobacterium branchiophilum FL-15

<400> SEQUENCE: 57

Asp Leu Gly Thr Asn Ser Ile Gly Trp Ala Val Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: N-terminal RuvC-like domain

<400> SEQUENCE: 58

Asp Leu Gly Thr Asn Ser Ile Gly Trp Ala Ile
1               5                   10

<210> SEQ ID NO 59
<211> LENGTH: 12
<212> TYPE: PRT
<213> ORGANISM: Bacteroides fragilis, NCTC 9343

<400> SEQUENCE: 59

Asp Leu Gly Thr Asn Ser Ile Gly Trp Ala Leu Val
1               5                   10

<210> SEQ ID NO 60
<211> LENGTH: 12
<212> TYPE: PRT
<213> ORGANISM: Fusobacterium nucleatum

<400> SEQUENCE: 60

Asp Ile Gly Thr Asn Ser Val Gly Trp Cys Val Thr
1               5                   10

<210> SEQ ID NO 61
<211> LENGTH: 12
<212> TYPE: PRT
```

```
<213> ORGANISM: Acidaminococcus sp. D21

<400> SEQUENCE: 61

Asp Ile Gly Thr Asn Ser Val Gly Tyr Ala Val Thr
1               5                   10

<210> SEQ ID NO 62
<211> LENGTH: 12
<212> TYPE: PRT
<213> ORGANISM: Coprococcus catus GD-7

<400> SEQUENCE: 62

Asp Met Gly Thr Gly Ser Leu Gly Trp Ala Val Thr
1               5                   10

<210> SEQ ID NO 63
<211> LENGTH: 12
<212> TYPE: PRT
<213> ORGANISM: Oenococcus kitaharae DSM 17330

<400> SEQUENCE: 63

Asp Ile Gly Thr Ser Ser Val Gly Trp Ala Ala Ile
1               5                   10

<210> SEQ ID NO 64
<211> LENGTH: 12
<212> TYPE: PRT
<213> ORGANISM: Catenibacterium mitsuokai DSM 15897

<400> SEQUENCE: 64

Asp Leu Gly Thr Gly Ser Val Gly Trp Ala Val Val
1               5                   10

<210> SEQ ID NO 65
<211> LENGTH: 12
<212> TYPE: PRT
<213> ORGANISM: Mycoplasma gallisepticum str. F

<400> SEQUENCE: 65

Asp Leu Gly Val Gly Ser Val Gly Trp Ala Ile Val
1               5                   10

<210> SEQ ID NO 66
<211> LENGTH: 12
<212> TYPE: PRT
<213> ORGANISM: Mycoplasma ovipneumoniae SC01

<400> SEQUENCE: 66

Asp Leu Gly Ile Ala Ser Ile Gly Trp Ala Ile Ile
1               5                   10

<210> SEQ ID NO 67
<211> LENGTH: 12
<212> TYPE: PRT
<213> ORGANISM: Mycoplasma canis PG 14

<400> SEQUENCE: 67

Asp Leu Gly Ile Ala Ser Val Gly Trp Ala Ile Val
1               5                   10

<210> SEQ ID NO 68
<211> LENGTH: 12
<212> TYPE: PRT
<213> ORGANISM: Mycoplasma synoviae 53
```

```
<400> SEQUENCE: 68

Asp Leu Gly Val Ala Ser Val Gly Trp Ser Ile Val
1               5                   10

<210> SEQ ID NO 69
<211> LENGTH: 12
<212> TYPE: PRT
<213> ORGANISM: Eubacterium rectale

<400> SEQUENCE: 69

Asp Ile Gly Ile Ala Ser Val Gly Trp Ala Ile Leu
1               5                   10

<210> SEQ ID NO 70
<211> LENGTH: 12
<212> TYPE: PRT
<213> ORGANISM: Enterococcus faecalis TX0012

<400> SEQUENCE: 70

Asp Leu Gly Ile Ser Ser Val Gly Trp Ser Val Ile
1               5                   10

<210> SEQ ID NO 71
<211> LENGTH: 12
<212> TYPE: PRT
<213> ORGANISM: Ilyobacter polytropus DSM 2926

<400> SEQUENCE: 71

Asp Ile Gly Ile Ala Ser Val Gly Trp Ser Val Ile
1               5                   10

<210> SEQ ID NO 72
<211> LENGTH: 12
<212> TYPE: PRT
<213> ORGANISM: Ruminococcus albus 8

<400> SEQUENCE: 72

Asp Val Gly Ile Gly Ser Ile Gly Trp Ala Val Ile
1               5                   10

<210> SEQ ID NO 73
<211> LENGTH: 12
<212> TYPE: PRT
<213> ORGANISM: Elusimicrobium minutum Pei191

<400> SEQUENCE: 73

Asp Leu Gly Val Gly Ser Ile Gly Phe Ala Ile Val
1               5                   10

<210> SEQ ID NO 74
<211> LENGTH: 12
<212> TYPE: PRT
<213> ORGANISM: Akkermansia muciniphila

<400> SEQUENCE: 74

Asp Ile Gly Tyr Ala Ser Ile Gly Trp Ala Val Ile
1               5                   10

<210> SEQ ID NO 75
<211> LENGTH: 12
<212> TYPE: PRT
<213> ORGANISM: Artificial Sequence
<220> FEATURE:
<223> OTHER INFORMATION: N-terminal RuvC-like domain
```

<400> SEQUENCE: 75

Asp Thr Gly Thr Asn Ser Leu Gly Trp Ala Ile Val
1               5                   10

<210> SEQ ID NO 76
<211> LENGTH: 12
<212> TYPE: PRT
<213> ORGANISM: Cand. Puniceispirillum marinum

<400> SEQUENCE: 76

Asp Leu Gly Thr Asn Ser Ile Gly Trp Cys Leu Leu
1               5                   10

<210> SEQ ID NO 77
<211> LENGTH: 12
<212> TYPE: PRT
<213> ORGANISM: Rhodospirillum rubrum

<400> SEQUENCE: 77

Asp Ile Gly Thr Asp Ser Leu Gly Trp Ala Val Phe
1               5                   10

<210> SEQ ID NO 78
<211> LENGTH: 12
<212> TYPE: PRT
<213> ORGANISM: Lactobacillus rhamnosus GG

<400> SEQUENCE: 78

Asp Ile Gly Ser Asn Ser Ile Gly Phe Ala Val Val
1               5                   10

<210> SEQ ID NO 79
<211> LENGTH: 12
<212> TYPE: PRT
<213> ORGANISM: Sphaerochaeta globus str. Buddy

<400> SEQUENCE: 79

Asp Leu Gly Val Gly Ser Ile Gly Val Ala Val Ala
1               5                   10

<210> SEQ ID NO 80
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 80

Asp Leu Gly Ile Ala Ser Cys Gly Trp Gly Val Val
1               5                   10

<210> SEQ ID NO 81
<211> LENGTH: 12
<212> TYPE: PRT
<213> ORGANISM: Mycoplasma mobile 163K

<400> SEQUENCE: 81

Asp Leu Gly Ile Ala Ser Val Gly Trp Cys Leu Thr
1               5                   10

<210> SEQ ID NO 82
<211> LENGTH: 12
<212> TYPE: PRT
<213> ORGANISM: Streptococcus thermophilus LMD-9

```
<400> SEQUENCE: 82

Asp Ile Gly Ile Gly Ser Val Gly Val Gly Ile Leu
1               5                   10

<210> SEQ ID NO 83
<211> LENGTH: 12
<212> TYPE: PRT
<213> ORGANISM: Staphylococcus lugdunensis M23590

<400> SEQUENCE: 83

Asp Ile Gly Ile Thr Ser Val Gly Tyr Gly Leu Ile
1               5                   10

<210> SEQ ID NO 84
<211> LENGTH: 12
<212> TYPE: PRT
<213> ORGANISM: Eubacterium dolichum DSM 3991

<400> SEQUENCE: 84

Asp Ile Gly Ile Thr Ser Val Gly Phe Gly Ile Ile
1               5                   10

<210> SEQ ID NO 85
<211> LENGTH: 12
<212> TYPE: PRT
<213> ORGANISM: Lactobacillus coryniformis KCTC 3535

<400> SEQUENCE: 85

Asp Val Gly Ile Thr Ser Thr Gly Tyr Ala Val Leu
1               5                   10

<210> SEQ ID NO 86
<211> LENGTH: 12
<212> TYPE: PRT
<213> ORGANISM: Nitratifractor salsuginis DSM 16511

<400> SEQUENCE: 86

Asp Leu Gly Ile Thr Ser Phe Gly Tyr Ala Ile Leu
1               5                   10

<210> SEQ ID NO 87
<211> LENGTH: 12
<212> TYPE: PRT
<213> ORGANISM: Bifidobacterium bifidum S17

<400> SEQUENCE: 87

Asp Ile Gly Asn Ala Ser Val Gly Trp Ser Ala Phe
1               5                   10

<210> SEQ ID NO 88
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 88

Asp Val Gly Thr Asn Ser Cys Gly Trp Val Ala Met
1               5                   10

<210> SEQ ID NO 89
<211> LENGTH: 12
<212> TYPE: PRT
<213> ORGANISM: Acidothermus cellulolyticus 11B
```

```
<400> SEQUENCE: 89

Asp Val Gly Glu Arg Ser Ile Gly Leu Ala Ala Val
1               5                   10

<210> SEQ ID NO 90
<211> LENGTH: 12
<212> TYPE: PRT
<213> ORGANISM: Bifidobacterium longum DJO10A

<400> SEQUENCE: 90

Asp Val Gly Leu Asn Ser Val Gly Leu Ala Ala Val
1               5                   10

<210> SEQ ID NO 91
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 91

Asp Val Gly Leu Met Ser Val Gly Leu Ala Ala Ile
1               5                   10

<210> SEQ ID NO 92
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 92

Asp Val Gly Thr Phe Ser Val Gly Leu Ala Ala Ile
1               5                   10

<210> SEQ ID NO 93
<211> LENGTH: 12
<212> TYPE: PRT
<213> ORGANISM: Staphylococcus pseudintermedius ED99

<400> SEQUENCE: 93

Asp Ile Gly Thr Gly Ser Val Gly Tyr Ala Cys Met
1               5                   10

<210> SEQ ID NO 94
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 94

Asp Leu Gly Thr Thr Ser Ile Gly Phe Ala His Ile
1               5                   10

<210> SEQ ID NO 95
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 95

Asp Leu Gly Thr Asn Ser Ile Gly Ser Ser Val Arg
1               5                   10
```

<210> SEQ ID NO 96
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 96

Asp Ile Gly Thr Asn Ser Ile Gly Trp Ala Val Ile
1               5                   10

<210> SEQ ID NO 97
<211> LENGTH: 12
<212> TYPE: PRT
<213> ORGANISM: Pasteurella multocida str. Pm70

<400> SEQUENCE: 97

Asp Leu Gly Ile Ala Ser Val Gly Trp Ala Val Val
1               5                   10

<210> SEQ ID NO 98
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 98

Asp Ile Gly Ile Ala Ser Val Gly Trp Ala Val Leu
1               5                   10

<210> SEQ ID NO 99
<211> LENGTH: 12
<212> TYPE: PRT
<213> ORGANISM: Helicobacter mustelae 12198

<400> SEQUENCE: 99

Asp Ile Gly Ile Ala Ser Ile Gly Trp Ala Val Ile
1               5                   10

<210> SEQ ID NO 100
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 100

Asp Ile Gly Ile Ala Ser Val Gly Trp Ala Ile Ile
1               5                   10

<210> SEQ ID NO 101
<211> LENGTH: 12
<212> TYPE: PRT
<213> ORGANISM: Clostridium cellulolyticum H10

<400> SEQUENCE: 101

Asp Val Gly Ile Ala Ser Val Gly Trp Ala Val Ile
1               5                   10

<210> SEQ ID NO 102
<211> LENGTH: 11
<212> TYPE: PRT
<213> ORGANISM: Artificial Sequence
<220> FEATURE:
<223> OTHER INFORMATION: N-terminal RuvC-like domain

<400> SEQUENCE: 102

Asp Ile Gly Ile Ala Ser Val Gly Trp Ala Leu
1               5                   10

<210> SEQ ID NO 103
<211> LENGTH: 12
<212> TYPE: PRT
<213> ORGANISM: Neisseria meningitidis

<400> SEQUENCE: 103

Asp Ile Gly Ile Ala Ser Val Gly Trp Ala Met Val
1               5                   10

<210> SEQ ID NO 104
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 104

Asp Ile Gly Ile Thr Ser Val Gly Trp Ala Val Ile
1               5                   10

<210> SEQ ID NO 105
<211> LENGTH: 12
<212> TYPE: PRT
<213> ORGANISM: Wolinella succinogenes DSM 1740

<400> SEQUENCE: 105

Asp Leu Gly Ile Ser Ser Leu Gly Trp Ala Ile Val
1               5                   10

<210> SEQ ID NO 106
<211> LENGTH: 12
<212> TYPE: PRT
<213> ORGANISM: Azospirillum sp. B510

<400> SEQUENCE: 106

Asp Leu Gly Thr Asn Ser Ile Gly Trp Gly Leu Leu
1               5                   10

<210> SEQ ID NO 107
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 107

Asp Leu Gly Ser Thr Ser Leu Gly Trp Ala Ile Phe
1               5                   10

<210> SEQ ID NO 108
<211> LENGTH: 12
<212> TYPE: PRT
<213> ORGANISM: Campylobacter jejuni, NCTC 11168

<400> SEQUENCE: 108

Asp Ile Gly Ile Ser Ser Ile Gly Trp Ala Phe Ser
1               5                   10

<210> SEQ ID NO 109
<211> LENGTH: 12

```
<212> TYPE: PRT
<213> ORGANISM: Parvibaculum lavamentivorans DS-1

<400> SEQUENCE: 109

Asp Ile Gly Thr Thr Ser Ile Gly Phe Ser Val Ile
1               5                   10

<210> SEQ ID NO 110
<211> LENGTH: 12
<212> TYPE: PRT
<213> ORGANISM: Dinoroseobacter shibae DFL 12

<400> SEQUENCE: 110

Asp Ile Gly Thr Ser Ser Ile Gly Trp Trp Leu Tyr
1               5                   10

<210> SEQ ID NO 111
<211> LENGTH: 12
<212> TYPE: PRT
<213> ORGANISM: Nitrobacter hamburgensis X14

<400> SEQUENCE: 111

Asp Leu Gly Ser Asn Ser Leu Gly Trp Phe Val Thr
1               5                   10

<210> SEQ ID NO 112
<211> LENGTH: 12
<212> TYPE: PRT
<213> ORGANISM: Bradyrhizobium sp. BTAi1

<400> SEQUENCE: 112

Asp Leu Gly Ala Asn Ser Leu Gly Trp Phe Val Val
1               5                   10

<210> SEQ ID NO 113
<211> LENGTH: 15
<212> TYPE: PRT
<213> ORGANISM: Artificial Sequence
<220> FEATURE:
<223> OTHER INFORMATION: N-terminal RuvC-like domain

<400> SEQUENCE: 113

Asp Ile Gly Leu Arg Ile Gly Ile Thr Ser Cys Gly Trp Ser Ile
1               5                   10                  15

<210> SEQ ID NO 114
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 114

Asp Met Gly Ala Lys Tyr Thr Gly Val Phe Tyr Ala
1               5                   10

<210> SEQ ID NO 115
<211> LENGTH: 12
<212> TYPE: PRT
<213> ORGANISM: Wolinella succinogenes DSM 1740

<400> SEQUENCE: 115

Asp Leu Gly Gly Lys Asn Thr Gly Phe Phe Ser Phe
1               5                   10
```

```
<210> SEQ ID NO 116
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 116

Asp Leu Gly Val Lys Asn Thr Gly Val Phe Ser Ala
1               5                   10

<210> SEQ ID NO 117
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 117

Asp Leu Gly Ala Lys Phe Thr Gly Val Ala Leu Tyr
1               5                   10

<210> SEQ ID NO 118
<211> LENGTH: 12
<212> TYPE: PRT
<213> ORGANISM: Legionella pneumophila str. Paris

<400> SEQUENCE: 118

Asp Leu Gly Gly Lys Phe Thr Gly Val Cys Leu Ser
1               5                   10

<210> SEQ ID NO 119
<211> LENGTH: 12
<212> TYPE: PRT
<213> ORGANISM: Artificial Sequence
<220> FEATURE:
<223> OTHER INFORMATION: N-terminal RuvC-like domain

<400> SEQUENCE: 119

Asp Leu Gly Gly Thr Tyr Thr Gly Thr Phe Ile Thr
1               5                   10

<210> SEQ ID NO 120
<211> LENGTH: 12
<212> TYPE: PRT
<213> ORGANISM: S. thermophilus

<400> SEQUENCE: 120

Asp Ile Gly Thr Asn Ser Val Gly Trp Ala Val Thr
1               5                   10

<210> SEQ ID NO 121
<211> LENGTH: 12
<212> TYPE: PRT
<213> ORGANISM: Eubacterium yurii

<400> SEQUENCE: 121

Asp Val Gly Thr Asn Ser Val Gly Trp Ala Val Thr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: N-terminal RuvC-like domain
```

```
<400> SEQUENCE: 122

Asp Met Gly Thr Asn Ser Val Gly Trp Ala Val Thr
1               5                   10

<210> SEQ ID NO 123
<211> LENGTH: 12
<212> TYPE: PRT
<213> ORGANISM: Solobacterium moorei F0204

<400> SEQUENCE: 123

Asp Val Gly Thr Ser Ser Val Gly Trp Ala Val Thr
1               5                   10

<210> SEQ ID NO 124
<211> LENGTH: 27
<212> TYPE: PRT
<213> ORGANISM: Treponema denticola

<400> SEQUENCE: 124

Asp Ile Asp His Ile Tyr Pro Gln Ser Lys Ile Lys Asp Asp Ser Ile
1               5                   10                  15

Ser Asn Arg Val Leu Val Cys Ser Ser Cys Asn
            20                  25

<210> SEQ ID NO 125
<211> LENGTH: 27
<212> TYPE: PRT
<213> ORGANISM: Coprococcus catus GD-7

<400> SEQUENCE: 125

Asp Ile Asp His Ile Tyr Pro Gln Ser Lys Thr Met Asp Asp Ser Leu
1               5                   10                  15

Asn Asn Arg Val Leu Val Lys Lys Asn Tyr Asn
            20                  25

<210> SEQ ID NO 126
<211> LENGTH: 27
<212> TYPE: PRT
<213> ORGANISM: Peptoniphilus duerdenii

<400> SEQUENCE: 126

Asp Gln Asp His Ile Tyr Pro Lys Ser Lys Ile Tyr Asp Asp Ser Leu
1               5                   10                  15

Glu Asn Arg Val Leu Val Lys Lys Asn Leu Asn
            20                  25

<210> SEQ ID NO 127
<211> LENGTH: 27
<212> TYPE: PRT
<213> ORGANISM: Catenibacterium mitsuokai DSM 15897

<400> SEQUENCE: 127

Gln Ile Asp His Ile Val Pro Gln Ser Leu Val Lys Asp Asp Ser Phe
1               5                   10                  15

Asp Asn Arg Val Leu Val Val Pro Ser Glu Asn
            20                  25

<210> SEQ ID NO 128
<211> LENGTH: 27
<212> TYPE: PRT
<213> ORGANISM: S. mutans

<400> SEQUENCE: 128
```

```
Asp Ile Asp His Ile Ile Pro Gln Ala Phe Ile Lys Asp Asn Ser Ile
1               5                   10                  15

Asp Asn Arg Val Leu Thr Ser Ser Lys Glu Asn
            20                  25

<210> SEQ ID NO 129
<211> LENGTH: 27
<212> TYPE: PRT
<213> ORGANISM: S. thermophilus

<400> SEQUENCE: 129

Asp Ile Asp His Ile Ile Pro Gln Ala Phe Leu Lys Asp Asn Ser Ile
1               5                   10                  15

Asp Asn Lys Val Leu Val Ser Ser Ala Ser Asn
            20                  25

<210> SEQ ID NO 130
<211> LENGTH: 27
<212> TYPE: PRT
<213> ORGANISM: Oenococcus kitaharae DSM 17330

<400> SEQUENCE: 130

Asp Ile Asp His Ile Ile Pro Gln Ala Tyr Thr Lys Asp Asn Ser Leu
1               5                   10                  15

Asp Asn Arg Val Leu Val Ser Asn Ile Thr Asn
            20                  25

<210> SEQ ID NO 131
<211> LENGTH: 27
<212> TYPE: PRT
<213> ORGANISM: L. inocua

<400> SEQUENCE: 131

Asp Ile Asp His Ile Val Pro Gln Ser Phe Ile Thr Asp Asn Ser Ile
1               5                   10                  15

Asp Asn Leu Val Leu Thr Ser Ser Ala Gly Asn
            20                  25

<210> SEQ ID NO 132
<211> LENGTH: 27
<212> TYPE: PRT
<213> ORGANISM: S. pyogenes

<400> SEQUENCE: 132

Asp Val Asp His Ile Val Pro Gln Ser Phe Leu Lys Asp Asp Ser Ile
1               5                   10                  15

Asp Asn Lys Val Leu Thr Arg Ser Asp Lys Asn
            20                  25

<210> SEQ ID NO 133
<211> LENGTH: 27
<212> TYPE: PRT
<213> ORGANISM: Acidaminococcus sp. D21

<400> SEQUENCE: 133

Asn Ile Asp His Ile Tyr Pro Gln Ser Met Val Lys Asp Asp Ser Leu
1               5                   10                  15

Asp Asn Lys Val Leu Val Gln Ser Glu Ile Asn
            20                  25

<210> SEQ ID NO 134
```

-continued

```
<211> LENGTH: 27
<212> TYPE: PRT
<213> ORGANISM: Lactobacillus rhamnosus GG

<400> SEQUENCE: 134

Asp Ile Asp His Ile Leu Pro Gln Ser Leu Ile Lys Asp Asp Ser Leu
1               5                   10                  15

Asp Asn Arg Val Leu Val Asn Ala Thr Ile Asn
            20                  25

<210> SEQ ID NO 135
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 135

Asp Ile Asp His Ile Leu Pro Gln Ser Phe Ile Lys Asp Asp Ser Leu
1               5                   10                  15

Glu Asn Arg Val Leu Val Lys Lys Ala Val Asn
            20                  25

<210> SEQ ID NO 136
<211> LENGTH: 27
<212> TYPE: PRT
<213> ORGANISM: Staphylococcus pseudintermedius ED99

<400> SEQUENCE: 136

Glu Val Asp His Ile Phe Pro Arg Ser Phe Ile Lys Asp Asp Ser Ile
1               5                   10                  15

Asp Asn Lys Val Leu Val Ile Lys Lys Met Asn
            20                  25

<210> SEQ ID NO 137
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 137

Glu Val Asp His Ile Ile Pro Arg Ser Tyr Ile Lys Asp Asp Ser Phe
1               5                   10                  15

Glu Asn Lys Val Leu Val Tyr Arg Glu Glu Asn
            20                  25

<210> SEQ ID NO 138
<211> LENGTH: 27
<212> TYPE: PRT
<213> ORGANISM: Bifidobacterium bifidum S17

<400> SEQUENCE: 138

Asp Ile Asp His Ile Ile Pro Gln Ala Val Thr Gln Asn Asp Ser Ile
1               5                   10                  15

Asp Asn Arg Val Leu Val Ala Arg Ala Glu Asn
            20                  25

<210> SEQ ID NO 139
<211> LENGTH: 27
<212> TYPE: PRT
<213> ORGANISM: Mycoplasma gallisepticum str. F

<400> SEQUENCE: 139
```

```
Glu Ile Asp His Ile Ile Pro Tyr Ser Ile Ser Phe Asp Asp Ser Ser
1               5                   10                  15

Ser Asn Lys Leu Leu Val Leu Ala Glu Ser Asn
            20                  25

<210> SEQ ID NO 140
<211> LENGTH: 27
<212> TYPE: PRT
<213> ORGANISM: Mycoplasma canis PG 14

<400> SEQUENCE: 140

Glu Ile Asp His Ile Ile Pro Tyr Ser Leu Cys Phe Asp Asp Ser Ser
1               5                   10                  15

Ala Asn Lys Val Leu Val His Lys Gln Ser Asn
            20                  25

<210> SEQ ID NO 141
<211> LENGTH: 27
<212> TYPE: PRT
<213> ORGANISM: Ilyobacter polytropus DSM 2926

<400> SEQUENCE: 141

Asp Ile Asp His Ile Ile Pro Tyr Ser Arg Ser Met Asp Asp Ser Tyr
1               5                   10                  15

Ser Asn Lys Val Leu Val Leu Ser Gly Glu Asn
            20                  25

<210> SEQ ID NO 142
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 142

Asp Ile Asp His Ile Ile Pro Tyr Ser Lys Ser Met Asp Asp Ser Phe
1               5                   10                  15

Asn Asn Lys Val Leu Cys Leu Ala Glu Glu Asn
            20                  25

<210> SEQ ID NO 143
<211> LENGTH: 27
<212> TYPE: PRT
<213> ORGANISM: Campylobacter jejuni

<400> SEQUENCE: 143

Glu Ile Asp His Ile Tyr Pro Tyr Ser Arg Ser Phe Asp Asp Ser Tyr
1               5                   10                  15

Met Asn Lys Val Leu Val Phe Thr Lys Gln Asn
            20                  25

<210> SEQ ID NO 144
<211> LENGTH: 27
<212> TYPE: PRT
<213> ORGANISM: Clostridium cellulolyticum H10

<400> SEQUENCE: 144

Gln Ile Asp His Ile Tyr Pro Tyr Ser Arg Ser Met Asp Asp Ser Tyr
1               5                   10                  15

Met Asn Lys Val Leu Val Leu Thr Asp Glu Asn
            20                  25
```

<210> SEQ ID NO 145
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 145

Glu Ile Asp His Ile Ile Pro Phe Ser Arg Ser Phe Asp Asp Ser Leu
1               5                   10                  15

Ser Asn Lys Ile Leu Val Leu Gly Ser Glu Asn
            20                  25

<210> SEQ ID NO 146
<211> LENGTH: 27
<212> TYPE: PRT
<213> ORGANISM: N. meningitides

<400> SEQUENCE: 146

Glu Ile Asp His Ala Leu Pro Phe Ser Arg Thr Trp Asp Asp Ser Phe
1               5                   10                  15

Asn Asn Lys Val Leu Val Leu Gly Ser Glu Asn
            20                  25

<210> SEQ ID NO 147
<211> LENGTH: 27
<212> TYPE: PRT
<213> ORGANISM: Pasteurella multocida str. Pm70

<400> SEQUENCE: 147

Glu Ile Asp His Ala Leu Pro Phe Ser Arg Thr Trp Asp Asp Ser Phe
1               5                   10                  15

Asn Asn Lys Val Leu Val Leu Ala Ser Glu Asn
            20                  25

<210> SEQ ID NO 148
<211> LENGTH: 27
<212> TYPE: PRT
<213> ORGANISM: Enterococcus faecalis TX0012

<400> SEQUENCE: 148

Glu Ile Asp His Ile Ile Pro Ile Ser Ile Ser Leu Asp Asp Ser Ile
1               5                   10                  15

Asn Asn Lys Val Leu Val Leu Ser Lys Ala Asn
            20                  25

<210> SEQ ID NO 149
<211> LENGTH: 27
<212> TYPE: PRT
<213> ORGANISM: Eubacterium dolichum DSM 3991

<400> SEQUENCE: 149

Glu Val Asp His Ile Ile Pro Ile Ser Ile Ser Leu Asp Asp Ser Ile
1               5                   10                  15

Thr Asn Lys Val Leu Val Thr His Arg Glu Asn
            20                  25

<210> SEQ ID NO 150
<211> LENGTH: 27
<212> TYPE: PRT
<213> ORGANISM: Artificial Sequence
<220> FEATURE:
<223> OTHER INFORMATION: HNH-LIKE domain -continued

<400> SEQUENCE: 150

Gln Val Asp His Ala Leu Pro Tyr Ser Arg Ser Tyr Asp Asp Ser Lys
1               5                   10                  15

Asn Asn Lys Val Leu Val Leu Thr His Glu Asn
            20                  25

<210> SEQ ID NO 151
<211> LENGTH: 27
<212> TYPE: PRT
<213> ORGANISM: Streptococcus thermophilus LMD-9

<400> SEQUENCE: 151

Glu Val Asp His Ile Leu Pro Leu Ser Ile Thr Phe Asp Asp Ser Leu
1               5                   10                  15

Ala Asn Lys Val Leu Val Tyr Ala Thr Ala Asn
            20                  25

<210> SEQ ID NO 152
<211> LENGTH: 27
<212> TYPE: PRT
<213> ORGANISM: Eubacterium rectale

<400> SEQUENCE: 152

Glu Ile Asp His Ile Ile Pro Arg Ser Ile Ser Phe Asp Asp Ala Arg
1               5                   10                  15

Ser Asn Lys Val Leu Val Tyr Arg Ser Glu Asn
            20                  25

<210> SEQ ID NO 153
<211> LENGTH: 27
<212> TYPE: PRT
<213> ORGANISM: Staphylococcus lugdunensis M23590

<400> SEQUENCE: 153

Glu Val Asp His Ile Ile Pro Arg Ser Val Ser Phe Asp Asn Ser Tyr
1               5                   10                  15

His Asn Lys Val Leu Val Lys Gln Ser Glu Asn
            20                  25

<210> SEQ ID NO 154
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 154

Asp Ile Asp His Ile Leu Pro Tyr Ser Ile Thr Phe Asp Asp Ser Phe
1               5                   10                  15

Arg Asn Lys Val Leu Val Thr Ser Gln Glu Asn
            20                  25

<210> SEQ ID NO 155
<211> LENGTH: 27
<212> TYPE: PRT
<213> ORGANISM: Wolinella succinogenes DSM 1740

<400> SEQUENCE: 155

Glu Ile Asp His Ile Leu Pro Arg Ser Arg Ser Ala Asp Asp Ser Phe
1               5                   10                  15

Ala Asn Lys Val Leu Cys Leu Ala Arg Ala Asn

```
                        20                  25

<210> SEQ ID NO 156
<211> LENGTH: 27
<212> TYPE: PRT
<213> ORGANISM: Cand. Puniceispirillum marinum

<400> SEQUENCE: 156

Glu Ile Glu His Leu Leu Pro Phe Ser Leu Thr Leu Asp Asp Ser Met
1               5                   10                  15

Ala Asn Lys Thr Val Cys Phe Arg Gln Ala Asn
            20                  25

<210> SEQ ID NO 157
<211> LENGTH: 27
<212> TYPE: PRT
<213> ORGANISM: Azospirillum sp. B510

<400> SEQUENCE: 157

Asp Ile Asp His Ile Leu Pro Phe Ser Val Ser Leu Asp Asp Ser Ala
1               5                   10                  15

Ala Asn Lys Val Val Cys Leu Arg Glu Ala Asn
            20                  25

<210> SEQ ID NO 158
<211> LENGTH: 27
<212> TYPE: PRT
<213> ORGANISM: Bradyrhizobium sp. BTAi1

<400> SEQUENCE: 158

Asp Ile Asp His Leu Ile Pro Phe Ser Ile Ser Trp Asp Asp Ser Ala
1               5                   10                  15

Ala Asn Lys Val Val Cys Met Arg Tyr Ala Asn
            20                  25

<210> SEQ ID NO 159
<211> LENGTH: 27
<212> TYPE: PRT
<213> ORGANISM: Nitrobacter hamburgensis X14

<400> SEQUENCE: 159

Asp Ile Asp His Ile Leu Pro Val Ala Met Thr Leu Asp Asp Ser Pro
1               5                   10                  15

Ala Asn Lys Ile Ile Cys Met Arg Tyr Ala Asn
            20                  25

<210> SEQ ID NO 160
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 160

Asp Val Asp His Ile Leu Pro Tyr Ser Arg Thr Leu Asp Asp Ser Phe
1               5                   10                  15

Pro Asn Arg Thr Leu Cys Leu Arg Glu Ala Asn
            20                  25

<210> SEQ ID NO 161
<211> LENGTH: 27
<212> TYPE: PRT
<213> ORGANISM: Artificial Sequence
```

-continued

```
<220> FEATURE:
<223> OTHER INFORMATION: HNH-LIKE domain

<400> SEQUENCE: 161

Glu Ile Glu His Ile Leu Pro Phe Ser Arg Thr Leu Asp Asp Ser Leu
1               5                   10                  15

Asn Asn Arg Thr Val Ala Met Arg Arg Ala Asn
            20                  25

<210> SEQ ID NO 162
<211> LENGTH: 27
<212> TYPE: PRT
<213> ORGANISM: Lactobacillus coryniformis KCTC 3535

<400> SEQUENCE: 162

Glu Val Asp His Ile Ile Pro Tyr Ser Ile Ser Trp Asp Asp Ser Tyr
1               5                   10                  15

Thr Asn Lys Val Leu Thr Ser Ala Lys Cys Asn
            20                  25

<210> SEQ ID NO 163
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 163

Gln Val Asp His Ile Leu Pro Trp Ser Arg Phe Gly Asp Asp Ser Tyr
1               5                   10                  15

Leu Asn Lys Thr Leu Cys Thr Ala Arg Ser Asn
            20                  25

<210> SEQ ID NO 164
<211> LENGTH: 27
<212> TYPE: PRT
<213> ORGANISM: Ralstonia syzygii R24

<400> SEQUENCE: 164

Gln Val Asp His Ile Leu Pro Phe Ser Lys Thr Leu Asp Asp Ser Phe
1               5                   10                  15

Ala Asn Lys Val Leu Ala Gln His Asp Ala Asn
            20                  25

<210> SEQ ID NO 165
<211> LENGTH: 27
<212> TYPE: PRT
<213> ORGANISM: Helicobacter mustelae 12198

<400> SEQUENCE: 165

Gln Ile Asp His Ala Phe Pro Leu Ser Arg Ser Leu Asp Asp Ser Gln
1               5                   10                  15

Ser Asn Lys Val Leu Cys Leu Thr Ser Ser Asn
            20                  25

<210> SEQ ID NO 166
<211> LENGTH: 27
<212> TYPE: PRT
<213> ORGANISM: Mycoplasma mobile 163K

<400> SEQUENCE: 166

Asp Ile Asp His Ile Val Pro Arg Ser Ile Ser Phe Asp Asp Ser Phe
1               5                   10                  15
```

```
Ser Asn Leu Val Ile Val Asn Lys Leu Asp Asn
            20                  25

<210> SEQ ID NO 167
<211> LENGTH: 27
<212> TYPE: PRT
<213> ORGANISM: Mycoplasma ovipneumoniae SC01

<400> SEQUENCE: 167

Glu Ile Glu His Ile Ile Pro Tyr Ser Met Ser Tyr Asp Asn Ser Gln
1               5                   10                  15

Ala Asn Lys Ile Leu Thr Glu Lys Ala Glu Asn
            20                  25

<210> SEQ ID NO 168
<211> LENGTH: 27
<212> TYPE: PRT
<213> ORGANISM: Mycoplasma synoviae 53

<400> SEQUENCE: 168

Glu Ile Asp His Val Ile Pro Tyr Ser Lys Ser Ala Asp Asp Ser Trp
1               5                   10                  15

Phe Asn Lys Leu Leu Val Lys Lys Ser Thr Asn
            20                  25

<210> SEQ ID NO 169
<211> LENGTH: 27
<212> TYPE: PRT
<213> ORGANISM: Aminomonas paucivorans DSM 12260

<400> SEQUENCE: 169

Glu Met Asp His Ile Leu Pro Tyr Ser Arg Ser Leu Asp Asn Gly Trp
1               5                   10                  15

His Asn Arg Val Leu Val His Gly Lys Asp Asn
            20                  25

<210> SEQ ID NO 170
<211> LENGTH: 27
<212> TYPE: PRT
<213> ORGANISM: Ruminococcus albus 8

<400> SEQUENCE: 170

Glu Val Asp His Ile Val Pro Tyr Ser Leu Ile Leu Asp Asn Thr Ile
1               5                   10                  15

Asn Asn Lys Ala Leu Val Tyr Ala Glu Glu Asn
            20                  25

<210> SEQ ID NO 171
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 171

Glu Ile Glu His Val Ile Pro Gln Ser Leu Tyr Phe Asp Asp Ser Phe
1               5                   10                  15

Ser Asn Lys Val Ile Cys Glu Ala Glu Val Asn
            20                  25

<210> SEQ ID NO 172
<211> LENGTH: 27
```

```
<212> TYPE: PRT
<213> ORGANISM: Bacteroides fragilis, NCTC 9343

<400> SEQUENCE: 172

Asp Ile Glu His Ile Ile Pro Gln Ala Arg Leu Phe Asp Asp Ser Phe
1               5                   10                  15

Ser Asn Lys Thr Leu Glu Ala Arg Ser Val Asn
            20                  25

<210> SEQ ID NO 173
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 173

Glu Ile Glu His Ile Val Pro Lys Ala Arg Val Phe Asp Asp Ser Phe
1               5                   10                  15

Ser Asn Lys Thr Leu Thr Phe His Arg Ile Asn
            20                  25

<210> SEQ ID NO 174
<211> LENGTH: 28
<212> TYPE: PRT
<213> ORGANISM: Finegoldia magna

<400> SEQUENCE: 174

Asp Lys Asp His Ile Ile Pro Gln Ser Met Lys Lys Asp Asp Ser Ile
1               5                   10                  15

Ile Asn Asn Leu Val Leu Val Asn Lys Asn Ala Asn
            20                  25

<210> SEQ ID NO 175
<211> LENGTH: 27
<212> TYPE: PRT
<213> ORGANISM: Parvibaculum lavamentivorans DS-1

<400> SEQUENCE: 175

Glu Val Glu His Ile Trp Pro Arg Ser Arg Ser Phe Asp Asn Ser Pro
1               5                   10                  15

Arg Asn Lys Thr Leu Cys Arg Lys Asp Val Asn
            20                  25

<210> SEQ ID NO 176
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 176

Ile Val Asn His Ile Ile Pro Tyr Asn Arg Ser Phe Asp Asp Thr Tyr
1               5                   10                  15

His Asn Arg Val Leu Thr Leu Thr Glu Thr Lys
            20                  25

<210> SEQ ID NO 177
<211> LENGTH: 27
<212> TYPE: PRT
<213> ORGANISM: Artificial Sequence
<220> FEATURE:
<223> OTHER INFORMATION: HNH-LIKE domain
```

```
<400> SEQUENCE: 177

Asp Met Glu His Thr Ile Pro Lys Ser Ile Ser Phe Asp Asn Ser Asp
1               5                   10                  15

Gln Asn Leu Thr Leu Cys Glu Ser Tyr Tyr Asn
            20                  25

<210> SEQ ID NO 178
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 178

Asp Ile Glu His Thr Ile Pro Arg Ser Ala Gly Gly Asp Ser Thr Lys
1               5                   10                  15

Met Asn Leu Thr Leu Cys Ser Ser Arg Phe Asn
            20                  25

<210> SEQ ID NO 179
<211> LENGTH: 27
<212> TYPE: PRT
<213> ORGANISM: Artificial Sequence
<220> FEATURE:
<223> OTHER INFORMATION: HNH-LIKE domain

<400> SEQUENCE: 179

Asp Ile Glu His Thr Ile Pro Arg Ser Ile Ser Gln Asp Asn Ser Gln
1               5                   10                  15

Met Asn Lys Thr Leu Cys Ser Leu Lys Phe Asn
            20                  25

<210> SEQ ID NO 180
<211> LENGTH: 27
<212> TYPE: PRT
<213> ORGANISM: Rhodospirillum rubrum

<400> SEQUENCE: 180

Asp Ile Asp His Val Ile Pro Leu Ala Arg Gly Gly Arg Asp Ser Leu
1               5                   10                  15

Asp Asn Met Val Leu Cys Gln Ser Asp Ala Asn
            20                  25

<210> SEQ ID NO 181
<211> LENGTH: 27
<212> TYPE: PRT
<213> ORGANISM: Elusimicrobium minutum Pei191

<400> SEQUENCE: 181

Asp Ile Glu His Leu Phe Pro Ile Ala Glu Ser Glu Asp Asn Gly Arg
1               5                   10                  15

Asn Asn Leu Val Ile Ser His Ser Ala Cys Asn
            20                  25

<210> SEQ ID NO 182
<211> LENGTH: 27
<212> TYPE: PRT
<213> ORGANISM: Sphaerochaeta globus str. Buddy

<400> SEQUENCE: 182

Asp Val Asp His Ile Phe Pro Arg Asp Asp Thr Ala Asp Asn Ser Tyr
1               5                   10                  15
```

Gly Asn Lys Val Val Ala His Arg Gln Cys Asn
            20                  25

<210> SEQ ID NO 183
<211> LENGTH: 27
<212> TYPE: PRT
<213> ORGANISM: Nitratifractor salsuginis DSM 16511

<400> SEQUENCE: 183

Asp Ile Glu His Ile Val Pro Gln Ser Leu Gly Gly Leu Ser Thr Asp
1               5                   10                  15

Tyr Asn Thr Ile Val Thr Leu Lys Ser Val Asn
            20                  25

<210> SEQ ID NO 184
<211> LENGTH: 27
<212> TYPE: PRT
<213> ORGANISM: Acidothermus cellulolyticus 11B

<400> SEQUENCE: 184

Glu Leu Asp His Ile Val Pro Arg Thr Asp Gly Gly Ser Asn Arg His
1               5                   10                  15

Glu Asn Leu Ala Ile Thr Cys Gly Ala Cys Asn
            20                  25

<210> SEQ ID NO 185
<211> LENGTH: 28
<212> TYPE: PRT
<213> ORGANISM: Bifidobacterium longum DJO10A

<400> SEQUENCE: 185

Glu Met Asp His Ile Val Pro Arg Lys Gly Val Gly Ser Thr Asn Thr
1               5                   10                  15

Arg Thr Asn Phe Ala Ala Val Cys Ala Glu Cys Asn
            20                  25

<210> SEQ ID NO 186
<211> LENGTH: 28
<212> TYPE: PRT
<213> ORGANISM: Artificial Sequence
<220> FEATURE:
<223> OTHER INFORMATION: HNH-LIKE domain

<400> SEQUENCE: 186

Glu Met Asp His Ile Val Pro Arg Lys Gly Val Gly Ser Thr Asn Thr
1               5                   10                  15

Arg Val Asn Leu Ala Ala Ala Cys Ala Ala Cys Asn
            20                  25

<210> SEQ ID NO 187
<211> LENGTH: 28
<212> TYPE: PRT
<213> ORGANISM: Artificial Sequence
<220> FEATURE:
<223> OTHER INFORMATION: HNH-LIKE domain

<400> SEQUENCE: 187

Glu Met Asp His Ile Val Pro Arg Ala Gly Gln Gly Ser Thr Asn Thr
1               5                   10                  15

Arg Glu Asn Leu Val Ala Val Cys His Arg Cys Asn
            20                  25

<210> SEQ ID NO 188

```
<211> LENGTH: 33
<212> TYPE: PRT
<213> ORGANISM: Artificial Sequence
<220> FEATURE:
<223> OTHER INFORMATION: HNH-LIKE domain

<400> SEQUENCE: 188

Glu Ile Asp His Ile Leu Pro Arg Ser Leu Ile Lys Asp Ala Arg Gly
1               5                   10                  15

Ile Val Phe Asn Ala Glu Pro Asn Leu Ile Tyr Ala Ser Ser Arg Gly
            20                  25                  30

Asn

<210> SEQ ID NO 189
<211> LENGTH: 33
<212> TYPE: PRT
<213> ORGANISM: Artificial Sequence
<220> FEATURE:
<223> OTHER INFORMATION: HNH-LIKE domain

<400> SEQUENCE: 189

Glu Ile Asp His Ile Ile Pro Arg Ser Leu Thr Gly Arg Thr Lys Lys
1               5                   10                  15

Thr Val Phe Asn Ser Glu Ala Asn Leu Ile Tyr Cys Ser Ser Lys Gly
            20                  25                  30

Asn

<210> SEQ ID NO 190
<211> LENGTH: 33
<212> TYPE: PRT
<213> ORGANISM: Artificial Sequence
<220> FEATURE:
<223> OTHER INFORMATION: HNH-LIKE domain

<400> SEQUENCE: 190

Glu Ile Asp His Ile Ile Pro Arg Ser Leu Thr Leu Lys Lys Ser Glu
1               5                   10                  15

Ser Ile Tyr Asn Ser Glu Val Asn Leu Ile Phe Val Ser Ala Gln Gly
            20                  25                  30

Asn

<210> SEQ ID NO 191
<211> LENGTH: 33
<212> TYPE: PRT
<213> ORGANISM: Legionella pneumophila str. Paris

<400> SEQUENCE: 191

Glu Ile Asp His Ile Tyr Pro Arg Ser Leu Ser Lys Lys His Phe Gly
1               5                   10                  15

Val Ile Phe Asn Ser Glu Val Asn Leu Ile Tyr Cys Ser Ser Gln Gly
            20                  25                  30

Asn

<210> SEQ ID NO 192
<211> LENGTH: 33
<212> TYPE: PRT
<213> ORGANISM: Wolinella succinogenes DSM 1740

<400> SEQUENCE: 192

Glu Ile Asp His Ile Leu Pro Arg Ser His Thr Leu Lys Ile Tyr Gly
1               5                   10                  15
```

Thr Val Phe Asn Pro Glu Gly Asn Leu Ile Tyr Val His Gln Lys Cys
            20                  25                  30

Asn

<210> SEQ ID NO 193
<211> LENGTH: 30
<212> TYPE: PRT
<213> ORGANISM: Artificial Sequence
<220> FEATURE:
<223> OTHER INFORMATION: HNH-LIKE domain

<400> SEQUENCE: 193

Glu Leu Asp His Ile Ile Pro Arg Ser His Lys Lys Tyr Gly Thr Leu
1               5                   10                  15

Asn Asp Glu Ala Asn Leu Ile Cys Val Thr Arg Gly Asp Asn
            20                  25                  30

<210> SEQ ID NO 194
<211> LENGTH: 27
<212> TYPE: PRT
<213> ORGANISM: Akkermansia muciniphila

<400> SEQUENCE: 194

Glu Leu Glu His Ile Val Pro His Ser Phe Arg Gln Ser Asn Ala Leu
1               5                   10                  15

Ser Ser Leu Val Leu Thr Trp Pro Gly Val Asn
            20                  25

<210> SEQ ID NO 195
<211> LENGTH: 27
<212> TYPE: PRT
<213> ORGANISM: Solobacterium moorei F0204

<400> SEQUENCE: 195

Asp Ile Asp His Ile Tyr Pro Arg Ser Lys Ile Lys Asp Ser Ile
1               5                   10                  15

Thr Asn Arg Val Leu Val Glu Lys Asp Ile Asn
            20                  25

<210> SEQ ID NO 196
<211> LENGTH: 28
<212> TYPE: PRT
<213> ORGANISM: Veillonella atypica ACS-134-V-Col7a

<400> SEQUENCE: 196

Tyr Asp Ile Asp His Ile Tyr Pro Arg Ser Leu Thr Lys Asp Asp Ser
1               5                   10                  15

Phe Asp Asn Leu Val Leu Cys Glu Arg Thr Ala Asn
            20                  25

<210> SEQ ID NO 197
<211> LENGTH: 28
<212> TYPE: PRT
<213> ORGANISM: Fusobacterium nucleatum

<400> SEQUENCE: 197

Asp Ile Asp His Ile Tyr Pro Arg Ser Lys Val Ile Lys Asp Asp Ser
1               5                   10                  15

Phe Asp Asn Leu Val Leu Val Leu Lys Asn Glu Asn
            20                  25

<210> SEQ ID NO 198

```
<211> LENGTH: 27
<212> TYPE: PRT
<213> ORGANISM: Filifactor alocis

<400> SEQUENCE: 198

Asp Arg Asp His Ile Tyr Pro Gln Ser Lys Ile Lys Asp Asp Ser Ile
1               5                   10                  15

Asp Asn Leu Val Leu Val Asn Lys Thr Tyr Asn
            20                  25

<210> SEQ ID NO 199
<211> LENGTH: 5
<212> TYPE: DNA
<213> ORGANISM: S. thermophilus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 199 nggng                                                          5

<210> SEQ ID NO 200
<211> LENGTH: 7
<212> TYPE: DNA
<213> ORGANISM: S. thermophilus
<220> FEATURE:
<221> NAME/KEY: misc_feature
<222> LOCATION: (1)..(2)
<223> OTHER INFORMATION: n is a, c, g, or t

<400> SEQUENCE: 200 nnagaaw                                                        7

<210> SEQ ID NO 201
<211> LENGTH: 4
<212> TYPE: DNA
<213> ORGANISM: S. mutans
<220> FEATURE:
<221> NAME/KEY: misc_feature
<222> LOCATION: (1)..(1)
<223> OTHER INFORMATION: n is a, c, g, or t

<400> SEQUENCE: 201 naar                                                           4

<210> SEQ ID NO 202
<211> LENGTH: 5
<212> TYPE: DNA
<213> ORGANISM: S. aureus
<220> FEATURE:
<221> NAME/KEY: misc_feature
<222> LOCATION: (1)..(2)
<223> OTHER INFORMATION: n is a, c, g, or t

<400> SEQUENCE: 202 nngrr                                                          5

<210> SEQ ID NO 203
<211> LENGTH: 6
<212> TYPE: DNA
<213> ORGANISM: S. aureus
<220> FEATURE:
<221> NAME/KEY: misc_feature
```

```
<222> LOCATION: (1)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 203 nngrrn                                                                     6

<210> SEQ ID NO 204
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 204 nngrrt                                                                     6

<210> SEQ ID NO 205
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 205 nngrrv                                                                     6

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Gly Gly Ser
1

<210> SEQ ID NO 207
<211> LENGTH: 4
<212> TYPE: PRT
<213> ORGANISM: Artificial Sequence
<220> FEATURE:
<223> OTHER INFORMATION: Synthetic

<400> SEQUENCE: 207

Gly Ser Gly Ser
1

<210> SEQ ID NO 208
<211> LENGTH: 4
<212> TYPE: PRT
<213> ORGANISM: Artificial Sequence
<220> FEATURE:
<223> OTHER INFORMATION: Synthetic

<400> SEQUENCE: 208
```

Gly Gly Gly Ser
1

<210> SEQ ID NO 209
<211> LENGTH: 5
<212> TYPE: PRT
<213> ORGANISM: Artificial Sequence
<220> FEATURE:
<223> OTHER INFORMATION: Synthetic

<400> SEQUENCE: 209

Gly Gly Gly Gly Ser
1               5

<210> SEQ ID NO 210
<211> LENGTH: 4
<212> TYPE: PRT
<213> ORGANISM: Artificial Sequence
<220> FEATURE:
<223> OTHER INFORMATION: Synthetic

<400> SEQUENCE: 210

Gly Gly Ser Gly
1

<210> SEQ ID NO 211
<211> LENGTH: 12
<212> TYPE: PRT
<213> ORGANISM: Artificial Sequence
<220> FEATURE:
<223> OTHER INFORMATION: Synthetic

<400> SEQUENCE: 211

Ser Gly Ser Glu Thr Pro Gly Thr Ser Glu Ser Ala
1               5                   10

<210> SEQ ID NO 212
<211> LENGTH: 16
<212> TYPE: PRT
<213> ORGANISM: Artificial Sequence
<220> FEATURE:
<223> OTHER INFORMATION: Synthetic

<400> SEQUENCE: 212

Ser Gly Ser Glu Thr Pro Gly Thr Ser Glu Ser Ala Thr Pro Glu Ser
1               5                   10                  15

<210> SEQ ID NO 213
<211> LENGTH: 21
<212> TYPE: PRT
<213> ORGANISM: Artificial Sequence
<220> FEATURE:
<223> OTHER INFORMATION: Synthetic

<400> SEQUENCE: 213

Ser Gly Ser Glu Thr Pro Gly Thr Ser Glu Ser Ala Thr Pro Glu Gly
1               5                   10                  15

Gly Ser Gly Gly Ser
            20

<210> SEQ ID NO 214
<211> LENGTH: 27
<212> TYPE: PRT
<213> ORGANISM: Artificial Sequence
<220> FEATURE:
<223> OTHER INFORMATION: Synthetic -continued

```
<400> SEQUENCE: 214

Gly Gly Ser Gly Gly Ser Gly Gly Ser Gly Gly Ser Gly
1               5                   10                  15

Gly Ser Gly Gly Ser Gly Gly Ser Gly Gly Ser
            20                  25

<210> SEQ ID NO 215
<211> LENGTH: 1699
<212> TYPE: PRT
<213> ORGANISM: Artificial Sequence
<220> FEATURE:
<223> OTHER INFORMATION: Synthetic: 6xHis-NLS-Halo-XTEN-Cas9

<400> SEQUENCE: 215

Met Lys His His His His His His Met Pro Lys Lys Arg Lys Val
1               5                   10                  15

Gly Gly Ser Gly Ala Glu Ile Gly Thr Gly Phe Pro Phe Asp Pro His
            20                  25                  30

Tyr Val Glu Val Leu Gly Glu Arg Met His Tyr Val Asp Val Gly Pro
        35                  40                  45

Arg Asp Gly Thr Pro Val Leu Phe Leu His Gly Asn Pro Thr Ser Ser
    50                  55                  60

Tyr Val Trp Arg Asn Ile Ile Pro His Val Ala Pro Thr His Arg Cys
65                  70                  75                  80

Ile Ala Pro Asp Leu Ile Gly Met Gly Lys Ser Asp Lys Pro Asp Leu
                85                  90                  95

Gly Tyr Phe Phe Asp Asp His Val Arg Phe Met Asp Ala Phe Ile Glu
            100                 105                 110

Ala Leu Gly Leu Glu Glu Val Val Leu Val Ile His Asp Trp Gly Ser
        115                 120                 125

Ala Leu Gly Phe His Trp Ala Lys Arg Asn Pro Glu Arg Val Lys Gly
    130                 135                 140

Ile Ala Phe Met Glu Phe Ile Arg Pro Ile Pro Thr Trp Asp Glu Trp
145                 150                 155                 160

Pro Glu Phe Ala Arg Glu Thr Phe Gln Ala Phe Arg Thr Thr Asp Val
                165                 170                 175

Gly Arg Lys Leu Ile Ile Asp Gln Asn Val Phe Ile Glu Gly Thr Leu
            180                 185                 190

Pro Met Gly Val Val Arg Pro Leu Thr Glu Val Glu Met Asp His Tyr
        195                 200                 205

Arg Glu Pro Phe Leu Asn Pro Val Asp Arg Glu Pro Leu Trp Arg Phe
    210                 215                 220

Pro Asn Glu Leu Pro Ile Ala Gly Glu Pro Ala Asn Ile Val Ala Leu
225                 230                 235                 240

Val Glu Glu Tyr Met Asp Trp Leu His Gln Ser Pro Val Pro Lys Leu
                245                 250                 255

Leu Phe Trp Gly Thr Pro Gly Val Leu Ile Pro Pro Ala Glu Ala Ala
            260                 265                 270

Arg Leu Ala Lys Ser Leu Pro Asn Cys Lys Ala Val Asp Ile Gly Pro
        275                 280                 285

Gly Leu Asn Leu Leu Gln Glu Asp Asn Pro Asp Leu Ile Gly Ser Glu
    290                 295                 300

Ile Ala Arg Trp Leu Ser Thr Leu Glu Ile Ser Gly Ser Gly Ser Glu
305                 310                 315                 320

Thr Pro Gly Thr Ser Glu Ser Ala Thr Pro Glu Ser Asp Lys Lys Tyr
```

-continued

```
                325                 330                 335
Ser Ile Gly Leu Asp Ile Gly Thr Asn Ser Val Gly Trp Ala Val Ile
                340                 345                 350
Thr Asp Glu Tyr Lys Val Pro Ser Lys Lys Phe Lys Val Leu Gly Asn
                355                 360                 365
Thr Asp Arg His Ser Ile Lys Lys Asn Leu Ile Gly Ala Leu Leu Phe
                370                 375                 380
Asp Ser Gly Glu Thr Ala Glu Ala Thr Arg Leu Lys Arg Thr Ala Arg
385                 390                 395                 400
Arg Arg Tyr Thr Arg Arg Lys Asn Arg Ile Cys Tyr Leu Gln Glu Ile
                405                 410                 415
Phe Ser Asn Glu Met Ala Lys Val Asp Asp Ser Phe Phe His Arg Leu
                420                 425                 430
Glu Glu Ser Phe Leu Val Glu Glu Asp Lys Lys His Glu Arg His Pro
                435                 440                 445
Ile Phe Gly Asn Ile Val Asp Glu Val Ala Tyr His Glu Lys Tyr Pro
                450                 455                 460
Thr Ile Tyr His Leu Arg Lys Lys Leu Val Asp Ser Thr Asp Lys Ala
465                 470                 475                 480
Asp Leu Arg Leu Ile Tyr Leu Ala Leu Ala His Met Ile Lys Phe Arg
                485                 490                 495
Gly His Phe Leu Ile Glu Gly Asp Leu Asn Pro Asp Asn Ser Asp Val
                500                 505                 510
Asp Lys Leu Phe Ile Gln Leu Val Gln Thr Tyr Asn Gln Leu Phe Glu
                515                 520                 525
Glu Asn Pro Ile Asn Ala Ser Gly Val Asp Ala Lys Ala Ile Leu Ser
                530                 535                 540
Ala Arg Leu Ser Lys Ser Arg Arg Leu Glu Asn Leu Ile Ala Gln Leu
545                 550                 555                 560
Pro Gly Glu Lys Lys Asn Gly Leu Phe Gly Asn Leu Ile Ala Leu Ser
                565                 570                 575
Leu Gly Leu Thr Pro Asn Phe Lys Ser Asn Phe Asp Leu Ala Glu Asp
                580                 585                 590
Ala Lys Leu Gln Leu Ser Lys Asp Thr Tyr Asp Asp Asp Leu Asp Asn
                595                 600                 605
Leu Leu Ala Gln Ile Gly Asp Gln Tyr Ala Asp Leu Phe Leu Ala Ala
                610                 615                 620
Lys Asn Leu Ser Asp Ala Ile Leu Leu Ser Asp Ile Leu Arg Val Asn
625                 630                 635                 640
Thr Glu Ile Thr Lys Ala Pro Leu Ser Ala Ser Met Ile Lys Arg Tyr
                645                 650                 655
Asp Glu His His Gln Asp Leu Thr Leu Leu Lys Ala Leu Val Arg Gln
                660                 665                 670
Gln Leu Pro Glu Lys Tyr Lys Glu Ile Phe Phe Asp Gln Ser Lys Asn
                675                 680                 685
Gly Tyr Ala Gly Tyr Ile Asp Gly Gly Ala Ser Gln Glu Glu Phe Tyr
                690                 695                 700
Lys Phe Ile Lys Pro Ile Leu Glu Lys Met Asp Gly Thr Glu Glu Leu
705                 710                 715                 720
Leu Val Lys Leu Asn Arg Glu Asp Leu Leu Arg Lys Gln Arg Thr Phe
                725                 730                 735
Asp Asn Gly Ser Ile Pro His Gln Ile His Leu Gly Glu Leu His Ala
                740                 745                 750
```

```
Ile Leu Arg Arg Gln Glu Asp Phe Tyr Pro Phe Leu Lys Asp Asn Arg
        755                 760                 765

Glu Lys Ile Glu Lys Ile Leu Thr Phe Arg Ile Pro Tyr Tyr Val Gly
    770                 775                 780

Pro Leu Ala Arg Gly Asn Ser Arg Phe Ala Trp Met Thr Arg Lys Ser
785                 790                 795                 800

Glu Glu Thr Ile Thr Pro Trp Asn Phe Glu Glu Val Val Asp Lys Gly
                805                 810                 815

Ala Ser Ala Gln Ser Phe Ile Glu Arg Met Thr Asn Phe Asp Lys Asn
            820                 825                 830

Leu Pro Asn Glu Lys Val Leu Pro Lys His Ser Leu Leu Tyr Glu Tyr
        835                 840                 845

Phe Thr Val Tyr Asn Glu Leu Thr Lys Val Lys Tyr Val Thr Glu Gly
    850                 855                 860

Met Arg Lys Pro Ala Phe Leu Ser Gly Glu Gln Lys Lys Ala Ile Val
865                 870                 875                 880

Asp Leu Leu Phe Lys Thr Asn Arg Lys Val Thr Val Lys Gln Leu Lys
                885                 890                 895

Glu Asp Tyr Phe Lys Lys Ile Glu Cys Phe Asp Ser Val Glu Ile Ser
            900                 905                 910

Gly Val Glu Asp Arg Phe Asn Ala Ser Leu Gly Thr Tyr His Asp Leu
        915                 920                 925

Leu Lys Ile Ile Lys Asp Lys Asp Phe Leu Asp Asn Glu Glu Asn Glu
    930                 935                 940

Asp Ile Leu Glu Asp Ile Val Leu Thr Leu Thr Leu Phe Glu Asp Arg
945                 950                 955                 960

Glu Met Ile Glu Glu Arg Leu Lys Thr Tyr Ala His Leu Phe Asp Asp
                965                 970                 975

Lys Val Met Lys Gln Leu Lys Arg Arg Arg Tyr Thr Gly Trp Gly Arg
            980                 985                 990

Leu Ser Arg Lys Leu Ile Asn Gly Ile Arg Asp Lys Gln Ser Gly Lys
        995                 1000                1005

Thr Ile Leu Asp Phe Leu Lys Ser Asp Gly Phe Ala Asn Arg Asn
        1010                1015                1020

Phe Met Gln Leu Ile His Asp Asp Ser Leu Thr Phe Lys Glu Asp
        1025                1030                1035

Ile Gln Lys Ala Gln Val Ser Gly Gln Gly Asp Ser Leu His Glu
        1040                1045                1050

His Ile Ala Asn Leu Ala Gly Ser Pro Ala Ile Lys Lys Gly Ile
        1055                1060                1065

Leu Gln Thr Val Lys Val Val Asp Glu Leu Val Lys Val Met Gly
        1070                1075                1080

Arg His Lys Pro Glu Asn Ile Val Ile Glu Met Ala Arg Glu Asn
        1085                1090                1095

Gln Thr Thr Gln Lys Gly Gln Lys Asn Ser Arg Glu Arg Met Lys
        1100                1105                1110

Arg Ile Glu Glu Gly Ile Lys Glu Leu Gly Ser Gln Ile Leu Lys
        1115                1120                1125

Glu His Pro Val Glu Asn Thr Gln Leu Gln Asn Glu Lys Leu Tyr
        1130                1135                1140

Leu Tyr Tyr Leu Gln Asn Gly Arg Asp Met Tyr Val Asp Gln Glu
        1145                1150                1155
```

```
Leu Asp Ile Asn Arg Leu Ser Asp Tyr Asp Val Asp His Ile Val
1160                1165                1170

Pro Gln Ser Phe Leu Lys Asp Asp Ser Ile Asp Asn Lys Val Leu
    1175                1180                1185

Thr Arg Ser Asp Lys Asn Arg Gly Lys Ser Asp Asn Val Pro Ser
    1190                1195                1200

Glu Glu Val Val Lys Lys Met Lys Asn Tyr Trp Arg Gln Leu Leu
    1205                1210                1215

Asn Ala Lys Leu Ile Thr Gln Arg Lys Phe Asp Asn Leu Thr Lys
    1220                1225                1230

Ala Glu Arg Gly Gly Leu Ser Glu Leu Asp Lys Ala Gly Phe Ile
    1235                1240                1245

Lys Arg Gln Leu Val Glu Thr Arg Gln Ile Thr Lys His Val Ala
    1250                1255                1260

Gln Ile Leu Asp Ser Arg Met Asn Thr Lys Tyr Asp Glu Asn Asp
    1265                1270                1275

Lys Leu Ile Arg Glu Val Lys Val Ile Thr Leu Lys Ser Lys Leu
    1280                1285                1290

Val Ser Asp Phe Arg Lys Asp Phe Gln Phe Tyr Lys Val Arg Glu
    1295                1300                1305

Ile Asn Asn Tyr His His Ala His Asp Ala Tyr Leu Asn Ala Val
    1310                1315                1320

Val Gly Thr Ala Leu Ile Lys Lys Tyr Pro Lys Leu Glu Ser Glu
    1325                1330                1335

Phe Val Tyr Gly Asp Tyr Lys Val Tyr Asp Val Arg Lys Met Ile
    1340                1345                1350

Ala Lys Ser Glu Gln Glu Ile Gly Lys Ala Thr Ala Lys Tyr Phe
    1355                1360                1365

Phe Tyr Ser Asn Ile Met Asn Phe Phe Lys Thr Glu Ile Thr Leu
    1370                1375                1380

Ala Asn Gly Glu Ile Arg Lys Arg Pro Leu Ile Glu Thr Asn Gly
    1385                1390                1395

Glu Thr Gly Glu Ile Val Trp Asp Lys Gly Arg Asp Phe Ala Thr
    1400                1405                1410

Val Arg Lys Val Leu Ser Met Pro Gln Val Asn Ile Val Lys Lys
    1415                1420                1425

Thr Glu Val Gln Thr Gly Gly Phe Ser Lys Glu Ser Ile Leu Pro
    1430                1435                1440

Lys Arg Asn Ser Asp Lys Leu Ile Ala Arg Lys Lys Asp Trp Asp
    1445                1450                1455

Pro Lys Lys Tyr Gly Gly Phe Asp Ser Pro Thr Val Ala Tyr Ser
    1460                1465                1470

Val Leu Val Val Ala Lys Val Glu Lys Gly Lys Ser Lys Lys Leu
    1475                1480                1485

Lys Ser Val Lys Glu Leu Leu Gly Ile Thr Ile Met Glu Arg Ser
    1490                1495                1500

Ser Phe Glu Lys Asn Pro Ile Asp Phe Leu Glu Ala Lys Gly Tyr
    1505                1510                1515

Lys Glu Val Lys Lys Asp Leu Ile Ile Lys Leu Pro Lys Tyr Ser
    1520                1525                1530

Leu Phe Glu Leu Glu Asn Gly Arg Lys Arg Met Leu Ala Ser Ala
    1535                1540                1545

Gly Glu Leu Gln Lys Gly Asn Glu Leu Ala Leu Pro Ser Lys Tyr
```

```
                    1550                1555                1560
Val Asn Phe Leu Tyr Leu Ala Ser His Tyr Glu Lys Leu Lys Gly
    1565                1570                1575

Ser Pro Glu Asp Asn Glu Gln Lys Gln Leu Phe Val Glu Gln His
    1580                1585                1590

Lys His Tyr Leu Asp Glu Ile Ile Glu Gln Ile Ser Glu Phe Ser
    1595                1600                1605

Lys Arg Val Ile Leu Ala Asp Ala Asn Leu Asp Lys Val Leu Ser
    1610                1615                1620

Ala Tyr Asn Lys His Arg Asp Lys Pro Ile Arg Glu Gln Ala Glu
    1625                1630                1635

Asn Ile Ile His Leu Phe Thr Leu Thr Asn Leu Gly Ala Pro Ala
    1640                1645                1650

Ala Phe Lys Tyr Phe Asp Thr Thr Ile Asp Arg Lys Arg Tyr Thr
    1655                1660                1665

Ser Thr Lys Glu Val Leu Asp Ala Thr Leu Ile His Gln Ser Ile
    1670                1675                1680

Thr Gly Leu Tyr Glu Thr Arg Ile Asp Leu Ser Gln Leu Gly Gly
    1685                1690                1695

Asp

<210> SEQ ID NO 216
<211> LENGTH: 1711
<212> TYPE: PRT
<213> ORGANISM: Artificial Sequence
<220> FEATURE:
<223> OTHER INFORMATION: Synthetic: 6xHis-NLS-Halo-GGS9-Cas9

<400> SEQUENCE: 216

Met Lys His His His His His His Met Pro Lys Lys Arg Lys Val
1               5                   10                  15

Gly Gly Ser Gly Ala Glu Ile Gly Thr Gly Phe Pro Phe Asp Pro His
                20                  25                  30

Tyr Val Glu Val Leu Gly Glu Arg Met His Tyr Val Asp Val Gly Pro
        35                  40                  45

Arg Asp Gly Thr Pro Val Leu Phe Leu His Gly Asn Pro Thr Ser Ser
    50                  55                  60

Tyr Val Trp Arg Asn Ile Ile Pro His Val Ala Pro Thr His Arg Cys
65                  70                  75                  80

Ile Ala Pro Asp Leu Ile Gly Met Gly Lys Ser Asp Lys Pro Asp Leu
                85                  90                  95

Gly Tyr Phe Phe Asp Asp His Val Arg Phe Met Asp Ala Phe Ile Glu
            100                 105                 110

Ala Leu Gly Leu Glu Glu Val Val Leu Val Ile His Asp Trp Gly Ser
        115                 120                 125

Ala Leu Gly Phe His Trp Ala Lys Arg Asn Pro Glu Arg Val Lys Gly
    130                 135                 140

Ile Ala Phe Met Glu Phe Ile Arg Pro Ile Pro Thr Trp Asp Glu Trp
145                 150                 155                 160

Pro Glu Phe Ala Arg Glu Thr Phe Gln Ala Phe Arg Thr Thr Asp Val
                165                 170                 175

Gly Arg Lys Leu Ile Ile Asp Gln Asn Val Phe Ile Glu Gly Thr Leu
            180                 185                 190

Pro Met Gly Val Val Arg Pro Leu Thr Glu Val Glu Met Asp His Tyr
        195                 200                 205
```

```
Arg Glu Pro Phe Leu Asn Pro Val Asp Arg Glu Pro Leu Trp Arg Phe
    210                 215                 220
Pro Asn Glu Leu Pro Ile Ala Gly Glu Pro Ala Asn Ile Val Ala Leu
225                 230                 235                 240
Val Glu Glu Tyr Met Asp Trp Leu His Gln Ser Pro Val Pro Lys Leu
                245                 250                 255
Leu Phe Trp Gly Thr Pro Gly Val Leu Ile Pro Pro Ala Glu Ala Ala
            260                 265                 270
Arg Leu Ala Lys Ser Leu Pro Asn Cys Lys Ala Val Asp Ile Gly Pro
        275                 280                 285
Gly Leu Asn Leu Leu Gln Glu Asp Asn Pro Asp Leu Ile Gly Ser Glu
    290                 295                 300
Ile Ala Arg Trp Leu Ser Thr Leu Glu Ile Ser Gly Thr Gly Gly Ser
305                 310                 315                 320
Gly Gly Ser Gly Gly Ser Gly Gly Ser Gly Gly Ser Gly Gly Ser Gly
                325                 330                 335
Gly Ser Gly Gly Ser Gly Gly Thr Asp Lys Lys Tyr Ser Ile Gly Leu
            340                 345                 350
Asp Ile Gly Thr Asn Ser Val Gly Trp Ala Val Ile Thr Asp Glu Tyr
        355                 360                 365
Lys Val Pro Ser Lys Lys Phe Lys Val Leu Gly Asn Thr Asp Arg His
    370                 375                 380
Ser Ile Lys Lys Asn Leu Ile Gly Ala Leu Leu Phe Asp Ser Gly Glu
385                 390                 395                 400
Thr Ala Glu Ala Thr Arg Leu Lys Arg Thr Ala Arg Arg Arg Tyr Thr
                405                 410                 415
Arg Arg Lys Asn Arg Ile Cys Tyr Leu Gln Glu Ile Phe Ser Asn Glu
            420                 425                 430
Met Ala Lys Val Asp Asp Ser Phe Phe His Arg Leu Glu Glu Ser Phe
        435                 440                 445
Leu Val Glu Glu Asp Lys Lys His Glu Arg His Pro Ile Phe Gly Asn
    450                 455                 460
Ile Val Asp Glu Val Ala Tyr His Glu Lys Tyr Pro Thr Ile Tyr His
465                 470                 475                 480
Leu Arg Lys Lys Leu Val Asp Ser Thr Asp Lys Ala Asp Leu Arg Leu
                485                 490                 495
Ile Tyr Leu Ala Leu Ala His Met Ile Lys Phe Arg Gly His Phe Leu
            500                 505                 510
Ile Glu Gly Asp Leu Asn Pro Asp Asn Ser Asp Val Asp Lys Leu Phe
        515                 520                 525
Ile Gln Leu Val Gln Thr Tyr Asn Gln Leu Phe Glu Glu Asn Pro Ile
    530                 535                 540
Asn Ala Ser Gly Val Asp Ala Lys Ala Ile Leu Ser Ala Arg Leu Ser
545                 550                 555                 560
Lys Ser Arg Arg Leu Glu Asn Leu Ile Ala Gln Leu Pro Gly Glu Lys
                565                 570                 575
Lys Asn Gly Leu Phe Gly Asn Leu Ile Ala Leu Ser Leu Gly Leu Thr
            580                 585                 590
Pro Asn Phe Lys Ser Asn Phe Asp Leu Ala Glu Asp Ala Lys Leu Gln
        595                 600                 605
Leu Ser Lys Asp Thr Tyr Asp Asp Asp Leu Asp Asn Leu Leu Ala Gln
    610                 615                 620
```

-continued

```
Ile Gly Asp Gln Tyr Ala Asp Leu Phe Leu Ala Ala Lys Asn Leu Ser
625                 630                 635                 640

Asp Ala Ile Leu Leu Ser Asp Ile Leu Arg Val Asn Thr Glu Ile Thr
            645                 650                 655

Lys Ala Pro Leu Ser Ala Ser Met Ile Lys Arg Tyr Asp Glu His His
            660                 665                 670

Gln Asp Leu Thr Leu Leu Lys Ala Leu Val Arg Gln Gln Leu Pro Glu
            675                 680                 685

Lys Tyr Lys Glu Ile Phe Phe Asp Gln Ser Lys Asn Gly Tyr Ala Gly
690                 695                 700

Tyr Ile Asp Gly Gly Ala Ser Gln Glu Glu Phe Tyr Lys Phe Ile Lys
705                 710                 715                 720

Pro Ile Leu Glu Lys Met Asp Gly Thr Glu Glu Leu Leu Val Lys Leu
            725                 730                 735

Asn Arg Glu Asp Leu Leu Arg Lys Gln Arg Thr Phe Asp Asn Gly Ser
            740                 745                 750

Ile Pro His Gln Ile His Leu Gly Glu Leu His Ala Ile Leu Arg Arg
            755                 760                 765

Gln Glu Asp Phe Tyr Pro Phe Leu Lys Asp Asn Arg Glu Lys Ile Glu
770                 775                 780

Lys Ile Leu Thr Phe Arg Ile Pro Tyr Tyr Val Gly Pro Leu Ala Arg
785                 790                 795                 800

Gly Asn Ser Arg Phe Ala Trp Met Thr Arg Lys Ser Glu Glu Thr Ile
            805                 810                 815

Thr Pro Trp Asn Phe Glu Glu Val Val Asp Lys Gly Ala Ser Ala Gln
            820                 825                 830

Ser Phe Ile Glu Arg Met Thr Asn Phe Asp Lys Asn Leu Pro Asn Glu
            835                 840                 845

Lys Val Leu Pro Lys His Ser Leu Leu Tyr Glu Tyr Phe Thr Val Tyr
850                 855                 860

Asn Glu Leu Thr Lys Val Lys Tyr Val Thr Glu Gly Met Arg Lys Pro
865                 870                 875                 880

Ala Phe Leu Ser Gly Glu Gln Lys Lys Ala Ile Val Asp Leu Leu Phe
            885                 890                 895

Lys Thr Asn Arg Lys Val Thr Val Lys Gln Leu Lys Glu Asp Tyr Phe
            900                 905                 910

Lys Lys Ile Glu Cys Phe Asp Ser Val Glu Ile Ser Gly Val Glu Asp
            915                 920                 925

Arg Phe Asn Ala Ser Leu Gly Thr Tyr His Asp Leu Leu Lys Ile Ile
930                 935                 940

Lys Asp Lys Asp Phe Leu Asp Asn Glu Glu Asn Glu Asp Ile Leu Glu
945                 950                 955                 960

Asp Ile Val Leu Thr Leu Thr Leu Phe Glu Asp Arg Glu Met Ile Glu
            965                 970                 975

Glu Arg Leu Lys Thr Tyr Ala His Leu Phe Asp Asp Lys Val Met Lys
            980                 985                 990

Gln Leu Lys Arg Arg Arg Tyr Thr Gly Trp Gly Arg Leu Ser Arg Lys
            995                 1000                1005

Leu Ile Asn Gly Ile Arg Asp Lys Gln Ser Gly Lys Thr Ile Leu
    1010                1015                1020

Asp Phe Leu Lys Ser Asp Gly Phe Ala Asn Arg Asn Phe Met Gln
    1025                1030                1035

Leu Ile His Asp Asp Ser Leu Thr Phe Lys Glu Asp Ile Gln Lys
```

-continued

```
            1040                1045                1050
Ala Gln Val Ser Gly Gln Gly Asp Ser Leu His Glu His Ile Ala
            1055                1060                1065
Asn Leu Ala Gly Ser Pro Ala Ile Lys Lys Gly Ile Leu Gln Thr
            1070                1075                1080
Val Lys Val Val Asp Glu Leu Val Lys Val Met Gly Arg His Lys
            1085                1090                1095
Pro Glu Asn Ile Val Ile Glu Met Ala Arg Glu Asn Gln Thr Thr
            1100                1105                1110
Gln Lys Gly Gln Lys Asn Ser Arg Glu Arg Met Lys Arg Ile Glu
            1115                1120                1125
Glu Gly Ile Lys Glu Leu Gly Ser Gln Ile Leu Lys Glu His Pro
            1130                1135                1140
Val Glu Asn Thr Gln Leu Gln Asn Glu Lys Leu Tyr Leu Tyr Tyr
            1145                1150                1155
Leu Gln Asn Gly Arg Asp Met Tyr Val Asp Gln Glu Leu Asp Ile
            1160                1165                1170
Asn Arg Leu Ser Asp Tyr Asp Val Asp His Ile Val Pro Gln Ser
            1175                1180                1185
Phe Leu Lys Asp Asp Ser Ile Asp Asn Lys Val Leu Thr Arg Ser
            1190                1195                1200
Asp Lys Asn Arg Gly Lys Ser Asp Asn Val Pro Ser Glu Glu Val
            1205                1210                1215
Val Lys Lys Met Lys Asn Tyr Trp Arg Gln Leu Leu Asn Ala Lys
            1220                1225                1230
Leu Ile Thr Gln Arg Lys Phe Asp Asn Leu Thr Lys Ala Glu Arg
            1235                1240                1245
Gly Gly Leu Ser Glu Leu Asp Lys Ala Gly Phe Ile Lys Arg Gln
            1250                1255                1260
Leu Val Glu Thr Arg Gln Ile Thr Lys His Val Ala Gln Ile Leu
            1265                1270                1275
Asp Ser Arg Met Asn Thr Lys Tyr Asp Glu Asn Asp Lys Leu Ile
            1280                1285                1290
Arg Glu Val Lys Val Ile Thr Leu Lys Ser Lys Leu Val Ser Asp
            1295                1300                1305
Phe Arg Lys Asp Phe Gln Phe Tyr Lys Val Arg Glu Ile Asn Asn
            1310                1315                1320
Tyr His His Ala His Asp Ala Tyr Leu Asn Ala Val Val Gly Thr
            1325                1330                1335
Ala Leu Ile Lys Lys Tyr Pro Lys Leu Glu Ser Glu Phe Val Tyr
            1340                1345                1350
Gly Asp Tyr Lys Val Tyr Asp Val Arg Lys Met Ile Ala Lys Ser
            1355                1360                1365
Glu Gln Glu Ile Gly Lys Ala Thr Ala Lys Tyr Phe Phe Tyr Ser
            1370                1375                1380
Asn Ile Met Asn Phe Phe Lys Thr Glu Ile Thr Leu Ala Asn Gly
            1385                1390                1395
Glu Ile Arg Lys Arg Pro Leu Ile Glu Thr Asn Gly Glu Thr Gly
            1400                1405                1410
Glu Ile Val Trp Asp Lys Gly Arg Asp Phe Ala Thr Val Arg Lys
            1415                1420                1425
Val Leu Ser Met Pro Gln Val Asn Ile Val Lys Lys Thr Glu Val
            1430                1435                1440
```

Gln Thr Gly Gly Phe Ser Lys Glu Ser Ile Leu Pro Lys Arg Asn
    1445              1450                1455

Ser Asp Lys Leu Ile Ala Arg Lys Lys Asp Trp Asp Pro Lys Lys
    1460              1465                1470

Tyr Gly Gly Phe Asp Ser Pro Thr Val Ala Tyr Ser Val Leu Val
    1475              1480                1485

Val Ala Lys Val Glu Lys Gly Lys Ser Lys Lys Leu Lys Ser Val
    1490              1495                1500

Lys Glu Leu Leu Gly Ile Thr Ile Met Glu Arg Ser Ser Phe Glu
    1505              1510                1515

Lys Asn Pro Ile Asp Phe Leu Glu Ala Lys Gly Tyr Lys Glu Val
    1520              1525                1530

Lys Lys Asp Leu Ile Ile Lys Leu Pro Lys Tyr Ser Leu Phe Glu
    1535              1540                1545

Leu Glu Asn Gly Arg Lys Arg Met Leu Ala Ser Ala Gly Glu Leu
    1550              1555                1560

Gln Lys Gly Asn Glu Leu Ala Leu Pro Ser Lys Tyr Val Asn Phe
    1565              1570                1575

Leu Tyr Leu Ala Ser His Tyr Glu Lys Leu Lys Gly Ser Pro Glu
    1580              1585                1590

Asp Asn Glu Gln Lys Gln Leu Phe Val Glu Gln His Lys His Tyr
    1595              1600                1605

Leu Asp Glu Ile Ile Glu Gln Ile Ser Glu Phe Ser Lys Arg Val
    1610              1615                1620

Ile Leu Ala Asp Ala Asn Leu Asp Lys Val Leu Ser Ala Tyr Asn
    1625              1630                1635

Lys His Arg Asp Lys Pro Ile Arg Glu Gln Ala Glu Asn Ile Ile
    1640              1645                1650

His Leu Phe Thr Leu Thr Asn Leu Gly Ala Pro Ala Ala Phe Lys
    1655              1660                1665

Tyr Phe Asp Thr Thr Ile Asp Arg Lys Arg Tyr Thr Ser Thr Lys
    1670              1675                1680

Glu Val Leu Asp Ala Thr Leu Ile His Gln Ser Ile Thr Gly Leu
    1685              1690                1695

Tyr Glu Thr Arg Ile Asp Leu Ser Gln Leu Gly Gly Asp
    1700              1705                1710

<210> SEQ ID NO 217
<211> LENGTH: 1700
<212> TYPE: PRT
<213> ORGANISM: Artificial Sequence
<220> FEATURE:
<223> OTHER INFORMATION: Synthetic: 6xHis-NLS-Cas9-XTEN-Halo

<400> SEQUENCE: 217

Met Lys His His His His His His Met Pro Lys Lys Arg Lys Val
1               5                   10                  15

Met Asp Lys Lys Tyr Ser Ile Gly Leu Asp Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

```
Lys Arg Thr Ala Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
                100                 105                 110

Phe Phe His Arg Leu Glu Glu Ser Phe Leu Val Glu Gly Asp Lys Lys
                115                 120                 125

His Glu Arg His Pro Ile Phe Gly Asn Ile Val Asp Glu Val Ala Tyr
            130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
                180                 185                 190

Asp Asn Ser Asp Val Asp Lys Leu Phe Ile Gln Leu Val Gln Thr Tyr
                195                 200                 205

Asn Gln Leu Phe Glu Glu Asn Pro Ile Asn Ala Ser Gly Val Asp Ala
                210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
                260                 265                 270

Asp Leu Ala Glu Asp Ala Lys Leu Gln Leu Ser Lys Asp Thr Tyr Asp
                275                 280                 285

Asp Asp Leu Asp Asn Leu Leu Ala Gln Ile Gly Asp Gln Tyr Ala Asp
                290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
                340                 345                 350

Ala Leu Val Arg Gln Gln Leu Pro Glu Lys Tyr Lys Glu Ile Phe Phe
                355                 360                 365

Asp Gln Ser Lys Asn Gly Tyr Ala Gly Tyr Ile Asp Gly Gly Ala Ser
                370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
                420                 425                 430

Gly Glu Leu His Ala Ile Leu Arg Arg Gln Glu Asp Phe Tyr Pro Phe
                435                 440                 445

Leu Lys Asp Asn Arg Glu Lys Ile Glu Lys Ile Leu Thr Phe Arg Ile
                450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495
```

```
Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
        530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
            565                 570                 575

Val Lys Gln Leu Lys Glu Asp Tyr Phe Lys Lys Ile Glu Cys Phe Asp
        580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
        610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
            645                 650                 655

His Leu Phe Asp Asp Lys Val Met Lys Gln Leu Lys Arg Arg Arg Tyr
        660                 665                 670

Thr Gly Trp Gly Arg Leu Ser Arg Lys Leu Ile Asn Gly Ile Arg Asp
            675                 680                 685

Lys Gln Ser Gly Lys Thr Ile Leu Asp Phe Leu Lys Ser Asp Gly Phe
690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
            725                 730                 735

His Glu His Ile Ala Asn Leu Ala Gly Ser Pro Ala Ile Lys Lys Gly
        740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
            805                 810                 815

Val Glu Asn Thr Gln Leu Gln Asn Glu Lys Leu Tyr Leu Tyr Tyr Leu
        820                 825                 830

Gln Asn Gly Arg Asp Met Tyr Val Asp Gln Glu Leu Asp Ile Asn Arg
        835                 840                 845

Leu Ser Asp Tyr Asp Val Asp His Ile Val Pro Gln Ser Phe Leu Lys
        850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
            885                 890                 895

Asn Tyr Trp Arg Gln Leu Leu Asn Ala Lys Leu Ile Thr Gln Arg Lys
        900                 905                 910

Phe Asp Asn Leu Thr Lys Ala Glu Arg Gly Gly Leu Ser Glu Leu Asp
```

```
                915                 920                 925
Lys Ala Gly Phe Ile Lys Arg Gln Leu Val Glu Thr Arg Gln Ile Thr
        930                 935                 940
Lys His Val Ala Gln Ile Leu Asp Ser Arg Met Asn Thr Lys Tyr Asp
945                 950                 955                 960
Glu Asn Asp Lys Leu Ile Arg Glu Val Lys Val Ile Thr Leu Lys Ser
                965                 970                 975
Lys Leu Val Ser Asp Phe Arg Lys Asp Phe Gln Phe Tyr Lys Val Arg
        980                 985                 990
Glu Ile Asn Asn Tyr His His Ala His Asp Ala Tyr Leu Asn Ala Val
                995                 1000                1005
Val Gly Thr Ala Leu Ile Lys Lys Tyr Pro Lys Leu Glu Ser Glu
        1010                1015                1020
Phe Val Tyr Gly Asp Tyr Lys Val Tyr Asp Val Arg Lys Met Ile
        1025                1030                1035
Ala Lys Ser Glu Gln Glu Ile Gly Lys Ala Thr Ala Lys Tyr Phe
        1040                1045                1050
Phe Tyr Ser Asn Ile Met Asn Phe Phe Lys Thr Glu Ile Thr Leu
        1055                1060                1065
Ala Asn Gly Glu Ile Arg Lys Arg Pro Leu Ile Glu Thr Asn Gly
        1070                1075                1080
Glu Thr Gly Glu Ile Val Trp Asp Lys Gly Arg Asp Phe Ala Thr
        1085                1090                1095
Val Arg Lys Val Leu Ser Met Pro Gln Val Asn Ile Val Lys Lys
        1100                1105                1110
Thr Glu Val Gln Thr Gly Gly Phe Ser Lys Glu Ser Ile Leu Pro
        1115                1120                1125
Lys Arg Asn Ser Asp Lys Leu Ile Ala Arg Lys Lys Asp Trp Asp
        1130                1135                1140
Pro Lys Lys Tyr Gly Gly Phe Asp Ser Pro Thr Val Ala Tyr Ser
        1145                1150                1155
Val Leu Val Val Ala Lys Val Glu Lys Gly Lys Ser Lys Lys Leu
        1160                1165                1170
Lys Ser Val Lys Glu Leu Leu Gly Ile Thr Ile Met Glu Arg Ser
        1175                1180                1185
Ser Phe Glu Lys Asn Pro Ile Asp Phe Leu Glu Ala Lys Gly Tyr
        1190                1195                1200
Lys Glu Val Lys Lys Asp Leu Ile Ile Lys Leu Pro Lys Tyr Ser
        1205                1210                1215
Leu Phe Glu Leu Glu Asn Gly Arg Lys Arg Met Leu Ala Ser Ala
        1220                1225                1230
Gly Glu Leu Gln Lys Gly Asn Glu Leu Ala Leu Pro Ser Lys Tyr
        1235                1240                1245
Val Asn Phe Leu Tyr Leu Ala Ser His Tyr Glu Lys Leu Lys Gly
        1250                1255                1260
Ser Pro Glu Asp Asn Glu Gln Lys Gln Leu Phe Val Glu Gln His
        1265                1270                1275
Lys His Tyr Leu Asp Glu Ile Ile Glu Gln Ile Ser Glu Phe Ser
        1280                1285                1290
Lys Arg Val Ile Leu Ala Asp Ala Asn Leu Asp Lys Val Leu Ser
        1295                1300                1305
Ala Tyr Asn Lys His Arg Asp Lys Pro Ile Arg Glu Gln Ala Glu
        1310                1315                1320
```

-continued

```
Asn Ile Ile His Leu Phe Thr Leu Thr Asn Leu Gly Ala Pro Ala
1325                1330                1335

Ala Phe Lys Tyr Phe Asp Thr Thr Ile Asp Arg Lys Arg Tyr Thr
1340                1345                1350

Ser Thr Lys Glu Val Leu Asp Ala Thr Leu Ile His Gln Ser Ile
1355                1360                1365

Thr Gly Leu Tyr Glu Thr Arg Ile Asp Leu Ser Gln Leu Gly Gly
1370                1375                1380

Asp Ser Gly Ser Glu Thr Pro Gly Thr Ser Glu Ser Ala Thr Pro
1385                1390                1395

Glu Ser Gly Gly Ser Gly Ala Glu Ile Gly Thr Gly Phe Pro Phe
1400                1405                1410

Asp Pro His Tyr Val Glu Val Leu Gly Glu Arg Met His Tyr Val
1415                1420                1425

Asp Val Gly Pro Arg Asp Gly Thr Pro Val Leu Phe Leu His Gly
1430                1435                1440

Asn Pro Thr Ser Ser Tyr Val Trp Arg Asn Ile Ile Pro His Val
1445                1450                1455

Ala Pro Thr His Arg Cys Ile Ala Pro Asp Leu Ile Gly Met Gly
1460                1465                1470

Lys Ser Asp Lys Pro Asp Leu Gly Tyr Phe Phe Asp Asp His Val
1475                1480                1485

Arg Phe Met Asp Ala Phe Ile Glu Ala Leu Gly Leu Glu Glu Val
1490                1495                1500

Val Leu Val Ile His Asp Trp Gly Ser Ala Leu Gly Phe His Trp
1505                1510                1515

Ala Lys Arg Asn Pro Glu Arg Val Lys Gly Ile Ala Phe Met Glu
1520                1525                1530

Phe Ile Arg Pro Ile Pro Thr Trp Asp Glu Trp Pro Glu Phe Ala
1535                1540                1545

Arg Glu Thr Phe Gln Ala Phe Arg Thr Thr Asp Val Gly Arg Lys
1550                1555                1560

Leu Ile Ile Asp Gln Asn Val Phe Ile Glu Gly Thr Leu Pro Met
1565                1570                1575

Gly Val Val Arg Pro Leu Thr Glu Val Glu Met Asp His Tyr Arg
1580                1585                1590

Glu Pro Phe Leu Asn Pro Val Asp Arg Glu Pro Leu Trp Arg Phe
1595                1600                1605

Pro Asn Glu Leu Pro Ile Ala Gly Glu Pro Ala Asn Ile Val Ala
1610                1615                1620

Leu Val Glu Glu Tyr Met Asp Trp Leu His Gln Ser Pro Val Pro
1625                1630                1635

Lys Leu Leu Phe Trp Gly Thr Pro Gly Val Leu Ile Pro Pro Ala
1640                1645                1650

Glu Ala Ala Arg Leu Ala Lys Ser Leu Pro Asn Cys Lys Ala Val
1655                1660                1665

Asp Ile Gly Pro Gly Leu Asn Leu Leu Gln Glu Asp Asn Pro Asp
1670                1675                1680

Leu Ile Gly Ser Glu Ile Ala Arg Trp Leu Ser Thr Leu Glu Ile
1685                1690                1695

Ser Gly
1700
```

<210> SEQ ID NO 218
<211> LENGTH: 1712
<212> TYPE: PRT
<213> ORGANISM: Artificial Sequence
<220> FEATURE:
<223> OTHER INFORMATION: Synthetic: 6xHis-NLS-Cas9-GGS9-Halo

<400> SEQUENCE: 218

```
Met Lys His His His His His His Met Pro Lys Lys Arg Lys Val
1               5                   10                  15

Met Asp Lys Lys Tyr Ser Ile Gly Leu Asp Ile Gly Thr Asn Ser Val
                20                  25                  30

Gly Trp Ala Val Ile Thr Asp Glu Tyr Lys Val Pro Ser Lys Lys Phe
            35                  40                  45

Lys Val Leu Gly Asn Thr Asp Arg His Ser Ile Lys Lys Asn Leu Ile
50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365
```

-continued

```
Asp Gln Ser Lys Asn Gly Tyr Ala Gly Tyr Ile Asp Gly Gly Ala Ser
    370                 375                 380
Gln Glu Glu Phe Tyr Lys Phe Ile Lys Pro Ile Leu Glu Lys Met Asp
385                 390                 395                 400
Gly Thr Glu Glu Leu Leu Val Lys Leu Asn Arg Glu Asp Leu Leu Arg
                405                 410                 415
Lys Gln Arg Thr Phe Asp Asn Gly Ser Ile Pro His Gln Ile His Leu
            420                 425                 430
Gly Glu Leu His Ala Ile Leu Arg Arg Gln Glu Asp Phe Tyr Pro Phe
        435                 440                 445
Leu Lys Asp Asn Arg Glu Lys Ile Glu Lys Ile Leu Thr Phe Arg Ile
450                 455                 460
Pro Tyr Tyr Val Gly Pro Leu Ala Arg Gly Asn Ser Arg Phe Ala Trp
465                 470                 475                 480
Met Thr Arg Lys Ser Glu Glu Thr Ile Thr Pro Trp Asn Phe Glu Glu
                485                 490                 495
Val Val Asp Lys Gly Ala Ser Ala Gln Ser Phe Ile Glu Arg Met Thr
                500                 505                 510
Asn Phe Asp Lys Asn Leu Pro Asn Glu Lys Val Leu Pro Lys His Ser
            515                 520                 525
Leu Leu Tyr Glu Tyr Phe Thr Val Tyr Asn Glu Leu Thr Lys Val Lys
        530                 535                 540
Tyr Val Thr Glu Gly Met Arg Lys Pro Ala Phe Leu Ser Gly Glu Gln
545                 550                 555                 560
Lys Lys Ala Ile Val Asp Leu Leu Phe Lys Thr Asn Arg Lys Val Thr
                565                 570                 575
Val Lys Gln Leu Lys Glu Asp Tyr Phe Lys Lys Ile Glu Cys Phe Asp
            580                 585                 590
Ser Val Glu Ile Ser Gly Val Glu Asp Arg Phe Asn Ala Ser Leu Gly
        595                 600                 605
Thr Tyr His Asp Leu Leu Lys Ile Ile Lys Asp Lys Asp Phe Leu Asp
610                 615                 620
Asn Glu Glu Asn Glu Asp Ile Leu Glu Asp Ile Val Leu Thr Leu Thr
625                 630                 635                 640
Leu Phe Glu Asp Arg Glu Met Ile Glu Glu Arg Leu Lys Thr Tyr Ala
                645                 650                 655
His Leu Phe Asp Asp Lys Val Met Lys Gln Leu Lys Arg Arg Arg Tyr
            660                 665                 670
Thr Gly Trp Gly Arg Leu Ser Arg Lys Leu Ile Asn Gly Ile Arg Asp
        675                 680                 685
Lys Gln Ser Gly Lys Thr Ile Leu Asp Phe Leu Lys Ser Asp Gly Phe
        690                 695                 700
Ala Asn Arg Asn Phe Met Gln Leu Ile His Asp Asp Ser Leu Thr Phe
705                 710                 715                 720
Lys Glu Asp Ile Gln Lys Ala Gln Val Ser Gly Gln Gly Asp Ser Leu
                725                 730                 735
His Glu His Ile Ala Asn Leu Ala Gly Ser Pro Ala Ile Lys Lys Gly
            740                 745                 750
Ile Leu Gln Thr Val Lys Val Val Asp Glu Leu Val Lys Val Met Gly
        755                 760                 765
Arg His Lys Pro Glu Asn Ile Val Ile Glu Met Ala Arg Glu Asn Gln
770                 775                 780
Thr Thr Gln Lys Gly Gln Lys Asn Ser Arg Glu Arg Met Lys Arg Ile
```

-continued

```
            785                 790                 795                 800
        Glu Glu Gly Ile Lys Glu Leu Gly Ser Gln Ile Leu Lys His Pro
                        805                 810                 815
        Val Glu Asn Thr Gln Leu Gln Asn Glu Lys Leu Tyr Leu Tyr Tyr Leu
                        820                 825                 830
        Gln Asn Gly Arg Asp Met Tyr Val Asp Gln Glu Leu Asp Ile Asn Arg
                        835                 840                 845
        Leu Ser Asp Tyr Asp Val Asp His Ile Val Pro Gln Ser Phe Leu Lys
                850                 855                 860
        Asp Asp Ser Ile Asp Asn Lys Val Leu Thr Arg Ser Asp Lys Asn Arg
        865                 870                 875                 880
        Gly Lys Ser Asp Asn Val Pro Ser Glu Glu Val Val Lys Met Lys
                        885                 890                 895
        Asn Tyr Trp Arg Gln Leu Leu Asn Ala Lys Leu Ile Thr Gln Arg Lys
                        900                 905                 910
        Phe Asp Asn Leu Thr Lys Ala Glu Arg Gly Gly Leu Ser Glu Leu Asp
                        915                 920                 925
        Lys Ala Gly Phe Ile Lys Arg Gln Leu Val Glu Thr Arg Gln Ile Thr
                930                 935                 940
        Lys His Val Ala Gln Ile Leu Asp Ser Arg Met Asn Thr Lys Tyr Asp
        945                 950                 955                 960
        Glu Asn Asp Lys Leu Ile Arg Glu Val Lys Val Ile Thr Leu Lys Ser
                        965                 970                 975
        Lys Leu Val Ser Asp Phe Arg Lys Asp Phe Gln Phe Tyr Lys Val Arg
                        980                 985                 990
        Glu Ile Asn Asn Tyr His His Ala His Asp Ala Tyr Leu Asn Ala Val
                        995                1000                1005
        Val Gly Thr Ala Leu Ile Lys Lys Tyr Pro Lys Leu Glu Ser Glu
                1010                1015                1020
        Phe Val Tyr Gly Asp Tyr Lys Val Tyr Asp Val Arg Lys Met Ile
                1025                1030                1035
        Ala Lys Ser Glu Gln Glu Ile Gly Lys Ala Thr Ala Lys Tyr Phe
                1040                1045                1050
        Phe Tyr Ser Asn Ile Met Asn Phe Phe Lys Thr Glu Ile Thr Leu
                1055                1060                1065
        Ala Asn Gly Glu Ile Arg Lys Arg Pro Leu Ile Glu Thr Asn Gly
                1070                1075                1080
        Glu Thr Gly Glu Ile Val Trp Asp Lys Gly Arg Asp Phe Ala Thr
                1085                1090                1095
        Val Arg Lys Val Leu Ser Met Pro Gln Val Asn Ile Val Lys Lys
                1100                1105                1110
        Thr Glu Val Gln Thr Gly Gly Phe Ser Lys Glu Ser Ile Leu Pro
                1115                1120                1125
        Lys Arg Asn Ser Asp Lys Leu Ile Ala Arg Lys Lys Asp Trp Asp
                1130                1135                1140
        Pro Lys Lys Tyr Gly Gly Phe Asp Ser Pro Thr Val Ala Tyr Ser
                1145                1150                1155
        Val Leu Val Val Ala Lys Val Glu Lys Gly Lys Ser Lys Lys Leu
                1160                1165                1170
        Lys Ser Val Lys Glu Leu Leu Gly Ile Thr Ile Met Glu Arg Ser
                1175                1180                1185
        Ser Phe Glu Lys Asn Pro Ile Asp Phe Leu Glu Ala Lys Gly Tyr
                1190                1195                1200
```

```
Lys Glu Val Lys Lys Asp Leu Ile Ile Lys Leu Pro Lys Tyr Ser
    1205                1210                1215

Leu Phe Glu Leu Glu Asn Gly Arg Lys Arg Met Leu Ala Ser Ala
    1220                1225                1230

Gly Glu Leu Gln Lys Gly Asn Glu Leu Ala Leu Pro Ser Lys Tyr
    1235                1240                1245

Val Asn Phe Leu Tyr Leu Ala Ser His Tyr Glu Lys Leu Lys Gly
    1250                1255                1260

Ser Pro Glu Asp Asn Glu Gln Lys Gln Leu Phe Val Glu Gln His
    1265                1270                1275

Lys His Tyr Leu Asp Glu Ile Ile Glu Gln Ile Ser Glu Phe Ser
    1280                1285                1290

Lys Arg Val Ile Leu Ala Asp Ala Asn Leu Asp Lys Val Leu Ser
    1295                1300                1305

Ala Tyr Asn Lys His Arg Asp Lys Pro Ile Arg Glu Gln Ala Glu
    1310                1315                1320

Asn Ile Ile His Leu Phe Thr Leu Thr Asn Leu Gly Ala Pro Ala
    1325                1330                1335

Ala Phe Lys Tyr Phe Asp Thr Thr Ile Asp Arg Lys Arg Tyr Thr
    1340                1345                1350

Ser Thr Lys Glu Val Leu Asp Ala Thr Leu Ile His Gln Ser Ile
    1355                1360                1365

Thr Gly Leu Tyr Glu Thr Arg Ile Asp Leu Ser Gln Leu Gly Gly
    1370                1375                1380

Asp Thr Gly Gly Ser Gly Gly Ser Gly Gly Ser Gly Gly Ser Gly
    1385                1390                1395

Gly Ser Gly Gly Ser Gly Gly Ser Gly Gly Ser Gly Gly Thr Gly
    1400                1405                1410

Gly Ser Gly Ala Glu Ile Gly Thr Gly Phe Pro Phe Asp Pro His
    1415                1420                1425

Tyr Val Glu Val Leu Gly Glu Arg Met His Tyr Val Asp Val Gly
    1430                1435                1440

Pro Arg Asp Gly Thr Pro Val Leu Phe Leu His Gly Asn Pro Thr
    1445                1450                1455

Ser Ser Tyr Val Trp Arg Asn Ile Ile Pro His Val Ala Pro Thr
    1460                1465                1470

His Arg Cys Ile Ala Pro Asp Leu Ile Gly Met Gly Lys Ser Asp
    1475                1480                1485

Lys Pro Asp Leu Gly Tyr Phe Phe Asp Asp His Val Arg Phe Met
    1490                1495                1500

Asp Ala Phe Ile Glu Ala Leu Gly Leu Glu Glu Val Val Leu Val
    1505                1510                1515

Ile His Asp Trp Gly Ser Ala Leu Gly Phe His Trp Ala Lys Arg
    1520                1525                1530

Asn Pro Glu Arg Val Lys Gly Ile Ala Phe Met Glu Phe Ile Arg
    1535                1540                1545

Pro Ile Pro Thr Trp Asp Glu Trp Pro Glu Phe Ala Arg Glu Thr
    1550                1555                1560

Phe Gln Ala Phe Arg Thr Thr Asp Val Gly Arg Lys Leu Ile Ile
    1565                1570                1575

Asp Gln Asn Val Phe Ile Glu Gly Thr Leu Pro Met Gly Val Val
    1580                1585                1590
```

```
Arg Pro Leu Thr Glu Val Glu Met Asp His Tyr Arg Glu Pro Phe
    1595                1600                1605

Leu Asn Pro Val Asp Arg Glu Pro Leu Trp Arg Phe Pro Asn Glu
    1610                1615                1620

Leu Pro Ile Ala Gly Glu Pro Ala Asn Ile Val Ala Leu Val Glu
    1625                1630                1635

Glu Tyr Met Asp Trp Leu His Gln Ser Pro Val Pro Lys Leu Leu
    1640                1645                1650

Phe Trp Gly Thr Pro Gly Val Leu Ile Pro Pro Ala Glu Ala Ala
    1655                1660                1665

Arg Leu Ala Lys Ser Leu Pro Asn Cys Lys Ala Val Asp Ile Gly
    1670                1675                1680

Pro Gly Leu Asn Leu Leu Gln Glu Asp Asn Pro Asp Leu Ile Gly
    1685                1690                1695

Ser Glu Ile Ala Arg Trp Leu Ser Thr Leu Glu Ile Ser Gly
    1700                1705                1710

<210> SEQ ID NO 219
<211> LENGTH: 3
<212> TYPE: DNA
<213> ORGANISM: S. mutans
<220> FEATURE:
<221> NAME/KEY: misc_feature
<222> LOCATION: (1)..(1)
<223> OTHER INFORMATION: n is a, c, g, or t

<400> SEQUENCE: 219 ngg                                                                3
```

CAS9 FUSION MOLECULES, GENE EDITING SYSTEMS, AND METHODS OF USE THEREOF

RELATED APPLICATIONS

This application is a 35 U.S.C. § 371 national stage filing of International Application No. PCT/US2017/027126, filed on Apr. 12, 2017, which in turn claims priority to U.S. Provisional Application No. 62/322,026, filed on Apr. 13, 2016, The entire contents of each of the aforementioned applications are expressly incorporated herein by reference.

SEQUENCE LISTING

The instant application contains a Sequence Listing which has been submitted electronically in ASCII format and is hereby incorporated by reference in its entirety. Said ASCII copy, created on Apr. 11, 2017, is named EM057PCT1_SL_2017-04-12.txt and is 251 KB in size.

FIELD OF THE INVENTION

The invention relates to Cas9 fusion molecules and methods and components for increasing editing of a target nucleic acid sequence by gene correction using an exogenous homologous region, and applications thereof.

BACKGROUND

The CRISPR (Clustered Regularly Interspaced Short Palindromic Repeats)/Cas (CRISPR-associated) system evolved in bacteria and archaea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains a sequence complimentary to the viral genome, mediates targeting of a Cas9 protein to the sequence in the viral genome. The Cas9 protein cleaves and thereby silences the viral target.

Recently, the CRISPR/Cas system has attracted widespread interest as a tool for genome editing through the generation of site-specific double strand breaks (DSBs). Current CRISPR/Cas systems that generate site-specific DSBs can be used to edit DNA in eukaryotic cells, e.g., by producing deletions, insertions and/or changes in nucleotide sequence.

Without wishing to be bound by any theory, it is thought that the mechanism by which an individual DSB is repaired varies depending on whether or not the DNA ends created by the DSB undergo endo- or exonucleolytic processing (also referred to as "end resection" or "processing"). When no end resection takes place, a DSB is generally repaired by a pathway referred to as classical non-homologous end joining (C-NHEJ). C-NHEJ is considered an "error-prone" pathway inasmuch as it leads in some cases to the formation of small insertions and deletions, though it may also result in perfect repair of DSBs without sequence alterations.

In contrast, if end resection does take place, the ends of a DSB may include one or more overhangs (for example, 3' overhangs or 5' overhangs), which can interact with nearby homologous sequences. Again, the mechanism by which the DSB is repaired may vary depending on the extent of processing. When the ends of a DSB undergo relatively limited end resection, the DSB is generally processed by alternative non-homologous end joining (ALT-NHEJ), a class of pathways that includes blunt end-joining (blunt EJ), microhomology mediated end joining (MMEJ), and synthesis dependent micro homology mediated end joining (SD-MMEJ). However, when end resection is extensive, the resulting overhangs may undergo strand invasion of highly homologous sequences (which can be endogenous sequences, for instance from a sister chromatid, or heterologous sequences from an exogenous template), followed by repair of the DSB by a homology-dependent recombination (HDR) pathway.

While a cell could, in theory, repair DNA breaks via any of a number of DNA damage repair pathways, in certain circumstances it is useful or desirable to manipulate the local environment in which the DSB is formed in order to drive a particular mode of repair. For instance, the addition of an exogenous homologous DNA sequence (also referred to as a "donor template" or "template nucleic acid") to a CRISPR/Cas system may tend to drive repair of DSBs through HDR-based gene correction. However, gene correction strategies that rely on exogenous donor templates are complicated by the potential for interactions between the donor template, the Cas9 and the guide RNA. At the same time, because the donor template is not a naturally occurring part of the CRISPR/Cas complex it may only be present and accessible at a fraction of the DSBs formed by the CRISPR/Cas system, and the desired gene correction may only occur in a fraction of instances.

SUMMARY

This disclosure provides systems, methods and compositions that facilitate gene correction by reconciling the need to localize the donor template at DSBs with the need to prevent interactions between the donor template and the guide RNA or the Cas9. In the various aspects of the disclosure, one or more Cas9 fusion molecules comprising a Cas9 polypeptide linked to a template nucleic acid sequence are utilized to increase the frequency and efficiency of DNA repair of DSBs using gene correction. The Cas9 fusion molecules of the invention comprise Cas9 molecules linked both covalently and non-covalently to template nucleic acids. While not wishing to be bound by theory, it is believed that, by optimizing the length of a linker between the Cas9 polypeptide and the template nucleic acid, hybridization of the template nucleic acid to a gRNA associated with the Cas9 molecule, and/or interactions between the template nucleic acid and DNA binding regions of Cas9, are reduced or even eliminated, while at the same time ensuring that the template nucleic acid is available to participate in HDR, thereby improving the efficiency of gene correction. In some cases, the efficiency of DNA repair via gene correction pathways may be significantly enhanced (e.g., doubled) when the donor template is linked to the Cas9 molecule, as compared to the un-linked molecule. Again, without wishing to be bound by any theory, it is also believed that by linking the donor template to the Cas9, the potential for degradation of the donor template (e.g., during trafficking into the nucleus) is reduced and nuclear localization of the template is improved.

In one aspect, this disclosure relates to compositions and methods for modifying a target nucleic acid in a cell, involving an enzymatically active Cas9 (eaCas9) fusion molecule. For example, the enzymatically active Cas9 (eaCas9) fusion molecule may be an eaCas9 molecule linked to a template nucleic acid.

In one embodiment, the eaCas9 molecule is covalently linked to the template nucleic acid. In certain embodiments, the eaCas9 molecule is covalently linked to the template nucleic acid using a polypeptide linker. In some embodiments, the polypeptide linker has a length sufficient to reduce or prevent hybridization of the template nucleic acid to a gRNA molecule associated with the eaCas9 molecule. In other embodiments, the polypeptide linker is sufficiently long to allow the eaCas9 molecule to bind to a target nucleic acid without steric interference. In other embodiments, the polypeptide linker is sufficiently long to allow the template nucleic acid to interact with the eaCas9 molecule without steric interference.

In certain embodiments, the polypeptide linker is between about 3 and about 100 amino acids in length. In some embodiments, the polypeptide linker is an XTEN linker, e.g., an XTEN linker with the amino acid sequence SGSETPGTSESATPES. In other embodiments, the polypeptide linker is a $GGS_9$ linker that is 27 amino acids in length. In other embodiments, the polypeptide linker is a $GGS_6$ linker that is 18 amino acids in length. In another embodiment, the polypeptide linker is a GGS linker that is 3 amino acids in length.

In one embodiment, the eaCas9 molecule is a variant eaCas9 molecule which has been modified to have at least one modification at a surface exposed residue. In some embodiments, the eaCas9 molecule has at least one modification a non-cysteine amino acid residue to a cysteine amino acid residue. In one embodiment, the eaCas9 molecule is a variant eaCas9 molecule which has a surface exposed thiol group.

In one embodiment, a template nucleic acid has a maleimide modification. In another embodiment, a variant eaCas9 molecule, for example, an eaCas9 molecule which has a surface exposed thiol group, is linked to the template nucleic acid having a maleimide modification using thiol coupling.

In one embodiment, an eaCas9 molecule which has a surface exposed thiol group, is linked to the template nucleic acid having an acrydite modification using thiol coupling.

In one embodiment, an eaCas9 molecule has been modified to have a succinimidyl-6-hydrazino-nicotinamide modification. In another embodiment, the succinimidyl-6-hydrazino-nicotinamide modified eaCas9 (i.e., the S-HyNic eaCas9 molecule) molecule is linked a template nucleic acid having a 4Fb modification, using amine coupling.

In one embodiment, an eaCas9 molecule has been modified to have a HaloTag®, a SNAP-tag®, a CLIP-tag®, a ACP-tag®, or a MCP-tag® linked to the eaCas9 molecule. For example, in certain embodiments, an eaCas9-HaloTag molecule is lined to a haloalkane modified template nucleic acid, e.g., using an $S_N2$ reaction.

In one embodiment, the eaCas9 molecule is covalently linked to the template nucleic acid using a synthetic linker. In certain embodiments, the eaCas9 molecule is a variant eaCas9 molecule which has been modified to have a N-[ε-Maleimidocaproic acid] hydrazide (EMCH) and a 1-ethyl-3-(3-dimethylaminopropyl) carbodiimide (EDC) coupling agent. In other embodiments, the template nucleic acid has a carboxy group, such that the variant eaCas9 molecule is linked to the template nucleic acid by conjugation of the carboxy group on the template nucleic acid to a primary amine of a hydrazine group on the variant Cas9 molecule which has been modified to have a N-[ε-Maleimidocaproic acid] hydrazide (EMCH) and a 1-ethyl-3-(3-dimethylaminopropyl) carbodiimide (EDC) coupling agent.

In one embodiment, the eaCas9 molecule is non-covalently linked to the template nucleic acid. In certain embodiments, the eaCas9 molecule is covalently linked to a first ligand, the template nucleic acid is covalently linked to a second ligand, and the first ligand and the second ligand are non-covalently linked to a ligand acceptor molecule. For example, in some embodiments, the first and second ligands are biotin. In some embodiments, the ligand acceptor molecule is streptavidin. In another embodiment, eaCas9 molecule non-covalently linked to the template nucleic acid, includes a linker between the eaCas9 molecule and the first ligand. In some embodiments, the linker is sufficiently long to allow the eaCas9 molecule to bind to a target nucleic acid. For example, the linker may be sufficiently long to allow the template nucleic acid to interact with the eaCas9 molecule without steric interference.

In one embodiment, the eaCas9 molecule is covalently linked to a polypeptide, and the polypeptide is non-covalently bound to the template nucleic acid. In some embodiments, the polypeptide is a nucleic acid binding protein. For example, the nucleic acid binding protein may be any one of Rad52, Rad52-yeast, RPA-4 subunit, BRCA2, Rad51, Rad51B, Rad51C, XRCC2, XRCC3, RecA, RadA, HNRNPA1, UP1 Filament of HNRNPA1, NABP2 (SSB1), NABP1 (SSB2), and UHRF1.

In one embodiment, a eaCas9 fusion molecule includes a template nucleic acid having a double stranded nucleic acid sequence or a single stranded nucleic acid sequence.

In one embodiment, a eaCas9 fusion molecule includes a wild-type Cas9 molecule

In one embodiment, a eaCas9 fusion molecule includes a Cas9 nickase molecule.

In one embodiment, a eaCas9 fusion molecule includes a split Cas9 molecule or an inducible Cas9 molecule.

In one embodiment, a gene editing system includes at least one eaCas9 fusion molecule having an eaCas9 molecule linked to a template nucleic acid and at least one gRNA molecule. In some embodiments, the gene editing system, which includes at least one gRNA molecule and a eaCas9 fusion molecule, are designed to associate with a target nucleic acid and generate a double strand break on the target nucleic acid. In some embodiments, the double strand break is repaired by at least one DNA repair pathway, thereby producing a modified target nucleic acid.

In one embodiment, a gene editing system includes a first eaCas9 fusion molecule, which includes a first Cas9 nickase molecule linked to a first template nucleic acid, a first gRNA molecule, a second eaCas9 fusion molecule, which includes a second Cas9 nickase molecule linked to a second template nucleic acid; and a second gRNA molecule.

In one embodiment, a gene editing system includes a first eaCas9 fusion molecule, which includes a first Cas9 nickase molecule linked to a template nucleic acid and a first gRNA molecule.

In one embodiment, a gene editing system includes a first eaCas9 fusion molecule, which includes a first Cas9 nickase molecule linked to a template nucleic acid, a first gRNA molecule, a second eaCas9 fusion, which includes a second Cas9 nickase molecule linked to a template nucleic acid and a first gRNA molecule.

In one embodiment, a gene editing system includes a first eaCas9 fusion molecule, which includes a first Cas9 nickase molecule linked to a first template nucleic acid, a first gRNA molecule, a second eaCas9 fusion molecule, which includes a second Cas9 nickase molecule linked to a second template nucleic acid, and a second gRNA molecule. In some embodiments, the first gRNA molecule and the first eaCas9 fusion molecule are designed to associate with a target nucleic acid and generate a first single strand break on a first strand of the target nucleic acid, and the second gRNA molecule and the second eaCas9 fusion molecule are designed to associate with the target nucleic acid and generate a second single strand break on a second strand of the target nucleic acid, forming a double strand break in the target nucleic acid having a first overhang and a second overhang, such that the double strand break is repaired by at least one DNA repair pathway, thereby producing a modified target nucleic acid.

In one embodiment, each Cas9 nickase molecule has N-terminal RuvC-like domain cleavage activity, but no HNH-like domain cleavage activity. In other embodiments, each Cas9 nickase molecule comprises an amino acid mutation at an amino acid position corresponding to amino acid position N863 of Streptococcus pyogenes Cas9.

In one embodiment, each Cas9 nickase molecule has HNH-like domain cleavage activity but no N-terminal RuvC-like domain cleavage activity. In other embodiments, each Cas9 nickase molecule comprises an amino acid mutation at an amino acid position corresponding to amino acid position D10 of Streptococcus pyogenes Cas9.

In one embodiment, a gene editing system includes an enzymatically inactive Cas9 (eiCas9) molecule In one embodiment, a cell includes a gene editing system as disclosed herein.

In one embodiment, a pharmaceutical composition includes a gene editing system as disclosed herein.

In one embodiment, a method of modifying a target nucleic acid in a cell includes contacting a cell with a gRNA molecule and an eaCas9 fusion molecule, which includes an eaCas9 molecule linked to a template nucleic acid. In some embodiments, the gRNA molecule and the eaCas9 fusion molecule associate with the target nucleic acid and generate a double strand break in the target nucleic acid, such that the double strand break is repaired by gene correction using the template nucleic acid of the eaCas9 fusion molecule.

In one embodiment, a method of modifying a target nucleic acid in a cell includes contacting a cell with a first gRNA molecule, a first eaCas9 molecule, a second gRNA molecule; and a second eaCas9 molecule; such that at least one of the first and second eaCas9 molecule is linked to a template nucleic acid, further such that the first gRNA molecule and the first eaCas9 molecule associate with the target nucleic acid and generate a first single strand cleavage event on a first strand of the target nucleic acid. In some embodiments, the second gRNA molecule and the second eaCas9 molecule associate with the target nucleic acid and generate a second single strand cleavage event on a second strand of the target nucleic acid, such that a double strand break having a first overhang and a second overhang is formed, and such that the first overhang and the second overhang in the target nucleic acid are repaired by gene correction using the template nucleic acid. In one embodiment, the first eaCas9 molecule is linked to the template nucleic acid. In another embodiment, both the first eaCas9 molecule and the second eaCas9 molecule are linked to the template nucleic acid.

In one embodiment, each eaCas9 has N-terminal RuvC-like domain cleavage activity, but no HNH-like domain cleavage activity. In another embodiment, each eaCas9 has an amino acid mutation at an amino acid position corresponding to amino acid position N863 of Streptococcus pyogenes Cas9.

In one embodiment, each eaCas9 has HNH-like domain cleavage activity but no N-terminal RuvC-like domain cleavage activity. In another embodiment, each eaCas9 has an amino acid mutation at an amino acid position corresponding to amino acid position D10 of Streptococcus pyogenes Cas9.

In one embodiment, the cell is a mammalian cell. In other embodiments, the cell is a human cell.

In one embodiment, a cell is altered by any of the methods disclosed or described herein.

In one embodiment, a pharmaceutical composition includes a cell altered by any of the methods disclosed or described herein.

In one embodiment, a nucleic acid molecule encodes at least one eaCas9 fusion molecule, which includes an eaCas9 molecule and a polypeptide. In some embodiments, the polypeptide is a nucleic acid binding protein. In some embodiments, the nucleic acid binding protein may be any one of Rad52, Rad52-yeast, RPA-4 subunit, BRCA2, Rad51, Rad51B, Rad51C, XRCC2, XRCC3, RecA, RadA, HNRNPA1, UP1 Filament of HNRNPA1, NABP2 (SSB1), NABP1 (SSB2), or UHRF1.

In one embodiment, a vector includes any of the nucleic acid molecules disclosed or described herein.

In one embodiment, a method of modifying a target nucleic acid in a cell, includes contacting the cell with a gRNA molecule and an eaCas9 fusion molecule, which includes an eaCas9 molecule linked to a template nucleic acid, such that the gRNA molecule and the eaCas9 fusion molecule associate with the target nucleic acid and generate a double strand break in the target nucleic acid. In some embodiments, a first overhang and a second overhang in the target nucleic acid are repaired by gene correction using the template nucleic acid in the eaCas9 fusion molecule, thereby modifying the target nucleic acid in the cell.

In one embodiment, a method of modifying a target nucleic acid in a cell includes contacting the cell with a first gRNA molecule, a first eaCas9 fusion molecule, which includes a first Cas9 nickase molecule linked to a first template nucleic acid, a second gRNA molecule, and a second eaCas9 fusion molecule, which includes a second Cas9 nickase molecule linked to a second template nucleic acid. In some embodiments, the first gRNA molecule and the first eaCas9 fusion molecule associate with the target nucleic acid and generate a first single strand cleavage event on a first strand of the target nucleic acid, and the second gRNA molecule and the second eaCas9 fusion molecule associate with the target nucleic acid and generate a second single strand cleavage event on a second strand of the target nucleic acid, forming a double strand break having a first overhang and a second overhang. In certain embodiments, the first overhang and the second overhang in the target nucleic acid are repaired by gene correction using the first and second template nucleic acid, thereby modifying the target nucleic acid in the cell.

Headings, including numeric and alphabetical headings and subheadings, are for organization and presentation and are not intended to be limiting.

Other features and advantages of the invention will be apparent from the detailed description, drawings, and from the claims.

BRIEF DESCRIPTION OF THE DRAWINGS

FIG. 5 depicts the normalized percentages of HDR editing efficiency using a nucleofection assay in U2OS cells. The results compare results obtained using a Cas9 protein fusion provided in Table 9 conjugated to a template nucleic acid with a Cas9-HaloTag protein molecule that is not conjugated to a template nucleic acid. The results demonstrate that the Cas9 fusion molecules increase HDR efficiency when conjugated to template nucleic acid compared to reactions performed with unconjugated template nucleic acid.

FIG. 6 depicts a scheme of generating a Cas9 fusion molecule by covalent conjugation of a single- or multi-cysteine variant Cas9 protein molecule to a template nucleic acid that contains an acrydite-modified template nucleic acid.

FIG. 8 depicts a scheme generating a Cas9 fusion molecule by non-covalent conjugation of a Cas9 protein molecule, covalently linked to biotin, and a template nucleic acid, covalently linked to biotin, via the interaction of the biotin moiety of the Cas9 protein molecule and the biotin moiety of the template nucleic acid with streptavidin.

DETAILED DESCRIPTION

Figure 1:
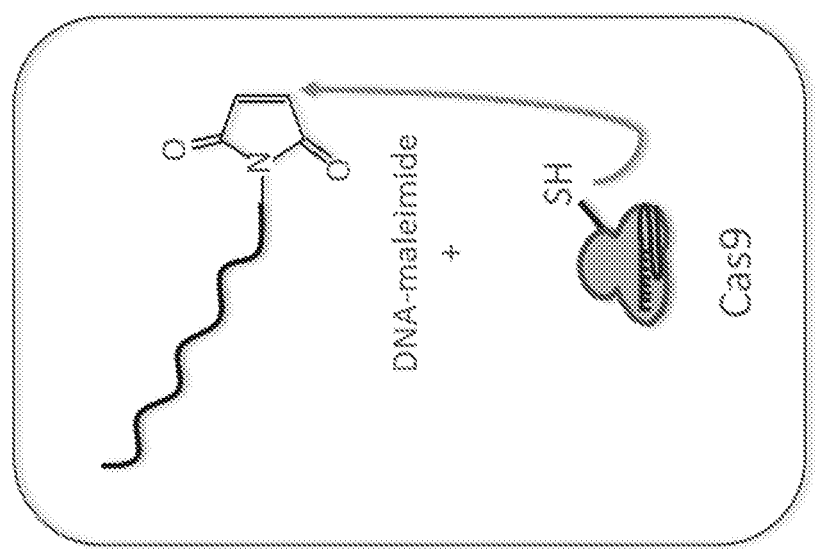
FIG. 1 depicts a scheme of generating a Cas9 fusion molecule by covalent conjugation of a single- or multi-cysteine variant Cas9 protein to a template nucleic acid that contains a 5'-maleimide-modification.

In order that the invention is understood, certain terms are herein defined.

Definitions

"Alt-HDR" or "alternative HDR," or alternative homology-directed repair, as used herein, refers to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Also, alt-HDR uses a single-stranded or nicked homologous nucleic acid for repair of the break.

"ALT-NHEJ" or "alternative NHEJ", or alternative non-homologous end joining, as used herein, is a type of alternative end joining repair process, and utilizes a different pathway than that of canonical NHEJ. In alternative NHEJ, a small degree of resection occurs at the break ends on both sides of the break to reveal single-stranded overhangs. Ligation or annealing of the overhangs results in the deletion of sequence. ALT-NHEJ is a category that includes microhomology-mediated end joining (MMEJ), blunt end joining (EJ), and synthesis-dependent microhomology-mediated end joining (SD-MMEJ). In MMEJ, microhomologies, or short spans of homologous sequences, e.g., 5 nucleotides or more, on the single-strand are aligned to guide repair, and leads to the deletion of sequence between the microhomologies.

"Amino acids" as used herein encompasses the canonical amino acids as well as analogs thereof. "Canonical HDR," or canonical homology-directed repair, as used herein, refers to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double-strand break, forming at least one single stranded portion of DNA. In a normal cell, HDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

"Canonical NHEJ", or canonical non-homologous end joining, as used herein, refers to the process of repairing double-strand breaks in which the break ends are directly ligated. This process does not require a homologous nucleic acid to guide the repair, and can result in deletion or insertion of one or more nucleotides. This process requires the Ku heterodimer (Ku70/Ku80), the catalytic subunit of DNA-PK (DN-PKcs), and/or DNA ligase XRCC4/LIG4. Unless indicated otherwise, the term "HDR" as used herein encompasses canonical HDR and alt-HDR.

A "Cas9 molecule," as used herein, refers to a Cas9 polypeptide or a nucleic acid encoding a Cas9 polypeptide. A "Cas9 polypeptide" is a polypeptide that can interact with a gRNA molecule and, in concert with the gRNA molecule, localize to a site comprising a target domain and, in certain embodiments, a PAM sequence. Cas9 molecules include both naturally occurring Cas9 molecules and Cas9 molecules and engineered, altered, or modified Cas9 molecules or Cas9 polypeptides that differ, e.g., by at least one amino acid residue, from a reference sequence, e.g., the most similar naturally occurring Cas9 molecule. (The terms altered, engineered or modified, as used in this context, refer merely to a difference from a reference or naturally occurring sequence, and impose no specific process or origin limitations.) A Cas9 molecule may be a Cas9 polypeptide or a nucleic acid encoding a Cas9 polypeptide. A Cas9 molecule may be a nuclease (an enzyme that cleaves both strands of a double-stranded nucleic acid), a nickase (an enzyme that cleaves one strand of a double-stranded nucleic acid), or an enzymatically inactive (or dead) Cas9 molecule. A Cas9 molecule having nuclease or nickase activity is referred to as an "enzymatically active Cas9 molecule" (an "eaCas9" molecule). A Cas9 molecule lacking the ability to cleave target nucleic acid is referred to as an "enzymatically inactive Cas9 molecule" (an "eiCas9" molecule). A Cas9 molecule may also be a split Cas9 molecule or an inducible Cas9 molecule, as described in more detail below.

In certain embodiments, a Cas9 molecule meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequences, e.g., naturally occurring Cas9 molecule.

In certain embodiments, a Cas9 molecule meets one or both of the following criteria: it has at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with, or it differs by no more than 1, 2, 3, 4, 5, 6, 7, 8, 9, 10, 11, 12, 13, 14, 15, 16, 17, 18, 19, 20, 25, 30, 35, 40, 35, 50, 55, 60, 65, 70, 75, 80, 85, 90, 95, 100, 150, 200, 250, 300, 350 or 400, amino acid residues from, the amino acid sequence of a reference sequences, e.g., naturally-occurring Cas9 molecule.

In certain embodiments, each domain of the Cas9 molecule (e.g., the domains named herein) will, independently have: at least 20, 30, 40, 50, 55, 60, 65, 70, 75, 80, 81, 82, 83, 84, 85, 86, 87, 88, 89, 90, 91, 92, 93, 94, 95, 96, 97, 98, 99, or 100% homology with such a domain described herein. In certain embodiments at least 1, 2, 3, 4, 5, of 6 domains will have, independently, at least 50, 60, 70, 80, 81, 82, 83, 84, 85, 86, 87, 88, 89, 90, 91, 92, 93, 94, 95, 96, 97, 98, 99, or 100% homology with a corresponding domain, while any remaining domains will be absent, or have less homology to their corresponding naturally occurring domains.

In certain embodiments, the Cas9 molecule is a *S. pyogenes* Cas9 variant. In certain embodiments, the Cas9 variant is the EQR variant. In certain embodiments, the Cas9 variant is the VRER variant. In certain embodiments, the eiCas9 molecule is a *S. pyogenes* Cas9 variant. In certain embodiments, the Cas9 variant is the EQR variant. In certain embodiments, the Cas9 variant is the VRER variant. In certain embodiments, a Cas9 system comprises a Cas9 molecule, e.g., a Cas9 molecule described herein, e.g., the Cas9 EQR variant or the Cas9 VRER variant.

In certain embodiments, the Cas9 molecule is a *S. aureus* Cas9 variant. In certain embodiments, the Cas9 variant is the KKH (E782K/N968K/R1015H) variant (see, e.g., Kleinstiver 2015, the entire contents of which are expressly incorporated herein by reference). In certain embodiments, the Cas9 variant is the E782K/K929R/R1015H variant (see, e.g., Kleinstiver 2015). In certain embodiments, the Cas9 variant is the E782K/K929R/N968K/R1015H variant (see, e.g., Kleinstiver 2015). In certain embodiments the Cas9 variant comprises one or more mutations in one of the following residues: E782, K929, N968, R1015. In certain embodiments the Cas9 variant comprises one or more of the following mutations: E782K, K929R, N968K, R1015H and R1015Q (see, e.g., Kleinstiver 2015). In certain embodiments, a Cas9 system comprises a Cas9 molecule, e.g., a Cas9 molecule described herein, e.g., the Cas9 KKH variant.

A "Cas9 fusion molecule", "Cas9 fusion protein", or "Cas9 fusion", as used herein, refers to a chimeric protein comprising a Cas9 molecule, e.g., Cas9 protein or Cas9 polypeptide, or a fragment thereof, linked to a template nucleic acid. In some embodiments, the template nucleic acid is a nucleic acid, e.g., DNA or RNA. In some embodiments, the template nucleic acid is single-stranded or double-stranded. In some embodiments the template nucleic acid is circular nucleic acid, while in other embodiments the template nucleic acid is linear nucleic acid. In certain embodiments, the Cas9 fusion molecule comprises a Cas9 molecule covalently linked to a template nucleic acid. In other embodiments, the Cas9 fusion molecule comprises a Cas9 molecule non-covalently linked to a template nucleic acid. In certain embodiments, a Cas9 fusion molecule is linked to more than one template nucleic acid.

As used herein, the term "Cas9 system" or "gene editing system" refers to a system capable of altering a target nucleic acid by one of many DNA repair pathways. In certain embodiments, the Cas9 system described herein promotes repair of a target nucleic acid via an HDR pathway. In some embodiments, a Cas9 system comprises a gRNA and a Cas9 molecule. In other embodiments, a Cas9 system comprises a gRNA and a Cas9 fusion molecule. In some embodiments, a Cas9 system further comprises a second gRNA. In yet another embodiment, a Cas9 system comprises a gRNA, a Cas9 molecule, and a second gRNA. In yet other embodiment, a Cas9 system comprises a gRNA, a Cas9 fusion molecule, and a second gRNA. In some embodiments, a Cas9 system comprises a gRNA, two Cas9 molecules, and a second gRNA. In some embodiments, a Cas9 system comprises a gRNA, two Cas9 fusion molecules, and a second gRNA. In some embodiments, a Cas9 system comprises a first gRNA, a second gRNA, a first Cas9 molecule, and a second Cas9 molecule. In other embodiments, a Cas9 system comprises a first gRNA, a second gRNA, a first Cas9 fusion molecule, and a second Cas9 fusion molecule. In some embodiments, a Cas9 system further comprises a template nucleic acid. In other embodiments, a Cas9 system further comprises a template nucleic acid provided by the Cas9 fusion molecule.

As used herein, the term "cleavage event" refers to a break in a nucleic acid molecule. A cleavage event may be a single-strand cleavage event, or a double-strand cleavage event. A single-strand cleavage event may result in a 5' overhang or a 3' overhang. A double-stranded cleavage event may result in blunt ends, two 5' overhangs, or two 3' overhangs.

A disorder "caused by" a mutation, as used herein, refers to a disorder that is made more likely or severe by the presence of the mutation, compared to a subject that does not have the mutation. The mutation need not be the only cause of a disorder, i.e., the disorder can still be caused by the mutation even if other causes, such as environmental factors or lifestyle factors, contribute causally to the disorder. In embodiments, the disorder is caused by the mutation if the mutation is a medically recognized risk factor for developing the disorder, and/or if a study has found that the mutation contributes causally to development of the disorder.

The term "covalent", as used herein, refers to a form of chemical bonding characterized by the sharing of one or more pairs of electrons between two components, producing a mutual attraction that holds the two components together. The sharing of the one or more pairs of electrons between two components may either be direct (e.g., via reactive groups on the surface the two components, e.g., a Cas9 polypeptide and a template nucleic acid) or indirect (via a linker molecule).

"Derived from", as used herein, refers to the source or origin of a molecular entity, e.g., a nucleic acid or protein. The source of a molecular entity may be naturally-occurring, recombinant, unpurified, or a purified molecular entity. For example, a polypeptide that is derived from a second polypeptide comprises an amino acid sequence that is identical or substantially similar, e.g., is more than 50% homologous to, the amino acid sequence of the second protein. The derived molecular entity, e.g., a nucleic acid or protein, can comprise one or more modifications, e.g., one or more amino acid or nucleotide changes.

"Domain," as used herein, is used to describe a segment of, or a portion of a protein or nucleic acid. Unless otherwise indicated, a domain is not required to have any specific functional property.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

As used herein, the term "endogenous" gene, "endogenous" nucleic acid, or "endogenous" homologous region refers to a native gene, nucleic acid, or region of a gene, which is in its natural location in the genome, e.g., chromosome or plasmid, of a cell. In contrast, the term "exogenous" gene or "exogenous" nucleic acid refers to a gene, nucleic acid, or region of a gene which is not native within a cell, but which is introduced into the cell during the methods of the invention. An exogenous gene or exogenous nucleic acid may be homologous to, or identical to, an endogenous gene or an endogenous nucleic acid.

As used herein, the term "endogenous homologous region" refers to an endogenous template nucleic acid sequence which is homologous to at least a portion of a target gene, and which can be used in conjunction with a Cas9 molecule and a gRNA molecule to modify, e.g., correct, a sequence of the target gene. In one embodiment, the endogenous homologous region is DNA. In another embodiment, the endogenous homologous region is double stranded DNA. In another embodiment, the endogenous homologous region is single stranded DNA. In one embodiment, the endogenous homologous region is at least 70%, 75%, 80%, 81%, 82%, 83%, 84%, 85%, 86%, 875, 885, 89%, 90%, 91%, 92%, 93%, 94%, 95%, 96%, 9%, 98%, or 99% homologous to at least a portion of the target gene.

As used herein, the term "enzymatically inactive Cas9" ("eiCas9") or eiCas9 polypeptide refers to Cas9 molecules having no, or no substantial, cleavage activity. For example, an eiCas9 molecule or eiCas9 polypeptide can lack cleavage activity or have substantially less, e.g., less than 20, 10, 5, 1 or 0.1% of the cleavage activity of a reference Cas9 molecule or eiCas9 polypeptide, as measured by an assay described herein.

In one embodiment, a Cas9 molecule is an eiCas9 molecule comprising one or more differences in a RuvC domain and/or in an HNH domain as compared to a reference Cas9 molecule, and the eiCas9 molecule does not cleave a nucleic acid, or cleaves with significantly less efficiency than does wild type, e.g., when compared with wild type in a cleavage assay, e.g., as described herein, cuts with less than 50, 25, 10, or 1% of a reference Cas9 molecule, as measured by an assay described herein. The reference Cas9 molecule can be a naturally occurring unmodified Cas9 molecule, e.g., a naturally occurring Cas9 molecule such as a Cas9 molecule of S. pyogenes, S. thermophilus, S. aureus, C. jejuni or N. meningitidis. In one embodiment, the reference Cas9 molecule is the naturally occurring Cas9 molecule having the closest sequence identity or homology. In one embodiment, the eiCas9 molecule lacks substantial cleavage activity associated with a RuvC domain and cleavage activity associated with an HNH domain.

Whether or not a particular sequence, e.g., a substitution, may affect one or more activity, such as targeting activity, cleavage activity, etc., can be evaluated or predicted, e.g., by evaluating whether the mutation is conservative. In one embodiment, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

Although an enzymatically inactive (eiCas9) Cas9 molecule itself can block transcription when recruited to early regions in the coding sequence, more robust repression can be achieved by fusing a transcriptional repression domain (for example KRAB, SID or ERD) to the Cas9 and recruiting it to the target knockdown position, e.g., within 1000 bp of sequence 3' of the start codon or within 500 bp of a promoter region 5' of the start codon of a gene. It is likely that targeting DNAseI hypersensitive sites (DHSs) of the promoter may yield more efficient gene repression or activation because these regions are more likely to be accessible to the Cas9 protein and are also more likely to harbor sites for endogenous transcription factors. Especially for gene repression, it is contemplated herein that blocking the binding site of an endogenous transcription factor would aid in downregulating gene expression. In one embodiment, one or more eiCas9 molecules may be used to block binding of one or more endogenous transcription factors. In another embodiment, an eiCas9 molecule can be fused to a chromatin modifying protein. Altering chromatin status can result in decreased expression of the target gene. One or more eiCas9 molecules fused to one or more chromatin modifying proteins may be used to alter chromatin status.

As used herein, "error-prone" repair refers to a DNA repair process that has a higher tendency to introduce mutations into the site being repaired. For instance, alt-NHEJ and SSA are error-prone pathways; C-NHEJ is also error prone because it sometimes leads to the creation of a small degree of alteration of the site (even though in some instances C-NHEJ results in error-free repair); and HR, alt-HR, and SSA in the case of a single-strand oligo donor are not error-prone. As used herein, the term "gRNA molecule" or "gRNA" refers to a guide RNA which is capable of targeting a Cas9 molecule to a target nucleic acid. In one embodiment, the term "gRNA molecule" refers to a guide ribonucleic acid. In another embodiment, the term "gRNA molecule" refers to a nucleic acid encoding a gRNA. In one embodiment, a gRNA molecule is non-naturally occurring. In one embodiment, a gRNA molecule is a synthetic gRNA molecule.

"Governing gRNA molecule," as used herein, refers to a gRNA molecule that comprises a targeting domain that is complementary to a target domain on a nucleic acid that comprises a sequence that encodes a component of the CRISPR/Cas system that is introduced into a cell or subject. A governing gRNA does not target an endogenous cell or subject sequence. In one embodiment, a governing gRNA molecule comprises a targeting domain that is complementary with a target sequence on: (a) a nucleic acid that encodes a Cas9 molecule; (b) a nucleic acid that encodes a gRNA molecule which comprises a targeting domain that targets a target gene (a target gene gRNA); or on more than one nucleic acid that encodes a CRISPR/Cas component, e.g., both (a) and (b). In one embodiment, a nucleic acid molecule that encodes a CRISPR/Cas component, e.g., that encodes a Cas9 molecule or a target gene gRNA molecule, comprises more than one target domain that is complementary with a governing gRNA targeting domain. While not wishing to be bound by theory, it is believed that a governing gRNA molecule complexes with a Cas9 molecule and results in Cas9 mediated inactivation of the targeted nucleic acid, e.g., by cleavage or by binding to the nucleic acid, and results in cessation or reduction of the production of a CRISPR/Cas system component. In one embodiment, the Cas9 molecule forms two complexes: a complex comprising a Cas9 molecule with a target gene gRNA molecule, which complex will alter the target gene; and a complex comprising a Cas9 molecule with a governing gRNA molecule, which complex will act to prevent further production of a CRISPR/Cas system component, e.g., a Cas9 molecule or a target gene gRNA molecule. In one embodiment, a governing gRNA molecule/Cas9 molecule complex binds to or promotes cleavage of a control region sequence, e.g., a promoter, operably linked to a sequence that encodes a Cas9 molecule, a sequence that encodes a transcribed region, an exon, or an intron, for the Cas9 molecule. In one embodiment, a governing gRNA molecule/Cas9 molecule complex binds to or promotes cleavage of a control region sequence, e.g., a promoter, operably linked to a gRNA molecule, or a sequence that encodes the gRNA molecule. In one embodiment, the governing gRNA molecule, e.g., a Cas9-targeting governing gRNA molecule, or a target gene gRNA-targeting governing gRNA molecule, limits the effect of the Cas9 molecule/target gene gRNA molecule complex-mediated gene targeting. In one embodiment, a governing gRNA places temporal, level of expression, or other limits, on activity of the Cas9 molecule/target gene gRNA molecule complex. In one embodiment, a governing gRNA reduces off-target or other unwanted activity. In one embodiment, a governing gRNA molecule inhibits, e.g., entirely or substantially entirely inhibits, the production of a component of the Cas9 system and thereby limits, or governs, its activity.

"HDR", or homology-directed repair, as used herein, refers to the process of repairing DNA damage using a homologous nucleic acid (e.g., an endogenous nucleic acid, e.g., a sister chromatid, or an exogenous nucleic acid, e.g., a template nucleic acid). HDR typically occurs when there has been significant resection at a double-strand break, forming at least one single stranded portion of DNA. HDR is a category that includes, for example, single-strand annealing (SSA), homologous recombination (HR), single strand template repair (SST-R), and a third, not yet fully characterized alternative homologous recombination (alt-HR) DNA repair pathway. In some embodiments, HDR includes gene conversion and gene correction. In some embodiments, the term HDR does not encompass canonical NHEJ (C-NHEJ). In some embodiments, the term HDR does not encompass alternative non-homologous end joining (Alt-NHEJ) (e.g., blunt end-joining (blunt EJ), (micro homology mediated end joining (MMEJ), and synthesis dependent microhomology-mediated end joining (SD-MMEJ)).

The terms "homology" or "identity," as used interchangeably herein, refer to sequence identity between two amino acid sequences or two nucleic acid sequences, with identity being a more strict comparison. The phrases "percent identity or homology" and "% identity or homology" refer to the percentage of sequence identity found in a comparison of two or more amino acid sequences or nucleic acid sequences. Two or more sequences can be anywhere from 0-100% identical, or any value there between. Identity can be determined by comparing a position in each sequence that can be aligned for purposes of comparison to a reference sequence. When a position in the compared sequence is occupied by the same nucleotide base or amino acid, then the molecules are identical at that position. A degree of identity of amino acid sequences is a function of the number of identical amino acids at positions shared by the amino acid sequences. A degree of identity between nucleic acid sequences is a function of the number of identical or matching nucleotides at positions shared by the nucleic acid sequences. A degree of homology of amino acid sequences is a function of the number of amino acids at positions shared by the polypeptide sequences.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

"Gene conversion", as used herein, refers to the process of repairing DNA damage by homology directed recombination (HDR) using an endogenous nucleic acid, e.g., a sister chromatid or a plasmid, as a template nucleic acid. Without being bound by theory, in some embodiments, BRCA1, BRCA2 and/or RAD51 are believed to be involved in gene conversion. In some embodiments, the endogenous nucleic acid is a nucleic acid sequence having homology, e.g., significant homology, with a fragment of DNA proximal to the site of the DNA lesion or mutation. In some embodiments, the template is not an exogenous nucleic acid.

"Gene correction", as used herein, refers to the process of repairing DNA damage by homology directed recombination using an exogenous nucleic acid, e.g., a donor template nucleic acid. In some embodiments, the exogenous nucleic acid is single-stranded. In some embodiments, the exogenous nucleic acid is double-stranded. In one embodiment, the donor template nucleic acid is a circular nucleic acid sequence. In another embodiment, the donor template nucleic acid is a linear nucleic acid sequence.

"Homologous recombination" or "HR" refers to a type of HDR DNA-repair which typically acts occurs when there has been significant resection at the double-strand break, forming at least one single stranded portion of DNA. In a normal cell, HR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded. In some embodiments, homologous recombination includes gene conversion.

"Ligand acceptor molecule," as used herein, refers to a substance or molecule that specifically interacts non-covalently with at least one ligand. In one embodiment, the ligand acceptor molecule is streptavidin.

The term "ligand," as used herein, refers to a substance or molecule that specifically interacts with another substance or molecule (e.g., a ligand acceptor molecule). In one embodiment, the ligand is biotin. In some embodiments, the ligand is a high-affinity ligand (e.g., a ligand that has high affinity for its receptor.

The term "linked" or "linkage" as used herein means an interaction between molecules or parts of molecules. Two molecules that are linked may be covalently linked or non-covalently linked.

The term "linker", as used herein, refers to a molecule which facilitates an interaction between molecules or parts of molecules. In one embodiment, a linker is a polypeptide linker. In another embodiment, a linker is a nucleic acid linker.

The term "peptide linker" or "polypeptide linker" as used herein means a peptide or polypeptide comprising two or more amino acids residues joined by peptide bonds. Such peptide or polypeptide linkers are well known in the art. Linkers comprise naturally occurring and/or non-naturally occurring peptides or polypeptides.

"Modulator," as used herein, refers to an entity, e.g., a compound, that can alter the activity (e.g., enzymatic activity, transcriptional activity, or translational activity), amount, distribution, or structure of a subject molecule or genetic sequence. In one embodiment, modulation comprises cleavage, e.g., breaking of a covalent or non-covalent bond, or the forming of a covalent or non-covalent bond, e.g., the attachment of a moiety, to the subject molecule. In one embodiment, a modulator alters the, three dimensional, secondary, tertiary, or quaternary structure, of a subject molecule. A modulator can increase, decrease, initiate, or eliminate a subject activity.

As used herein, the term "mutation" refers to a change in the sequence of a nucleic acid as compared to a wild-type sequence of the nucleic acid, resulting a variant form of the nucleic acid. A mutation in a nucleic acid may be caused by the alteration of a single base pair in the nucleic acid, or the insertion, deletion, or rearrangement of larger sections of the nucleic acid. A mutation in a gene may result in variants of the protein encoded by the gene which are associated with genetic disorders.

The term "non-covalent bond" refers to a variety of interactions between molecules or parts of molecules that are not covalent in nature, which provide force to hold the molecules or parts of molecules together usually in a specific orientation or conformation. Such non-covalent interactions include inter alia ionic bonds, hydrophobic interactions, hydrogen bonds, Van-der-Waals forces, and dipole-dipole bonds.

"Non-homologous end joining" or "NHEJ," as used herein, refers to ligation mediated repair and/or non-template mediated repair including canonical NHEJ (cNHEJ), alternative NHEJ (altNHEJ), microhomology-mediated end joining (MMEJ), single-strand annealing (SSA), and synthesis-dependent microhomology-mediated end joining (SD-MMEJ). Unless indicate otherwise, "NHEJ" as used herein encompasses canonical NHEJ, alt-NHEJ, MMEJ, SSA and SD-MMEJ.

"Polypeptide," as used herein, refers to a polymer of amino acids.

The term "protein", as used herein, is intended to refer to a biomolecule comprised of amino acids arranged in the form of a polypeptide. A protein may be a full-length protein, or a fragment thereof.

As used herein, the term "processing," with respect to overhangs, refers to either the endonucleolytic processing or the exonucleolytic processing of a break in a nucleic acid molecule. In one embodiment, processing of a 5' overhang in a nucleic acid molecule may result in a 3' overhang. In another embodiment, processing of a 3' overhang in a nucleic acid molecule may result in a 5' overhang.

A "reference molecule," as used herein, refers to a molecule to which a modified or candidate molecule is compared. For example, a reference Cas9 molecule refers to a Cas9 molecule to which a modified or candidate Cas9 molecule is compared. The modified or candidate molecule may me compared to the reference molecule on the basis of sequence (e.g., the modified or candidate may have X % sequence identity or homology with the reference molecule) or activity (e.g., the modified or candidate molecule may have X % of the activity of the reference molecule). For example, where the reference molecule is a Cas9 molecule, a modified or candidate may be characterized as having no more than 10% of the nuclease activity of the reference Cas9 molecule. Examples of reference Cas9 molecules include naturally occurring unmodified Cas9 molecules, e.g., a naturally occurring Cas9 molecule from *S. pyogenes, S. aureus, S. thermophilus* or *N. meningitidis*. In certain embodiments, the reference Cas9 molecule is the naturally occurring Cas9 molecule having the closest sequence identity or homology with the modified or candidate Cas9 molecule to which it is being compared. In certain embodiments, the reference Cas9 molecule is a parental molecule having a naturally occurring or known sequence on which a mutation has been made to arrive at the modified or candidate Cas9 molecule.

"Replacement," or "replaced," as used herein with reference to a modification of a molecule does not require a process limitation but merely indicates that the replacement entity is present.

"Resection", as used herein, refers to exonuclease-mediated digestion of one strand of a double-stranded DNA molecule, which results in a single-stranded overhang. Resection may occur, e.g., on one or both sides of a double-stranded break. Resection can be measured by, for instance, extracting genomic DNA, digesting it with an enzyme that selectively degrades dsDNA, and performing quantitative PCR using primers spanning the DSB site, e.g., as described herein.

"SSA" or "Single-strand Annealing", as used herein, refers to the process where RAD52 as opposed to RAD51 in the HR pathways, binds to the single stranded portion of DNA and promotes annealing of the two single stranded DNA segments at repetitive regions. Once RAD52 binds XFP/ERCC1 removes DNA flaps to make the DNA more suitable for ligation.

"Subject," as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In one embodiment, the subject is a human. In another embodiment, the subject is poultry. In another embodiment, the subject is piscine. In certain embodiments, the subject is a human, and in certain of these embodiments the human is an infant, child, young adult, or adult.

As used herein, the terms "target nucleic acid" or "target gene" refer to a nucleic acid which is being targeted for alteration, e.g., by gene correction, by a Cas9 system described herein. In certain embodiments, a target nucleic acid comprises one gene. In certain embodiments, a target nucleic acid may comprise one or more genes, e.g., two genes, three genes, four genes, or five genes. In one embodiment, a target nucleic acid may comprise a promoter region, or control region, of a gene. In one embodiment, a target nucleic acid may comprise an intron of a gene. In another embodiment, a target nucleic acid may comprise an exon of a gene. In one embodiment, a target nucleic acid may comprise a coding region of gene. In one embodiment, a target nucleic acid may comprise a non-coding region of a gene.

"Target position" as used herein, refers to a site on a target nucleic acid that is modified by a Cas9 molecule-dependent or a Cas9 fusion molecule-dependent process. For example, the target position can be modified by a Cas9 molecule-mediated cleavage (or a Cas9 fusion molecule-mediated cleavage) of the target nucleic acid and template nucleic acid directed modification, e.g., correction, of the target position. In one embodiment, a target position can be a site between two nucleotides, e.g., adjacent nucleotides, on the target nucleic acid into which one or more nucleotides is added based on homology with a template nucleic acid. The target position may comprise one or more nucleotides that are altered, e.g., corrected, based on homology with a template nucleic acid. In another embodiment, the target position may comprise one or more nucleotides that are deleted based on homology with a template nucleic acid. In one embodiment, the target position is within a "target sequence" (e.g., the sequence to which the gRNA binds). In one embodiment, a target position is upstream or downstream of a target sequence (e.g., the sequence to which the gRNA binds).

"Target region," "target domain," or "target sequence," as used herein, is a nucleic acid sequence that comprises a target position and at least one nucleotide position outside the target position. In certain embodiments, the target position is flanked by sequences of the target position region, i.e., the target position is disposed in the target position region such that there are target position region sequences both 5' and 3' to the target position. In certain embodiments, the target position region provides sufficient sequences on each side (i.e., 5' and 3') of the target position to allow gene correction of the target position, wherein the gene correction uses an exogenous sequence homologous with the target position region as a template.

A "template nucleic acid," "exogenous homologous region," "donor nucleic acid," "exogenous template," or "donor template" as that term is used herein, refers to a nucleic acid sequence which can be used in conjunction with a Cas9 molecule (or a Cas9 fusion molecule) and a gRNA molecule and services as a guide for altering the structure of a target position. In some embodiments, the template nucleic acid is homologous to at least a portion of a target gene, and which can be used in conjunction with a Cas9 molecule and a gRNA molecule to modify, e.g., correct, a sequence of the target gene. In one embodiment, the target nucleic acid is modified to have the some or all of the sequence of the template nucleic acid, typically at or near cleavage site(s). In some embodiments, the template nucleic acid is a nucleic acid, e.g., DNA or RNA. In one embodiment, the template nucleic acid is single stranded. In an alternate embodiment, the template nucleic acid is double stranded. In one embodiment, the template nucleic acid is DNA, e.g., double stranded DNA. In an alternate embodiment, the template nucleic acid is single stranded DNA. In one embodiment, the template nucleic acid is encoded on the same vector backbone, e.g., AAV genome, plasmid DNA, as the Cas9 and gRNA. In one embodiment, the template nucleic acid is excised from a vector backbone in vivo, e.g., it is flanked by gRNA recognition sequences. In one embodiment, the template nucleic acid comprises endogenous genomic sequence. In one embodiment, the template nucleic acid is an RNA. In some embodiments the template nucleic acid is circular nucleic acid. In other embodiments, the template nucleic acid is linear nucleic acid.

In one embodiment, the template nucleic acid alters the structure of the target position by participating in a homology directed repair event, e.g., a gene correction event. In one embodiment, the template nucleic acid alters the sequence of the target position. In one embodiment, the template nucleic acid results in the incorporation of a modified, or non-naturally occurring base into the target nucleic acid.

Typically, the template sequence undergoes a breakage mediated or catalyzed recombination with the target sequence. In one embodiment, the template nucleic acid includes sequence that corresponds to a site on the target sequence that is cleaved by an eaCas9 mediated cleavage event. In one embodiment, the template nucleic acid includes sequence that corresponds to both, a first site on the target sequence that is cleaved in a first Cas9 mediated event, and a second site on the target sequence that is cleaved in a second Cas9 mediated event.

In one embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a gene, e.g., a gene described herein, can be used to alter the structure of a target sequence. The template sequence can be used to alter an unwanted structure, e.g., an unwanted or mutant nucleotide.

A template nucleic acid typically comprises the following components:

[5' homology arm]-[replacement sequence]-[3' homology arm].

The homology arms provide for recombination into the chromosome, thus replacing the undesired element, e.g., a mutation or signature, with a replacement sequence, e.g., the desired, or corrected sequence. In one embodiment, the homology arms flank the most distal cleavage sites.

In one embodiment, the 3' end of the 5' homology arm is the position next to the 5' end of the replacement sequence. In one embodiment, the 5' homology arm can extend at least 10, 20, 30, 40, 50, 100, 200, 300, 400, 500, 600, 700, 800, 900, 1000, 1500, 2000, 3000, 4000, or 5000 nucleotides 5' from the 5' end of the replacement sequence.

In one embodiment, the 5' end of the 3' homology arm is the position next to the 3' end of the replacement sequence. In one embodiment, the 3' homology arm can extend at least 10, 20, 30, 40, 50, 100, 200, 300, 400, 500, 600, 700, 800, 900, 1000, 1500, 2000, 3000, 4000, or 5000 nucleotides 3' from the 3' end of the replacement sequence.

In one embodiment, to correct a mutation, the homology arms, e.g., the 5' and 3' homology arms, may each comprise about 1000 base pairs (bp) of sequence flanking the most distal gRNAs (e.g., 1000 bp of sequence on either side of the mutation).

It is contemplated herein that one or both homology arms may be shortened to avoid including certain sequence repeat elements, e.g., Alu repeats or LINE elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

It is contemplated herein that template nucleic acids for correcting a mutation may be designed for use as a single-stranded oligonucleotide, e.g., a single-stranded oligodeoxynucleotide (ssODN). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made. In some embodiments, a longer homology arm is made by a method other than chemical synthesis, e.g., by denaturing a long double stranded nucleic acid and purifying one of the strands, e.g., by affinity for a strand-specific sequence anchored to a solid substrate.

While not wishing to be bound by theory, in some embodiments HDR proceeds more efficiently when the template nucleic acid has extended homology 5' to a nick, (i.e., in the 5' direction of the nicked strand). A nick, as referred to herein, refers to a single strand break in a nucleic acid. Accordingly, in some embodiments, the template nucleic acid has a longer homology arm and a shorter homology arm, wherein the longer homology arm can anneal 5' of the nick. In some embodiments, the arm that can anneal 5' to the nick is at least 25, 50, 75, 100, 125, 150, 175, or 200, 300, 400, 500, 600, 700, 800, 900, 1000, 1500, 2000, 3000, 4000, or 5000 nucleotides from the nick or the 5' or 3' end of the replacement sequence. In some embodiments, the arm that can anneal 5' to the nick is at least 10%, 20%, 30%, 40%, or 50% longer than the arm that can anneal 3' to the nick. In some embodiments, the arm that can anneal 5' to the nick is at least 2×, 3×, 4×, or 5× longer than the arm that can anneal 3' to the nick. Depending on whether a ssDNA template can anneal to the intact strand or the nicked strand, the homology arm that anneals 5' to the nick may be at the 5' end of the ssDNA template or the 3' end of the ssDNA template, respectively.

Similarly, in some embodiments, the template nucleic acid has a 5' homology arm, a replacement sequence, and a 3' homology arm, such that the template nucleic acid has extended homology to the 5' of the nick. For example, the 5' homology arm and 3' homology arm may be substantially the same length, but the replacement sequence may extend farther 5' of the nick than 3' of the nick. In some embodiments, the replacement sequence extends at least 10%, 20%, 30%, 40%, 50%, 2×, 3×, 4×, or 5× further to the 5' end of the nick than the 3' end of the nick.

While not wishing to be bound by theory, in some embodiments HDR proceeds more efficiently when the template nucleic acid is centered on the nick. Accordingly, in some embodiments, the template nucleic acid has two homology arms that are essentially the same size. For instance, the first homology arm of a template nucleic acid may have a length that is within 10%, 9%, 8%, 7%, 6%, 5%, 4%, 3%, 2%, or 1% of the second homology arm of the template nucleic acid.

Similarly, in some embodiments, the template nucleic acid has a 5' homology arm, a replacement sequence, and a 3' homology arm, such that the template nucleic acid extends substantially the same distance on either side of the nick. For example, the homology arms may have different lengths, but the replacement sequence may be selected to compensate for this. For example, the replacement sequence may extend further 5' from the nick than it does 3' of the nick, but the homology arm 5' of the nick is shorter than the homology arm 3' of the nick, to compensate. The converse is also possible, e.g., that the replacement sequence may extend further 3' from the nick than it does 5' of the nick, but the homology arm 3' of the nick is shorter than the homology arm 5' of the nick, to compensate.

A "variant Cas9 molecule," as used herein refers to a Cas9 molecule with at least one modification, e.g., a mutation or chemical modification to at least one amino acid residue of the wild-type Cas9 molecule.

Exemplary Arrangements of Linear Nucleic Acid Template Systems

In one embodiment, the template nucleic acid is double stranded. In one embodiment, the template nucleic acid is single stranded. In one embodiment, the nucleic acid template system comprises a single stranded portion and a double stranded portion. In one embodiment, the template nucleic acid comprises about 50 to 100, e.g., 55 to 95, 60 to 90, 65 to 85, or 70 to 80, base pairs, homology on either side of the nick and/or replacement sequence. In one embodiment, the template nucleic acid comprises about 50, 55, 60, 65, 70, 75, 80, 85, 90, 95, or 100 base pairs homology 5' of the nick or replacement sequence, 3' of the nick or replacement sequence, or both 5' and 3' of the nick or replacement sequences.

In one embodiment, the template nucleic acid comprises about 150 to 200, e.g., 155 to 195, 160 to 190, 165 to 185, or 170 to 180, base pairs homology 3' of the nick and/or replacement sequence. In one embodiment, the template nucleic acid comprises about 150, 155, 160, 165, 170, 175, 180, 185, 190, 195, or 200 base pairs homology 3' of the nick or replacement sequence. In one embodiment, the template nucleic acid comprises less than about 100, 90, 80, 70, 60, 50, 40, 30, 20, 15, or 10 base pairs homology 5' of the nick or replacement sequence.

In one embodiment, the template nucleic acid comprises about 150 to 200, e.g., 155 to 195, 160 to 190, 165 to 185, or 170 to 180, base pairs homology 5' of the nick and/or replacement sequence. In one embodiment, the template nucleic acid comprises about 150, 155, 160, 165, 170, 175, 180, 185, 190, 195, or 200 base pairs homology 5' of the nick or replacement sequence. In one embodiment, the template nucleic acid comprises less than about 100, 90, 80, 70, 60, 50, 40, 30, 20, 15, or 10 base pairs homology 3' of the nick or replacement sequence.

Exemplary Template Nucleic Acids

In one embodiment, the template nucleic acid is a single stranded nucleic acid. In another embodiment, the template nucleic acid is a double stranded nucleic acid. In some embodiments, the template nucleic acid comprises a nucleotide sequence, e.g., of one or more nucleotides, that will be added to or will create a change in, or correct the sequence of the target nucleic acid to a desired sequence. In other embodiments, the template nucleic acid comprises a nucleotide sequence that may be used to modify the target position. In other embodiments, the template nucleic acid comprises a nucleotide sequence, e.g., of one or more nucleotides, that corresponds to wild type sequence of the target nucleic acid, e.g., of the target position.

The template nucleic acid may comprise a replacement sequence. A replacement sequence, as the term is used herein, refers to a sequence which will serve as the template for making the desired change, or correction, in the target nucleic acid. The replacement sequence is homologous, but not identical to, the target nucleic acid. In some embodiments, the template nucleic acid comprises a 5' homology arm. In other embodiments, the template nucleic acid comprises a 3' homology arm.

In embodiments, the template nucleic acid is linear double stranded DNA. The length may be, e.g., about 150-200 base pairs, e.g., about 150, 160, 170, 180, 190, or 200 base pairs. The length may be, e.g., at least 150, 160, 170, 180, 190, or 200 base pairs. In some embodiments, the length is no greater than 150, 160, 170, 180, 190, or 200 base pairs. In some embodiments, a double stranded template nucleic acid has a length of about 160 base pairs, e.g., about 155-165, 150-170, 140-180, 130-190, 120-200, 110-210, 100-220, 90-230, or 80-240 base pairs.

The template nucleic acid can be linear single stranded DNA. In embodiments, the template nucleic acid is (i) linear single stranded DNA that can anneal to the nicked strand of the target nucleic acid, (ii) linear single stranded DNA that can anneal to the intact strand of the target nucleic acid, (iii) linear single stranded DNA that can anneal to the transcribed strand of the target nucleic acid, (iv) linear single stranded DNA that can anneal to the non-transcribed strand of the target nucleic acid, or more than one of the preceding. The length may be, e.g., about 150-200 nucleotides, e.g., about 150, 160, 170, 180, 190, or 200 nucleotides. The length may be, e.g., at least 150, 160, 170, 180, 190, or 200 nucleotides. In some embodiments, the length is no greater than 150, 160, 170, 180, 190, or 200 nucleotides. In some embodiments, a single stranded template nucleic acid has a length of about 160 nucleotides, e.g., about 155-165, 150-170, 140-180, 130-190, 120-200, 110-210, 100-220, 90-230, or 80-240 nucleotides.

In some embodiments, the template nucleic acid is circular double stranded DNA, e.g., a plasmid. In some embodiments, the template nucleic acid comprises about 500 to 1000 base pairs of homology on either side of the replacement sequence and/or the nick. In some embodiments, the template nucleic acid comprises about 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence.

In some embodiments, the template nucleic acid is an adenovirus vector, e.g., an AAV vector, e.g., a ssDNA molecule of a length and sequence that allows it to be packaged in an AAV capsid. The vector may be, e.g., less than 5 kb and may contain an ITR sequence that promotes packaging into the capsid. The vector may be integration-deficient. In some embodiments, the template nucleic acid comprises about 150 to 1000 nucleotides of homology on either side of the replacement sequence and/or the nick. In some embodiments, the template nucleic acid comprises about 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at least 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at most 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence.

In some embodiments, the template nucleic acid is a lentiviral vector, e.g., an IDLV (integration deficiency lentivirus). In some embodiments, the template nucleic acid comprises about 500 to 1000 base pairs of homology on either side of the replacement sequence and/or the nick. In some embodiments, the template nucleic acid comprises about 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence.

In one embodiment, the template nucleic acid comprises one or more mutations, e.g., silent mutations, that prevent Cas9 from recognizing and cleaving the template nucleic acid. The template nucleic acid may comprise, e.g., at least 1, 2, 3, 4, 5, 10, 20, or 30 silent mutations relative to the corresponding sequence in the genome of the cell to be altered. In embodiments, the template nucleic acid comprises at most 2, 3, 4, 5, 10, 20, 30, or 50 silent mutations relative to the corresponding sequence in the genome of the cell to be altered. In one embodiment, the cDNA comprises one or more mutations, e.g., silent mutations that prevent Cas9 from recognizing and cleaving the template nucleic acid. The template nucleic acid may comprise, e.g., at least 1, 2, 3, 4, 5, 10, 20, or 30 silent mutations relative to the corresponding sequence in the genome of the cell to be altered. In embodiments, the template nucleic acid comprises at most 2, 3, 4, 5, 10, 20, 30, or 50 silent mutations relative to the corresponding sequence in the genome of the cell to be altered.

In one embodiment, the template nucleic acid alters the structure of the target position by participating in a homology directed repair event. In one embodiment, the template nucleic acid alters the sequence of the target position. In one embodiment, the template nucleic acid results in the incorporation of a modified, or non-naturally occurring base into the target nucleic acid.

Typically, the template sequence undergoes a breakage mediated or catalyzed recombination with the target sequence. In one embodiment, the template nucleic acid includes sequence that corresponds to a site on the target sequence that is cleaved by an eaCas9 mediated cleavage event. In one embodiment, the template nucleic acid includes sequence that corresponds to both, a first site on the target sequence that is cleaved in a first Cas9 mediated event, and a second site on the target sequence that is cleaved in a second Cas9 mediated event.

In one embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position can be used to alter the structure of a target sequence. The template sequence can be used to alter an unwanted structure, e.g., an unwanted or mutant nucleotide.

Table 1 below provides exemplary template nucleic acids. In one embodiment, the template nucleic acid includes the 5' homology arm and the 3' homology arm of a row from Table 1. In another embodiment, a 5' homology arm from the first column can be combined with a 3' homology arm from Table 1. In each embodiment, a combination of the 5' and 3' homology arms include a replacement sequence.

TABLE 1

| Length of the 5' homology arm (the number of nucleotides) | Replacement Sequence | Length of the 3' homology arm (the number of nucleotides) |
| --- | --- | --- |
| 10 or more | | 10 or more |
| 20 or more | | 20 or more |
| 50 or more | | 50 or more |
| 100 or more | | 100 or more |
| 150 or more | | 150 or more |
| 200 or more | | 200 or more |
| 250 or more | | 250 or more |
| 300 or more | | 300 or more |
| 350 or more | | 350 or more |
| 400 or more | | 400 or more |
| 450 or more | | 450 or more |
| 500 or more | | 500 or more |
| 550 or more | | 550 or more |
| 600 or more | | 600 or more |
| 650 or more | | 650 or more |
| 700 or more | | 700 or more |
| 750 or more | | 750 or more |
| 800 or more | | 800 or more |
| 850 or more | | 850 or more |
| 900 or more | | 900 or more |
| 1000 or more | | 1000 or more |
| 1100 or more | | 1100 or more |
| 1200 or more | | 1200 or more |
| 1300 or more | | 1300 or more |
| 1400 or more | | 1400 or more |
| 1500 or more | | 1500 or more |
| 1600 or more | | 1600 or more |
| 1700 or more | | 1700 or more |
| 1800 or more | | 1800 or more |
| 1900 or more | | 1900 or more |
| 1200 or more | | 1200 or more |

TABLE 1-continued

| Length of the 5' homology arm (the number of nucleotides) | Replacement Sequence | Length of the 3' homology arm (the number of nucleotides) |
| --- | --- | --- |
| At least 50 but not long enough to include a repeated element. | | At least 50 but not long enough to include a repeated element. |
| At least 100 but not long enough to include a repeated element. | | At least 100 but not long enough to include a repeated element. |
| At least 150 but not long enough to include a repeated element. | | At least 150 but not long enough to include a repeated element. |
| 5 to 100 nucleotides | | 5 to 100 nucleotides |
| 10 to 150 nucleotides | | 10 to 150 nucleotides |
| 20 to 150 nucleotides | | 20 to 150 nucleotides |

"Treat," "treating" and "treatment," as used herein, mean the treatment of a disease in a mammal, e.g., in a human, including (a) inhibiting the disease, i.e., arresting or preventing its development or progression; (b) relieving the disease, i.e., causing regression of the disease state; and (c) relieving one or more symptoms of the disease; and (d) curing the disease.

"Prevent," "preventing" and "prevention," as used herein, means the prevention of a disease in a mammal, e.g., in a human, including (a) avoiding or precluding the disease; (b) affecting the predisposition toward the disease (c) preventing or delaying the onset of at least one symptom of the disease.

An "up-regulator", as used herein, refers to an agent that directly increases the activity of a specified biological pathway. Directly increasing the activity of the pathway refers to (i) the up-regulator binding to a component of that pathway (e.g., a protein that acts in the pathway or an mRNA encoding that protein) and increasing the level or activity of that component, e.g., by increasing the concentration or specific activity of that component, or (ii) the up-regulator is an added amount of a component that is ordinarily present in the pathway at a given level, e.g., an overexpressed protein. An up-regulator may, e.g., speed up one of the steps of that pathway or increase the level or activity of a component in that pathway. An up-regulator may be, e.g., a protein in the pathway, e.g., one may overexpress a protein that is ordinarily in the pathway to increase the overall activity of the pathway. The pathway may be, e.g., a DNA damage repair pathway, for example, HDR, e.g., gene correction. In one embodiment, the increased level or activity is compared to what would be seen in the absence of the up-regulator.

"Wild type", as used herein, refers to a gene or polypeptide which has the characteristics, e.g., the nucleotide or amino acid sequence, of a gene or polypeptide from a naturally-occurring source. The term "wild type" typically includes the most frequent observation of a particular gene or polypeptide in a population of organisms found in nature.

"X" as used herein in the context of an amino acid sequence, refers to any amino acid (e.g., any of the twenty natural amino acids) unless otherwise specified.

I. Cas9 Fusion Molecules

Various types of Cas9 fusion molecules or Cas9 fusion polypeptides are disclosed herein. In some embodiments, a Cas9 fusion molecule is a chimeric protein comprising a Cas9 protein or a Cas9 polypeptide, or a fragment thereof, covalently linked to at least one template nucleic acid. In other embodiments, a Cas9 fusion molecule is a chimeric protein comprising a Cas9 protein or a Cas9 polypeptide, or a fragment thereof, non-covalently linked to at least one template nucleic acid. Exemplary Cas9 fusion molecules are provided below.

Cas9-Template Nucleic Acid Covalent Fusions

Cas9 molecules of the invention can be directly linked to a template nucleic acid by various forms of covalent attachment, each of which are described in the subsections, below.

Linkers to Connect Cas9 Molecules to a Template Nucleic Acid

In one embodiment, a linker covalently connects a Cas9 molecule to a template nucleic acid to form a Cas9 fusion molecule. A linker may be a short peptide sequence that connects a protein domain and a nucleic acid (e.g., DNA or RNA). Linkers may be composed of flexible residues like glycine and serine so that the adjacent protein domains are free to move relative to one another. In certain embodiments, the linker has sufficient length and flexibility to allow a Cas9 molecule to bind to a target nucleic acid, e.g., so that the binding event is not sterically prohibited.

In one embodiment, a linker is attached to the C-terminus of a Cas9 molecule. Alternatively, a linker is attached to the N-terminus of a Cas9 molecule. In another embodiment, the linker is attached to a position other than the C-terminus or the N-terminus of a Cas9 molecule, e.g., an internal residue of the Cas9 molecule.

In one embodiment, a linker is attached to the C-terminus of the template nucleic acid. Alternatively, the linker is attached to the N-terminus of the template nucleic acid.

In one embodiment, the linker is attached to the 5' end of the template nucleic acid. In another embodiment, the linker is attached to the 3' end of the template nucleic acid. In yet another embodiment, the linker is attached to a residue other than the 5'-end or the 3'-end of the donor nucleic acid (e.g., an internal nucleic acid residue).

In some embodiments, the linker from about 3 to 100 amino acids in length. The linker may be, e.g., 3-10, 6-10, 10-15, 15-20, 20-30, 30-40, 40-50, 50-60, 60-70, 70-80, 80-90 or 90-100 amino acids in length. The linker may be, e.g., at least 3, 6, 7, 8, 9, 10, 15, 20, 30, 40, 50, 60, 70, 80 or 90 amino acids in length. In other embodiments, the linker is, e.g., at most 7, 8, 9, 10, 15, 20, 30, 40, 50, 60, 70, 80, 90 or 100 amino acids in length. Ranges comprising any combination of these endpoints are also envisioned.

In some embodiments, the linker is encoded by a nucleic acid sequence comprising about 9 to about 300 nucleotides or base pairs. The nucleic acid may be, e.g., 9-300, 9-210, 9-99, 9-45 nucleotides in length. The linker may be, e.g., at least 9, 21, 45, 99, or 210 nucleotides in length. In some embodiments, the linker is, e.g., at most 9, 18, 21, 45, 99, or 210 nucleotides in length. Ranges comprising any combination of these endpoints are also envisioned.

In some embodiments, the linker comprises glycine and serine residues. In some embodiments the linker consists of glycine and serine residues. For instance, the linker may comprise one or more modules such as GGS, GSGS, GGGS, GGGGS or GGSG. In some embodiments, the linker comprises a plurality of modules comprising glycine and serine, e.g., at least 2, 3, 4, 5, 10, or 15 of these modules, and/or at most 3, 4, 5, 10, 15, or 20 of these modules, or any combination of these endpoints. In some embodiments, each module in the linker has the same sequence, and in other embodiments, at least two modules in a linker have different sequences from each other.

In some embodiments, the linker is an XTEN linker or a variation of an XTEN linker such as SGSETPGTSESA, SGSETPGTSESATPES, or SGSETPGTSESATPEGGSGGS. Additional information on the XTEN linker may be found in Schellenberger et al. (2009), NATURE BIOTECHNOLOGY 27: 1186-1190, the entire contents of which are incorporated herein by reference.

Exemplary linker modules are given in Table 2:

| Linker | SEQ ID NO |
|---|---|
| GGS | 206 |
| GSGS | 207 |
| GGGS | 208 |
| GGGGS | 209 |
| GGSG | 210 |
| SGSETPGTSESA | 211 |
| SGSETPGTSESATPES | 212 |
| SGSETPGTSESATPEGGSGGS | 213 |
| GGSGGSGGSGGSGGSGGSGGSGGSGGS | 214 |

Additional exemplary linker modules are given in Table 3:

| Name | Description | Length (nt) |
|---|---|---|
| BBa_J176131 | PLrigid | 60 |
| BBa_J18920 | 2aa GS linker | 6 |
| BBa_J18921 | 6aa [GS]x linker | 18 |
| BBa_J18922 | 10aa [GS]x linker | 30 |
| BBa_K105012 | 10 aa flexible protein domain linker | 30 |
| BBa_K133132 | 8 aa protein domain linker | 24 |
| BBa_K1486003 | flexible linker 2x (GGGS) | 24 |
| BBa_K1486004 | flexible linker 2x (GGGGS) | 30 |
| BBa_K1486037 | linker | 39 |
| BBa_K157009 | Split fluorophore linker; Freiburg standard | 51 |
| BBa_K157013 | 15 aa flexible glycine-serine protein domain linker; Freiburg standard | 45 |
| BBa_K243004 | Short Linker (Gly-Gly-Ser-Gly) | 12 |
| BBa_K243005 | Middle Linker ( Gly-Gly-Ser-Gly)x2 | 24 |
| BBa_K243006 | Long Linker (Gly-Gly-Ser-Gly)x3 | 36 |
| BBa_K243029 | GSAT Linker | 108 |
| BBa_K243030 | SEG | 108 |
| BBa_K404300 | SEG-Linker | 108 |
| BBa_K404301 | GSAT-Linker | 108 |
| BBa_K404303 | Z-EGFR-1907_Short-Linker | 192 |
| BBa_K404304 | Z-EGFR-1907_Middle-Linker | 204 |
| BBa_K404305 | Z-EGFR-1907_Long-Linker | 216 |
| BBa_K404306 | Z-EGFR-1907_SEG-Linker | 288 |
| BBa_K416001 | (Gly4Ser)3 Flexible Peptide Linker | 45 |
| BBa_K648005 | Short Fusion Protein Linker: GGSG with standard 25 prefix/suffix | 12 |
| BBa_K648006 | Long 10AA Fusion Protein Linker with Standard 25 Prefix/Suffix | 30 |
| BBa_K648007 | Medium 6AA Fusion Protein Linker: GGSGGS with Standard 25 Prefix/Suffix | 18 |

In another embodiment, linkers can comprise a direct bond or an atom such as, e.g., an oxygen (O) or sulfur (S), a unit such as —NR— wherein R is hydrogen or alkyl, —C(O)—, —C(O)O—, —C(O)NH—, SO, $SO_2$, —$SO_2$NH— or a chain of atoms, such as substituted or unsubstituted alkyl, substituted or unsubstituted alkenyl, substituted or unsubstituted alkynyl, arylalkyl, heteroarylalkyl. In some embodiments, one or more methylenes in the chain of atoms can be replaced with one or more of O, S, S(O), $SO_2$, —$SO_2$NH—, —NR—, —$NR_2$, —C(O)—, —C(O)O—, —C(O)NH—, a cleavable linking group, substituted or unsubstituted aryl, substituted or unsubstituted heteroaryl, and substituted or unsubstituted heterocyclic.

In some embodiments, the template nucleic acid is attached to the Cas9 molecule through a linker that is itself stable under physiological conditions, such as an alkylene chain, and does not result in release of the donor nucleic acid sequence from the Cas9 molecule for at least 2, 3, 4, 5, 10, 15, 24 or 48 hours or for at least 1, 2, 3, 4, 5 or 10 days when administered to a subject. In some embodiments, the template nucleic acid and the Cas9 molecule comprise residues of a functional groups through which reaction and linkage of the donor nucleic acid sequence to the Cas9 molecule was achieved. In some embodiments, the functional groups, which may be the same or different, terminal or internal, of the donor nucleic acid sequence or Cas9 molecule comprise an amino, acid, imidazole, hydroxyl, thio, acyl halide, —HC=CH—, —C≡C— group, or derivative thereof. In some embodiments, the linker comprises a hydrocarbylene group wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, C(=X) (wherein X is $NR_1$, O or S), —$NR_1$—, —$NR_1$C(O)—, —C(O)$NR_1$—, —S(O)$_n$—, —$NR_1$S(O)$_n$—, —S(O)$_n NR_1$—, —$NR_1$C(O)—$NR_1$—; and $R_1$, independently for each occurrence, represents H or a lower alkyl and wherein n is 0, 1, or 2.

In some embodiments, the linker comprises an alkylene moiety or a heteroalkylene moiety (e.g., an alkylene glycol moiety such as ethylene glycol). In some embodiments, a linker comprises a poly-L-glutamic acid, polylactic acid, poly(ethyleneimine), an oligosaccharide, an amino acid (e.g., glycine), an amino acid chain, or any other suitable linkage. The linker groups can be biologically inactive, such as a PEG, polyglycolic acid, or polylactic acid chain. In certain embodiments, the linker group represents a derivatized or non-derivatized amino acid (e.g., glycine).

The Cas9 molecule attached to the linker may be any Cas9 molecule described herein, e.g., a nickase Cas9 molecule, or a Cas9 molecule capable of making a double stranded break.

Direct Cross-Linking Using a Maleimide-Modified Template Nucleic Acid

In one embodiment, a maleimide-modified template nucleic acid is cross-linked to a Cas9 molecule to form a Cas9 fusion molecule.

In one embodiment, template nucleic acid is prepared such that some or all of the sequence contain a maleimide-modification. In some embodiments, template nucleic acid is prepared such that some or all of the sequence maleimide-modified at its 5'-end. In one embodiment, the template nucleic acid is single stranded. In an alternate embodiment, the template nucleic acid is double stranded. In one embodiment, the template nucleic acid is DNA, e.g., double stranded DNA. In an alternate embodiment, the template nucleic acid is single stranded DNA.

In one embodiment, the Cas9 molecule is a wild-type molecule. In other embodiments, the Cas9 molecule is not a wild-type molecule. In certain embodiments, the Cas9 molecule has at least one modification. In another embodiment, the Cas9 molecule has at least one modification at a surface-exposed amino acid residue. In other embodiments, the Cas9 molecule has at least one mutation. In other embodiments, the Cas9 molecule has at least one mutation that results in a change from a non-cysteine amino acid residue to a cysteine amino acid residue. In other embodiments, the at least one mutation is a mutation forms a cysteine-variant Cas9 molecule (e.g., a Cas9 molecule having at least one cysteine residue). In certain embodiments, the cysteine-variant Cas9 molecule has more than one cysteine residue.

In other embodiments, the Cas9 fusion molecule is formed by nature of the formation of a covalent bond between the cysteine-variant Cas9 molecule (e.g., a Cas9 molecule with at least one surface exposed cysteine residue) and the maleimide-modified template nucleic acid. Without being bound by theory, in some embodiments, it is believed that the at least one surface exposed thiol groups on the cysteine-variant Cas9 molecule is reactive with the α,β-unsaturated carbonyl component of the maleimide-modified template nucleic acid.

The Cas9 molecule attached to the maleimide-modified template nucleic acid may be any Cas9 molecule described herein, e.g., a nickase Cas9 molecule or a Cas9 molecule capable of making a double stranded break.

Direct Cross-Linking Via Formation of a Bis-Aryl Hydrazine-Based Conjugate

In one embodiment, a 5'-4-Formylbenzamide (4FB)-modified template nucleic acid is cross-linked to a 6-hydrazino-nicotinamide (HyNic)-modified Cas9 molecule to form a Cas9 fusion molecule.

In one embodiment, a template nucleic acid is synthesized to have the some or all of the sequence 4FB-modified. In some embodiments, the template nucleic acid is prepared such that the some or all of the sequence 4FB-modified at its 5'-end. In one embodiment, the template nucleic acid is single stranded. In an alternate embodiment, the template nucleic acid is double stranded. In one embodiment, the template nucleic acid is DNA, e.g., double stranded DNA. In an alternate embodiment, the template nucleic acid is single stranded DNA.

In one embodiment, the Cas9 molecule is a wild-type molecule. In other embodiments, the Cas9 molecule is not a wild-type molecule. In certain embodiments, the Cas9 molecule has at least one modification. In another embodiment, the Cas9 molecule has at least one modification at a surface-exposed amino acid residue. In another embodiment, the Cas9 molecule has at least one modification at a surface-exposed amino acid residue that is characterized as possessing a primary amine group. In some embodiments, the at least one modification forms a 6-hydrazino-nicotinamide (HyNic)-modified Cas9 molecule. In certain embodiments, the variant Cas9 molecule has more than one 6-hydrazino-nicotinamide (HyNic) modification.

In other embodiments, the Cas9 fusion molecule is formed by nature of the formation of a covalent bond between the 6-hydrazino-nicotinamide (HyNic)-modified Cas9 molecule and the 4FB-modified template nucleic acid. Without being bound by theory, in some embodiments, it is believed that a succinimidyl ester functionality of S-HyNic readily reacts with an amine moiety (e.g., a primary amine) on the surface of a Cas9 molecule to form a 6-hydrazino-nicotinamide (HyNic)-modified Cas9 molecule. Without being bound by theory, in some embodiments, it is believed that the at least one surface exposed hydrazino-nicotinamide (HyNic) moiety on the 6-hydrazino-nicotinamide (HyNic)-modified Cas9 molecule is reactive with the formylbenzamide (4FB) moiety of the 4FB-modified template nucleic acid to form a stable bis-aryl hydrazine conjugate.

The Cas9 molecule attached to the maleimide-modified template nucleic acid may be any Cas9 molecule described herein, e.g., a nickase Cas9 molecule or a Cas9 molecule capable of making a double stranded break.

Direct Cross-Linking Using a N-Terminal and/or C-Terminal Cas9 Fusion Molecule

Nucleic acid sequences encoding a Cas9 fusion molecule are also provided herein.

In one embodiment, a nucleic acid encoding a Cas9 fusion molecule can be a synthetic nucleic acid sequence. For example, the synthetic nucleic acid molecule can further be chemically modified, e.g., as described below.

In one embodiment, a vector can comprise a nucleic acid sequence that encodes a Cas9 fusion molecule. In another embodiment, a vector can comprise a sequence encoding a polypeptide tag (a HaloTag® molecule, a SNAP-tag®, a CLIP-tag®, a ACP-tag® or a MCP-tag®), fused, e.g., to a Cas9 fusion molecule nucleic acid sequence. For example, a vector can comprise a sequence encoding a polypeptide tag (HaloTag® molecule, a SNAP-tag®, a CLIP-tag®, a ACP-tag® or a MCP-tag®) fused to the sequence encoding a Cas9 molecule. In some embodiments, the sequence encoding a polypeptide tag is fused to the N-terminus of the sequence encoding the Cas9 molecule. In other embodiments, the sequence encoding a polypeptide tag is fused to the C-terminus of the sequence encoding the Cas9 molecule. In certain embodiments, the vector comprises a sequence encoding a linker between the sequence encoding a polypeptide tag and the sequence encoding a Cas9 molecule.

In one embodiments, a Cas9 fusion molecule comprises a polypeptide tag (e.g., a HaloTag® molecule, a SNAP-tag®, a CLIP-tag®, a ACP-tag® or a MCP-tag®) fused to a Cas9 molecule. In certain embodiments, a Cas9 fusion molecule comprises a HaloTag fused to the N-terminus of the Cas9 molecule. In another embodiment, a Cas9 fusion molecule comprises a HaloTag fused to the C-terminus of the Cas9 molecule. In certain embodiments, a Cas9 fusion molecule comprises a HaloTag fused to a linker sequence (e.g., an XTEN linker, a GGS9 linker, a GGS6 linker, or a GGS linker) fused to the N-terminus of the Cas9 molecule. In another embodiment, a Cas9 fusion molecule comprises a HaloTag fused to a linker sequence (e.g., an XTEN linker, a GGS9 linker, a GGS6 linker, or a GGS linker) fused to the C-terminus of the Cas9 molecule.

In one embodiment, the polypeptide tag is a molecule comprising at least one modification. In another embodiment, the polypeptide tag has at least one modification at a surface-exposed amino acid residue. In other embodiments, the polypeptide tag has at least one mutation. In some embodiments, the at least one mutation comprises a H272F mutation (e.g., a HaloTag-variant).

In one embodiment, a template nucleic acid is synthesized to have the some or all of the sequence modified to contain a primary halogen (e.g., a haloalkane-modified template nucleic acid). In some embodiments, a template nucleic acid is synthesized to have the some or all of the sequence modified to contain a primary halogen at its 5'-end. In some embodiments, a template nucleic acid is synthesized to have the some or all of the sequence modified to contain a primary halogen at its 3'-end. In other embodiments, a template nucleic acid is synthesized to have the some or all of the sequence modified to contain a primary halogen at an internal position of the template nucleic acid. In one embodiment, the template nucleic acid is single stranded. In an alternate embodiment, the template nucleic acid is double stranded. In one embodiment, the template nucleic acid is DNA, e.g., double stranded DNA. In an alternate embodiment, the template nucleic acid is single stranded DNA.

In other embodiments, the Cas9 fusion molecule is formed by nature of the formation of a covalent bond between the polypeptide tag (e.g., a HaloTag-variant) of the Cas9 fusion molecule and the primary halogen of the template nucleic acid. Without being bound by theory, in some embodiments, it is believed that certain active site residues of the HaloTag-variant readily reacts via a nucleophilic attack with the at least one primary halogen on the template nucleic acid to form a stable conjugate.

The Cas9 fusion molecule described herein may be any Cas9 molecule described herein, e.g., a Cas9 nickase molecule, or a Cas9 molecule capable of making a double stranded break.

Direct Cross-Linking Using an Acrydite-Modified Template Nucleic Acid

In one embodiment, an acrydite-modified template nucleic acid is cross-linked to a Cas9 molecule to form a Cas9 fusion molecule.

In one embodiment, a template nucleic acid is prepared such that some or all of the sequence is acrydite-modified. In some embodiments, template nucleic acid is prepared such that some or all of the sequence is acrydite-modified at its 5'-end. In some embodiments, template nucleic acid is prepared such that some or all of the sequence is acrydite-modified at its 3'-end. In some embodiments, template nucleic acid is prepared such that some or all of the sequence is acrydite-modified at an internal position of the template nucleic acid. In one embodiment, the template nucleic acid is single stranded. In an alternate embodiment, the template nucleic acid is double stranded. In one embodiment, the template nucleic acid is DNA, e.g., double stranded DNA. In an alternate embodiment, the template nucleic acid is single stranded DNA.

In one embodiment, the Cas9 molecule is a wild-type molecule. In other embodiments, the Cas9 molecule is not a wild-type molecule. In certain embodiments, the Cas9 molecule has at least one modification. In another embodiment, the Cas9 molecule has at least one modification at a surface-exposed amino acid residue. In other embodiments, the Cas9 molecule has at least one mutation. In other embodiments, the Cas9 molecule has at least one mutation that results in a change from a non-cysteine amino acid residue to a cysteine amino acid residue. In some embodiments, the at least one mutation is a mutation that forms a cysteine-variant Cas9 molecule (e.g., a Cas9 molecule having at least one cysteine residue). In certain embodiments, the cysteine-variant Cas9 molecule has more than one cysteine residue.

In other embodiments, the Cas9 fusion molecule is formed by nature of the formation of a covalent bond between the cysteine-variant Cas9 molecule (e.g., a Cas9 molecule with at least one surface exposed cysteine residue) and the acrydite-modified template nucleic acid. Without being bound by theory, in some embodiments, it is believed that the at least one surface exposed thiol group (e.g., a surface exposed cysteine) on the cysteine-variant Cas9 molecule is reactive with the acrylic acid moiety of the acrydite-modified template nucleic acid.

The Cas9 molecule attached to the acrydite-modified template nucleic acid may be any Cas9 molecule described herein, e.g., a Cas9 nickase molecule, or a Cas9 molecule capable of making a double stranded break.

Direct Cross-Linking Using Heterobifunctional Cross-linkers EMCH/EDC

In one embodiment, a carboxy-modified template nucleic acid is cross-linked to a N-[ε-Maleimidocaproic acid] hydrazide (EMCH)-modified Cas9 molecule via 1-ethyl-3-(3-dimethylaminopropyl) carbodiimide (EDC)-based coupling to form a Cas9 fusion molecule.

In one embodiment, a template nucleic acid is prepared such that some or all of the sequence is carboxy-modified (e.g., a template nucleic acid with an exposed carboxyl group). In some embodiments, a template nucleic acid is prepared such that some or all of the sequence is carboxy-modified at its 5'-end. In some embodiments, a template nucleic acid is prepared so that some or all of the sequence carboxy-modified at its 3'-end. In some embodiments, a template nucleic acid is prepared such that some or all of the sequence carboxy-modified at an internal position of the template nucleic acid. In one embodiment, the template nucleic acid is single stranded. In an alternate embodiment, the template nucleic acid is double stranded. In one embodiment, the template nucleic acid is DNA, e.g., double stranded DNA. In an alternate embodiment, the template nucleic acid is single stranded DNA.

In one embodiment, a carboxy-modified template nucleic acid is coupled to 1-ethyl-3-(3-dimethylaminopropyl) carbodiimide (EDC) to form an activated carboxy-modified template nucleic acid (e.g., a carboxy-modified template nucleic acid coupled to EDC) comprising an O-acylisourea ester.

In one embodiment, the Cas9 molecule is a wild-type molecule. In other embodiments, the Cas9 molecule is not a wild-type molecule. In certain embodiments, the Cas9 molecule has at least one modification. In another embodiment, the Cas9 molecule has at least one modification at a surface-exposed amino acid residue. In other embodiments, the Cas9 molecule has at least one mutation. In another embodiment, the Cas9 molecule has at least one mutation at a surface-exposed amino acid residue that contains a thiol group. In some embodiments, the at least one mutation is a mutation that forms a cysteine variant Cas9 molecule (e.g., a Cas9 molecule having at least one cysteine residue). In other embodiments, the Cas9 molecule has at least one mutation that results in a change from a non-cysteine amino acid residue to a cysteine amino acid residue. In certain embodiments, the variant Cas9 molecule has more than one cysteine residue. In some embodiments, the at least one modification forms a N-[ε-Maleimidocaproic acid] hydrazide (EMCH)-variant Cas9 molecule. In certain embodiments, the N-[ε-Maleimidocaproic acid] hydrazide (EMCH)-variant Cas9 molecule has more than one EMCH modification.

In other embodiments, the Cas9 fusion molecule is formed by nature of the formation of a covalent bond between the EMCH-variant Cas9 molecule and the activated carboxy-modified template nucleic acid (e.g., a carboxy-modified template nucleic acid coupled to EDC). Without being bound by theory, in some embodiments, it is believed that a primary amine component of the EMCH-variant Cas9 molecule readily reacts with the O-acylisourea ester of the activated carboxy-modified template nucleic acid (e.g., a carboxy-modified template nucleic acid coupled to EDC) to form a stable conjugate.

The Cas9 molecule attached to the maleimide-modified template nucleic acid may be any Cas9 molecule described herein, e.g., a Cas9 nickase molecule, or a Cas9 molecule capable of making a double stranded break.

Cas9-Donor Template Non-Covalent Fusions

Cas9 fusion molecules described herein may also be linked to a template nucleic acid by various forms of non-covalent attachment. Non-covalent interactions generally include hydrogen bonds, ionic bonds, van der Waals interactions, and hydrophobic interactions. Non-covalent linkages are described in more detail in the subsections, below.

Non-Covalent Attachment Using Biotin and Streptavidin to Form Cas9 Fusion Molecules In one embodiment, a Cas9 molecule is non-covalently attached to a template nucleic acid using biotin and streptavidin to form a Cas9 fusion molecule.

In one embodiment, a Cas9 molecule is covalently linked to a first ligand. In some embodiments, the first ligand is biotin. In certain embodiments, the Cas9 molecule comprises a linker between the Cas9 molecule and the first ligand. In other embodiments, the linker between the Cas9 molecule and the first ligand is sufficiently long to allow the Cas9 molecule to bind to a target nucleic acid and the exogenous donor template sequence without steric interference. In one embodiment, the linker comprises a polypeptide. In other embodiments, the polypeptide comprises serine, glycine, or glycine and serine. In other embodiments, the polypeptide comprises a XTEN-based linker. In some embodiments, the length of the linker varies from at least 3 amino acid residues to at least 60 amino acids in length. In one embodiment, the first ligand is an affinity ligand (e.g., a high affinity ligand).

In one embodiment, a template nucleic acid is covalently linked to a second ligand. In some embodiments, the second ligand is biotin. In one embodiment, the second ligand is an affinity ligand (e.g., a high affinity ligand).

In another embodiment, a ligand acceptor protein is bound non-covalently and directly to both the first and second affinity ligand (e.g., a high affinity ligand) at distinct ligand binding sites on a ligand acceptor protein. In certain embodiments, the ligand acceptor protein is streptavidin. Without being bound by theory, in some embodiments, it is believed that by nature of the ability of the ligand acceptor protein binding to a first and a second affinity ligand (e.g., a high affinity ligand), a Cas9 molecule is non-covalently linked to a template nucleic acid forming a Cas9 fusion molecule.

The Cas9 molecule non-covalently attached to a template nucleic acid may be any Cas9 molecule described herein, e.g., a Cas9 nickase molecule, or a Cas9 molecule capable of making a double stranded break.

Non-Covalent Attachment Using Nucleic Acid Binding Proteins to Form Cas9 Fusion Molecules In one embodiment, a Cas9 molecule is non-covalently attached to a template nucleic acid using a nucleic acid binding protein to form a Cas9 fusion molecule. For example, an eaCas9 molecule may be covalently linked to a polypeptide, e.g., a nucleic acid binding protein wherein the polypeptide is non-covalently bound to the template nucleic acid.

Nucleic acid binding proteins are well known to one of ordinary skill in the art. For example, nucleic acid binding proteins include, but are not limited to, Rad52, Rad52-yeast, RPA-4 subunit, BRCA2, Rad51, Rad51B, Rad51C, XRCC2, XRCC3, RecA, RadA, HNRNPA1, UP1 Filament of HNRNPA1, NABP2 (SSB1), NABP1 (SSB2), and UHRF1.

The Cas9 molecule non-covalently attached to a template nucleic acid may be any Cas9 molecule described herein, e.g., a Cas9 nickase molecule, or a Cas9 molecule capable of making a double stranded break.

Guide RNA (gRNA) Molecules

A gRNA molecule, as that term is used herein, refers to a nucleic acid that promotes the specific targeting or homing of a gRNA molecule/Cas9 molecule complex to a target nucleic acid. gRNA molecules can be unimolecular (having a single RNA molecule) (e.g., chimeric or modular (comprising more than one, and typically two, separate RNA molecules). The gRNA molecules provided herein comprise a targeting domain comprising, consisting of, or consisting essentially of a nucleic acid sequence fully or partially complementary to a target domain. In certain embodiments, the gRNA molecule further comprises one or more additional domains, including for example a first complementarity domain, a linking domain, a second complementarity domain, a proximal domain, a tail domain, and a 5' extension domain. Each of these domains is discussed in detail below. Additional details on gRNAs are provided in Section I entitled "gRNA molecules" of PCT Application WO 2015/048577, the entire contents of which are expressly incorporated herein by reference. In certain embodiments, one or more of the domains in the gRNA molecule comprises an amino acid sequence identical to or sharing sequence homology with a naturally occurring sequence, e.g., from *S. pyogenes, S. aureus,* or *S. thermophilus.*

In certain embodiments, a unimolecular, or chimeric, gRNA comprises, preferably from 5' to 3':
  a targeting domain complementary to a target domain in a target gene;
  a first complementarity domain;
  a linking domain;
  a second complementarity domain (which is complementary to the first complementarity domain);
  a proximal domain; and
  optionally, a tail domain.

In certain embodiments, a modular gRNA comprises:
  a first strand comprising, preferably from 5' to 3':
    a targeting domain (which is complementary to a target domain in the target gene); and
    a first complementarity domain; and
  a second strand, comprising, preferably from 5' to 3':
    optionally, a 5' extension domain;
    a second complementarity domain;
    a proximal domain; and
    optionally, a tail domain.

Each of these domains are described in more detail, below.

Targeting Domain

The targeting domain (sometimes referred to alternatively as the guide sequence or complementarity region) comprises, consists of, or consists essentially of a nucleic acid sequence that is complementary or partially complementary to a target nucleic acid sequence, e.g., a target nucleic acid sequence in a target gene. The nucleic acid sequence in a target gene to which all or a portion of the targeting domain is complementary or partially complementary is referred to herein as the target domain. In certain embodiments, the target domain comprises a target position within the target gene. In other embodiments, a target position lies outside (i.e., upstream or downstream of) the target domain. In certain embodiments, the target domain is located entirely within a target gene, e.g., in a coding region, an intron, or an exon. In other embodiments, all or part of the target domain is located outside of a target gene, e.g., in a control region or in a non-coding region.

Methods for selecting targeting domains are known in the art (see, e.g., Fu 2014; Sternberg 2014).

The strand of the target nucleic acid comprising the target domain is referred to herein as the "complementary strand" because it is complementary to the targeting domain sequence. Since the targeting domain is part of a gRNA molecule, it comprises the base uracil (U) rather than thymine (T); conversely, any DNA molecule encoding the gRNA molecule will comprise thymine rather than uracil. In a targeting domain/target domain pair, the uracil bases in the targeting domain will pair with the adenine bases in the target domain. In certain embodiments, the degree of complementarity between the targeting domain and target domain is sufficient to allow targeting of a Cas9 molecule to the target nucleic acid.

In certain embodiments, the targeting domain comprises a core domain and an optional secondary domain. In certain of these embodiments, the core domain is located 3' to the secondary domain, and in certain of these embodiments the core domain is located at or near the 3' end of the targeting domain. In certain of these embodiments, the core domain consists of or consists essentially of about 8 to about 13 nucleotides at the 3' end of the targeting domain. In certain embodiments, only the core domain is complementary or partially complementary to the corresponding portion of the target domain, and in certain of these embodiments the core domain is fully complementary to the corresponding portion of the target domain. In other embodiments, the secondary domain is also complementary or partially complementary to a portion of the target domain. In certain embodiments, the core domain is complementary or partially complementary to a core domain target in the target domain, while the secondary domain is complementary or partially complementary to a secondary domain target in the target domain. In certain embodiments, the core domain and secondary domain have the same degree of complementarity with their respective corresponding portions of the target domain. In other embodiments, the degree of complementarity between the core domain and its target and the degree of complementarity between the secondary domain and its target may differ. In certain of these embodiments, the core domain may have a higher degree of complementarity for its target than the secondary domain, whereas in other embodiments the secondary domain may have a higher degree of complementarity than the core domain.

In certain embodiments, the targeting domain and/or the core domain within the targeting domain is 3 to 100, 5 to 100, 10 to 100, or 20 to 100 nucleotides in length, and in certain of these embodiments the targeting domain or core domain is 3 to 15, 3 to 20, 5 to 20, 10 to 20, 15 to 20, 5 to 50, 10 to 50, or 20 to 50 nucleotides in length. In certain embodiments, the targeting domain and/or the core domain within the targeting domain is 6, 7, 8, 9, 10, 11, 12, 13, 14, 15, 16, 17, 18, 19, 20, 21, 22, 23, 24, 25, or 26 nucleotides in length. In certain embodiments, the targeting domain and/or the core domain within the targeting domain is 6+/−2, 7+/−2, 8+/−2, 9+/−2, 10+/−2, 10+/−4, 10+/−5, 11+/−2, 12+/−2, 13+/−2, 14+/−2, 15+/−2, or 16+−2, 20+/−5, 30+/−5, 40+/−5, 50+/−5, 60+/−5, 70+/−5, 80+/−5, 90+/−5, or 100+/−5 nucleotides in length.

In certain embodiments wherein the targeting domain includes a core domain, the core domain is 3 to 20 nucleotides in length, and in certain of these embodiments the core domain 5 to 15 or 8 to 13 nucleotides in length. In certain embodiments wherein the targeting domain includes a secondary domain, the secondary domain is 0, 1, 2, 3, 4, 5, 6, 7, 8, 9, 10, 11, 12, 13, 14 or 15 nucleotides in length. In certain embodiments wherein the targeting domain comprises a core domain that is 8 to 13 nucleotides in length, the targeting domain is 26, 25, 24, 23, 22, 21, 20, 19, 18, 17, or 16 nucleotides in length, and the secondary domain is 13 to 18, 12 to 17, 11 to 16, 10 to 15, 9 to 14, 8 to 13, 7 to 12, 6 to 11, 5 to 10, 4 to 9, or 3 to 8 nucleotides in length, respectively.

In certain embodiments, the targeting domain is fully complementary to the target domain. Likewise, where the targeting domain comprises a core domain and/or a secondary domain, in certain embodiments one or both of the core domain and the secondary domain are fully complementary to the corresponding portions of the target domain. In other embodiments, the targeting domain is partially complementary to the target domain, and in certain of these embodiments where the targeting domain comprises a core domain and/or a secondary domain, one or both of the core domain and the secondary domain are partially complementary to the corresponding portions of the target domain. In certain of these embodiments, the nucleic acid sequence of the targeting domain, or the core domain or targeting domain within the targeting domain, is at least 80%, 85%, 90%, or 95% complementary to the target domain or to the corresponding portion of the target domain. In certain embodiments, the targeting domain and/or the core or secondary domains within the targeting domain include one or more nucleotides that are not complementary with the target domain or a portion thereof, and in certain of these embodiments the targeting domain and/or the core or secondary domains within the targeting domain include 1, 2, 3, 4, 5, 6, 7, or 8 nucleotides that are not complementary with the target domain. In certain embodiments, the core domain includes 1, 2, 3, 4, or 5 nucleotides that are not complementary with the corresponding portion of the target domain. In certain embodiments wherein the targeting domain includes one or more nucleotides that are not complementary with the target domain, one or more of said non-complementary nucleotides are located within five nucleotides of the 5' or 3' end of the targeting domain. In certain of these embodiments, the targeting domain includes 1, 2, 3, 4, or 5 nucleotides within five nucleotides of its 5' end, 3' end, or both its 5' and 3' ends that are not complementary to the target domain. In certain embodiments wherein the targeting domain includes two or more nucleotides that are not complementary to the target domain, two or more of said non-complementary nucleotides are adjacent to one another, and in certain of these embodiments the two or more consecutive non-complementary nucleotides are located within five nucleotides of the 5' or 3' end of the targeting domain. In other embodiments, the two or more consecutive non-complementary nucleotides are both located more than five nucleotides from the 5' and 3' ends of the targeting domain.

In one embodiment, the gRNA molecule, e.g., a gRNA molecule comprising a targeting domain, which is complementary with the target gene, is a modular gRNA molecule. In another embodiment, the gRNA molecule is a unimolecular or chimeric gRNA molecule.

In one embodiment, the nucleic acid encodes a gRNA molecule, e.g., the first gRNA molecule, comprising a targeting domain comprising a sequence that is the same as, or differs by no more than 1, 2, 3, 4, or 5 nucleotides from, a targeting domain sequence described herein. In one embodiment, the nucleic acid encodes a gRNA molecule comprising a targeting domain described herein.

In certain embodiments, the targeting domain comprises 16 nucleotides. In certain embodiments, the targeting domain comprises 17 nucleotides. In certain embodiments, the targeting domain comprises 18 nucleotides. In certain embodiments, the targeting domain comprises 19 nucleotides. In certain embodiments, the targeting domain comprises 20 nucleotides. In certain embodiments, the targeting domain comprises 21 nucleotides. In certain embodiments, the targeting domain comprises 22 nucleotides. In certain embodiments, the targeting domain comprises 23 nucleotides. In certain embodiments, the targeting domain comprises 24 nucleotides. In certain embodiments, the targeting domain comprises 25 nucleotides. In certain embodiments, the targeting domain comprises 26 nucleotides.

In certain embodiments, the targeting domain which is complementary with the target gene is 16 nucleotides or more in length. In certain embodiments, the targeting domain is 16 nucleotides in length. In certain embodiments, the targeting domain is 17 nucleotides in length. In another embodiment, the targeting domain is 18 nucleotides in length. In still another embodiment, the targeting domain is 19 nucleotides in length. In still another embodiment, the targeting domain is 20 nucleotides in length. In still another embodiment, the targeting domain is 21 nucleotides in length. In still another embodiment, the targeting domain is 22 nucleotides in length. In still another embodiment, the targeting domain is 23 nucleotides in length. In still another embodiment, the targeting domain is 24 nucleotides in length. In still another embodiment, the targeting domain is 25 nucleotides in length. In still another embodiment, the targeting domain is 26 nucleotides in length.

In one embodiment, a nucleic acid encodes a modular gRNA molecule, e.g., one or more nucleic acids encode a modular gRNA molecule. In another embodiment, a nucleic acid encodes a chimeric gRNA molecule. The nucleic acid may encode a gRNA molecule, e.g., the first gRNA molecule, comprising a targeting domain comprising 16 nucleotides or more in length. In one embodiment, the nucleic acid encodes a gRNA molecule, e.g., the first gRNA molecule, comprising a targeting domain that is 16 nucleotides in length. In another embodiment, the nucleic acid encodes a gRNA molecule, e.g., the first gRNA molecule, comprising a targeting domain that is 17 nucleotides in length. In still another embodiment, the nucleic acid encodes a gRNA molecule, e.g., the first gRNA molecule, comprising a targeting domain that is 18 nucleotides in length. In still another embodiment, the nucleic acid encodes a gRNA molecule, e.g., the first gRNA molecule, comprising a targeting domain that is 19 nucleotides in length. In still another embodiment, the nucleic acid encodes a gRNA molecule, e.g., the first gRNA molecule, comprising a targeting domain that is 20 nucleotides in length. In still another embodiment, the nucleic acid encodes a gRNA molecule, e.g., the first gRNA molecule, comprising a targeting domain that is 21 nucleotides in length. In still another embodiment, the nucleic acid encodes a gRNA molecule, e.g., the first gRNA molecule, comprising a targeting domain that is 22 nucleotides in length. In still another embodiment, the nucleic acid encodes a gRNA molecule, e.g., the first gRNA molecule, comprising a targeting domain that is 23 nucleotides in length. In still another embodiment, the nucleic acid encodes a gRNA molecule, e.g., the first gRNA molecule, comprising a targeting domain that is 24 nucleotides in length. In still another embodiment, the nucleic acid encodes a gRNA molecule, e.g., the first gRNA molecule, comprising a targeting domain that is 25 nucleotides in length. In still another embodiment, the nucleic acid encodes a gRNA molecule, e.g., the first gRNA molecule, comprising a targeting domain that is 26 nucleotides in length.

In certain embodiments, the targeting domain, core domain, and/or secondary domain do not comprise any modifications. In other embodiments, the targeting domain, core domain, and/or secondary domain, or one or more nucleotides therein, have a modification, including but not limited to the modifications set forth below. In certain embodiments, one or more nucleotides of the targeting domain, core domain, and/or secondary domain may comprise a 2' modification (e.g., a modification at the 2' position on ribose), e.g., a 2-acetylation, e.g., a 2' methylation. In certain embodiments, the backbone of the targeting domain can be modified with a phosphorothioate. In certain embodiments, modifications to one or more nucleotides of the targeting domain, core domain, and/or secondary domain render the targeting domain and/or the gRNA comprising the targeting domain less susceptible to degradation or more bio-compatible, e.g., less immunogenic. In certain embodiments, the targeting domain and/or the core or secondary domains include 1, 2, 3, 4, 5, 6, 7, or 8 or more modifications, and in certain of these embodiments the targeting domain and/or core or secondary domains include 1, 2, 3, or 4 modifications within five nucleotides of their respective 5' ends and/or 1, 2, 3, or 4 modifications within five nucleotides of their respective 3' ends. In certain embodiments, the targeting domain and/or the core or secondary domains comprise modifications at two or more consecutive nucleotides.

In certain embodiments wherein the targeting domain includes core and secondary domains, the core and secondary domains contain the same number of modifications. In certain of these embodiments, both domains are free of modifications. In other embodiments, the core domain includes more modifications than the secondary domain, or vice versa.

In certain embodiments, modifications to one or more nucleotides in the targeting domain, including in the core or secondary domains, are selected to not interfere with targeting efficacy, which can be evaluated by testing a candidate modification using a system as set forth below. gRNAs having a candidate targeting domain having a selected length, sequence, degree of complementarity, or degree of modification can be evaluated using a system as set forth below. The candidate targeting domain can be placed, either alone or with one or more other candidate changes in a gRNA molecule/Cas9 molecule system known to be functional with a selected target, and evaluated.

In certain embodiments, all of the modified nucleotides are complementary to and capable of hybridizing to corresponding nucleotides present in the target domain. In another embodiment, 1, 2, 3, 4, 5, 6, 7 or 8 or more modified nucleotides are not complementary to or capable of hybridizing to corresponding nucleotides present in the target domain.

First and Second Complementarity Domains

The first and second complementarity (sometimes referred to alternatively as the crRNA-derived hairpin sequence and tracrRNA-derived hairpin sequences, respectively) domains are fully or partially complementary to one another. In certain embodiments, the degree of complementarity is sufficient for the two domains to form a duplexed region under at least some physiological conditions. In certain embodiments, the degree of complementarity between the first and second complementarity domains, together with other properties of the gRNA, is sufficient to allow targeting of a Cas9 molecule to a target nucleic acid.

In certain embodiments the first and/or second complementarity domain includes one or more nucleotides that lack complementarity with the corresponding complementarity domain. In certain embodiments, the first and/or second complementarity domain includes 1, 2, 3, 4, 5, or 6 nucleotides that do not complement with the corresponding complementarity domain. For example, the second complementarity domain may contain 1, 2, 3, 4, 5, or 6 nucleotides that do not pair with corresponding nucleotides in the first complementarity domain. In certain embodiments, the nucleotides on the first or second complementarity domain that do not complement with the corresponding complementarity domain loop out from the duplex formed between the first and second complementarity domains. In certain of these embodiments, the unpaired loop-out is located on the second complementarity domain, and in certain of these embodiments the unpaired region begins 1, 2, 3, 4, 5, or 6 nucleotides from the 5' end of the second complementarity domain.

In certain embodiments, the first complementarity domain is 5 to 30, 5 to 25, 7 to 25, 5 to 24, 5 to 23, 7 to 22, 5 to 22, 5 to 21, 5 to 20, 7 to 18, 7 to 15, 9 to 16, or 10 to 14 nucleotides in length, and in certain of these embodiments the first complementarity domain is 5, 6, 7, 8, 9, 10, 11, 12, 13, 14, 15, 16, 17, 18, 19, 20, 21, 22, 23, 24, or 25 nucleotides in length. In certain embodiments, the second complementarity domain is 5 to 27, 7 to 27, 7 to 25, 5 to 24, 5 to 23, 5 to 22, 5 to 21, 7 to 20, 5 to 20, 7 to 18, 7 to 17, 9 to 16, or 10 to 14 nucleotides in length, and in certain of these embodiments the second complementarity domain is 5, 6, 7, 8, 9, 10, 11, 12, 13, 14, 15, 16, 17, 18, 19, 20, 21, 22, 23, 24, 25, or 26 nucleotides in length. In certain embodiments, the first and second complementarity domains are each independently 6+/−2, 7+/−2, 8+/−2, 9+/−2, 10+/−2, 11+/−2, 12+/−2, 13+/−2, 14+/−2, 15+/−2, 16+/−2, 17+/−2, 18+/−2, 19+/−2, or 20+/−2, 21+/−2, 22+/−2, 23+/−2, or 24+/−2 nucleotides in length. In certain embodiments, the second complementarity domain is longer than the first complementarity domain, e.g., 2, 3, 4, 5, or 6 nucleotides longer.

In certain embodiments, the first and/or second complementarity domains each independently comprise three subdomains, which, in the 5' to 3' direction are: a 5' subdomain, a central subdomain, and a 3' subdomain. In certain embodiments, the 5' subdomain and 3' subdomain of the first complementarity domain are fully or partially complementary to the 3' subdomain and 5' subdomain, respectively, of the second complementarity domain.

In certain embodiments, the 5' subdomain of the first complementarity domain is 4 to 9 nucleotides in length, and in certain of these embodiments the 5' domain is 4, 5, 6, 7, 8, or 9 nucleotides in length. In certain embodiments, the 5' subdomain of the second complementarity domain is 3 to 25, 4 to 22, 4 to 18, or 4 to 10 nucleotides in length, and in certain of these embodiments the 5' domain is 3, 4, 5, 6, 7, 8, 9, 10, 11, 12, 13, 14, 15, 16, 17, 18, 19, 20, 21, 22, 23, 24, or 25 nucleotides in length. In certain embodiments, the central subdomain of the first complementarity domain is 1, 2, or 3 nucleotides in length. In certain embodiments, the central subdomain of the second complementarity domain is 1, 2, 3, 4, or 5 nucleotides in length. In certain embodiments, the 3' subdomain of the first complementarity domain is 3 to 25, 4 to 22, 4 to 18, or 4 to 10 nucleotides in length, and in certain of these embodiments the 3' subdomain is 3, 4, 5, 6, 7, 8, 9, 10, 11, 12, 13, 14, 15, 16, 17, 18, 19, 20, 21, 22, 23, 24, or 25 nucleotides in length. In certain embodiments, the 3' subdomain of the second complementarity domain is 4 to 9, e.g., 4, 5, 6, 7, 8 or 9 nucleotides in length.

The first and/or second complementarity domains can share homology with, or be derived from, naturally occurring or reference first and/or second complementarity domain. In certain of these embodiments, the first and/or second complementarity domains have at least 50%, 60%, 70%, 80%, 85%, 90%, or 95% homology with, or differ by no more than 1, 2, 3, 4, 5, or 6 nucleotides from, the naturally occurring or reference first and/or second complementarity domain. In certain of these embodiments, the first and/or second complementarity domains may have at least 50%, 60%, 70%, 80%, 85%, 90%, or 95% homology with homology with a first and/or second complementarity domain from *S. pyogenes* or *S. aureus*.

In certain embodiments, the first and/or second complementarity domains do not comprise any modifications. In other embodiments, the first and/or second complementarity domains or one or more nucleotides therein have a modification, including but not limited to a modification set forth below. In certain embodiments, one or more nucleotides of the first and/or second complementarity domain may comprise a 2' modification (e.g., a modification at the 2' position on ribose), e.g., a 2-acetylation, e.g., a 2' methylation. In certain embodiments, the backbone of the targeting domain can be modified with a phosphorothioate. In certain embodiments, modifications to one or more nucleotides of the first and/or second complementarity domain render the first and/or second complementarity domain and/or the gRNA comprising the first and/or second complementarity less susceptible to degradation or more bio-compatible, e.g., less immunogenic. In certain embodiments, the first and/or second complementarity domains each independently include 1, 2, 3, 4, 5, 6, 7, or 8 or more modifications, and in certain of these embodiments the first and/or second complementarity domains each independently include 1, 2, 3, or 4 modifications within five nucleotides of their respective 5' ends, 3' ends, or both their 5' and 3' ends. In other embodiments, the first and/or second complementarity domains each independently contain no modifications within five nucleotides of their respective 5' ends, 3' ends, or both their 5' and 3' ends. In certain embodiments, one or both of the first and second complementarity domains comprise modifications at two or more consecutive nucleotides.

In certain embodiments, modifications to one or more nucleotides in the first and/or second complementarity domains are selected to not interfere with targeting efficacy, which can be evaluated by testing a candidate modification in a system as set forth below. gRNAs having a candidate first or second complementarity domain having a selected length, sequence, degree of complementarity, or degree of modification can be evaluated in a system as set forth below. The candidate complementarity domain can be placed, either alone or with one or more other candidate changes in a gRNA molecule/Cas9 molecule system known to be functional with a selected target, and evaluated.

In certain embodiments, the duplexed region formed by the first and second complementarity domains is, for example, 6, 7, 8, 9, 10, 11, 12, 13, 14, 15, 16, 17, 18, 19, 20, 21, or 22 bp in length, excluding any looped out or unpaired nucleotides.

In certain embodiments, the first and second complementarity domains, when duplexed, comprise 11 paired nucleotides (see, for e.g., gRNA of SEQ ID NO:5). In certain embodiments, the first and second complementarity domains, when duplexed, comprise 15 paired nucleotides (see, e.g., gRNA of SEQ ID NO:27). In certain embodiments, the first and second complementarity domains, when duplexed, comprise 16 paired nucleotides (see, e.g., gRNA of SEQ ID NO:28). In certain embodiments, the first and second complementarity domains, when duplexed, comprise 21 paired nucleotides (see, e.g., gRNA of SEQ ID NO:29).

In certain embodiments, one or more nucleotides are exchanged between the first and second complementarity domains to remove poly-U tracts. For example, nucleotides 23 and 48 or nucleotides 26 and 45 of the gRNA of SEQ ID NO:5 may be exchanged to generate the gRNA of SEQ ID NOs:30 or 31, respectively. Similarly, nucleotides 23 and 39 of the gRNA of SEQ ID NO:29 may be exchanged with nucleotides 50 and 68 to generate the gRNA of SEQ ID NO:32.

Linking Domain

The linking domain is disposed between and serves to link the first and second complementarity domains in a unimolecular or chimeric gRNA. In certain embodiments, part of the linking domain is from a crRNA-derived region, and another part is from a tracrRNA-derived region.

In certain embodiments, the linking domain links the first and second complementarity domains covalently. In certain of these embodiments, the linking domain consists of or comprises a covalent bond. In other embodiments, the linking domain links the first and second complementarity domains non-covalently. In certain embodiments, the linking domain is ten or fewer nucleotides in length, e.g., 1, 2, 3, 4, 5, 6, 7, 8, 9, or 10 nucleotides. In other embodiments, the linking domain is greater than 10 nucleotides in length, e.g., 11, 12, 13, 14, 15, 16, 17, 18, 19, 20, 21, 22, 23, 24, or 25 or more nucleotides. In certain embodiments, the linking domain is 2 to 50, 2 to 40, 2 to 30, 2 to 20, 2 to 10, 2 to 5, 10 to 100, 10 to 90, 10 to 80, 10 to 70, 10 to 60, 10 to 50, 10 to 40, 10 to 30, 10 to 20, 10 to 15, 20 to 100, 20 to 90, 20 to 80, 20 to 70, 20 to 60, 20 to 50, 20 to 40, 20 to 30, or 20 to 25 nucleotides in length. In certain embodiments, the linking domain is 10+/−5, 20+/−5, 20+/−10, 30+/−5, 30+/−10, 40+/−5, 40+/−10, 50+/−5, 50+/−10, 60+/−5, 60+/−10, 70+/−5, 70+/−10, 80+/−5, 80+/−10, 90+/−5, 90+/−10, 100+/−5, or 100+/−10 nucleotides in length.

In certain embodiments, the linking domain shares homology with, or is derived from, a naturally occurring sequence, e.g., the sequence of a tracrRNA that is 5' to the second complementarity domain. In certain embodiments, the linking domain has at least 50%, 60%, 70%, 80%, 90%, or 95% homology with or differs by no more than 1, 2, 3, 4, 5, or 6 nucleotides from a linking domain disclosed herein.

In certain embodiments, the linking domain does not comprise any modifications. In other embodiments, the linking domain or one or more nucleotides therein have a modification, including but not limited to the modifications set forth below. In certain embodiments, one or more nucleotides of the linking domain may comprise a 2' modification (e.g., a modification at the 2' position on ribose), e.g., a 2-acetylation, e.g., a 2' methylation. In certain embodiments, the backbone of the linking domain can be modified with a phosphorothioate. In certain embodiments, modifications to one or more nucleotides of the linking domain render the linking domain and/or the gRNA comprising the linking domain less susceptible to degradation or more bio-compatible, e.g., less immunogenic. In certain embodiments, the linking domain includes 1, 2, 3, 4, 5, 6, 7, or 8 or more modifications, and in certain of these embodiments the linking domain includes 1, 2, 3, or 4 modifications within five nucleotides of its 5' and/or 3' end. In certain embodiments, the linking domain comprises modifications at two or more consecutive nucleotides.

In certain embodiments, modifications to one or more nucleotides in the linking domain are selected to not interfere with targeting efficacy, which can be evaluated by testing a candidate modification in a system as set forth below. gRNAs having a candidate linking domain having a selected length, sequence, degree of complementarity, or degree of modification can be evaluated in a system as set forth below. The candidate linking domain can be placed, either alone or with one or more other candidate changes in a gRNA molecule/Cas9 molecule system known to be functional with a selected target, and evaluated.

In certain embodiments, the linking domain comprises a duplexed region, typically adjacent to or within 1, 2, or 3 nucleotides of the 3' end of the first complementarity domain and/or the 5' end of the second complementarity domain. In certain of these embodiments, the duplexed region of the linking region is 10+/−5, 15+/−5, 20+/−5, 20+/−10, or 30+/−5 bp in length. In certain embodiments, the duplexed region of the linking domain is 1, 2, 3, 4, 5, 6, 7, 8, 9, 10, 11, 12, 13, 14, or 15 bp in length. In certain embodiments, the sequences forming the duplexed region of the linking domain are fully complementarity. In other embodiments, one or both of the sequences forming the duplexed region contain one or more nucleotides (e.g., 1, 2, 3, 4, 5, 6, 7, or 8 nucleotides) that are not complementary with the other duplex sequence.

5' Extension Domain

In certain embodiments, a modular gRNA as disclosed herein comprises a 5' extension domain, i.e., one or more additional nucleotides 5' to the second complementarity domain. In certain embodiments, the 5' extension domain is 2 to 10 or more, 2 to 9, 2 to 8, 2 to 7, 2 to 6, 2 to 5, or 2 to 4 nucleotides in length, and in certain of these embodiments the 5' extension domain is 2, 3, 4, 5, 6, 7, 8, 9, or 10 or more nucleotides in length.

In certain embodiments, the 5' extension domain nucleotides do not comprise modifications, e.g., modifications of the type provided below. However, in certain embodiments, the 5' extension domain comprises one or more modifications, e.g., modifications that it render it less susceptible to degradation or more bio-compatible, e.g., less immunogenic. By way of example, the backbone of the 5' extension domain can be modified with a phosphorothioate, or other modification(s) as set forth below. In certain embodiments, a nucleotide of the 5' extension domain can comprise a 2' modification (e.g., a modification at the 2' position on ribose), e.g., a 2-acetylation, e.g., a 2' methylation, or other modification(s) as set forth below.

In certain embodiments, the 5' extension domain can comprise as many as 1, 2, 3, 4, 5, 6, 7, or 8 modifications. In certain embodiments, the 5' extension domain comprises as many as 1, 2, 3, or 4 modifications within 5 nucleotides of its 5' end, e.g., in a modular gRNA molecule. In certain embodiments, the 5' extension domain comprises as many as 1, 2, 3, or 4 modifications within 5 nucleotides of its 3' end, e.g., in a modular gRNA molecule.

In certain embodiments, the 5' extension domain comprises modifications at two consecutive nucleotides, e.g., two consecutive nucleotides that are within 5 nucleotides of the 5' end of the 5' extension domain, within 5 nucleotides of the 3' end of the 5' extension domain, or more than 5 nucleotides away from one or both ends of the 5' extension domain. In certain embodiments, no two consecutive nucleotides are modified within 5 nucleotides of the 5' end of the 5' extension domain, within 5 nucleotides of the 3' end of the 5' extension domain, or within a region that is more than 5 nucleotides away from one or both ends of the 5' extension domain. In certain embodiments, no nucleotide is modified within 5 nucleotides of the 5' end of the 5' extension domain, within 5 nucleotides of the 3' end of the 5' extension domain, or within a region that is more than 5 nucleotides away from one or both ends of the 5' extension domain.

Modifications in the 5' extension domain can be selected so as to not interfere with gRNA molecule efficacy, which can be evaluated by testing a candidate modification in a system as set forth below. gRNAs having a candidate 5' extension domain having a selected length, sequence, degree of complementarity, or degree of modification, can be evaluated in a system as set forth below. The candidate 5' extension domain can be placed, either alone, or with one or more other candidate changes in a gRNA molecule/Cas9 molecule system known to be functional with a selected target and evaluated.

In certain embodiments, the 5' extension domain has at least 60, 70, 80, 85, 90, or 95% homology with, or differs by no more than 1, 2, 3, 4, 5, or 6 nucleotides from, a reference 5' extension domain, e.g., a naturally occurring, e.g., an S. pyogenes, S. aureus, or S. thermophilus, 5' extension domain, or a 5' extension domain described herein.

Proximal Domain

In certain embodiments, the proximal domain is 5 to 20 or more nucleotides in length, e.g., 5, 6, 7, 8, 9, 10, 11, 12, 13, 14, 15, 16, 17, 18, 19, 20, 21, 22, 23, 24, 25, or 26 nucleotides in length. In certain of these embodiments, the proximal domain is 6+/−2, 7+/−2, 8+/−2, 9+/−2, 10+/−2, 11+/−2, 12+/−2, 13+/−2, 14+/−2, 14+/−2, 16+/−2, 17+/−2, 18+/−2, 19+/−2, or 20+/−2 nucleotides in length. In certain embodiments, the proximal domain is 5 to 20, 7, to 18, 9 to 16, or 10 to 14 nucleotides in length.

In certain embodiments, the proximal domain can share homology with or be derived from a naturally occurring proximal domain. In certain of these embodiments, the proximal domain has at least 50%, 60%, 70%, 80%, 85%, 90%, or 95% homology with or differs by no more than 1, 2, 3, 4, 5, or 6 nucleotides from a proximal domain disclosed herein, e.g., an S. pyogenes, S. aureus, or S. thermophilus proximal domain.

In certain embodiments, the proximal domain does not comprise any modifications. In other embodiments, the proximal domain or one or more nucleotides therein have a modification, including but not limited to the modifications set forth in herein. In certain embodiments, one or more nucleotides of the proximal domain may comprise a 2' modification (e.g., a modification at the 2' position on ribose), e.g., a 2-acetylation, e.g., a 2' methylation. In certain embodiments, the backbone of the proximal domain can be modified with a phosphorothioate. In certain embodiments, modifications to one or more nucleotides of the proximal domain render the proximal domain and/or the gRNA comprising the proximal domain less susceptible to degradation or more bio-compatible, e.g., less immunogenic. In certain embodiments, the proximal domain includes 1, 2, 3, 4, 5, 6, 7, or 8 or more modifications, and in certain of these embodiments the proximal domain includes 1, 2, 3, or 4 modifications within five nucleotides of its 5' and/or 3' end. In certain embodiments, the proximal domain comprises modifications at two or more consecutive nucleotides.

In certain embodiments, modifications to one or more nucleotides in the proximal domain are selected to not interfere with targeting efficacy, which can be evaluated by testing a candidate modification in a system as set forth below. gRNAs having a candidate proximal domain having a selected length, sequence, degree of complementarity, or degree of modification can be evaluated in a system as set forth below. The candidate proximal domain can be placed, either alone or with one or more other candidate changes in a gRNA molecule/Cas9 molecule system known to be functional with a selected target, and evaluated.

Tail Domain

A broad spectrum of tail domains are suitable for use in the gRNA molecules disclosed herein.

In certain embodiments, the tail domain is absent. In other embodiments, the tail domain is 1 to 100 or more nucleotides in length, e.g., 1, 2, 3, 4, 5, 6, 7, 8, 9, 10, 20, 30, 40, 50, 60, 70, 80, 90, or 100 nucleotides in length. In certain embodiments, the tail domain is 1 to 5, 1 to 10, 1 to 15, 1 to 20, 1 to 50, 10 to 100, 20 to 100, 10 to 90, 20 to 90, 10 to 80, 20 to 80, 10 to 70, 20 to 70, 10 to 60, 20 to 60, 10 to 50, 20 to 50, 10 to 40, 20 to 40, 10 to 30, 20 to 30, 20 to 25, 10 to 20, or 10 to 15 nucleotides in length. In certain embodiments, the tail domain is 5+/−5, 10+/−5, 20+/−10, 20+/−5, 25+/−10, 30+/−10, 30+/−5, 40+/−10, 40+/−5, 50+/−10, 50+/−5, 60+/−10, 60+/−5, 70+/−10, 70+/−5, 80+/−10, 80+/−5, 90+/−10, 90+/−5, 100+/−10, or 100+/−5 nucleotides in length, In certain embodiments, the tail domain can share homology with or be derived from a naturally occurring tail domain or the 5' end of a naturally occurring tail domain. In certain of these embodiments, the proximal domain has at least 50%, 60%, 70%, 80%, 85%, 90%, or 95% homology with or differs by no more than 1, 2, 3, 4, 5, or 6 nucleotides from a naturally occurring tail domain disclosed herein, e.g., an S. pyogenes, S. aureus, or S. thermophilus tail domain.

In certain embodiments, the tail domain includes sequences that are complementary to each other and which, under at least some physiological conditions, form a duplexed region. In certain of these embodiments, the tail domain comprises a tail duplex domain which can form a tail duplexed region. In certain embodiments, the tail duplexed region is 3, 4, 5, 6, 7, 8, 9, 10, 11, or 12 bp in length. In certain embodiments, the tail domain comprises a single stranded domain 3' to the tail duplex domain that does not form a duplex. In certain of these embodiments, the single stranded domain is 3 to 10 nucleotides in length, e.g., 3, 4, 5, 6, 7, 8, 9, 10, or 4 to 6 nucleotides in length.

In certain embodiments, the tail domain does not comprise any modifications. In other embodiments, the tail domain or one or more nucleotides therein have a modification, including but not limited to the modifications set forth herein. In certain embodiments, one or more nucleotides of the tail domain may comprise a 2' modification (e.g., a modification at the 2' position on ribose), e.g., a 2-acetylation, e.g., a 2' methylation. In certain embodiments, the backbone of the tail domain can be modified with a phosphorothioate. In certain embodiments, modifications to one or more nucleotides of the tail domain render the tail domain and/or the gRNA comprising the tail domain less susceptible to degradation or more bio-compatible, e.g., less immunogenic. In certain embodiments, the tail domain includes 1, 2, 3, 4, 5, 6, 7, or 8 or more modifications, and in certain of these embodiments the tail domain includes 1, 2, 3, or 4 modifications within five nucleotides of its 5' and/or 3' end. In certain embodiments, the tail domain comprises modifications at two or more consecutive nucleotides.

In certain embodiments, modifications to one or more nucleotides in the tail domain are selected to not interfere with targeting efficacy, which can be evaluated by testing a candidate modification as set forth below. gRNAs having a candidate tail domain having a selected length, sequence, degree of complementarity, or degree of modification can be evaluated using a system as set forth below. The candidate tail domain can be placed, either alone or with one or more other candidate changes in a gRNA molecule/Cas9 molecule system known to be functional with a selected target, and evaluated.

In certain embodiments, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. When a U6 promoter is used for in vivo transcription, these nucleotides may be the sequence UUUUUU. When an H1 promoter is used for transcription, these nucleotides may be the sequence UUUU. When alternate pol-III promoters are used, these nucleotides may be various numbers of uracil bases depending on, e.g., the termination signal of the pol-III promoter, or they may include alternate bases.

In certain embodiments, the proximal and tail domain taken together comprise, consist of, or consist essentially of the sequence set forth in SEQ ID NOs: 33, 34, 35, 36, or 38.

Exemplary Unimolecular/Chimeric gRNAs

In certain embodiments, a gRNA as disclosed herein has the structure: 5' [targeting domain]-[first complementarity domain]-[linking domain]-[second complementarity domain]-[proximal domain]-[tail domain]-3', wherein:

the targeting domain comprises a core domain and optionally a secondary domain, and is 10 to 50 nucleotides in length;

the first complementarity domain is 5 to 25 nucleotides in length and, in certain embodiments has at least 50, 60, 70, 80, 85, 90, or 95% homology with a reference first complementarity domain disclosed herein;

the linking domain is 1 to 5 nucleotides in length;

the second complementarity domain is 5 to 27 nucleotides in length and, in certain embodiments has at least 50, 60, 70, 80, 85, 90, or 95% homology with a reference second complementarity domain disclosed herein;

the proximal domain is 5 to 20 nucleotides in length and, in certain embodiments has at least 50, 60, 70, 80, 85, 90, or 95% homology with a reference proximal domain disclosed herein; and the tail domain is absent or a nucleotide sequence is 1 to 50 nucleotides in length and, in certain embodiments has at least 50, 60, 70, 80, 85, 90, or 95% homology with a reference tail domain disclosed herein.

In certain embodiments, a unimolecular gRNA as disclosed herein comprises, preferably from 5' to 3':

a targeting domain, e.g., comprising 10-50 nucleotides;

a first complementarity domain, e.g., comprising 15, 16, 17, 18, 19, 20, 21, 22, 23, 24, 25, or 26 nucleotides;

a linking domain;

a second complementarity domain;

a proximal domain; and a tail domain, wherein, (a) the proximal and tail domain, when taken together, comprise at least 15, 18, 20, 25, 30, 31, 35, 40, 45, 49, 50, or 53 nucleotides;

(b) there are at least 15, 18, 20, 25, 30, 31, 35, 40, 45, 49, 50, or 53 nucleotides 3' to the last nucleotide of the second complementarity domain; or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the sequence from (a), (b), and/or (c) has at least 50%, 60%, 70%, 75%, 80%, 85%, 90%, 95%, or 99% homology with the corresponding sequence of a naturally occurring gRNA, or with a gRNA described herein.

In certain embodiments, the proximal and tail domain, when taken together, comprise at least 15, 18, 20, 25, 30, 31, 35, 40, 45, 49, 50, or 53 nucleotides.

In certain embodiments, there are at least 15, 18, 20, 25, 30, 31, 35, 40, 45, 49, 50, or 53 nucleotides 3' to the last nucleotide of the second complementarity domain.

In certain embodiments, there are at least 16, 19, 21, 26, 31, 32, 36, 41, 46, 50, 51, or 54 nucleotides 3' to the last nucleotide of the second complementarity domain that are complementary to the corresponding nucleotides of the first complementarity domain.

In certain embodiments, the targeting domain consists of, consists essentially of, or comprises 16, 17, 18, 19, 20, 21, 22, 23, 24, 25, or 26 nucleotides (e.g., 16, 17, 18, 19, 20, 21, 22, 23, 24, 25, or 26 consecutive nucleotides) complementary or partially complementary to the target domain or a portion thereof, e.g., the targeting domain is 16, 17, 18, 19, 20, 21, 22, 23, 24, 25, or 26 nucleotides in length. In certain of these embodiments, the targeting domain is complementary to the target domain over the entire length of the targeting domain, the entire length of the target domain, or both.

In certain embodiments, a unimolecular or chimeric gRNA molecule disclosed herein (comprising a targeting domain, a first complementary domain, a linking domain, a second complementary domain, a proximal domain and, optionally, a tail domain) comprises the amino acid sequence set forth in SEQ ID NO:45, wherein the targeting domain is listed as 20 N's (residues 1-20) but may range in length from 16 to 26 nucleotides, and wherein the final six residues (residues 97-102) represent a termination signal for the U6 promoter buy may be absent or fewer in number. In certain embodiments, the unimolecular, or chimeric, gRNA molecule is a *S. pyogenes* gRNA molecule.

In certain embodiments, a unimolecular or chimeric gRNA molecule disclosed herein (comprising a targeting domain, a first complementary domain, a linking domain, a second complementary domain, a proximal domain and, optionally, a tail domain) comprises the amino acid sequence set forth in SEQ ID NO:40, wherein the targeting domain is listed as 20 Ns (residues 1-20) but may range in length from 16 to 26 nucleotides, and wherein the final six residues (residues 97-102) represent a termination signal for the U6 promoter but may be absent or fewer in number. In certain embodiments, the unimolecular or chimeric gRNA molecule is an *S. aureus* gRNA molecule.

Exemplary Modular gRNAs

In certain embodiments, a modular gRNA disclosed herein comprises:
  a first strand comprising, preferably from 5' to 3';
    a targeting domain, e.g., comprising 15, 16, 17, 18, 19, 20, 21, 22, 23, 24, 25, or 26 nucleotides;
    a first complementarity domain; and
  a second strand, comprising, preferably from 5' to 3':
    optionally a 5' extension domain;
    a second complementarity domain;
    a proximal domain; and
    a tail domain,
  wherein:
  (a) the proximal and tail domain, when taken together, comprise at least 15, 18, 20, 25, 30, 31, 35, 40, 45, 49, 50, or 53 nucleotides;
  (b) there are at least 15, 18, 20, 25, 30, 31, 35, 40, 45, 49, 50, or 53 nucleotides 3' to the last nucleotide of the second complementarity domain; or
  (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the sequence from (a), (b), or (c), has at least 60, 75, 80, 85, 90, 95, or 99% homology with the corresponding sequence of a naturally occurring gRNA, or with a gRNA described herein.

In certain embodiments, the proximal and tail domain, when taken together, comprise at least 15, 18, 20, 25, 30, 31, 35, 40, 45, 49, 50, or 53 nucleotides.

In certain embodiments, there are at least 15, 18, 20, 25, 30, 31, 35, 40, 45, 49, 50, or 53 nucleotides 3' to the last nucleotide of the second complementarity domain.

In certain embodiments, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain. In certain embodiments, the targeting domain comprises, has, or consists of, 16, 17, 18, 19, 20, 21, 22, 23, 24, 25, or 26 nucleotides (e.g., 16, 17, 18, 19, 20, 21, 22, 23, 24, 25, or 26 consecutive nucleotides) having complementarity with the target domain, e.g., the targeting domain is 16, 17, 18, 19, 20, 21, 22, 23, 24, 25, or 26 nucleotides in length.

In certain embodiments, the targeting domain consists of, consists essentially of, or comprises 16, 17, 18, 19, 20, 21, 22, 23, 24, 25, or 26 nucleotides (e.g., 16, 17, 18, 19, 20, 21, 22, 23, 24, 25, or 26 consecutive nucleotides) complementary to the target domain or a portion thereof. In certain of these embodiments, the targeting domain is complementary to the target domain over the entire length of the targeting domain, the entire length of the target domain, or both.

In certain embodiments, the targeting domain comprises, has, or consists of, 16 nucleotides (e.g., 16 consecutive nucleotides) having complementarity with the target domain, e.g., the targeting domain is 16 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 16 nucleotides (e.g., 16 consecutive nucleotides) having complementarity with the target domain, e.g., the targeting domain is 16 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 16 nucleotides (e.g., 16 consecutive nucleotides) having complementarity with the target domain, e.g., the targeting domain is 16 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain has, or consists of, 17 nucleotides (e.g., 17 consecutive nucleotides) having complementarity with the target domain, e.g., the targeting domain is 17 nucleotides in length; and the proximal and tail domain, when taken together, comprise at least 15, 18, 20, 25, 30, 31, 35, 40, 45, 49, 50, or 53 nucleotides.

In certain embodiments, the targeting domain has, or consists of, 17 nucleotides (e.g., 17 consecutive nucleotides) having complementarity with the target domain, e.g., the targeting domain is 17 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain has, or consists of, 17 nucleotides (e.g., 17 consecutive nucleotides) having complementarity with the target domain, e.g., the targeting domain is 17 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain has, or consists of, 18 nucleotides (e.g., 18 consecutive nucleotides) having complementarity with the target domain, e.g., the targeting domain is 18 nucleotides in length; and the proximal and tail domain, when taken together, comprise at least 15, 18, 20, 25, 30, 31, 35, 40, 45, 49, 50, or 53 nucleotides.

In certain embodiments, the targeting domain has, or consists of, 18 nucleotides (e.g., 18 consecutive nucleotides) having complementarity with the target domain, e.g., the targeting domain is 18 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain has, or consists of, 18 nucleotides (e.g., 18 consecutive nucleotides) having complementarity with the target domain, e.g., the targeting domain is 18 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 19 nucleotides (e.g., 19 consecutive nucleotides) having complementarity with the target domain, e.g., the targeting domain is 19 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 19 nucleotides (e.g., 19 consecutive nucleotides) having complementarity with the target domain, e.g., the targeting domain is 19 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 19 nucleotides (e.g., 19 consecutive nucleotides) having complementarity with the target domain, e.g., the targeting domain is 19 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 20 nucleotides (e.g., 20 consecutive nucleotides) having complementarity with the target domain, e.g., the targeting domain is 20 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 20 nucleotides (e.g., 20 consecutive nucleotides) having complementarity with the target domain, e.g., the targeting domain is 20 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 20 nucleotides (e.g., 20 consecutive nucleotides) having complementarity with the target domain, e.g., the targeting domain is 20 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 21 nucleotides (e.g., 21 consecutive nucleotides) having complementarity with the target domain, e.g., the targeting domain is 21 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 21 nucleotides (e.g., 21 consecutive nucleotides) having complementarity with the target domain, e.g., the targeting domain is 21 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 21 nucleotides (e.g., 21 consecutive nucleotides) having complementarity with the target domain, e.g., the targeting domain is 21 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 22 nucleotides (e.g., 22 consecutive nucleotides) having complementarity with the target domain, e.g., the targeting domain is 22 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 22 nucleotides (e.g., 22 consecutive nucleotides) having complementarity with the target domain, e.g., the targeting domain is 22 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 22 nucleotides (e.g., 22 consecutive nucleotides) having complementarity with the target domain, e.g., the targeting domain is 22 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 23 nucleotides (e.g., 23 consecutive nucleotides) having complementarity with the target domain, e.g., the targeting domain is 23 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 23 nucleotides (e.g., 23 consecutive nucleotides) having complementarity with the target domain, e.g., the targeting domain is 23 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 23 nucleotides (e.g., 23 consecutive nucleotides) having complementarity with the target domain, e.g., the targeting domain is 23 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 24 nucleotides (e.g., 24 consecutive nucleotides) having complementarity with the target domain, e.g., the targeting domain is 24 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 24 nucleotides (e.g., 24 consecutive nucleotides) having complementarity with the target domain, e.g., the targeting domain is 24 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 24 nucleotides (e.g., 24 consecutive nucleotides) having complementarity with the target domain, e.g., the targeting domain is 24 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 25 nucleotides (e.g., 25 consecutive nucleotides) having complementarity with the target domain, e.g., the targeting domain is 25 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 25 nucleotides (e.g., 25 consecutive nucleotides) having complementarity with the target domain, e.g., the targeting domain is 25 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 25 nucleotides (e.g., 25 consecutive nucleotides) having complementarity with the target domain, e.g., the targeting domain is 25 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 26 nucleotides (e.g., 26 consecutive nucleotides) having complementarity with the target domain, e.g., the targeting domain is 26 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 26 nucleotides (e.g., 26 consecutive nucleotides) having complementarity with the target domain, e.g., the targeting domain is 26 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 26 nucleotides (e.g., 26 consecutive nucleotides) having complementarity with the target domain, e.g., the targeting domain is 26 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

Methods for Designing gRNA Molecules

Methods for selecting, designing, and validating targeting domains for use in the gRNAs described herein are provided. Exemplary targeting domains for incorporation into gRNAs are also provided herein.

Methods for selection and validation of target sequences as well as off-target analyses have been described (see, e.g., Mali 2013; Hsu 2013; Fu 2014; Heigwer 2014; Bae 2014; and Xiao 2014). For example, a software tool can be used to optimize the choice of potential targeting domains corresponding to a user's target sequence, e.g., to minimize total off-target activity across the genome. Off-target activity may be other than cleavage. For each possible targeting domain choice using S. pyogenes Cas9, the tool can identify all off-target sequences (preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible targeting domain is then ranked according to its total predicted off-target cleavage; the top-ranked targeting domains represent those that are likely to have the greatest on-target cleavage and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate targeting domains and gRNAs comprising those targeting domains can be functionally evaluated by using methods known in the art and/or as set forth herein.

As a non-limiting example, targeting domains for use in gRNAs for use with S. pyogenes, and S. aureus Cas9s were identified using a DNA sequence searching algorithm. 17-mer and 20-mer targeting domains were designed for S. pyogenes targets, while 18-mer, 19-mer, 20-mer, 21-mer, 22-mer, 23-mer, and 24-mer targeting domains were designed for S. aureus targets. gRNA design was carried out using a custom gRNA design software based on the public tool cas-offinder (Bae 2014). This software scores guides after calculating their genome-wide off-target propensity. Typically matches ranging from perfect matches to 7 mismatches are considered for guides ranging in length from 17 to 24. Once the off-target sites are computationally-determined, an aggregate score is calculated for each guide and summarized in a tabular output using a web-interface. In addition to identifying potential target sites adjacent to PAM sequences, the software also identifies all PAM adjacent sequences that differ by 1, 2, 3 or more than 3 nucleotides from the selected target sites. Genomic DNA sequences for a target gene may be obtained from the UCSC Genome browser and sequences screened for repeat elements using the publically available RepeatMasker program. Repeat-Masker searches input DNA sequences for repeated elements and regions of low complexity. The output is a detailed annotation of the repeats present in a given query sequence.

Following identification, targeting domains were ranked into tiers based on their distance to the target site, their orthogonality and presence of a 5' G (based on identification of close matches in the human genome containing a relevant PAM e.g., NGG PAM for *S. pyogenes*, NNGRRT or NNGRRV PAM for *S. aureus*. Orthogonality refers to the number of sequences in the human genome that contain a minimum number of mismatches to the target sequence. A "high level of orthogonality" or "good orthogonality" may, for example, refer to 20-mer targeting domains that have no identical sequences in the human genome besides the intended target, nor any sequences that contain one or two mismatches in the target sequence. Targeting domains with good orthogonality are selected to minimize off-target DNA cleavage.

Targeting domains were identified for both single-gRNA nuclease cleavage and for a dual-gRNA paired "nickase" strategy. Criteria for selecting targeting domains and the determination of which targeting domains can be incorporated into a gRNA and used for the dual-gRNA paired "nickase" strategy is based on two considerations:
1. gRNA pairs should be oriented on the DNA such that PAMs are facing out and cutting with the D10A Cas9 nickase will result in 5' overhangs.
2. An assumption that cleaving with dual nickase pairs will result in deletion of the entire intervening sequence at a reasonable frequency. However, cleaving with dual nickase pairs can also result in indel mutations at the site of only one of the gRNA molecules. Candidate pair members can be tested for how efficiently they remove the entire sequence versus causing indel mutations at the target site of one gRNA molecule.

Other gRNA Design Strategy

In certain embodiments, two or more (e.g., three or four) gRNA molecules are used with one Cas9 molecule. In another embodiment, when two or more (e.g., three or four) gRNAs are used with two or more Cas9 molecules, at least one Cas9 molecule is from a different species than the other Cas9 molecule(s). For example, when two gRNA molecules are used with two Cas9 molecules, one Cas9 molecule can be from one species and the other Cas9 molecule can be from a different species. Both Cas9 species are used to generate a single or double-strand break, as desired.

In certain embodiments, dual targeting is used to create two nicks on opposite DNA strands by using Cas9 nickases (e.g., a *S. pyogenes* Cas9 nickase) with two targeting domains that are complementary to opposite DNA strands, e.g., a gRNA molecule comprising any minus strand targeting domain may be paired any gRNA molecule comprising a plus strand targeting domain provided that the two gRNAs are oriented on the DNA such that PAMs face outward and the distance between the 5' ends of the gRNAs is 0-50 bp. When selecting gRNA molecules for use in a nickase pair, one gRNA molecule targets a domain in the complementary strand and the second gRNA molecule targets a domain in the non-complementary strand, e.g., a gRNA comprising any minus strand targeting domain may be paired any gRNA molecule comprising a plus strand targeting domain targeting the same target position. In certain embodiments, two 20-mer gRNAs are used to target two Cas9 nucleases (e.g., two *S. pyogenes* Cas9 nucleases) or two Cas9 nickases (e.g., two *S. pyogenes* Cas9 nickases). Any of the targeting domains described herein can be used with a Cas9 molecule that generates a single-strand break (i.e., a *S. pyogenes* or *S. aureus* Cas9 nickase) or with a Cas9 molecule that generates a double-strand break (i.e., *S. pyogenes* or *S. aureus* Cas9 nuclease).

gRNA molecules, as described herein, may comprise from 5' to 3': a targeting domain (comprising a "core domain", and optionally a "secondary domain"); a first complementarity domain; a linking domain; a second complementarity domain; a proximal domain; and a tail domain. In one embodiment, the proximal domain and tail domain are taken together as a single domain.

In one embodiment, a gRNA molecule comprises a linking domain of no more than 25 nucleotides in length; a proximal and tail domain, that taken together, are at least 20 nucleotides in length; and a targeting domain equal to or greater than 16, 17, 18, 19, 20, 21, 22, 23, 24, 25 or 26 nucleotides in length.

In another embodiment, a gRNA molecule comprises a linking domain of no more than 25 nucleotides in length; a proximal and tail domain, that taken together, are at least 25 nucleotides in length; and a targeting domain equal to or greater than 16, 17, 18, 19, 20, 21, 22, 23, 24, 25 or 26 nucleotides in length.

In another embodiment, a gRNA molecule comprises a linking domain of no more than 25 nucleotides in length; a proximal and tail domain, that taken together, are at least 30 nucleotides in length; and a targeting domain equal to or greater than 16, 17, 18, 19, 20, 21, 22, 23, 24, 25 or 26 nucleotides in length.

In another embodiment, a gRNA molecule comprises a linking domain of no more than 25 nucleotides in length; a proximal and tail domain, that taken together, are at least 40 nucleotides in length; and a targeting domain equal to or greater than 16, 17, 18, 19, 20, 21, 22, 23, 24, 25 or 26 nucleotides in length.

When two gRNAs are designed for use with two Cas9 molecules, the two Cas9 molecules may be from different species. Both Cas9 species may be used to generate a single or double strand break, as desired.

It is contemplated herein that any upstream gRNA described herein may be paired with any downstream gRNA described herein. When an upstream gRNA designed for use with one species of Cas9 molecule is paired with a downstream gRNA designed for use from a different species of Cas9 molecule, both Cas9 species are used to generate a single or double-strand break, as desired.

Cas9 Molecules

Cas9 molecules of a variety of species can be used in the methods and compositions described herein. While *S. pyogenes* and *S. aureus* Cas9 molecules are the subject of much of the disclosure herein, Cas9 molecules of, derived from, or based on the Cas9 proteins of other species listed herein can be used as well. These include, for example, Cas9 molecules from *Acidovorax avenae, Actinobacillus pleuropneumoniae, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida,*

*Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*. In some embodiments, the Cas9 molecule is a split Cas9 molecule or an inducible Cas9 molecule, as described in more detail in WO15/089427 and WO14/018423, the entire contents of each of which are expressly incorporated herein by reference.

Cas9 Domains

Crystal structures have been determined for two different naturally occurring bacterial Cas9 molecules (Jinek et al. 2014) and for *S. pyogenes* Cas9 with a guide RNA (e.g., a synthetic fusion of crRNA and tracrRNA) (Nishimasu et al. 2014; and Anders 2014).

A naturally-occurring Cas9 molecule comprises two lobes: a recognition (REC) lobe and a nuclease (NUC) lobe; each of which further comprise domains described herein. The domain nomenclature and the numbering of the amino acid residues encompassed by each domain used throughout this disclosure is as described previously in (Nishimasu 2014). The numbering of the amino acid residues is with reference to Cas9 from *S. pyogenes*.

The REC lobe comprises the arginine-rich bridge helix (BH), the REC1 domain, and the REC2 domain. The REC lobe does not share structural similarity with other known proteins, indicating that it is a Cas9-specific functional domain. The BH domain is a long a helix and arginine rich region and comprises amino acids 60-93 of the sequence of *S. pyogenes* Cas9. The REC1 domain is important for recognition of the repeat:anti-repeat duplex, e.g., of a gRNA or a tracrRNA, and is therefore critical for Cas9 activity by recognizing the target sequence. The REC1 domain comprises two REC1 motifs at amino acids 94 to 179 and 308 to 717 of the sequence of *S. pyogenes* Cas9. These two REC1 domains, though separated by the REC2 domain in the linear primary structure, assemble in the tertiary structure to form the REC1 domain. The REC2 domain, or parts thereof, may also play a role in the recognition of the repeat:anti-repeat duplex. The REC2 domain comprises amino acids 180-307 of the sequence of *S. pyogenes* Cas9.

The NUC lobe comprises the RuvC domain, the HNH domain, and the PAM-interacting (PI) domain. The RuvC domain shares structural similarity to retroviral integrase superfamily members and cleaves a single strand, e.g., the non-complementary strand of the target nucleic acid molecule. The RuvC domain is assembled from the three split RuvC motifs (RuvC I, RuvCII, and RuvCIII, which are often commonly referred to in the art as RuvCI domain, or N-terminal RuvC domain, RuvCII domain, and RuvCIII domain) at amino acids 1-59, 718-769, and 909-1098, respectively, of the sequence of *S. pyogenes* Cas9. Similar to the REC1 domain, the three RuvC motifs are linearly separated by other domains in the primary structure, however in the tertiary structure, the three RuvC motifs assemble and form the RuvC domain. The HNH domain shares structural similarity with HNH endonucleases, and cleaves a single strand, e.g., the complementary strand of the target nucleic acid molecule. The HNH domain lies between the RuvC II-III motifs and comprises amino acids 775-908 of the sequence of *S. pyogenes* Cas9. The PI domain interacts with the PAM of the target nucleic acid molecule, and comprises amino acids 1099-1368 of the sequence of *S. pyogenes* Cas9.

RuvC-Like Domain and an HNH-Like Domain

In certain embodiments, a Cas9 molecule or Cas9 polypeptide comprises an HNH-like domain and a RuvC-like domain and in certain of these embodiments cleavage activity is dependent on the RuvC-like domain and the HNH-like domain. A Cas9 molecule or Cas9 polypeptide can comprise one or more of a RuvC-like domain and an HNH-like domain. In certain embodiments, a Cas9 molecule or Cas9 polypeptide comprises a RuvC-like domain, e.g., a RuvC-like domain described below, and/or an HNH-like domain, e.g., an HNH-like domain described below.

RuvC-Like Domains

In certain embodiments, a RuvC-like domain cleaves, a single strand, e.g., the non-complementary strand of the target nucleic acid molecule. The Cas9 molecule or Cas9 polypeptide can include more than one RuvC-like domain (e.g., one, two, three or more RuvC-like domains). In certain embodiments, a RuvC-like domain is at least 5, 6, 7, 8 amino acids in length but not more than 20, 19, 18, 17, 16 or 15 amino acids in length. In certain embodiments, the Cas9 molecule or Cas9 polypeptide comprises an N-terminal RuvC-like domain of about 10 to 20 amino acids, e.g., about 15 amino acids in length.

N-Terminal RuvC-Like Domains

Some naturally occurring Cas9 molecules comprise more than one RuvC-like domain with cleavage being dependent on the N-terminal RuvC-like domain. Accordingly, a Cas9 molecule or Cas9 polypeptide can comprise an N-terminal RuvC-like domain. Exemplary N-terminal RuvC-like domains are described below.

In certain embodiments, a Cas9 molecule or Cas9 polypeptide comprises an N-terminal RuvC-like domain comprising an amino acid sequence of Formula I:

$$D-X_1-G-X_2-X_3-X_4-X_5-G-X_6-X_7-X_8-X_9, \quad \text{(SEQ ID NO: 8)}$$

wherein, $X_1$ is selected from I, V, M, L and T (e.g., selected from I, V, and L);

$X_2$ is selected from T, I, V, S, N, Y, E and L (e.g., selected from T, V, and I);

$X_3$ is selected from N, S, G, A, D, T, R, M and F (e.g., A or N);

$X_4$ is selected from S, Y, N and F (e.g., 5);

$X_5$ is selected from V, I, L, C, T and F (e.g., selected from V, I and L);

$X_6$ is selected from W, F, V, Y, S and L (e.g., W);

$X_7$ is selected from A, S, C, V and G (e.g., selected from A and S);

$X_8$ is selected from V, I, L, A, M and H (e.g., selected from V, I, M and L); and $X_9$ is selected from any amino acid or is absent (e.g., selected from T, V, I, L, Δ, F, S, A, Y, M and R, or, e.g., selected from T, V, I, L and Δ).

In certain embodiments, the N-terminal RuvC-like domain differs from a sequence of SEQ ID NO:8, by as many as 1 but no more than 2, 3, 4, or 5 residues.

In certain embodiments, the N-terminal RuvC-like domain is cleavage competent.

In other embodiments, the N-terminal RuvC-like domain is cleavage incompetent.

In certain embodiments, a Cas9 molecule or Cas9 polypeptide comprises an N-terminal RuvC-like domain comprising an amino acid sequence of Formula II:

$$\text{D-X}_1\text{-G-X}_2\text{-X}_3\text{-S-X}_5\text{-G-X}_6\text{-X}_7\text{-X}_8\text{-X}_9, \quad \text{(SEQ ID NO: 9)}$$

wherein $X_1$ is selected from I, V, M, L and T (e.g., selected from I, V, and L);

$X_2$ is selected from T, I, V, S, N, Y, E and L (e.g., selected from T, V, and I);

$X_3$ is selected from N, S, G, A, D, T, R, M and F (e.g., A or N);

$X_5$ is selected from V, I, L, C, T and F (e.g., selected from V, I and L);

$X_6$ is selected from W, F, V, Y, S and L (e.g., W);

$X_7$ is selected from A, S, C, V and G (e.g., selected from A and S);

$X_8$ is selected from V, I, L, A, M and H (e.g., selected from V, I, M and L); and $X_9$ is selected from any amino acid or is absent (e.g., selected from T, V, I, L, Δ, F, S, A, Y, M and R or selected from e.g., T, V, I, L and Δ).

In certain embodiments, the N-terminal RuvC-like domain differs from a sequence of SEQ ID NO:9 by as many as 1 but not more than 2, 3, 4, or 5 residues.

In certain embodiments, the N-terminal RuvC-like domain comprises an amino acid sequence of Formula III:

$$\text{D-I-G-X}_2\text{-X}_3\text{-S-V-G-W-A-X}_8\text{-X}_9, \quad \text{(SEQ ID NO: 10)}$$

wherein $X_2$ is selected from T, I, V, S, N, Y, E and L (e.g., selected from T, V, and I);

$X_3$ is selected from N, S, G, A, D, T, R, M and F (e.g., A or N);

$X_8$ is selected from V, I, L, A, M and H (e.g., selected from V, I, M and L); and $X_9$ is selected from any amino acid or is absent (e.g., selected from T, V, I, L, Δ, F, S, A, Y, M and R or selected from e.g., T, V, I, L and Δ).

In certain embodiments, the N-terminal RuvC-like domain differs from a sequence of SEQ ID NO:10 by as many as 1 but not more than, 2, 3, 4, or 5 residues.

In certain embodiments, the N-terminal RuvC-like domain comprises an amino acid sequence of Formula IV:

$$\text{D-I-G-T-N-S-V-G-W-A-V-X}, \quad \text{(SEQ ID NO: 11)}$$

wherein

X is a non-polar alkyl amino acid or a hydroxyl amino acid, e.g., X is selected from V, I, L and T.

In certain embodiments, the N-terminal RuvC-like domain differs from a sequence of SEQ ID NO:11 by as many as 1 but not more than 2, 3, 4, or 5 residues.

In certain embodiments, the N-terminal RuvC-like domain differs from a sequence of an N-terminal RuvC like domain disclosed herein, e.g., in any one of SEQ ID Nos: 54-103, as many as 1 but no more than 2, 3, 4, or 5 residues. In certain embodiments, 1, 2, 3 or all of the highly conserved residues of SEQ ID Nos: 54-103 are present.

In certain embodiment, the N-terminal RuvC-like domain differs from a sequence of an N-terminal RuvC-like domain disclosed herein, e.g., in any one of SEQ ID Nos: 104-177, as many as 1 but no more than 2, 3, 4, or 5 residues. In certain embodiments, 1, 2, or all of the highly conserved residues identified of SEQ ID Nos: 104-177 are present.

Additional RuvC-Like Domains

In addition to the N-terminal RuvC-like domain, the Cas9 molecule or Cas9 polypeptide can comprise one or more additional RuvC-like domains. In certain embodiments, the Cas9 molecule or Cas9 polypeptide can comprise two additional RuvC-like domains. Preferably, the additional RuvC-like domain is at least 5 amino acids in length and, e.g., less than 15 amino acids in length, e.g., 5 to 10 amino acids in length, e.g., 8 amino acids in length.

An additional RuvC-like domain can comprise an amino acid sequence of Formula V:

$$\text{I-X}_1\text{-X}_2\text{-E-X}_3\text{-A-R-E}, \quad \text{(SEQ ID NO: 12)}$$

wherein $X_1$ is V or H;

$X_2$ is I, L or V (e.g., I or V); and $X_3$ is M or T.

In certain embodiments, the additional RuvC-like domain comprises an amino acid sequence of Formula VI:

$$\text{I-V-X}_2\text{-E-M-A-R-E}, \quad \text{(SEQ ID NO: 13)}$$

wherein $X_2$ is I, L or V (e.g., I or V).

An additional RuvC-like domain can comprise an amino acid sequence of Formula VII:

$$\text{H-H-A-X}_1\text{-D-A-X2-X}_3, \quad \text{(SEQ ID NO: 14)}$$

wherein $X_1$ is H or L;

$X_2$ is R or V; and $X_3$ is E or V.

In certain embodiments, the additional RuvC-like domain comprises the amino acid sequence: H-H-A-H-D-A-Y-L (SEQ ID NO:15).

In certain embodiments, the additional RuvC-like domain differs from a sequence of SEQ ID NOs: 12-15 by as many as 1 but not more than 2, 3, 4, or 5 residues.

In certain embodiment, the sequence flanking the N-terminal RuvC-like domain has the amino acid sequence of Formula VIII:

$$\text{K-X}_1'\text{-Y-X}_2'\text{-X}_3'\text{-X}_4'\text{-Z-T-D-X}_9'\text{-Y}, \quad \text{(SEQ ID NO: 16)}$$

wherein $X_1'$ is selected from K and P;

$X_2'$ is selected from V, L, I, and F (e.g., V, I and L);

$X_3'$ is selected from G, A and S (e.g., G);

$X_4'$ is selected from L, I, V and F (e.g., L);

$X_9'$ is selected from D, E, N and Q; and

Z is an N-terminal RuvC-like domain, e.g., as described above, e.g., having 5 to 20 amino acids.

HNH-Like Domains

In certain embodiments, an HNH-like domain cleaves a single stranded complementary domain, e.g., a complementary strand of a double stranded nucleic acid molecule. In certain embodiments, an HNH-like domain is at least 15, 20, or 25 amino acids in length but not more than 40, 35, or 30 amino acids in length, e.g., 20 to 35 amino acids in length, e.g., 25 to 30 amino acids in length. Exemplary HNH-like domains are described below.

In certain embodiments, a Cas9 molecule or Cas9 polypeptide comprises an HNH-like domain having an amino acid sequence of Formula IX:

(SEQ ID NO: 17)
$X_1$-$X_2$-$X_3$-H-$X_4$-$X_5$-P-$X_6$-$X_7$-$X_8$-$X_9$-$X_{10}$-$X_{11}$-$X_{12}$-$X_{13}$-$X_{14}$-$X_{15}$-N-$X_{16}$-$X_{17}$-$X_{18}$-$X_{19}$-$X_{20}$-$X_{21}$-$X_{22}$-$X_{23}$-N, wherein
$X_1$ is selected from D, E, Q and N (e.g., D and E);
$X_2$ is selected from L, I, R, Q, V, M and K;
$X_3$ is selected from D and E;
$X_4$ is selected from I, V, T, A and L (e.g., A, I and V);
$X_5$ is selected from V, Y, I, L, F and W (e.g., V, I and L);
$X_6$ is selected from Q, H, R, K, Y, I, L, F and W;
$X_7$ is selected from S, A, D, T and K (e.g., S and A);
$X_8$ is selected from F, L, V, K, Y, M, I, R, A, E, D and Q (e.g., F);
$X_9$ is selected from L, R, T, I, V, S, C, Y, K, F and G;
$X_{10}$ is selected from K, Q, Y, T, F, L, W, M, A, E, G, and S;
$X_{11}$ is selected from D, S, N, R, L and T (e.g., D);
$X_{12}$ is selected from D, N and S;
$X_{13}$ is selected from S, A, T, G and R (e.g., 5);
$X_{14}$ is selected from I, L, F, S, R, Y, Q, W, D, K and H (e.g., I, L and F);
$X_{15}$ is selected from D, S, I, N, E, A, H, F, L, Q, M, G, Y and V;
$X_{16}$ is selected from K, L, R, M, T and F (e.g., L, R and K);
$X_{17}$ is selected from V, L, I, A and T;
$X_{18}$ is selected from L, I, V and A (e.g., L and I);
$X_{19}$ is selected from T, V, C, E, S and A (e.g., T and V);
$X_{20}$ is selected from R, F, T, W, E, L, N, C, K, V, S, Q, I, Y, H and A;
$X_{21}$ is selected from S, P, R, K, N, A, H, Q, G and L;
$X_{22}$ is selected from D, G, T, N, S, K, A, I, E, L, Q, R and Y; and
$X_{23}$ is selected from K, V, A, E, Y, I, C, L, S, T, G, K, M, D and F.

In certain embodiments, a HNH-like domain differs from a sequence of SEQ ID NO: 17 by at least one but not more than, 2, 3, 4, or 5 residues.

In certain embodiments, the HNH-like domain is cleavage competent.

In other embodiments, the HNH-like domain is cleavage incompetent.

In certain embodiments, a Cas9 molecule or Cas9 polypeptide comprises an HNH-like domain comprising an amino acid sequence of Formula X:

(SEQ ID NO: 18)
$X_1$-$X_2$-$X_3$-H-$X_4$-$X_5$-P-$X_6$-S-$X_8$-$X_9$-$X_{10}$-D-D-S-$X_{14}$-$X_{15}$-N-K-V-L-$X_{19}$-$X_{20}$-$X_{21}$-$X_{22}$-$X_{23}$-N, wherein
$X_1$ is selected from D and E;
$X_2$ is selected from L, I, R, Q, V, M and K;
$X_3$ is selected from D and E;
$X_4$ is selected from I, V, T, A and L (e.g., A, I and V);
$X_5$ is selected from V, Y, I, L, F and W (e.g., V, I and L);
$X_6$ is selected from Q, H, R, K, Y, I, L, F and W;
$X_8$ is selected from F, L, V, K, Y, M, I, R, A, E, D and Q (e.g., F);
$X_9$ is selected from L, R, T, I, V, S, C, Y, K, F and G;
$X_{10}$ is selected from K, Q, Y, T, F, L, W, M, A, E, G, and S;
$X_{14}$ is selected from I, L, F, S, R, Y, Q, W, D, K and H (e.g., I, L and F);
$X_{15}$ is selected from D, S, I, N, E, A, H, F, L, Q, M, G, Y and V;
$X_{19}$ is selected from T, V, C, E, S and A (e.g., T and V);
$X_{20}$ is selected from R, F, T, W, E, L, N, C, K, V, S, Q, I, Y, H and A;
$X_{21}$ is selected from S, P, R, K, N, A, H, Q, G and L;
$X_{22}$ is selected from D, G, T, N, S, K, A, I, E, L, Q, R and Y; and
$X_{23}$ is selected from K, V, A, E, Y, I, C, L, S, T, G, K, M, D and F.

In certain embodiments, the HNH-like domain differs from a sequence of SEQ ID NO: 18 by 1, 2, 3, 4, or 5 residues.

In certain embodiments, a Cas9 molecule or Cas9 polypeptide comprises an HNH-like domain comprising an amino acid sequence of Formula XI:

(SEQ ID NO: 19)
$X_1$-V-$X_3$-H-I-V-P-$X_6$-S-$X_8$-$X_9$-$X_{10}$-D-D-S-$X_{14}$-$X_{15}$-N-K-V-L-T-$X_{20}$-$X_{21}$-$X_{22}$-$X_{23}$-N, wherein
$X_1$ is selected from D and E;
$X_3$ is selected from D and E;
$X_6$ is selected from Q, H, R, K, Y, I, L and W;
$X_8$ is selected from F, L, V, K, Y, M, I, R, A, E, D and Q (e.g., F);
$X_9$ is selected from L, R, T, I, V, S, C, Y, K, F and G;
$X_{10}$ is selected from K, Q, Y, T, F, L, W, M, A, E, G, and S;
$X_{14}$ is selected from I, L, F, S, R, Y, Q, W, D, K and H (e.g., I, L and F);
$X_{15}$ is selected from D, S, I, N, E, A, H, F, L, Q, M, G, Y and V;
$X_{20}$ is selected from R, F, T, W, E, L, N, C, K, V, S, Q, I, Y, H and A;
$X_{21}$ is selected from S, P, R, K, N, A, H, Q, G and L;
$X_{22}$ is selected from D, G, T, N, S, K, A, I, E, L, Q, R and Y; and
$X_{23}$ is selected from K, V, A, E, Y, I, C, L, S, T, G, K, M, D and F.

In certain embodiments, the HNH-like domain differs from a sequence of SEQ ID NO: 19 by 1, 2, 3, 4, or 5 residues.

In certain embodiments, a Cas9 molecule or Cas9 polypeptide comprises an HNH-like domain having an amino acid sequence of Formula XII:

(SEQ ID NO: 20)
D-$X_2$-D-H-I-$X_5$-P-Q-$X_7$-F-$X_9$-$X_{10}$-D-$X_{12}$-S-I-D-N-$X_{16}$-V-L-$X_{19}$-$X_{20}$-S-$X_{22}$-$X_{23}$-N, wherein
$X_2$ is selected from I and V;
$X_5$ is selected from I and V;
$X_7$ is selected from A and S;
$X_9$ is selected from I and L;
$X_{10}$ is selected from K and T;
$X_{12}$ is selected from D and N;
$X_{16}$ is selected from R, K and L;
$X_{19}$ is selected from T and V;
$X_{20}$ is selected from S and R;
$X_{22}$ is selected from K, D and A; and $X_{23}$ is selected from E, K, G and N (e.g., the Cas9 molecule or Cas9 polypeptide can comprise an HNH-like domain as described herein).

In certain embodiments, the HNH-like domain differs from a sequence of SEQ ID NO: 20 by as many as 1 but not more than 2, 3, 4, or 5 residues.

In certain embodiments, a Cas9 molecule or Cas9 polypeptide comprises the amino acid sequence of formula XIII:

(SEQ ID NO: 21)
L-Y-Y-L-Q-N-G-$X_1$'-D-M-Y-$X_2$'-$X_3$'-X4'-$X_5$'-L-D-I-$X_6$'-$X_7$'-L-S-$X_8$'-Y-Z-N-R-$X_9$'-K-$X_{10}$'-D-$X_{11}$'-V-P, wherein
 $X_1$' is selected from K and R;
 $X_2$' is selected from V and T;
 $X_3$' is selected from G and D;
 $X_4$' is selected from E, Q and D;
 $X_5$' is selected from E and D;
 $X_6$' is selected from D, N and H;
 $X_7$' is selected from Y, R and N;
 $X_8$' is selected from Q, D and N;
 $X_9$' is selected from G and E;
 $X_{10}$' is selected from S and G;
 $X_{11}$' is selected from D and N; and
 Z is an HNH-like domain, e.g., as described above.

In certain embodiment, a Cas9 molecule or Cas9 polypeptide comprises an amino acid sequence that differs from a sequence of SEQ ID NO:21 by as many as 1 but not more than 2, 3, 4, or 5 residues.

In certain embodiments, the HNH-like domain differs from a sequence of an HNH-like domain disclosed herein by as many as 1 but not more than 2, 3, 4, or 5 residues. In certain embodiments, 1 or both of the highly conserved residues of are present.

In certain embodiments, the HNH-like domain differs from a sequence of an HNH-like domain disclosed herein by as many as 1 but not more than 2, 3, 4, or 5 residues. In certain embodiments, 1, 2, all 3 of the highly conserved residues are present.

Inducible Cas9 Molecules and Gene Editing Systems

In some embodiments, the Cas9 fusion molecule comprises an inducible Cas9 molecule, as described in more detail in WO15/089427 and WO14/018423, the entire contents of each of which are expressly incorporated herein by reference. Inducible Cas9 molecules are summarized briefly, below.

In one aspect, disclosed herein is a non-naturally occurring or engineered gene editing system, comprising a Cas9 molecule, which may comprise at least one switch, wherein the activity of said gene editing system is controlled by contact with at least one inducer energy source as to the switch. In an embodiment, the control as to the at least one switch or the activity of the gene editing system may be activated, enhanced, terminated or repressed. The contact with the at least one inducer energy source may result in a first effect and a second effect. The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of the gene editing system. In one embodiment, the first effect and the second effect may occur in a cascade.

In one embodiment, the Cas9 molecule may further comprise at least one nuclear localization signal (NLS), nuclear export signal (NES), functional domain, flexible linker, mutation, deletion, alteration or truncation. The one or more of the NLS, the NES or the functional domain may be conditionally activated or inactivated. In another embodiment, the mutation may be one or more of a mutation in a transcription factor homology region, a mutation in a DNA binding domain (such as mutating basic residues of a basic helix loop helix), a mutation in an endogenous NLS or a mutation in an endogenous NES. The disclosure comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source may be abscisic acid (ABA), doxycycline (DOX), cumate, rapamycin, 4-hydroxytamoxifen (40HT), estrogen or ecdysone. The disclosure also provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment, the at least one switch may be selected from the group consisting of tetracycline (Tet)/DOX inducible systems, light inducible systems, ABA inducible systems, cumate repressor/operator systems, 40HT/estrogen inducible systems, ecdysone-based inducible systems and FKBP12/FRAP (FKBP12-rapamycin complex) inducible systems.

The at least one functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase or histone tail protease.

Specifically, the disclosure provides for systems or methods as described herein, wherein the gene editing system may comprise a vector system comprising: a) a first regulatory element operably linked to a gene editing system guide RNA that targets a locus of interest, b) a second regulatory inducible element operably linked to a Cas9 fusion protein, wherein components (a) and (b) may be located on same or different vectors of the system, wherein the guide RNA targets DNA of the locus of interest, wherein the Cas9 fusion protein and the guide RNA do not naturally occur together. In a preferred embodiment of the invention, the Cas9 fusion protein comprises an inducible Cas9 enzyme. The invention also provides for the vector being a AAV or a lentivirus.

Split Cas9 Molecules and Gene Editing Systems

In some embodiments, the Cas9 fusion molecule comprises a split Cas9 molecule, as described in more detail in WO15/089427 and WO14/018423, the entire contents of each of which are expressly incorporated herein by reference. Split Cas9 molecules are summarized briefly, below.

In an aspect, disclosed herein is a non-naturally occurring or engineered inducible CRISPR enzyme, e.g., Cas9 enzyme, comprising: a first CRISPR enzyme fusion construct attached to a first half of an inducible dimer and a second CRISPR enzyme fusion construct attached to a second half of the inducible dimer, wherein the first CRISPR enzyme fusion construct is operably linked to one or more nuclear localization signals, wherein the second CRISPR enzyme fusion construct is operably linked to one or more nuclear export signals, wherein contact with an inducer energy source brings the first and second halves of the inducible dimer together, wherein bringing the first and second halves of the inducible dimer together allows the first and second CRISPR enzyme fusion constructs to constitute a functional gene editing system.

In another aspect, in the inducible gene editing system, the inducible dimer is or comprises or consists essentially of or consists of an inducible heterodimer. In an aspect, in inducible gene editing system, the first half or a first portion or a first fragment of the inducible heterodimer is or comprises or consists of or consists essentially of an FKBP, optionally FKBP 12. In an aspect, in the inducible gene editing system, the second half or a second portion or a second fragment of the inducible heterodimer is or comprises or consists of or consists essentially of FRB. In one aspect, in the inducible gene editing system, the arrangement of the first CRISPR enzyme fusion construct is or comprises or consists of or consists essentially of N' terminal Cas9 part-FRB-NES. In another aspect, in the inducible gene editing system, the arrangement of the first CRISPR enzyme fusion construct is or comprises or consists of or consists essentially of NES-N' terminal Cas9 part-FRB-NES. In one aspect in the inducible gene editing system, the arrangement of the second CRISPR enzyme fusion construct is or comprises or consists essentially of or consists of C terminal Cas9 part-FKBP-NLS. In another aspect, in the inducible gene editing system, the arrangement of the second CRISPR enzyme fusion construct is or comprises or consists of or consists essentially of NLS-C terminal Cas9 part-FKBP-NLS. In an aspect, in inducible gene editing system there can be a linker that separates the Cas9 part from the half or portion or fragment of the inducible dimer. In an aspect, in the inducible gene editing system, the inducer energy source is or comprises or consists essentially of or consists of rapamycin. In an aspect, in inducible gene editing system, the inducible dimer is an inducible homodimer. In an aspect, in inducible gene editing system, the CRISPR enzyme is Cas9, e.g., SpCas9 or SaCas9. In an aspect in an gene editing system, the Cas9 is split into two parts at any one of the following split points, according or with reference to SpCas9: a split position between 202A/203S; a split position between 255F/256D; a split position between 310E/311I; a split position between 534R/535; a split position between 572E/573C; a split position between 713S/714G; a split position between 1003L/104E; a split position between 1 G54G/1 Q55E; a split position between 1114N/1115S; a split position between 1152K/1153S; a split position between 1245K/1246G; or a split between 1098 and 1099. In an aspect, in the inducible gene editing system, one or more functional domains are associated with one or both parts of the Cas9 enzyme, e.g., the functional domains optionally including a transcriptional activator, a transcriptional or a nuclease such as a fok I nuclease. In an aspect, in the inducible gene editing system, the functional gene editing system binds to the target sequence and the enzyme is a deadCas9, optionally having a diminished nuclease activity of at least 97%, or 100% (or no more than 3% and advantageously 0%) nuclease activity) as compared with the CRISPR enzyme not having the at least one mutation. In an aspect, in the inducible gene editing system, the deadCas9 (CRISPR enzyme) comprises two or more mutations wherein two or more of DIG, E762, H840, N854, N863, or D986 according to SpCas9 protein or any corresponding ortholog or N580 according to SaCas9 protein are mutated, or the CRISPR enzyme comprises at least one mutation, e.g., wherein at least H840 is mutated. The disclosure further provides, a polynucleotide encoding the inducible gene editing system as herein discussed.

Also disclosed herein is a vector for delivery of the first CRISPR enzyme fusion construct, attached to a first half or portion or fragment of an inducible dimer and operably linked to one or more nuclear localization signals, according as herein discussed. In an aspect, disclosed herein is a vector for delivery of the second CRISPR enzyme fusion construct, attached to a second half or portion or fragment of an inducible dimer and operably linked to one or more nuclear export signals.

Cas9 Activities

In certain embodiments, the Cas9 molecule or Cas9 polypeptide is capable of cleaving a target nucleic acid molecule. Typically wild-type Cas9 molecules cleave both strands of a target nucleic acid molecule. Cas9 molecules and Cas9 polypeptides can be engineered to alter nuclease cleavage (or other properties), e.g., to provide a Cas9 molecule or Cas9 polypeptide which is a nickase, or which lacks the ability to cleave target nucleic acid. A Cas9 molecule or Cas9 polypeptide that is capable of cleaving a target nucleic acid molecule is referred to herein as an eaCas9 (an enzymatically active Cas9) molecule or eaCas9 polypeptide.

In certain embodiments, an eaCas9 molecule or eaCas9 polypeptide comprises one or more of the following enzymatic activities:

a nickase activity, i.e., the ability to cleave a single strand, e.g., the non-complementary strand or the complementary strand, of a nucleic acid molecule;

a double stranded nuclease activity, i.e., the ability to cleave both strands of a double stranded nucleic acid and create a double stranded break, which in one embodiment is the presence of two nickase activities;

an endonuclease activity;

an exonuclease activity; and a helicase activity, i.e., the ability to unwind the helical structure of a double stranded nucleic acid.

In certain embodiments, an enzymatically active Cas9 or eaCas9 molecule or eaCas9 polypeptide cleaves both DNA strands and results in a double stranded break. In certain embodiments, an eaCas9 molecule or eaCas9 polypeptide cleaves only one strand, e.g., the strand to which the gRNA hybridizes to, or the strand complementary to the strand the gRNA hybridizes with. In one embodiment, an eaCas9 molecule or eaCas9 polypeptide comprises cleavage activity associated with an HNH domain. In one embodiment, an eaCas9 molecule or eaCas9 polypeptide comprises cleavage activity associated with a RuvC domain. In one embodiment, an eaCas9 molecule or eaCas9 polypeptide comprises cleavage activity associated with an HNH domain and cleavage activity associated with a RuvC domain. In one embodiment, an eaCas9 molecule or eaCas9 polypeptide comprises an active, or cleavage competent, HNH domain and an inactive, or cleavage incompetent, RuvC domain. In one embodiment, an eaCas9 molecule or eaCas9 polypeptide comprises an inactive, or cleavage incompetent, HNH domain and an active, or cleavage competent, RuvC domain.

Some Cas9 molecules or Cas9 polypeptides have the ability to interact with a gRNA molecule, and in conjunction with the gRNA molecule localize to a core target domain, but are incapable of cleaving the target nucleic acid, or incapable of cleaving at efficient rates. Cas9 molecules having no, or no substantial, cleavage activity are referred to herein as an eiCas9 molecule or eiCas9 polypeptide. For example, an eiCas9 molecule or eiCas9 polypeptide can lack cleavage activity or have substantially less, e.g., less than 20, 10, 5, 1 or 0.1% of the cleavage activity of a reference Cas9 molecule or eiCas9 polypeptide, as measured by an assay described herein.

Targeting and PAMs

A Cas9 molecule or Cas9 polypeptide that can interact with a gRNA molecule and, in concert with the gRNA molecule, localizes to a site which comprises a target domain, and in certain embodiments, a PAM sequence.

In certain embodiments, the ability of an eaCas9 molecule or eaCas9 polypeptide to interact with and cleave a target nucleic acid is PAM sequence dependent. A PAM sequence is a sequence in the target nucleic acid. In one embodiment, cleavage of the target nucleic acid occurs upstream from the PAM sequence. eaCas9 molecules from different bacterial species can recognize different sequence motifs (e.g., PAM sequences). In one embodiment, an eaCas9 molecule of *S. pyogenes* recognizes the sequence motif NGG and directs cleavage of a target nucleic acid sequence 1 to 10, e.g., 3 to 5, bp upstream from that sequence (see, e.g., Mali 2013). In one embodiment, an eaCas9 molecule of *S. thermophilus* recognizes the sequence motif NGGNG and/or NNAGAAW (W=A or T) and directs cleavage of a target nucleic acid sequence 1 to 10, e.g., 3 to 5, bp upstream from these sequences (see, e.g., Horvath 2010; Deveau 2008). In one embodiment, an eaCas9 molecule of *S. nutans* recognizes the sequence motif NGG and/or NAAR (R=A or G) and directs cleavage of a target nucleic acid sequence 1 to 10, e.g., 3 to 5, bp upstream from this sequence (see, e.g., Deveau 2008). In one embodiment, an eaCas9 molecule of *S. aureus* recognizes the sequence motif NNGRR (R=A or G) and directs cleavage of a target nucleic acid sequence 1 to 10, e.g., 3 to 5, bp upstream from that sequence. In one embodiment, an eaCas9 molecule of *S. aureus* recognizes the sequence motif NNGRRN (R=A or G) and directs cleavage of a target nucleic acid sequence 1 to 10, e.g., 3 to 5, bp upstream from that sequence. In one embodiment, an eaCas9 molecule of *S. aureus* recognizes the sequence motif NNGRRT (R=A or G) and directs cleavage of a target nucleic acid sequence 1 to 10, e.g., 3 to 5, base pairs upstream from that sequence. In one embodiment, an eaCas9 molecule of *S. aureus* recognizes the sequence motif NNGRRV (R=A or G) and directs cleavage of a target nucleic acid sequence 1 to 10, e.g., 3 to 5, bp upstream from that sequence. The ability of a Cas9 molecule to recognize a PAM sequence can be determined, e.g., using a transformation assay as described in Jinek 2012. In the aforementioned embodiments, N can be any nucleotide residue, e.g., any of A, G, C, or T.

As is discussed herein, Cas9 molecules can be engineered to alter the PAM specificity of the Cas9 molecule.

Exemplary naturally occurring Cas9 molecules have been described previously (see, e.g., Chylinski 2013). Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. aureus, S. pyogenes* (e.g., strain SF370, MGAS10270, MGAS10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. anginosus* (e.g., strain F0211), *S. agalactiae* (e.g., strain NEM316, A909), *Listeria monocytogenes* (e.g., strain F6854), *Listeria innocua* (*L. innocua*, e.g., strain Clip11262), *Enterococcus italicus* (e.g., strain DSM 15952), or *Enterococcus faecium* (e.g., strain 1,231,408).

In certain embodiments, a Cas9 molecule or Cas9 polypeptide comprises an amino acid sequence: having 60%, 65%, 70%, 75%, 80%, 85%, 90%, 95%, 96%, 97%, 98% or 99% homology with; differs at no more than, 2, 5, 10, 15, 20, 30, or 40% of the amino acid residues when compared with; differs by at least 1, 2, 5, 10 or 20 amino acids, but by no more than 100, 80, 70, 60, 50, 40 or 30 amino acids from; or is identical to any Cas9 molecule sequence described herein, or to a naturally occurring Cas9 molecule sequence, e.g., a Cas9 molecule from a species listed herein (e.g., SEQ ID NO:1-4 or described in Chylinski 2013 or Hou 2013). In one embodiment, the Cas9 molecule or Cas9 polypeptide comprises one or more of the following activities: a nickase activity; a double stranded cleavage activity (e.g., an endonuclease and/or exonuclease activity); a helicase activity; or the ability, together with a gRNA molecule, to localize to a target nucleic acid.

A comparison of the sequence of a number of Cas9 molecules indicate that certain regions are conserved. These are identified below as:

region 1 (residues 1 to 180, or in the case of region 1, residues 120 to 180)

region 2 (residues 360 to 480);

region 3 (residues 660 to 720);

region 4 (residues 817 to 900); and region 5 (residues 900 to 960).

In one embodiment, a Cas9 molecule or Cas9 polypeptide comprises regions 1-5, together with sufficient additional Cas9 molecule sequence to provide a biologically active molecule, e.g., a Cas9 molecule having at least one activity described herein. In one embodiment, each of regions 1-5, independently, have 50%, 60%, 70%, 80%, 85%, 90%, 95%, 96%, 97%, 98% or 99% homology with the corresponding residues of a Cas9 molecule or Cas9 polypeptide described herein, e.g., a sequence from SEQ ID Nos: 1-4.

In one embodiment, a Cas9 molecule or Cas9 polypeptide comprises an amino acid sequence referred to as region 1:

having 50%, 60%, 70%, 80%, 85%, 90%, 95%, 96%, 97%, 98% or 99% homology with amino acids 1-180 of the amino acid sequence of Cas9 of *S. pyogenes*;

differs by at least 1, 2, 5, 10 or 20 amino acids but by no more than 90, 80, 70, 60, 50, 40 or 30 amino acids from amino acids 1-180 of the amino acid sequence of Cas9 of *S. pyogenes, S. thermophilus, S. mutans*, or *Listeria innocua*; or is identical to amino acids 1-180 of the amino acid sequence of Cas9 of *S. pyogenes, S. thermophilus, S. mutans*, or *L. innocua*.

In one embodiment, a Cas9 molecule or Cas9 polypeptide comprises an amino acid sequence referred to as region 1':

having 55%, 60%, 65%, 70%, 75%, 80%, 85%, 90%, 95%, 96%, 97%, 98% or 99% homology with amino acids 120-180 of the amino acid sequence of Cas9 of *S. pyogenes, S. thermophilus, S. mutans* or *L. innocua*;

differs by at least 1, 2, or 5 amino acids but by no more than 35, 30, 25, 20 or 10 amino acids from amino acids 120-180 of the amino acid sequence of Cas9 of *S. pyogenes, S. thermophilus, S. mutans*, or *L. innocua*; or is identical to amino acids 120-180 of the amino acid sequence of Cas9 of *S. pyogenes, S. thermophilus, S. mutans*, or *L. innocua*.

In one embodiment, a Cas9 molecule or Cas9 polypeptide comprises an amino acid sequence referred to as region 2:

having 50%, 55%, 60%, 65%, 70%, 75%, 80%, 85%, 90%, 95%, 96%, 97%, 98% or 99% homology with amino acids 360-480 of the amino acid sequence of Cas9 of *S. pyogenes, S. thermophilus, S. mutans*, or *L. innocua*;

differs by at least 1, 2, or 5 amino acids but by no more than 35, 30, 25, 20 or 10 amino acids from amino acids 360-480 of the amino acid sequence of Cas9 of *S. pyogenes, S. thermophilus, S. mutans*, or *L. innocua*; or is identical to amino acids 360-480 of the amino acid sequence of Cas9 of *S. pyogenes, S. thermophilus, S. mutans*, or *L. innocua*.

In certain embodiments, a Cas9 molecule or Cas9 polypeptide comprises an amino acid sequence referred to as region 3:

having 55%, 60%, 65%, 70%, 75%, 80%, 85%, 90%, 95%, 96%, 97%, 98%, or 99% homology with amino acids 660-720 of the amino acid sequence of Cas9 of *S. pyogenes, S. thermophilus, S. mutans* or *L. innocua*;

differs by at least 1, 2, or 5 amino acids but by no more than 35, 30, 25, 20 or 10 amino acids from amino acids 660-720 of the amino acid sequence of Cas9 of *S. pyogenes, S. thermophilus, S. mutans* or *L. innocua*; or is identical to amino acids 660-720 of the amino acid sequence of Cas9 of *S. pyogenes, S. thermophilus, S. mutans* or *L. innocua*.

In one embodiment, a Cas9 molecule or Cas9 polypeptide comprises an amino acid sequence referred to as region 4:

having 50%, 55%, 60%, 65%, 70%, 75%, 80%, 85%, 90%, 95%, 96%, 97%, 98%, or 99% homology with amino acids 817-900 of the amino acid sequence of Cas9 of *S. pyogenes, S. thermophilus, S. mutans*, or *L. innocua*;

differs by at least 1, 2, or 5 amino acids but by no more than 35, 30, 25, 20 or 10 amino acids from amino acids 817-900 of the amino acid sequence of Cas9 of *S. pyogenes, S. thermophilus, S. mutans*, or *L. innocua*; or is identical to amino acids 817-900 of the amino acid sequence of Cas9 of *S. pyogenes, S. thermophilus, S. mutans*, or *L. innocua*.

In one embodiment, a Cas9 molecule or Cas9 polypeptide comprises an amino acid sequence referred to as region 5:

having 50%, 55%, 60%, 65%, 70%, 75%, 80%, 85%, 90%, 95%, 96%, 97%, 98%, or 99% homology with amino acids 900-960 of the amino acid sequence of Cas9 of *S. pyogenes, S. thermophilus, S. mutans*, or *L. innocua*;

differs by at least 1, 2, or 5 amino acids but by no more than 35, 30, 25, 20 or 10 amino acids from amino acids 900-960 of the amino acid sequence of Cas9 of *S. pyogenes, S. thermophilus, S. mutans*, or *L. innocua*; or is identical to amino acids 900-960 of the amino acid sequence of Cas9 of *S. pyogenes, S. thermophilus, S. mutans*, or *L. innocua*.

Engineered or Altered Cas9 Molecules and Cas9 Polypeptides

Cas9 molecules and Cas9 polypeptides described herein can possess any of a number of properties, including: nickase activity, nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In certain embodiments, a Cas9 molecule or Cas9 polypeptide can include all or a subset of these properties. In a typical embodiment, a Cas9 molecule or Cas9 polypeptide has the ability to interact with a gRNA molecule and, in concert with the gRNA molecule, localize to a site in a nucleic acid. Other activities, e.g., PAM specificity, cleavage activity, or helicase activity can vary more widely in Cas9 molecules and Cas9 polypeptides.

Cas9 molecules include engineered Cas9 molecules and engineered Cas9 polypeptides (engineered, as used in this context, means merely that the Cas9 molecule or Cas9 polypeptide differs from a reference sequences, and implies no process or origin limitation). An engineered Cas9 molecule or Cas9 polypeptide can comprise altered enzymatic properties, e.g., altered nuclease activity, (as compared with a naturally occurring or other reference Cas9 molecule) or altered helicase activity. As discussed herein, an engineered Cas9 molecule or Cas9 polypeptide can have nickase activity (as opposed to double-strand nuclease activity). In one embodiment an engineered Cas9 molecule or Cas9 polypeptide can have an alteration that alters its size, e.g., a deletion of amino acid sequence that reduces its size, e.g., without significant effect on one or more, or any Cas9 activity. In one embodiment, an engineered Cas9 molecule or Cas9 polypeptide can comprise an alteration that affects PAM recognition. For example, an engineered Cas9 molecule can be altered to recognize a PAM sequence other than that recognized by the endogenous wild-type PI domain. In one embodiment a Cas9 molecule or Cas9 polypeptide can differ in sequence from a naturally occurring Cas9 molecule but not have significant alteration in one or more Cas9 activities.

Cas9 molecules or Cas9 polypeptides with desired properties can be made in a number of ways, e.g., by alteration of a parental, e.g., naturally occurring, Cas9 molecules or Cas9 polypeptides, to provide an altered Cas9 molecule or Cas9 polypeptide having a desired property. For example, one or more mutations or differences relative to a parental Cas9 molecule, e.g., a naturally occurring or engineered Cas9 molecule, can be introduced. Such mutations and differences comprise: substitutions (e.g., conservative substitutions or substitutions of non-essential amino acids); insertions; or deletions. In one embodiment, a Cas9 molecule or Cas9 polypeptide can comprises one or more mutations or differences, e.g., at least 1, 2, 3, 4, 5, 10, 15, 20, 30, 40 or 50 mutations but less than 200, 100, or 80 mutations relative to a reference, e.g., a parental, Cas9 molecule.

In certain embodiments, a mutation or mutations do not have a substantial effect on a Cas9 activity, e.g., a Cas9 activity described herein. In other embodiments, a mutation or mutations have a substantial effect on a Cas9 activity, e.g., a Cas9 activity described herein.

Non-Cleaving and Modified-Cleavage Cas9 Molecules and Cas9 Polypeptides

In one embodiment, a Cas9 molecule or Cas9 polypeptide comprises a cleavage property that differs from naturally occurring Cas9 molecules, e.g., that differs from the naturally occurring Cas9 molecule having the closest homology. For example, a Cas9 molecule or Cas9 polypeptide can differ from naturally occurring Cas9 molecules, e.g., a Cas9 molecule of S. pyogenes, as follows: its ability to modulate, e.g., decreased or increased, cleavage of a double stranded nucleic acid (endonuclease and/or exonuclease activity), e.g., as compared to a naturally occurring Cas9 molecule (e.g., a Cas9 molecule of S. pyogenes); its ability to modulate, e.g., decreased or increased, cleavage of a single-strand of a nucleic acid, e.g., a non-complementary strand of a nucleic acid molecule or a complementary strand of a nucleic acid molecule (nickase activity), e.g., as compared to a naturally occurring Cas9 molecule (e.g., a Cas9 molecule of S. pyogenes); or the ability to cleave a nucleic acid molecule, e.g., a double stranded or single stranded nucleic acid molecule, can be eliminated.

In certain embodiments, an eaCas9 molecule or eaCas9 polypeptide comprises one or more of the following activities: cleavage activity associated with an N-terminal RuvC-like domain; cleavage activity associated with an HNH-like domain; cleavage activity associated with an HNH-like domain and cleavage activity associated with an N-terminal RuvC-like domain.

In certain embodiments, an eaCas9 molecule or eaCas9 polypeptide comprises an active, or cleavage competent, HNH-like domain (e.g., an HNH-like domain described herein) and an inactive, or cleavage incompetent, N-terminal RuvC-like domain. An exemplary inactive, or cleavage incompetent N-terminal RuvC-like domain can have a mutation of an aspartic acid in an N-terminal RuvC-like domain, e.g., an aspartic acid at position 10 of SEQ ID NO:2, e.g., can be substituted with an alanine. In one embodiment, the eaCas9 molecule or eaCas9 polypeptide differs from wild-type in the N-terminal RuvC-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of S. pyogenes, S. aureus, or S. thermophilus. In one embodiment, the reference Cas9 molecule is the naturally occurring Cas9 molecule having the closest sequence identity or homology.

In certain embodiments, an eaCas9 molecule or eaCas9 polypeptide comprises an inactive, or cleavage incompetent, HNH domain and an active, or cleavage competent, N-terminal RuvC-like domain (e.g., a RuvC-like domain described herein). Exemplary inactive, or cleavage incompetent HNH-like domains can have a mutation at one or more of: a histidine in an HNH-like domain, for example, at position 856 of the S. pyogenes Cas9 sequence (SEQ ID NO:2), e.g., can be substituted with an alanine; and one or more asparagines in an HNH-like domain, for example, at position 870 and/or 879 of the S. pyogenes Cas9 sequence (SEQ ID NO:2) e.g., can be substituted with an alanine. In one embodiment, the eaCas9 differs from wild-type in the HNH-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of S. pyogenes, S. aureus, or S. thermophilus. In one embodiment, the reference Cas9 molecule is the naturally occurring Cas9 molecule having the closest sequence identity or homology.

In certain embodiments, exemplary Cas9 activities comprise one or more of PAM specificity, cleavage activity, and helicase activity. A mutation(s) can be present, e.g., in: one or more RuvC domains, e.g., an N-terminal RuvC domain; an HNH domain; a region outside the RuvC domains and the HNH domain. In one embodiment, a mutation(s) is present in a RuvC domain. In one embodiment, a mutation(s) is present in an HNH domain. In one embodiment, mutations are present in both a RuvC domain and an HNH domain.

Exemplary mutations that may be made in the RuvC domain or HNH domain with reference to the S. pyogenes Cas9 sequence include: D10A, E762A, H840A, N854A, N863A and/or D986A. Exemplary mutations that may be made in the RuvC domain with reference to the S. aureus Cas9 sequence include N580A.

In one embodiment, a Cas9 molecule is an eiCas9 molecule comprising one or more differences in a RuvC domain and/or in an HNH domain as compared to a reference Cas9 molecule, and the eiCas9 molecule does not cleave a nucleic acid, or cleaves with significantly less efficiency than does wild type, e.g., when compared with wild type in a cleavage assay, e.g., as described herein, cuts with less than 50, 25, 10, or 1% of a reference Cas9 molecule, as measured by an assay described herein.

Whether or not a particular sequence, e.g., a substitution, may affect one or more activity, such as targeting activity, cleavage activity, etc., can be evaluated or predicted, e.g., by evaluating whether the mutation is conservative. In one embodiment, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

In one embodiment, a Cas9 molecule comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of *S aureus* or *S. pyogenes* as follows: its ability to modulate, e.g., decreased or increased, cleavage of a double stranded break (endonuclease and/or exonuclease activity), e.g., as compared to a naturally occurring Cas9 molecule (e.g., a Cas9 molecule of *S aureus* or *S. pyogenes*); its ability to modulate, e.g., decreased or increased, cleavage of a single-strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of *S aureus* or *S. pyogenes*); or the ability to cleave a nucleic acid molecule, e.g., a double stranded or single stranded nucleic acid molecule, can be eliminated. In certain embodiments, the nickase is *S. aureus* Cas9-derived nickase comprising the sequence of SEQ ID NO: 214 (D10A) or SEQ ID NO: 215 (N580A) (Friedland 2015).

In certain embodiments, the altered Cas9 molecule is an eaCas9 molecule comprising one or more of the following activities: cleavage activity associated with a RuvC domain; cleavage activity associated with an HNH domain; cleavage activity associated with an HNH domain and cleavage activity associated with a RuvC domain.

In one embodiment, the altered Cas9 molecule is an eiCas9 molecule which does not cleave a nucleic acid molecule (either double stranded or single stranded nucleic acid molecules) or cleaves a nucleic acid molecule with significantly less efficiency, e.g., less than 20, 10, 5, 1 or 0.1% of the cleavage activity of a reference Cas9 molecule, e.g., as measured by an assay described herein. The reference Cas9 molecule can be a naturally occurring unmodified Cas9 molecule, e.g., a naturally occurring Cas9 molecule such as a Cas9 molecule of *S. pyogenes, S. thermophilus, S. aureus, C. jejuni* or *N. meningitidis*. In one embodiment, the reference Cas9 molecule is the naturally occurring Cas9 molecule having the closest sequence identity or homology. In one embodiment, the eiCas9 molecule lacks substantial cleavage activity associated with a RuvC domain and cleavage activity associated with an HNH domain.

In certain embodiments, the altered Cas9 molecule or Cas9 polypeptide, e.g., an eaCas9 molecule or eaCas9 polypeptide, can be a fusion, e.g., of two of more different Cas9 molecules, e.g., of two or more naturally occurring Cas9 molecules of different species. For example, a fragment of a naturally occurring Cas9 molecule of one species can be fused to a fragment of a Cas9 molecule of a second species. As an example, a fragment of a Cas9 molecule of *S. pyogenes* comprising an N-terminal RuvC-like domain can be fused to a fragment of Cas9 molecule of a species other than *S. pyogenes* (e.g., *S. thermophilus*) comprising an HNH-like domain.

Cas9 with Altered or No PAM Recognition

Naturally-occurring Cas9 molecules can recognize specific PAM sequences, for example the PAM recognition sequences described above for, e.g., *S. pyogenes, S. thermophilus, S. nutans*, and *S. aureus*.

In certain embodiments, a Cas9 molecule or Cas9 polypeptide has the same PAM specificities as a naturally occurring Cas9 molecule. In other embodiments, a Cas9 molecule or Cas9 polypeptide has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule or Cas9 polypeptide recognizes in order to decrease off-target sites and/or improve specificity; or eliminate a PAM recognition requirement. In certain embodiments, a Cas9 molecule or Cas9 polypeptide can be altered, e.g., to increase length of PAM recognition sequence and/or improve Cas9 specificity to high level of identity (e.g., 98%, 99% or 100% match between gRNA and a PAM sequence), e.g., to decrease off-target sites and/or increase specificity. In certain embodiments, the length of the PAM recognition sequence is at least 4, 5, 6, 7, 8, 9, 10 or 15 amino acids in length. In one embodiment, the Cas9 specificity requires at least 90%, 95%, 96%, 97%, 98%, 99% or more homology between the gRNA and the PAM sequence. Cas9 molecules or Cas9 polypeptides that recognize different PAM sequences and/or have reduced off-target activity can be generated using directed evolution. Exemplary methods and systems that can be used for directed evolution of Cas9 molecules are described (see, e.g., Esvelt 2011). Candidate Cas9 molecules can be evaluated, e.g., by methods described below.

Size-Optimized Cas9 Molecules

Engineered Cas9 molecules and engineered Cas9 polypeptides described herein include a Cas9 molecule or Cas9 polypeptide comprising a deletion that reduces the size of the molecule while still retaining desired Cas9 properties, e.g., essentially native conformation, Cas9 nuclease activity, and/or target nucleic acid molecule recognition. Provided herein are Cas9 molecules or Cas9 polypeptides comprising one or more deletions and optionally one or more linkers, wherein a linker is disposed between the amino acid residues that flank the deletion. Methods for identifying suitable deletions in a reference Cas9 molecule, methods for generating Cas9 molecules with a deletion and a linker, and methods for using such Cas9 molecules will be apparent to one of ordinary skill in the art upon review of this document.

A Cas9 molecule, e.g., a *S. aureus* or *S. pyogenes* Cas9 molecule, having a deletion is smaller, e.g., has reduced number of amino acids, than the corresponding naturally-occurring Cas9 molecule. The smaller size of the Cas9 molecules allows increased flexibility for delivery methods, and thereby increases utility for genome-editing. A Cas9 molecule can comprise one or more deletions that do not substantially affect or decrease the activity of the resultant Cas9 molecules described herein. Activities that are retained in the Cas9 molecules comprising a deletion as described herein include one or more of the following:

a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which in one embodiment is the presence of two nickase activities; an endonuclease activity; an exonuclease activity; a helicase activity, i.e., the ability to unwind the helical structure of a double stranded nucleic acid; and recognition activity of a nucleic acid molecule, e.g., a target nucleic acid or a gRNA molecule.

Activity of the Cas9 molecules described herein can be assessed using the activity assays described herein or in the art.

Identifying Regions Suitable for Deletion

Suitable regions of Cas9 molecules for deletion can be identified by a variety of methods. Naturally-occurring orthologous Cas9 molecules from various bacterial species can be modeled onto the crystal structure of S. *pyogenes* Cas9 (Nishimasu 2014) to examine the level of conservation across the selected Cas9 orthologs with respect to the three-dimensional conformation of the protein. Less conserved or unconserved regions that are spatially located distant from regions involved in Cas9 activity, e.g., interface with the target nucleic acid molecule and/or gRNA, represent regions or domains are candidates for deletion without substantially affecting or decreasing Cas9 activity.

Nucleic Acids Encoding Cas9 Molecules

Nucleic acids encoding the Cas9 molecules or Cas9 polypeptides, e.g., an eaCas9 molecule or eaCas9 polypeptides are provided herein. Exemplary nucleic acids encoding Cas9 molecules or Cas9 polypeptides have been described previously (see, e.g., Cong 2013; Wang 2013; Mali 2013; Jinek 2012).

In one embodiment, a nucleic acid encoding a Cas9 molecule or Cas9 polypeptide can be a synthetic nucleic acid sequence. For example, the synthetic nucleic acid molecule can be chemically modified, e.g., as described herein. In one embodiment, the Cas9 mRNA has one or more (e.g., all of the following properties: it is capped, polyadenylated, substituted with 5-methylcytidine and/or pseudouridine.

In addition, or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

In addition, or alternatively, a nucleic acid encoding a Cas9 molecule or Cas9 polypeptide may comprise a nuclear localization sequence (NLS). Nuclear localization sequences are known in the art.

An exemplary codon optimized nucleic acid sequence encoding a Cas9 molecule of S. *pyogenes* is set forth in SEQ ID NO: 22. The corresponding amino acid sequence of an S. *pyogenes* Cas9 molecule is set forth in SEQ ID NO: 23.

Exemplary codon optimized nucleic acid sequence encoding a Cas9 molecule of S. *aureus* is set forth in SEQ ID NO: 26, 39, 213 and 214.

If any of the above Cas9 sequences are fused with a peptide or polypeptide at the C-terminus, it is understood that the stop codon will be removed.

Other Cas Molecules and Cas Polypeptides

Various types of Cas molecules or Cas polypeptides can be used to practice the inventions disclosed herein. In some embodiments, Cas molecules of Type II Cas systems are used. In other embodiments, Cas molecules of other Cas systems are used. For example, Type I or Type III Cas molecules may be used. Exemplary Cas molecules (and Cas systems) have been described previously (see, e.g., Haft 2005; Makarova 2011). Exemplary Cas molecules (and Cas systems) are also shown in Table 4.

TABLE 4

Cas Systems

| Gene name‡ | System type or subtype | Name from Haft 2005§ | Structure of encoded protein (PDB accessions)¶ | Families (and superfamily) of encoded protein#** | Representatives |
|---|---|---|---|---|---|
| cas1 | Type I<br>Type II<br>Type III | cas1 | 3GOD, 3LFX and 2YZS | COG1518 | SERP2463, SPy1047 and ygbT |
| cas2 | Type I<br>Type II<br>Type III | cas2 | 2IVY, 2I8E and 3EXC | COG1343 and COG3512 | SERP2462, SPy1048, SPy1723 (N-terminal domain) and ygbF |
| cas3' | Type I‡‡ | cas3 | NA | COG1203 | APE1232 and ygcB |
| cas3" | Subtype I-A<br>Subtype I-B | NA | NA | COG2254 | APE1231 and BH0336 |
| cas4 | Subtype I-A<br>Subtype I-B<br>Subtype I-C<br>Subtype I-D<br>Subtype II-B | cas4 and csa1 | NA | COG1468 | APE1239 and BH0340 |
| cas5 | Subtype I-A<br>Subtype I-B<br>Subtype I-C<br>Subtype I-E | cas5a, cas5d, cas5e, cas5h, cas5p, cas5t and cmx5 | 3KG4 | COG1688 (RAMP) | APE1234, BH0337, devS and ygcI |
| cas6 | Subtype I-A<br>Subtype I-B<br>Subtype I-D<br>Subtype III-A• Subtype III-B | cas6 and cmx6 | 3I4H | COG1583 and COG5551 (RAMP) | PF1131 and slr7014 |
| cas6e | Subtype I-E | cse3 | 1WJ9 | (RAMP) | ygcH |
| cas6f | Subtype I-F | csy4 | 2XLJ | (RAMP) | y1727 |
| cas7 | Subtype I-A<br>Subtype I-B<br>Subtype I-C<br>Subtype I-E | csa2, csd2, cse4, csh2, csp1 and cst2 | NA | COG1857 and COG3649 (RAMP) | devR and ygcJ |
| cas8a1 | Subtype I-A‡‡ | cmx1, cst1, csx8, csx13 and CXXC-CXXC | NA | BH0338-like | LA3191§§ and PG2018§§ |

TABLE 4-continued

Cas Systems

| Gene name‡ | System type or subtype | Name from Haft 2005§ | Structure of encoded protein (PDB accessions)¶ | Families (and superfamily) of encoded protein#** | Representatives |
|---|---|---|---|---|---|
| cas8a2 | Subtype I-A‡‡ | csa4 and csx9 | NA | PH0918 | AF0070, AF1873, MJ0385, PF0637, PH0918 and SSO1401 |
| cas8b | Subtype I-B‡‡ | csh1 and TM1802 | NA | BH0338-like | MTH1090 and TM1802 |
| cas8c | Subtype I-C‡‡ | csd1 and csp2 | NA | BH0338-like | BH0338 |
| cas9 | Type II‡‡ | csn1 and csx12 | NA | COG3513 | FTN_0757 and SPy1046 |
| cas10 | Type III‡‡ | cmr2, csm1 and csx11 | NA | COG1353 | MTH326, Rv2823c§§ and TM1794§§ |
| cas10d | Subtype I-D‡‡ | csc3 | NA | COG1353 | slr7011 |
| csy1 | Subtype I-F‡‡ | csy1 | NA | y1724-like | y1724 |
| csy2 | Subtype I-F | csy2 | NA | (RAMP) | y1725 |
| csy3 | Subtype I-F | csy3 | NA | (RAMP) | y1726 |
| cse1 | Subtype I-E‡‡ | cse1 | NA | YgcL-like | ygcL |
| cse2 | Subtype I-E | cse2 | 2ZCA | YgcK-like | ygcK |
| csc1 | Subtype I-D | csc1 | NA | alr1563-like (RAMP) | alr1563 |
| csc2 | Subtype I-D | csc1 and csc2 | NA | COG1337 (RAMP) | slr7012 |
| csa5 | Subtype I-A | csa5 | NA | AF1870 | AF1870, MJ0380, PF0643 and SSO1398 |
| csn2 | Subtype II-A | csn2 | NA | SPy1049-like | SPy1049 |
| csm2 | Subtype III-A‡‡ | csm2 | NA | COG1421 | MTH1081 and SERP2460 |
| csm3 | Subtype III-A | csc2 and csm3 | NA | COG1337 (RAMP) | MTH1080 and SERP2459 |
| csm4 | Subtype III-A | csm4 | NA | COG1567 (RAMP) | MTH1079 and SERP2458 |
| csm5 | Subtype III-A | csm5 | NA | COG1332 (RAMP) | MTH1078 and SERP2457 |
| csm6 | Subtype III-A | APE2256 and csm6 | 2WTE | COG1517 | APE2256 and SSO1445 |
| cmr1 | Subtype III-B | cmr1 | NA | COG1367 (RAMP) | PF1130 |
| cmr3 | Subtype III-B | cmr3 | NA | COG1769 (RAMP) | PF1128 |
| cmr4 | Subtype III-B | cmr4 | NA | COG1336 (RAMP) | PF1126 |
| cmr5 | Subtype III-B‡‡ | cmr5 | 2ZOP and 2OEB | COG3337 | MTH324 and PF1125 |
| cmr6 | Subtype III-B | cmr6 | NA | COG1604 (RAMP) | PF1124 |
| csb1 | Subtype I-U | GSU0053 | NA | (RAMP) | Balac_1306 and GSU0053 |
| csb2 | Subtype I-U§§ | NA | NA | (RAMP) | Balac_1305 and GSU0054 |
| csb3 | Subtype I-U | NA | NA | (RAMP) | Balac_1303§§ |
| csx17 | Subtype I-U | NA | NA | NA | Btus_2683 |
| csx14 | Subtype I-U | NA | NA | NA | GSU0052 |
| csx10 | Subtype I-U | csx10 | NA | (RAMP) | Caur_2274 |
| csx16 | Subtype III-U | VVA1548 | NA | NA | VVA1548 |
| csaX | Subtype III-U | csaX | NA | NA | SSO1438 |
| csx3 | Subtype III-U | csx3 | NA | NA | AF1864 |
| csx1 | Subtype III-U | csa3, csx1, csx2, DXTHG, NE0113 and TIGR02710 | 1XMX and 2I71 | COG1517 and COG4006 | MJ1666, NE0113, PF1127 and TM1812 |
| csx15 | Unknown | NA | NA | TTE2665 | TTE2665 |
| csf1 | Type U | csf1 | NA | NA | AFE_1038 |
| csf2 | Type U | csf2 | NA | (RAMP) | AFE_1039 |

TABLE 4-continued

Cas Systems

| Gene name‡ | System type or subtype | Name from Haft 2005§ | Structure of encoded protein (PDB accessions)¶ | Families (and superfamily) of encoded protein#** | Representatives |
|---|---|---|---|---|---|
| csf3 | Type U | csf3 | NA | (RAMP) | AFE_1040 |
| csf4 | Type U | csf4 | NA | NA | AFE_1037 |

Functional Analysis of Candidate Molecules

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule have been described previously (Jinek 2012).

Binding and Cleavage Assay: Testing the Endonuclease Activity of Cas9 Molecule

The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and ~3-6 pmol (~20-40 mCi) [γ-32P]-ATP in 1×T4 polynucleotide kinase reaction buffer at 37° C. for 30 min, in a 50 μL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM MgCl2, 1 mM DTT, 5% glycerol) in a total volume of 9 μL. Reactions are initiated by the addition of 1 μl target DNA (10 nM) and incubated for 1 h at 37° C. Reactions are quenched by the addition of 20 μL of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cas9 molecule.

Binding Assay: Testing the Binding of Cas9 Molecule to Target DNA

Exemplary methods for evaluating the binding of Cas9 molecule to target DNA have been described previously (Jinek 2012).

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1×TBE. DNA bands are visualized by UV shadowing, excised, and eluted by soaking gel pieces in DEPC-treated $H_2O$. Eluted DNA is ethanol precipitated and dissolved in DEPC-treated $H_2O$. DNA samples are 5' end labeled with [γ-32P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM $MgCl_2$, 1 mM DTT and 10% glycerol in a total volume of 10 μL. Cas9 protein molecule is programmed with equimolar amounts of pre-annealed gRNA molecule and titrated from 100 pM to 1 μM. Radiolabeled DNA is added to a final concentration of 20 pM. Samples are incubated for 1 h at 37° C. and resolved at 4° C. on an 8% native polyacrylamide gel containing 1×TBE and 5 mM $MgCl_2$. Gels are dried and DNA visualized by phosphorimaging.

Differential Scanning Fluorimetry (DSF)

The thermostability of Cas9 molecule-gRNA ribonucleoprotein (RNP) complexes can be measured via DSF. This technique measures the thermostability of a protein, which can increase under favorable conditions such as the addition of a binding RNA molecule, e.g., a gRNA.

The assay is performed using two different protocols, one to test the best stoichiometric ratio of gRNA:Cas9 protein and another to determine the best solution conditions for RNP formation.

To determine the best solution to form RNP complexes, a 2 μM solution of Cas9 in water+10×SYPRO Orange® (Life Technologies cat #S-6650) and dispensed into a 384 well plate. An equimolar amount of gRNA diluted in solutions with varied pH and salt is then added. After incubating at room temperature for 10 min. and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with 2 μM Cas 9 in optimal buffer from the assay above and incubating at RT for 10 min in a 384 well plate. An equal volume of optimal buffer+10×SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Resection Assay: Testing a Cas9 to Promote Resection

The ability of a Cas9 to promote resection can be evaluated by measuring the levels of single stranded DNA at specific double strand break sites in human cells using quantitative methods (as described in Zhou 2014). In this assay, a cell line is delivered, e.g., by transfection, a candidate Cas9 or a candidate Cas9 fusion protein. The cells are cultured for a sufficient amount of time to allow nuclease activity and resection to occur. Genomic DNA is carefully extracted using a method in which cells are embedded in low-gelling point agar that protects the DNA from shearing and damage during extraction. The genomic DNA is digested with a restriction enzyme that selectively cuts double-stranded DNA. Primers for quantitative PCR that span up to 5 kb of the double strand break site are designed. The results from the PCR reaction show the levels of single strand DNA detected at each of the primer positions. Thus, the length and the level of resection promoted by the candidate Cas9 or Cas9 fusion protein can be determined from this assay.

Other qualitative assays for identifying the occurrence of resection include the detection of proteins or protein complexes that bind to single-stranded DNA after resection has occurred, e.g., RPA foci, Rad51 foci, or BrDU detection by immunofluorescence. Antibodies for RPA protein and Rad51 are known in the art.

Genome Editing Approaches

Mutations in a target gene may be corrected using one of the approaches discussed herein. In one embodiment, a mutation in a target gene is corrected by homology directed repair (HDR) using an exogenously provided template nucleic acid, referred to herein as "gene correction". In another embodiment, a mutation in a target gene is corrected by homology directed repair without using an exogenously provided template nucleic acid, referred to herein as gene correction.

HDR Repair and Template Nucleic Acids

In certain embodiments of the methods provided herein, HDR-mediated sequence alteration is used to alter and/or correct (e.g., repair or edit) the sequence of one or more nucleotides in a genome (e.g., a point mutation in a target gene). While not wishing to be bound by theory, it is believed that HDR-mediated alteration of a target sequence within a target gene occurs by HDR with an exogenously provided donor template or template nucleic acid in a process referred to herein as gene correction. For example, the donor template or template nucleic acid provides for alteration of the target sequence. It is contemplated that a plasmid donor can be used as a template for homologous recombination. It is further contemplated that a single stranded donor template can be used as a template for alteration of the target sequence by alternate methods of HDR (e.g., single-strand annealing) between the target sequence and the donor template. Donor template-effected alteration of a target sequence depends on cleavage by a Cas9 molecule. Cleavage by Cas9 can comprise a double-strand break or two single-strand breaks.

In one embodiment, the target position or target position regions has at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, or 99% homology with an endogenous homologous sequence.

In one embodiment, the target position region, except for the target position, differs by 1, 2, 3, 4, 5, 10, 25, 50, 100 or fewer, nucleotides with an endogenous homologous sequence.

In one embodiment, the target position region has at least 50%, 60%, 70%, 80%, 90%, 92%, 94%, 96%, 98%, or 99% homology with an endogenous homologous sequence over at least 10, 20, 30, 40, 50, 100, 200, 300, 400, 500, 750, 1,000, 2500, 5000, or 10000 nucleotides.

In one embodiment, the target position region, except for the target position, differs by 1, 2, 3, 4, 5, 10, 25, 50, 100 or fewer, nucleotides with an endogenous homologous sequence over at least 10, 20, 30, 40, 50, 100, 200, 300, 400, 500, 750, 1,000, 2500, 5000, or 10000 nucleotides.

In one embodiment, the endogenous homologous sequence comprises a domain, e.g., a catalytic domain, a domain that binds a target, a structural domain, found in the gene that comprises the target position.

In certain embodiments of the methods provided herein, HDR-mediated alteration is used to alter a single nucleotide in a target sequence. These embodiments may utilize either one double-strand break or two single-strand breaks. In certain embodiments, a single nucleotide alteration is incorporated using (1) one double-strand break, (2) two single-strand breaks, (3) two double-strand breaks with a break occurring on each side of the target position, (4) one double-strand break and two single-strand breaks with the double-strand break and two single-strand breaks occurring on each side of the target position (5) four single-strand breaks with a pair of single stranded breaks occurring on each side of the target position, or (6) one single-strand break.

In certain embodiments wherein a single-stranded template nucleic acid is used, the target position can be altered by alternative HDR.

Donor template-effected alteration of a target position depends on cleavage by a Cas9 molecule. Cleavage by Cas9 can comprise a nick, a double-strand break, or two single-strand breaks, e.g., one on each strand of the target nucleic acid. After introduction of the breaks on the target nucleic acid, resection occurs at the break ends resulting in single stranded overhanging DNA regions.

In canonical HDR, a double-stranded donor template is introduced, comprising homologous sequence to the target nucleic acid that will either be directly incorporated into the target nucleic acid or used as a template to change the sequence of the target nucleic acid. After resection at the break, repair can progress by different pathways, e.g., by the double Holliday junction model (or double-strand break repair, DSBR, pathway) or the synthesis-dependent strand annealing (SDSA) pathway. In the double Holliday junction model, strand invasion by the two single stranded overhangs of the target nucleic acid to the homologous sequences in the donor template occurs, resulting in the formation of an intermediate with two Holliday junctions. The junctions migrate as new DNA is synthesized from the ends of the invading strand to fill the gap resulting from the resection. The end of the newly synthesized DNA is ligated to the resected end, and the junctions are resolved, resulting in the alteration of the target nucleic acid, e.g., incorporation of the altered sequence of the donor template at the corresponding target position. Crossover with the donor template may occur upon resolution of the junctions. In the SDSA pathway, only one single stranded overhang invades the donor template and new DNA is synthesized from the end of the invading strand to fill the gap resulting from resection. The newly synthesized DNA then anneals to the remaining single stranded overhang, new DNA is synthesized to fill in the gap, and the strands are ligated to produce the altered DNA duplex.

In alternative HDR, a single-strand donor template, e.g., template nucleic acid, is introduced. A nick, single-strand break, or double-strand break at the target nucleic acid, for altering a desired target position, is mediated by a Cas9 molecule, e.g., described herein, and resection at the break occurs to reveal single stranded overhangs. Incorporation of the sequence of the template nucleic acid to correct or alter the target position of the target nucleic acid typically occurs by the SDSA pathway, as described above.

Additional details on template nucleic acids are provided in Section IV entitled "Template nucleic acids" in International Application PCT/US2014/057905, now published as WO2015/048577, the entire contents of which are expressly incorporated herein by reference.

In certain embodiments, double-strand cleavage is effected by a Cas9 molecule having cleavage activity associated with an HNH-like domain and cleavage activity associated with a RuvC-like domain, e.g., an N-terminal RuvC-like domain, e.g., a wild type Cas9. Such embodiments require only a single gRNA molecule.

In certain embodiments, one single-strand break, or nick, is effected by a Cas9 molecule having nickase activity, e.g., a Cas9 nickase as described herein. A nicked target nucleic acid can be a substrate for alt-HDR.

In other embodiments, two single-strand breaks, or nicks, are effected by a Cas9 molecule having nickase activity, e.g., cleavage activity associated with an HNH-like domain or cleavage activity associated with an N-terminal RuvC-like domain. Such embodiments usually require two gRNAs, one for placement of each single-strand break. In one embodiment, the Cas9 molecule having nickase activity cleaves the strand to which the gRNA hybridizes, but not the strand that is complementary to the strand to which the gRNA hybridizes. In one embodiment, the Cas9 molecule having nickase activity does not cleave the strand to which the gRNA hybridizes, but rather cleaves the strand that is complementary to the strand to which the gRNA hybridizes.

In certain embodiments, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HNH activity and will cut on the strand to which the gRNA hybridizes (e.g., the complementary strand, which does not have the NGG PAM on it). In other embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA). In other embodiments, a Cas9 molecule having an N863 mutation, e.g., the N863A mutation, mutation can be used as a nickase. N863A inactivates HNH therefore the Cas9 nickase has (only) RuvC activity and cuts on the non-complementary strand (the strand that has the NGG PAM and whose sequence is identical to the gRNA).

In certain embodiments, in which a nickase and two gRNAs are used to position two single-strand nicks, one nick is on the + strand and one nick is on the − strand of the target nucleic acid. The PAMs can be outwardly facing or inwardly facing. The gRNAs can be selected such that the gRNAs are separated by, from about 0-50, 0-100, or 0-200 nucleotides. In one embodiment, there is no overlap between the target sequences that are complementary to the targeting domains of the two gRNAs. In one embodiment, the gRNAs do not overlap and are separated by as much as 50, 100, or 200 nucleotides. In one embodiment, the use of two gRNAs can increase specificity, e.g., by decreasing off-target binding (Ran 2013).

In certain embodiments, a single nick can be used to induce HDR, e.g., alt-HDR. It is contemplated herein that a single nick can be used to increase the ratio of HR to NHEJ at a given cleavage site. In certain embodiments, a single-strand break is formed in the strand of the target nucleic acid to which the targeting domain of said gRNA is complementary. In certain embodiments, a single-strand break is formed in the strand of the target nucleic acid other than the strand to which the targeting domain of said gRNA is complementary.

Placement of Double-Strand or Single-Strand Breaks Relative to the Target Position A double-strand break or single-strand break in one of the strands should be sufficiently close to target position that an alteration is produced in the desired region, e.g., correction of a mutation occurs. In certain embodiments, the distance is not more than 50, 100, 200, 300, 350 or 400 nucleotides. While not wishing to be bound by theory, in certain embodiments, it is believed that the break should be sufficiently close to target position such that the target position is within the region that is subject to exonuclease-mediated removal during end resection. If the distance between the target position and a break is too great, the sequence desired to be altered may not be included in the end resection and, therefore, may not be altered, as donor sequence, either exogenously provided donor sequence or endogenous genomic donor sequence, in some embodiments is only used to alter sequence within the end resection region.

In certain embodiments, the gRNA targeting domain is configured such that a cleavage event, e.g., a double-strand or single-strand break, is positioned within 1, 2, 3, 4, 5, 10, 15, 20, 25, 30, 35, 40, 45, 50, 60, 70, 80, 90, 100, 150 or 200 nucleotides of the region desired to be altered, e.g., a mutation. The break, e.g., a double-strand or single-strand break, can be positioned upstream or downstream of the region desired to be altered, e.g., a mutation. In some embodiments, a break is positioned within the region desired to be altered, e.g., within a region defined by at least two mutant nucleotides. In some embodiments, a break is positioned immediately adjacent to the region desired to be altered, e.g., immediately upstream or downstream of a mutation.

In certain embodiments, a single-strand break is accompanied by an additional single-strand break, positioned by a second gRNA molecule, as discussed below. For example, the targeting domains bind configured such that a cleavage event, e.g., the two single-strand breaks, are positioned within 1, 2, 3, 4, 5, 10, 15, 20, 25, 30, 35, 40, 45, 50, 60, 70, 80, 90, 100, 150 or 200 nucleotides of a target position. In one embodiment, the first and second gRNA molecules are configured such that when guiding a Cas9 nickase, a single-strand break is accompanied by an additional single-strand break, positioned by a second gRNA, sufficiently close to one another to result in alteration of the desired region. In one embodiment, the first and second gRNA molecules are configured such that a single-strand break positioned by said second gRNA is within 10, 20, 30, 40, or 50 nucleotides of the break positioned by said first gRNA molecule, e.g., when the Cas9 is a nickase. In one embodiment, the two gRNA molecules are configured to position cuts at the same position, or within a few nucleotides of one another, on different strands, e.g., essentially mimicking a double-strand break.

In certain embodiments, in which a gRNA (unimolecular (or chimeric) or modular gRNA) and Cas9 nuclease induce a double-strand break for the purpose of inducing HDR-mediated alteration, the cleavage site is between 0-200 bp (e.g., 0-175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In certain embodiments, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In certain embodiments, one can promote HDR by using nickases to generate a break with overhangs. While not wishing to be bound by theory, the single stranded nature of the overhangs can enhance the cell's likelihood of repairing the break by HDR as opposed to, e.g., NHEJ. Specifically, in certain embodiments, HDR is promoted by selecting a first gRNA that targets a first nickase to a first target sequence, and a second gRNA that targets a second nickase to a second target sequence which is on the opposite DNA strand from the first target sequence and offset from the first nick.

In certain embodiment, the targeting domain of a gRNA molecule is configured to position a cleavage event sufficiently far from a preselected nucleotide, e.g., the nucleotide of a coding region, such that the nucleotide is not altered. In certain embodiments, the targeting domain of a gRNA molecule is configured to position an intronic cleavage event sufficiently far from an intron/exon border, or naturally occurring splice signal, to avoid alteration of the exonic sequence or unwanted splicing events. The gRNA molecule may be a first, second, third and/or fourth gRNA molecule, as described herein.

Placement of a First Break and a Second Break Relative to Each Other

In certain embodiments, a double-strand break can be accompanied by an additional double-strand break, positioned by a second gRNA molecule, as is discussed below.

In certain embodiments, a double-strand break can be accompanied by two additional single-strand breaks, positioned by a second gRNA molecule and a third gRNA molecule.

In certain embodiments, a first and second single-strand breaks can be accompanied by two additional single-strand breaks positioned by a third gRNA molecule and a fourth gRNA molecule.

When two or more gRNAs are used to position two or more cleavage events, e.g., double-strand or single-strand breaks, in a target nucleic acid, it is contemplated that the two or more cleavage events may be made by the same or different Cas9 proteins. For example, when two gRNAs are used to position two double stranded breaks, a single Cas9 nuclease may be used to create both double stranded breaks. When two or more gRNAs are used to position two or more single stranded breaks (nicks), a single Cas9 nickase may be used to create the two or more nicks. When two or more gRNAs are used to position at least one double stranded break and at least one single stranded break, two Cas9 proteins may be used, e.g., one Cas9 nuclease and one Cas9 nickase. It is contemplated that when two or more Cas9 proteins are used that the two or more Cas9 proteins may be delivered sequentially to control specificity of a double stranded versus a single stranded break at the desired position in the target nucleic acid.

In some embodiments, the targeting domain of the first gRNA molecule and the targeting domain of the second gRNA molecules are complementary to opposite strands of the target nucleic acid molecule. In some embodiments, the gRNA molecule and the second gRNA molecule are configured such that the PAMs are oriented outward. In some embodiments, the gRNA molecule and the second gRNA molecule are configured such that the PAMs are oriented inward.

In certain embodiments, two gRNA are selected to direct Cas9-mediated cleavage at two positions that are a preselected distance from each other. In certain embodiments, the two points of cleavage are on opposite strands of the target nucleic acid. In some embodiments, the two cleavage points form a blunt ended break, and in other embodiments, they are offset so that the DNA ends comprise one or two overhangs (e.g., one or more 5' overhangs and/or one or more 3' overhangs). In some embodiments, each cleavage event is a nick. In some embodiments, the nicks are close enough together that they form a break that is recognized by the double stranded break machinery (as opposed to being recognized by, e.g., the SSBr machinery). In certain embodiments, the nicks are far enough apart that they create an overhang that is a substrate for HDR, i.e., the placement of the breaks mimics a DNA substrate that has experienced some resection. For instance, in some embodiments the nicks are spaced to create an overhang that is a substrate for processive resection. In some embodiments, the two breaks are spaced within 25-65 nucleotides of each other. The two breaks may be, e.g., about 25, 30, 35, 40, 45, 50, 55, 60 or 65 nucleotides of each other. The two breaks may be, e.g., at least about 25, 30, 35, 40, 45, 50, 55, 60 or 65 nucleotides of each other. The two breaks may be, e.g., at most about 30, 35, 40, 45, 50, 55, 60 or 65 nucleotides of each other. In embodiments, the two breaks are about 25-30, 30-35, 35-40, 40-45, 45-50, 50-55, 55-60, or 60-65 nucleotides of each other.

In some embodiments, the break that mimics a resected break comprises a 3' overhang (e.g., generated by a DSB and a nick, where the nick leaves a 3' overhang), a 5' overhang (e.g., generated by a DSB and a nick, where the nick leaves a 5' overhang), a 3' and a 5' overhang (e.g., generated by three cuts), two 3' overhangs (e.g., generated by two nicks that are offset from each other), or two 5' overhangs (e.g., generated by two nicks that are offset from each other).

In certain embodiments, in which two gRNAs (independently, unimolecular (or chimeric) or modular gRNA) complexing with Cas9 nickases induce two single-strand breaks for the purpose of inducing HDR-mediated alteration (e.g., correction), the closer nick is between 0-200 bp (e.g., 0-175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, or 75 to 100 bp) away from the target position and the two nicks will ideally be within 25-65 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, 20, 10, or 5 bp away from each other). In certain embodiments, the cleavage site is between 0-100 bp (e.g., 0 to 75, 0 to 50, 0 to 25, 25 to 100, 25 to 75, 25 to 50, 50 to 100, 50 to 75, or 75 to 100 bp) away from the target position.

In some embodiments, two gRNAs, e.g., independently, unimolecular (or chimeric) or modular gRNA, are configured to position a double-strand break on both sides of a target position. In other embodiments, three gRNAs, e.g., independently, unimolecular (or chimeric) or modular gRNA, are configured to position a double-strand break (i.e., one gRNA complexes with a Cas9 nuclease) and two single-strand breaks or paired single stranded breaks (i.e., two gRNAs complex with Cas9 nickases) on either side of the target position. In other embodiments, four gRNAs, e.g., independently, unimolecular (or chimeric) or modular gRNA, are configured to generate two pairs of single stranded breaks (i.e., two pairs of two gRNA molecules complex with Cas9 nickases) on either side of the target position. The double-strand break(s) or the closer of the two single-strand nicks in a pair will ideally be within 0-500 bp of the target position (e.g., no more than 450, 400, 350, 300, 250, 200, 150, 100, 50 or 25 bp from the target position). When nickases are used, the two nicks in a pair are, in certain embodiments, within 25-65 bp of each other (e.g., between 25 to 55, 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, 20, or 10 bp).

When two gRNAs are used to target Cas9 molecules to breaks, different combinations of Cas9 molecules are envisioned. In some embodiments, a first gRNA is used to target a first Cas9 molecule to a first target position, and a second gRNA is used to target a second Cas9 molecule to a second target position. In some embodiments, the first Cas9 molecule creates a nick on the first strand of the target nucleic acid, and the second Cas9 molecule creates a nick on the opposite strand, resulting in a double stranded break (e.g., a blunt ended cut or a cut with overhangs).

Different combinations of nickases can be chosen to target one single stranded break to one strand and a second single stranded break to the opposite strand. When choosing a combination, one can take into account that there are nickases having one active RuvC-like domain, and nickases having one active HNH domain. In certain embodiments, a RuvC-like domain cleaves the non-complementary strand of the target nucleic acid molecule. In certain embodiments, an HNH-like domain cleaves a single stranded complementary domain, e.g., a complementary strand of a double stranded nucleic acid molecule. Generally, if both Cas9 molecules have the same active domain (e.g., both have an active RuvC domain or both have an active HNH domain), one will choose two gRNAs that bind to opposite strands of the target. In more detail, in some embodiments, a first gRNA is complementary with a first strand of the target nucleic acid and binds a nickase having an active RuvC-like domain and causes that nickase to cleave the strand that is non-complementary to that first gRNA, i.e., a second strand of the target nucleic acid; and a second gRNA is complementary with a second strand of the target nucleic acid and binds a nickase having an active RuvC-like domain and causes that nickase to cleave the strand that is non-complementary to that second gRNA, i.e., the first strand of the target nucleic acid. Conversely, In some embodiments, a first gRNA is complementary with a first strand of the target nucleic acid and binds a nickase having an active HNH domain and causes that nickase to cleave the strand that is complementary to that first gRNA, i.e., a first strand of the target nucleic acid; and a second gRNA is complementary with a second strand of the target nucleic acid and binds a nickase having an active HNH domain and causes that nickase to cleave the strand that is complementary to that second gRNA, i.e., the second strand of the target nucleic acid. In another arrangement, if one Cas9 molecule has an active RuvC-like domain and the other Cas9 molecule has an active HNH domain, the gRNAs for both Cas9 molecules can be complementary to the same strand of the target nucleic acid, so that the Cas9 molecule with the active RuvC-like domain will cleave the non-complementary strand and the Cas9 molecule with the HNH domain will cleave the complementary strand, resulting in a double stranded break.

In one embodiment, the cleavage event comprises one or more breaks, e.g., one or more single-strand breaks, one or more double-strand breaks, or a combination thereof.

In one embodiment, the cleavage event comprises any one of the following: (a) one single-strand break; (b) two single-strand breaks; (c) three single-strand breaks; (d) four single-strand breaks; (e) one double-strand break; (f) two double-strand breaks; (g) one single-strand break and one double-strand break; (h) two single-strand breaks and one double-strand break; or (i) any combination thereof.

In one embodiment, the gRNA molecule and the second gRNA molecule position a cleavage event on each strand of a target nucleic acid.

In one embodiment, the cleavage event flanks the target position, and wherein the terminus (created by the cleavage event) closest to the target position, for each cleavage event, is a 5' terminus, e.g., resulting in a 5' overhang.

While not wishing to be bound by theory, it believed that, in one embodiment, the sequence exposed by a cleavage event (e.g., a single-strand cleavage event) mediated by a gRNA molecule and a Cas9 fusion molecule (e.g., a Cas9 nickase, e.g., a Cas9 molecule containing D10A or N863A mutation) may affect (e.g., increase or decrease) gene correction efficiency. For example, the sequence exposed by the cleavage event can include a 5' overhang, a 3' overhang, a product of the nucleolytic processing of a 5' overhang, a product of the nucleolytic processing of a 3' overhang, or any combination thereof. In one embodiment, the exposed sequence comprises or consists of a 5' overhang. In another embodiment, the exposed sequence comprises or consists of a 3' overhang. In one embodiment, the exposed sequence comprises or consists of a product of the nucleolytic processing of a 5' overhang. In another embodiment, the exposed sequence comprises or consists of a product of the nucleolytic processing of a 3' overhang.

In one embodiment, the 5' overhang is between 1 and 20000 nucleotides, 5 and 20000 nucleotides, 10 and 20000 nucleotides, 20 and 20000 nucleotides, 30 and 20000 nucleotides, between 35 and 20000 nucleotides, between 40 and 20000 nucleotides, between 50 and 20000 nucleotides, between 1000 and 10000 nucleotides, or between 500 and 5000 nucleotides in length, e.g., between 1 and 100 nucleotides, between 1 and 50 nucleotides, between 1 and 25 nucleotides, between 40 and 60 nucleotides, between 40 and 55 nucleotides, or between 45 and 50 nucleotides in length, e.g., at least about 1, 5, 10, 20, 30, 35, 40, 45, 50, 75, 100, 200, 300, 400, 500, 750, 1000, 2000, 3000, 4000, 5000, 6000, 7000, 8000, 9000, 10000, or 15000 nucleotides in length. The sequence exposed by the Cas9 fusion molecule/gRNA molecule mediated cleavage event can constitute a substrate used for homology search in gene correction.

In one embodiment, the exposed sequence differs by 1, 2, 3, 4, 5, 10, 25, 50, 100 or fewer, nucleotides with an endogenous homologous sequence. In one embodiment, the exposed sequence has at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, or 99% homology with an endogenous homologous sequence over at least 10, 20, 30, 40, 50, 100, 200, 300, 400, 500, 750, 1000, 2500, 5000, or 10000 nucleotides. In one embodiment, the exposed sequence differs by 1, 2, 3, 4, 5, 10, 25, 50, 100 or fewer, nucleotides with an endogenous homologous sequence over at least 10, 20, 30, 40, 50, 100, 200, 300, 400, 500, 750, 1000, 2500, 5000, or 10000 nucleotides.

In one embodiment, the cleavage event flanks the target position, and the terminus (created by a cleavage event) closest to the target position, for each cleavage event, is a 3' terminus, e.g., resulting a 3' overhang.

In one embodiment, the 3' overhang is between 1 and 20000 nucleotides, 5 and 20000 nucleotides, 10 and 20000 nucleotides, 20 and 20000 nucleotides, between 30 and 20000 nucleotides, between 35 and 20000 nucleotides, between 40 and 20000 nucleotides, between 50 and 20000 nucleotides, between 1000 and 10000 nucleotides, or between 500 and 5000 nucleotides in length, e.g., between 1 and 100 nucleotides, between 1 and 50 nucleotides, between 1 and 25 nucleotides, between 40 and 60 nucleotides, between 40 and 55 nucleotides, or between 45 and 50 nucleotides in length, e.g., at least about 30, 35, 40, 45, 50, 75, 100, 200, 300, 400, 500, 750, 1000, 2000, 3000, 4000, 5000, 6000, 7000, 8000, 9000, 10000, or 15000 nucleotides in length.

In one embodiment, the distance between the cleavage event and the target position is between 10 and 10000 nucleotides in length, e.g., between 50 and 5000 nucleotides, between 100 and 1000 nucleotides, between 200 and 800 nucleotides, between 400 and 600 nucleotides, between 100 and 500 nucleotides, or between 500 and 1000 nucleotides in length, e.g., at least about 20, 30, 40, 50, 75, 100, 200, 300, 400, 500, 750, 1000, 2000, 3000, 4000, 5000, 6000, 7000, 8000, 9000, or 10000 nucleotides in length.

In one embodiment, the cleavage event comprises a single-strand break, and wherein the distance between the single-strand break and the target position is between 10 and 10000 nucleotides in length, e.g., between 50 and 5000 nucleotides, between 100 and 1000 nucleotides, between 200 and 800 nucleotides, between 400 and 600 nucleotides, between 100 and 500 nucleotides, or between 500 and 1000 nucleotides in length, e.g., at least about 20, 30, 40, 50, 75, 100, 200, 300, 400, 500, 750, 1000, 2000, 3000, 4000, 5000, 6000, 7000, 8000, 9000, or 10000 nucleotides in length.

In one embodiment, the cleavage event comprises two, three or four single-strand breaks, and wherein the distance between each of the single-strand breaks and the target position is between 10 and 10000 nucleotides in length, e.g., between 50 and 5000 nucleotides, between 100 and 1000 nucleotides, between 200 and 800 nucleotides, between 400 and 600 nucleotides, between 100 and 500 nucleotides, or between 500 and 1000 nucleotides in length, e.g., at least about 20, 30, 40, 50, 75, 100, 200, 300, 400, 500, 750, 1000, 2000, 3000, 4000, 5000, 6000, 7000, 8000, 9000, or 10000 nucleotides in length.

In one embodiment, the cleavage event comprises a double-strand break, and wherein the distance between the double-strand break and the target position is between 10 and 10000 nucleotides in length, e.g., between 50 and 5000 nucleotides, between 100 and 1000 nucleotides, between 200 and 800 nucleotides, between 400 and 600 nucleotides, between 100 and 500 nucleotides, or between 500 and 1000 nucleotides in length, e.g., at least about 20, 30, 40, 50, 75, 100, 200, 300, 400, 500, 750, 1000, 2000, 3000, 4000, 5000, 6000, 7000, 8000, 9000, or 10000 nucleotides in length.

In one embodiment, the cleavage event comprises two double-strand breaks, and wherein the distance between each of the double-strand breaks and the target position is between 10 and 10000 nucleotides in length, e.g., between 50 and 5000 nucleotides, between 100 and 1000 nucleotides, between 200 and 800 nucleotides, between 400 and 600 nucleotides, between 100 and 500 nucleotides, or between 500 and 1000 nucleotides in length, e.g., at least about 20, 30, 40, 50, 75, 100, 200, 300, 400, 500, 750, 1000, 2000, 3000, 4000, 5000, 6000, 7000, 8000, 9000, or 10000 nucleotides in length.

In one embodiment, the cleavage event comprises a single-strand break and a double-strand break, wherein the distance between the single-strand break and the target position is between 10 and 10000 nucleotides in length, e.g., between 50 and 5000 nucleotides or between 100 and 1000 nucleotides in length, e.g., about 20, 30, 40, 50, 75, 100, 200, 300, 400, 500, 750, 1000, 2000, 3000, 4000, 5000, 6000, 7000, 8000, 9000, or 10000 nucleotides in length, and wherein the distance between the double-strand break and the target position is between 10 and 10000 nucleotides in length, e.g., between 50 and 5000 nucleotides or between 100 and 1000 nucleotides in length, e.g., at least about 20, 30, 40, 50, 75, 100, 200, 300, 400, 500, 750, 1000, 2000, 3000, 4000, 5000, 6000, 7000, 8000, 9000, or 10000 nucleotides in length.

In one embodiment, the cleavage event comprises two single-strand breaks and a double-strand break, wherein the distance between each of the single-strand breaks and the target position is between 10 and 10000 nucleotides in length, e.g., between 50 and 5000 nucleotides or between 100 and 1000 nucleotides in length, e.g., about 20, 30, 40, 50, 75, 100, 200, 300, 400, 500, 750, 1000, 2000, 3000, 4000, 5000, 6000, 7000, 8000, 9000, or 10000 nucleotides in length, and wherein the distance between the double-strand break and the target position is between 10 and 10000 nucleotides in length, e.g., between 50 and 5000 nucleotides or between 100 and 1000 nucleotides in length, e.g., at least about 20, 30, 40, 50, 75, 100, 200, 300, 400, 500, 750, 1000, 2000, 3000, 4000, 5000, 6000, 7000, 8000, 9000, or 10000 nucleotides in length.

In one embodiment, the cleavage event comprises two or more single-strand breaks, two or more double-strand breaks, or two single-strand breaks and one double-strand breaks, wherein the distance between any of the two breaks that are present on the same strand is between 30 and 20000 nucleotides, 40 and 20000 nucleotides, or 50 and 20000 nucleotides in length, e.g., between 1000 and 10000 nucleotides or between 500 and 5000 nucleotides in length, e.g., between 40 and 60 nucleotides, between 40 and 55 nucleotides, or between 45 and 50 nucleotides in length, e.g., at least about 30, 35, 40, 45, 50, 75, 100, 200, 300, 400, 500, 750, 1000, 2000, 3000, 4000, 5000, 6000, 7000, 8000, 9000, 10000, or 15000 nucleotides in length.

In one embodiment, the cleavage event comprises two or more single-strand breaks, two or more double-strand breaks, or two single-strand breaks and one double-strand breaks, wherein the distance between at least two breaks that are present on different strands is between 30 and 20000 nucleotides, 40 and 20000 nucleotides, or 50 and 20000 nucleotides in length, e.g., between 1000 and 10000 nucleotides or between 500 and 5000 nucleotides in length, e.g., between 40 and 60 nucleotides, between 40 and 55 nucleotides, or between 45 and 50 nucleotides in length, e.g., at least about 30, 35, 40, 45, 50, 75, 100, 200, 300, 400, 500, 750, 1000, 2000, 3000, 4000, 5000, 6000, 7000, 8000, 9000, 10000, or 15000 nucleotides in length.

In one embodiment, the cleavage event comprises two single-strand breaks, wherein the distance between the two single breaks is between 30 and 20000 nucleotides, 40 and 20000 nucleotides, or 50 and 20000 nucleotides in length, e.g., between 1000 and 10000 nucleotides or between 500 and 5000 nucleotides in length, e.g., between 40 and 60 nucleotides, between 40 and 55 nucleotides, or between 45 and 50 nucleotides in length, e.g., at least about 30, 35, 40, 45, 50, 75, 100, 200, 300, 400, 500, 750, 1000, 2000, 3000, 4000, 5000, 6000, 7000, 8000, 9000, 10000, or 15000 nucleotides in length. In one embodiment, the single-strand breaks are present on different strands. In another embodiment, the single-strand breaks are present on the same strand. In one embodiment, the cleavage event further comprises one or more (e.g., two) of single-strand break, double-strand break, or both.

In one embodiment, the Cas9 molecule comprises HNH-like domain cleavage activity but has no, or no significant, N-terminal RuvC-like domain cleavage activity. In one embodiment, the eaCas9 molecule is an HNH-like domain nickase, e.g., the Cas9 molecule comprises a mutation at D10, e.g., D10A. In another embodiment, the eaCas9 molecule comprises N-terminal RuvC-like domain cleavage activity but has no, or no significant, HNH-like domain cleavage activity. In one embodiment, the Cas9 molecule is an N-terminal RuvC-like domain nickase, e.g., the eaCas9 molecule comprises a mutation at N863, e.g., N863A.

In one embodiment, the first gRNA molecule positions a cleavage event on a strand that does not bind to the first gRNA molecule.

In one embodiment, the second gRNA molecule positions a cleavage event on a strand that does not bind to the second gRNA molecule.

In one embodiment, the first gRNA molecule positions a cleavage event on a strand that does not bind to the first gRNA and the second gRNA molecule positions a cleavage event on a strand that does not bind to the second gRNA molecule, and wherein the gRNA molecule and the second gRNA molecule bind to different strands, e.g., resulting in a 3' overhang on each strand.

In one embodiment, the first gRNA molecule positions a cleavage event 5' to the target position on the first strand. In one embodiment, the second gRNA molecule positions a cleavage event 3' to the target position (relative to the target position on the first strand) on the second strand. In one embodiment, the second gRNA molecule positions a cleavage event 5' to the target position on the second strand. In one embodiment, the first gRNA molecule positions a cleavage event 5' to the target position on the first strand, and wherein the second gRNA molecule positions a cleavage event 3' to the target position (relative to the target position on the first strand) on the second strand. In one embodiment, the first gRNA molecule positions a cleavage event 3' to the target position on the first strand.

In one embodiment, the second gRNA molecule positions a cleavage event 5' to the target position (relative to the target position on the first strand) on the second strand. In one embodiment, the first gRNA molecule positions a cleavage event 3' to the target position on the first strand, and wherein the second gRNA molecule positions a cleavage event 5' to the target position (relative to the target position on the first strand) on the second strand. In one embodiment, the first gRNA molecule positions a cleavage event 5' to the target position on the first strand, and wherein the second gRNA molecule positions a cleavage event 5' to the target position (relative to the target position on the first strand) on the second strand, e.g., to produce a 5' overhang. In one embodiment, the first gRNA molecule positions a cleavage event 3' to the target position on the first strand, and wherein the second gRNA molecule positions a cleavage event 3' to the target position (relative to the target position on the first strand) on the second strand, e.g., to produce a 5' overhang. In one embodiment, the first gRNA molecule positions a cleavage event 5' to the target position on the first strand, and wherein the second gRNA molecule positions a cleavage event 5' to the target position (relative to the target position on the first strand) on the second strand, e.g., to produce a 3' overhang. In one embodiment, the first gRNA molecule positions a cleavage event 3' to the target position on the first strand, and wherein the second gRNA molecule positions a cleavage event 3' to the target position (relative to the target position on the first strand) on the second strand, e.g., to produce a 3' overhang. In one embodiment, the target position comprises a mutation. In one embodiment, the mutation is associated with a disease phenotype.

In one embodiment, the first gRNA molecule positions a cleavage event on a strand that binds to the gRNA molecule.

In one embodiment, the second gRNA molecule positions a cleavage event on a strand that binds to the second gRNA molecule.

In one embodiment, the first gRNA molecule positions a cleavage event on a strand that binds to the gRNA and the second gRNA molecule positions a cleavage event on a strand that binds to the second gRNA molecule, and wherein the first gRNA molecule and the second gRNA molecule bind to different strands, e.g., resulting in a 5' overhang on each strand.

In one embodiment, the gRNA molecule, together with the Cas9 molecule (e.g., a nickase), positions a cleavage event on a strand (e.g., a first strand or a second strand), In one embodiment, the gRNA molecule positions a cleavage event 5' to the target position on the first strand. This embodiment allows the use of a single Cas9 molecule, e.g., a single Cas9 molecule that is a nickase (e.g., a Cas9 molecule with a D10A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment, the gRNA molecule positions a cleavage event 3' to the target position (relative to the target position on the first strand) on the second strand. This embodiment allows the use of a single Cas9 molecule, e.g., a single Cas9 molecule that is a nickase (e.g., a Cas9 molecule with a D10A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment, the gRNA molecule positions a cleavage event 3' to the target position on the first strand. This embodiment allows the use of a single Cas9 molecule, e.g., a single Cas9 molecule that is a nickase (e.g., a Cas9 molecule with a D10A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment, the gRNA molecule positions a cleavage event 5' to the target position (relative to the target position on the first strand) on the second strand. This embodiment allows the use of a single Cas9 molecule, e.g., a single Cas9 molecule that is a nickase (e.g., a Cas9 molecule with a D10A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment, the gRNA molecule positions a cleavage event 5' to the target position on the first strand. This embodiment allows the use of a single Cas9 molecule, e.g., a single Cas9 molecule that is a nickase (e.g., a Cas9 molecule with an N863A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment, the gRNA molecule positions a cleavage event 3' to the target position (relative to the target position on the first strand) on the second strand. This embodiment allows the use of a single Cas9 molecule, e.g., a single Cas9 molecule that is a nickase (e.g., a Cas9 molecule with an N863A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment, the gRNA molecule positions a cleavage event 3' to the target position on the first strand. This embodiment allows the use of a single Cas9 molecule, e.g., a single Cas9 molecule that is a nickase (e.g., a Cas9 molecule with an N863A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment, the gRNA molecule positions a cleavage event 5' to the target position (relative to the target position on the first strand) on the second strand. This embodiment allows the use of a single Cas9 molecule, e.g., a single Cas9 molecule that is a nickase (e.g., a Cas9 molecule with an N863A mutation), e.g., to place a single-strand cleavage event sufficiently close to the target position (e.g., within 10000, 9000, 8000, 7000, 6000, 5000, 4000, 3000, 2000, 1000, 800, 600, 500, 400, 300, 200, 100, 75, 50, 40, 30, 20, 10, 5, or 1 bp to the target position).

In one embodiment the gRNA molecule, together with the Cas9 molecule (e.g., a nickase), positions a cleavage event on the strand that binds to the gRNA molecule; and the second gRNA molecule, together with the Cas9 molecule, positions a cleavage event on the strand that binds to the second gRNA molecule, wherein the gRNA molecule and the second gRNA molecule bind to different strands, the gRNA molecule positions a cleavage event 5' to the target position on the first strand, and the second gRNA molecule positions a cleavage event 3' to the target position (relative to the target position on the first strand) on the second strand. This embodiment allows the use of a single Cas9 molecule, e.g., a single Cas9 molecule that is a nickase (e.g., a Cas9 molecule with a D10A mutation), e.g., to place single-strand cleavage events on each side of the target position.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (a nickase), positions a cleavage event on the strand other than the strand that binds to the gRNA molecule; and
the second gRNA molecule, together with the Cas9 molecule, positions a cleavage event on the strand other than the strand that binds to the second gRNA molecule,
wherein:
the gRNA molecule and the second gRNA molecule bind to different strands,
the gRNA molecule positions a cleavage event 5' to the target position on the first strand, and
the second gRNA molecule positions a cleavage event 3' to the target position (relative to the target position on the first strand) on the second strand. This embodiment allows the use of a single Cas9 molecule, e.g., a single Cas9 molecule that is a nickase (e.g., a Cas9 molecule with an N863A mutation), e.g., to place single-strand cleavage events on each side of the target position.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (a nickase), positions a cleavage event on the strand that binds to the gRNA molecule; and
the second gRNA molecule, together with the Cas9 molecule, positions a cleavage event on the strand that binds to the second gRNA molecule,
wherein:
the gRNA molecule and the second gRNA molecule bind to different strands,
the gRNA molecule positions a cleavage event 3' to the target position on the first strand, and
the second gRNA molecule positions a cleavage event 5' to the target position (relative to the target position on the first strand) on the second strand. This embodiment allows the use of a single Cas9 molecule, e.g., a single Cas9 molecule that is a nickase (e.g., a Cas9 molecule with a D10A mutation), e.g., to place single-strand cleavage events on each side of the target position.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (a nickase), positions a cleavage event on the strand other than the strand that binds to the gRNA molecule; and
the second gRNA molecule, together with the Cas9 molecule, positions a cleavage event on the strand other than the strand that binds to the second gRNA molecule,
wherein:
the gRNA molecule and the second gRNA molecule bind to different strands,
the gRNA molecule positions a cleavage event 3' to the target position on the first strand, and
the second gRNA molecule positions a cleavage event 5' to the target position (relative to the target position on the first strand) on the second strand. This embodiment allows the use of a single Cas9 molecule, e.g., a single Cas9 molecule that is a nickase (e.g., a Cas9 molecule with a N863A mutation), e.g., to place single-strand cleavage events on each side of the target position.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (e.g., a nickase), positions a cleavage event on the strand that binds to the gRNA molecule; and
the second gRNA molecule, together with the Cas9 molecule, positions a cleavage event on the strand that binds to the second gRNA molecule,
wherein:
the gRNA molecule and the second gRNA molecule bind to different strands,
the gRNA molecule positions a cleavage event 5' to the target position on the first strand, and
the second gRNA molecule positions a cleavage event 5' to the target position (relative to the target position on the first strand) on the second strand, e.g., to produce a 5' overhang. This embodiment allows the use of a single Cas9 molecule, e.g., a single Cas9 molecule that is a nickase (e.g., a Cas9 molecule with a D10A mutation), e.g., to place single-strand cleavage events on one side of the target position, e.g., to produce a 5' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (a nickase), positions a cleavage event on the strand other than the strand that binds to the gRNA molecule; and
the second gRNA molecule, together with the Cas9 molecule, positions a cleavage event on the strand other than the strand that binds to the second gRNA molecule,
wherein:
the gRNA molecule and the second gRNA molecule bind to different strands,
the gRNA molecule positions a cleavage event 5' to the target position on the first strand, and
the second gRNA molecule positions a cleavage event 5' to the target position (relative to the target position on the first strand) on the second strand, e.g., to produce a 5' overhang. This embodiment allows the use of a single Cas9 molecule, e.g., a single Cas9 molecule that is a nickase (e.g., a Cas9 molecule with an N863A mutation), e.g., to place single-strand cleavage events on each side of the target position, e.g., to produce a 5' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (e.g., a nickase), positions a cleavage event on the strand that binds to the gRNA molecule; and
the second gRNA molecule, together with the Cas9 molecule, positions a cleavage event on the strand that binds to the second gRNA molecule,
wherein:
the gRNA molecule and the second gRNA molecule bind to different strands,
the gRNA molecule positions a cleavage event 3' to the target position on the first strand, and
the second gRNA molecule positions a cleavage event 3' to the target position (relative to the target position on the first strand) on the second strand, e.g., to produce a 5' overhang. This embodiment allows the use of a single Cas9 molecule, e.g., a single Cas9 molecule that is a nickase (e.g., a Cas9 molecule with a D10A mutation), e.g., to place single-strand cleavage events on one side of the target position, e.g., to produce a 5' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (a nickase), positions a cleavage event on the strand other than the strand that binds to the gRNA molecule; and
the second gRNA molecule, together with the Cas9 molecule, positions a cleavage event on the strand other than the strand that binds to the second gRNA molecule,
wherein:
the gRNA molecule and the second gRNA molecule bind to different strands,
the gRNA molecule positions a cleavage event 3' to the target position on the first strand, and
the second gRNA molecule positions a cleavage event 3' to the target position (relative to the target position on the first strand) on the second strand, e.g., to produce a 5' overhang. This embodiment allows the use of a single Cas9 molecule, e.g., a single Cas9 molecule that is a nickase (e.g., a Cas9 molecule with an N863A mutation), e.g., to place single-strand cleavage events on each side of the target position, e.g., to produce a 5' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:
the gRNA molecule, together with the Cas9 molecule (e.g., a nickase), positions a cleavage event on the strand that binds to the gRNA molecule; and
the second gRNA molecule, together with the Cas9 molecule, positions a cleavage event on the strand that binds to the second gRNA molecule,
wherein:
the gRNA molecule and the second gRNA molecule bind to different strands,
the gRNA molecule positions a cleavage event 5' to the target position on the first strand, and
the second gRNA molecule positions a cleavage event 5' to the target position (relative to the target position on the first strand) on the second strand, e.g., to produce a 3' overhang. This embodiment allows the use of a single Cas9 molecule, e.g., a single Cas9 molecule that is a nickase (e.g., a Cas9 molecule with a D10A mutation), e.g., to place single-strand cleavage events on one side of the target position, e.g., to produce a 3' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:

the gRNA molecule, together with the Cas9 molecule (a nickase), positions a cleavage event on the strand other than the strand that binds to the gRNA molecule; and the second gRNA molecule, together with the Cas9 molecule, positions a cleavage event on the strand other than the strand that binds to the second gRNA molecule, wherein:

the gRNA molecule and the second gRNA molecule bind to different strands, the gRNA molecule positions a cleavage event 5' to the target position on the first strand, and the second gRNA molecule positions a cleavage event 5' to the target position (relative to the target position on the first strand) on the second strand, e.g., to produce a 3' overhang. This embodiment allows the use of a single Cas9 molecule, e.g., a single Cas9 molecule that is a nickase (e.g., a Cas9 molecule with an N863A mutation), e.g., to place single-strand cleavage events on each side of the target position, e.g., to produce a 3' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:

the gRNA molecule, together with the Cas9 molecule (e.g., a nickase), positions a cleavage event on the strand that binds to the gRNA molecule; and the second gRNA molecule, together with the Cas9 molecule, positions a cleavage event on the strand that binds to the second gRNA molecule, wherein:

the gRNA molecule and the second gRNA molecule bind to different strands, the gRNA molecule positions a cleavage event 3' to the target position on the first strand, and the second gRNA molecule positions a cleavage event 3' to the target position (relative to the target position on the first strand) on the second strand, e.g., to produce a 3' overhang. This embodiment allows the use of a single Cas9 molecule, e.g., a single Cas9 molecule that is a nickase (e.g., a Cas9 molecule with a D10A mutation), e.g., to place single-strand cleavage events on one side of the target position, e.g., to produce a 3' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

In one embodiment:

the gRNA molecule, together with the Cas9 molecule (a nickase), positions a cleavage event on the strand other than the strand that binds to the gRNA molecule; and the second gRNA molecule, together with the Cas9 molecule, positions a cleavage event on the strand other than the strand that binds to the second gRNA molecule, wherein:

the gRNA molecule and the second gRNA molecule bind to different strands, the gRNA molecule positions a cleavage event 3' to the target position on the first strand, and the second gRNA molecule positions a cleavage event 3' to the target position (relative to the target position on the first strand) on the second strand, e.g., to produce a 3' overhang. This embodiment allows the use of a single Cas9 molecule, e.g., a single Cas9 molecule that is a nickase (e.g., a Cas9 molecule with an N863A mutation), e.g., to place single-strand cleavage events on each side of the target position, e.g., to produce a 3' overhang.

In one embodiment, the cleavage event positioned by the gRNA molecule and the cleavage event positioned by the second gRNA molecule are separated by 10 to 10000, 10 to 5000, 10 to 2500, 10 to 1000, 10 to 750, 10 to 500, 10 to 400, 10 to 300, 10 to 200, 10 to 100, 10 to 75, 10 to 50, or 10 to 25 base pairs.

Homology Arms of the Donor Template

A homology arm should extend at least as far as the region in which end resection may occur, e.g., in order to allow the resected single stranded overhang to find a complementary region within the donor template. The overall length could be limited by parameters such as plasmid size or viral packaging limits. In one embodiment, a homology arm does not extend into repeated elements, e.g., Alu repeats or LINE repeats.

Exemplary homology arm lengths include at least 50, 100, 250, 500, 750, 1000, 2000, 3000, 4000, or 5000 nucleotides. In some embodiments, the homology arm length is 50-100, 100-250, 250-500, 500-750, 750-1000, 1000-2000, 2000-3000, 3000-4000, or 4000-5000 nucleotides.

Target position, as used herein, refers to a site on a target nucleic acid (e.g., the chromosome) that is modified by a Cas9 molecule-dependent process. For example, the target position can be a modified Cas9 molecule cleavage of the target nucleic acid and template nucleic acid directed modification, e.g., correction, of the target position. In one embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In one embodiment, the target position is within a target sequence (e.g., the sequence to which the gRNA binds). In one embodiment, a target position is upstream or downstream of a target sequence (e.g., the sequence to which the gRNA binds).

A template nucleic acid, as that term is used herein, refers to a nucleic acid sequence which can be used in conjunction with a Cas9 molecule and a gRNA molecule to alter the structure of a target position. In certain embodiments, the target nucleic acid is modified to have the some or all of the sequence of the template nucleic acid, typically at or near cleavage site(s). In one embodiment, the template nucleic acid is single stranded. In certain embodiments, the template nucleic acid is double stranded. In certain embodiments, the template nucleic acid is DNA, e.g., double stranded DNA. In other embodiments, the template nucleic acid is single stranded DNA. In certain embodiments, the template nucleic acid is encoded on the same vector backbone, e.g., AAV genome, plasmid DNA, as the Cas9 and gRNA. In one embodiment, the template nucleic acid is excised from a vector backbone in vivo, e.g., it is flanked by gRNA recognition sequences. In certain embodiments, the template nucleic acid comprises endogenous genomic sequence. In certain embodiments, a template nucleic acid is a template nucleic acid covalently linked to the Cas9 molecule. In certain embodiments, a template nucleic acid is a template nucleic acid non-covalently linked to the Cas9 molecule.

In certain embodiments, the template nucleic acid alters the structure of the target position by participating in an HDR event. In certain embodiments, the template nucleic acid alters the sequence of the target position. In certain embodiments, the template nucleic acid results in the incorporation of a modified, or non-naturally occurring base into the target nucleic acid.

Typically, the template sequence undergoes a breakage mediated or catalyzed recombination with the target sequence. In certain embodiments, the template nucleic acid includes sequence that corresponds to a site on the target sequence that is cleaved by an eaCas9 mediated cleavage event. In certain embodiments, the template nucleic acid includes sequence that corresponds to both, a first site on the target sequence that is cleaved in a first Cas9 mediated event, and a second site on the target sequence that is cleaved in a second Cas9 mediated event.

In one embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in the target gene can be used to alter the structure of a target sequence (e.g., to correct a mutation present in a target position of an endogenous target gene). The template sequence can be used to alter an unwanted structure, e.g., an unwanted or mutant nucleotide.

A template nucleic acid typically comprises the following components:

[5' homology arm]-[replacement sequence]-[3' homology arm].

The homology arms provide for recombination into the chromosome, thus replacing the undesired element, e.g., a mutation or signature, with the replacement sequence. In certain embodiments, the homology arms flank the most distal cleavage sites.

In certain embodiments, the 3' end of the 5' homology arm is the position next to the 5' end of the replacement sequence. In one embodiment, the 5' homology arm can extend at least 10, 20, 30, 40, 50, 100, 200, 300, 400, 500, 600, 700, 800, 900, 1000, 1500, 2000, 3000, 4000, or 5000 nucleotides 5' from the 5' end of the replacement sequence.

In certain embodiments, the 5' end of the 3' homology arm is the position next to the 3' end of the replacement sequence. In certain embodiments, the 3' homology arm can extend at least 10, 20, 30, 40, 50, 100, 200, 300, 400, 500, 600, 700, 800, 900, 1000, 1500, 2000, 3000, 4000, or 5000 nucleotides 3' from the 3' end of the replacement sequence.

In certain embodiments, to alter one or more nucleotides at a target position (e.g., to correct a mutation), the homology arms, e.g., the 5' and 3' homology arms, may each comprise about 1000 bp of sequence flanking the most distal gRNAs (e.g., 1000 bp of sequence on either side of the target position (e.g., the mutation).

It is contemplated herein that one or both homology arms may be shortened to avoid including certain sequence repeat elements, e.g., Alu repeats or LINE elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

It is contemplated herein that template nucleic acids for altering the sequence (e.g., correcting a mutation) of a target position may be designed for use as a single-stranded oligonucleotide, e.g., a single-stranded oligodeoxynucleotide (ssODN). When using a ssODN, 5' and 3' homology arms may range up to about 200 bp in length, e.g., at least 25, 50, 75, 100, 125, 150, 175, or 200 bp in length. Longer homology arms are also contemplated for ssODNs as improvements in oligonucleotide synthesis continue to be made. In some embodiments, a longer homology arm is made by a method other than chemical synthesis, e.g., by denaturing a long double stranded nucleic acid and purifying one of the strands, e.g., by affinity for a strand-specific sequence anchored to a solid substrate.

While not wishing to be bound by theory, in certain embodiments alt-HDR proceeds more efficiently when the template nucleic acid has extended homology 5' to the nick (i.e., in the 5' direction of the nicked strand). Accordingly, in some embodiments, the template nucleic acid has a longer homology arm and a shorter homology arm, wherein the longer homology arm can anneal 5' of the nick. In some embodiments, the arm that can anneal 5' to the nick is at least 25, 50, 75, 100, 125, 150, 175, or 200, 300, 400, 500, 600, 700, 800, 900, 1000, 1500, 2000, 3000, 4000, or 5000 nucleotides from the nick or the 5' or 3' end of the replacement sequence. In some embodiments, the arm that can anneal 5' to the nick is at least 10%, 20%, 30%, 40%, or 50% longer than the arm that can anneal 3' to the nick. In some embodiments, the arm that can anneal 5' to the nick is at least 2x, 3x, 4x, or 5x longer than the arm that can anneal 3' to the nick. Depending on whether a ssDNA template can anneal to the intact strand or the nicked strand, the homology arm that anneals 5' to the nick may be at the 5' end of the ssDNA template or the 3' end of the ssDNA template, respectively.

Similarly, in some embodiments, the template nucleic acid has a 5' homology arm, a replacement sequence, and a 3' homology arm, such that the template nucleic acid has extended homology to the 5' of the nick. For example, the 5' homology arm and 3' homology arm may be substantially the same length, but the replacement sequence may extend farther 5' of the nick than 3' of the nick. In some embodiments, the replacement sequence extends at least 10%, 20%, 30%, 40%, 50%, 2x, 3x, 4x, or 5x further to the 5' end of the nick than the 3' end of the nick.

While not wishing to be bound by theory, In some embodiments, alt-HDR proceeds more efficiently when the template nucleic acid is centered on the nick. Accordingly, in some embodiments, the template nucleic acid has two homology arms that are essentially the same size. For instance, the first homology arm of a template nucleic acid may have a length that is within 10%, 9%, 8%, 7%, 6%, 5%, 4%, 3%, 2%, or 1% of the second homology arm of the template nucleic acid.

Similarly, in some embodiments, the template nucleic acid has a 5' homology arm, a replacement sequence, and a 3' homology arm, such that the template nucleic acid extends substantially the same distance on either side of the nick. For example, the homology arms may have different lengths, but the replacement sequence may be selected to compensate for this. For example, the replacement sequence may extend further 5' from the nick than it does 3' of the nick, but the homology arm 5' of the nick is shorter than the homology arm 3' of the nick, to compensate. The converse is also possible, e.g., that the replacement sequence may extend further 3' from the nick than it does 5' of the nick, but the homology arm 3' of the nick is shorter than the homology arm 5' of the nick, to compensate.

Exemplary Template Nucleic Acids

In a preferred embodiment, and in order to increase DNA repair via gene correction, the template nucleic acid is linked to the Cas9 molecule as part of a Cas9 fusion molecule. In certain embodiments, the template nucleic acid is double stranded. In other embodiments, the template nucleic acid is single stranded. In certain embodiments, the template nucleic acid comprises a single stranded portion and a double stranded portion. In certain embodiments, the template nucleic acid comprises about 50 to 100, e.g., 55 to 95, 60 to 90, 65 to 85, or 70 to 80 bp, homology on either side of the nick and/or replacement sequence. In certain embodiments, the template nucleic acid comprises about 50, 55, 60, 65, 70, 75, 80, 85, 90, 95, or 100 bp homology 5' of the nick or replacement sequence, 3' of the nick or replacement sequence, or both 5' and 3' of the nick or replacement sequences.

In certain embodiments, the template nucleic acid comprises about 150 to 200 bp, e.g., 155 to 195, 160 to 190, 165 to 185, or 170 to 180 bp, homology 3' of the nick and/or replacement sequence. In certain embodiments, the template nucleic acid comprises about 150, 155, 160, 165, 170, 175, 180, 185, 190, 195, or 200 bp homology 3' of the nick or replacement sequence. In some embodiments, the template nucleic acid comprises less than about 100, 90, 80, 70, 60, 50, 40, 30, 20, 15, or 10 bp homology 5' of the nick or replacement sequence.

In certain embodiments, the template nucleic acid comprises about 150 to 200 bp, e.g., 155 to 195, 160 to 190, 165 to 185, or 170 to 180 bp, homology 5' of the nick and/or replacement sequence. In certain embodiments, the template nucleic acid comprises about 150, 155, 160, 165, 170, 175, 180, 185, 190, 195, or 200 bp homology 5' of the nick or replacement sequence. In certain embodiments, the template nucleic acid comprises less than about 100, 90, 80, 70, 60, 50, 40, 30, 20, 15, or 10 bp homology 3' of the nick or replacement sequence.

In certain embodiments, the template nucleic acid comprises a nucleotide sequence, e.g., of one or more nucleotides, that will be added to or will template a change in the target nucleic acid. In other embodiments, the template nucleic acid comprises a nucleotide sequence that may be used to modify the target position. In other embodiments, the template nucleic acid comprises a nucleotide sequence, e.g., of one or more nucleotides, that corresponds to wild type sequence of the target nucleic acid, e.g., of the target position.

The template nucleic acid may comprise a replacement sequence. In some embodiments, the template nucleic acid comprises a 5' homology arm. In some embodiments, the template nucleic acid comprises a 3' homology arm.

In certain embodiments, the template nucleic acid is linear double stranded DNA. The length may be, e.g., about 150-200 bp, e.g., about 150, 160, 170, 180, 190, or 200 bp. The length may be, e.g., at least 150, 160, 170, 180, 190, or 200 bp. In some embodiments, the length is no greater than 150, 160, 170, 180, 190, or 200 bp. In some embodiments, a double stranded template nucleic acid has a length of about 160 bp, e.g., about 155-165, 150-170, 140-180, 130-190, 120-200, 110-210, 100-220, 90-230, or 80-240 bp.

The template nucleic acid can be linear single stranded DNA. In certain embodiments, the template nucleic acid is (i) linear single stranded DNA that can anneal to the nicked strand of the target nucleic acid, (ii) linear single stranded DNA that can anneal to the intact strand of the target nucleic acid, (iii) linear single stranded DNA that can anneal to the plus strand of the target nucleic acid, (iv) linear single stranded DNA that can anneal to the minus strand of the target nucleic acid, or more than one of the preceding. The length may be, e.g., about 150-200 nucleotides, e.g., about 150, 160, 170, 180, 190, or 200 nucleotides. The length may be, e.g., at least 150, 160, 170, 180, 190, or 200 nucleotides. In some embodiments, the length is no greater than 150, 160, 170, 180, 190, or 200 nucleotides. In some embodiments, a single stranded template nucleic acid has a length of about 160 nucleotides, e.g., about 155-165, 150-170, 140-180, 130-190, 120-200, 110-210, 100-220, 90-230, or 80-240 nucleotides.

In some embodiments, the template nucleic acid is circular double stranded DNA, e.g., a plasmid. In some embodiments, the template nucleic acid comprises about 500 to 1000 bp of homology on either side of the replacement sequence and/or the nick. In some embodiments, the template nucleic acid comprises about 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 bp of homology 5' of the nick or replacement sequence, 3' of the nick or replacement sequence, or both 5' and 3' of the nick or replacement sequence.

In certain embodiments, one or both homology arms may be shortened to avoid including certain sequence repeat elements, e.g., Alu repeats, LINE elements. For example, a 5' homology arm may be shortened to avoid a sequence repeat element, while a 3' homology arm may be shortened to avoid a sequence repeat element. In some embodiments, both the 5' and the 3' homology arms may be shortened to avoid including certain sequence repeat elements.

In some embodiments, the Cas9 fusion molecule, comprising the template nucleic acid, is in an adenovirus vector, e.g., an AAV vector, e.g., a ssDNA molecule of a length and sequence that allows it to be packaged in an AAV capsid. The vector may be, e.g., less than 5 kb and may contain an ITR sequence that promotes packaging into the capsid. The vector may be integration-deficient. In some embodiments, the template nucleic acid comprises about 150 to 1000 nucleotides of homology on either side of the replacement sequence and/or the nick. In some embodiments, the template nucleic acid comprises about 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at least 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at most 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence.

In some embodiments, the Cas9 fusion molecule, comprising the template nucleic acid, is in a lentiviral vector, e.g., an IDLV (integration deficiency lentivirus). In some embodiments, the template nucleic acid comprises about 500 to 1000 base pairs of homology on either side of the replacement sequence and/or the nick. In some embodiments, the template nucleic acid comprises about 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 bp of homology 5' of the nick or replacement sequence, 3' of the nick or replacement sequence, or both 5' and 3' of the nick or replacement sequence.

In certain embodiments, the template nucleic acid alters the structure of the target position by participating in an HDR event. In some embodiments, the template nucleic acid alters the sequence of the target position. In some embodiments, the template nucleic acid results in the incorporation of a modified, or non-naturally occurring nucleotide base into the target nucleic acid.

Typically, the template sequence undergoes a breakage mediated or catalyzed recombination with the target sequence. In some embodiments, the template nucleic acid includes sequence that corresponds to a site on the target sequence that is cleaved by an eaCas9 mediated cleavage event. In some embodiments, the template nucleic acid includes sequence that corresponds to both, a first site on the target sequence that is cleaved in a first Cas9 mediated event, and a second site on the target sequence that is cleaved in a second Cas9 mediated event.

In some embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introduction of a stop codon, insertion of an amino acid residue, deletion of an amino acid residue, or a nonsense mutation.

In some embodiments, the template nucleic acid can include sequence which results in an alteration in a noncoding sequence, e.g., an alteration in an exon or in a 5' or 3' non-translated or non-transcribed region. Such alterations include an alteration in a control element, e.g., a promoter or enhancer, or an alteration in a cis-acting or trans-acting control element.

In some embodiments, a template nucleic acid having homology with a target position can be used to alter the structure of a target sequence. The template nucleic acid sequence can be used to alter an unwanted structure, e.g., an unwanted or mutant nucleotide.

In some embodiments, shorter homology arms, e.g., 5' and/or 3' homology arms may be used. In certain embodiments, the length of the 5' homology arm is about 5 to about 100 nucleotides. In some embodiments, the length of the 5' homology arm is about 10 to about 150 nucleotides. In some embodiments, the length of the 5' homology arm is about 20 to about 150 nucleotides. In certain embodiments, the length of the 5' homology arm is about 10, 20, 50, 100, 150, 200, 250, 300, 350, 400, 450, 500, 550, 600, 650, 700, 750, 800, 850, 900, 950, 1000, 1100, 1200, or more nucleotides in length.

In certain embodiments, the length of the 3' homology arm is about 5 to about 100 nucleotides. In some embodiments, the length of the 3' homology arm is about 10 to about 150 nucleotides. In some embodiments, the length of the 3' homology arm is about 20 to about 150 nucleotides. In certain embodiments, the length of the 3' homology arm is about 10, 20, 50, 100, 150, 200, 250, 300, 350, 400, 450, 500, 550, 600, 650, 700, 750, 800, 850, 900, 950, 1000, 1100, 1200, or more nucleotides in length.

It is contemplated herein that one or both homology arms may be shortened to avoid including certain sequence repeat elements, e.g., Alu repeats, LINE elements. For example, a 5' homology arm may be shortened to avoid a sequence repeat element. In one embodiment, a 3' homology arm may be shortened to avoid a sequence repeat element. In one embodiment, both the 5' and the 3' homology arms may be shortened to avoid including certain sequence repeat elements. In some embodiments, the length of the 5' homology arm is at least 50 nucleotides in length, but not long enough to include a repeated element. In some embodiments, the length of the 5' homology arm is at least 100 nucleotides in length, but not long enough to include a repeated element. In some embodiments, the length of the 5' homology arm is at least 150 nucleotides in length, but not long enough to include a repeated element. In some embodiments, the length of the 3' homology arm is at least 50 nucleotides in length, but not long enough to include a repeated element. In some embodiments, the length of the 3' homology arm is at least 100 nucleotides in length, but not long enough to include a repeated element. In some embodiments, the length of the 3' homology arm is at least 150 nucleotides in length, but not long enough to include a repeated element.

It is contemplated herein that template nucleic acids for correcting a mutation may be designed for use as a single-stranded oligonucleotide (ssODN), e.g., a single-stranded oligodeoxynucleotide. When using a ssODN, 5' and 3' homology arms may range up to about 200 bp in length, e.g., at least 25, 50, 75, 100, 125, 150, 175, or 200 bp in length. Longer homology arms are also contemplated for ssODNs as improvements in oligonucleotide synthesis continue to be made.

Silent Mutations in the Template Nucleic Acid

It is contemplated herein that Cas9 could potentially cleave donor constructs either prior to or following homology directed repair (e.g., homologous recombination), resulting in a possible non-homologous-end-joining event and further DNA sequence mutation at the chromosomal locus of interest. Therefore, to avoid cleavage of the donor sequence before and/or after Cas9-mediated homology directed repair, in some embodiments, alternate versions of the donor sequence may be used where silent mutations are introduced. These silent mutations may disrupt Cas9 binding and cleavage, but not disrupt the amino acid sequence of the repaired gene. For example, mutations may include those made to a donor sequence to repair the target gene, the mutant form of which can cause disease.

Increasing Gene Correction

In certain embodiments of the methods provided herein, the frequency of preferred repair outcomes generated using a Cas9 fusion molecule described herein may be increased as compared to the frequency of preferred repair outcomes with a Cas9 fusion molecule and a template nucleic acid which are not fused. In some embodiments, the frequency of gene correction resulting from a Cas9 fusion molecule induced-lesion in a target position of a target cell overexpressing a gene correction pathway component is increased at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, or more, as compared to the frequency of gene correction resulting from a Cas9 molecule and a target nucleic acid which are not fused in a target position.

In some embodiments, the frequency of gene correction resulting from a Cas9 fusion molecule induced-lesion in a target position of a target cell overexpressing a gene correction pathway component is increased at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 150%, at least about 200%, at least about 300%, at least about 400%, at least about 500%, at least about 600%, at least about 700%, at least about 800%, at least about 900%, or more.

NHEJ Approaches for Gene Targeting

In certain embodiments of the methods provided herein, NHEJ-mediated deletion is used to delete all or part of a target gene. As described herein, nuclease-induced NHEJ can also be used to remove (e.g., delete) sequences in a gene of interest.

While not wishing to be bound by theory, it is believed that, in certain embodiments, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, e.g., resection, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily reach greater than 100-200 bp. In some embodiments, the deletion is at least about 1, 2, 3, 4, 5, 6, 7, 8, 9, 10, 11, 12, 13, 14, 15, 16, 17, 18, 19, 20, 30, 40, 47, 50, 75, 100, 200, 300, 400, 500, 750, 1000, 2000, 3000, 4000, 5000, 6000, 7000, 8000, 9000, 10000, 15000, 20000, 25000, 30000, 40000, 50000, 60000, 70000, 80000, 90000, 100000, 200000, 300000, 400000, 500000, 600000, 700000, 800000, 900000, 1000000 or more nucleotides in length. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double-strand cleaving eaCas9 molecules and single strand, or nickase, eaCas9 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

Placement of Double-Strand or Single-Strand Breaks Relative to the Target Position In certain embodiments, in which a gRNA and Cas9 nuclease generate a double-strand break for the purpose of inducing NHEJ-mediated indels, a gRNA, e.g., a unimolecular (or chimeric) or modular gRNA molecule, is configured to position one double-strand break in close proximity to a nucleotide of the target position. In one embodiment, the cleavage site is between 0-30 bp away from the target position (e.g., less than 30, 25, 20, 15, 10, 9, 8, 7, 6, 5, 4, 3, 2 or 1 bp from the target position).

In certain embodiments, in which two gRNAs complexing with Cas9 nickases induce two single-strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In certain embodiments, the gRNAs are configured to position cuts at the same position, or within a few nucleotides of one another, on different strands, essentially mimicking a double-strand break. In certain embodiments, the closer nick is between 0-30 bp away from the target position (e.g., less than 30, 25, 20, 15, 10, 9, 8, 7, 6, 5, 4, 3, 2, or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20, or 10 bp). In certain embodiments, the gRNAs are configured to place a single-strand break on either side of a nucleotide of the target position.

Both double-strand cleaving eaCas9 molecules and single strand, or nickase, eaCas9 molecules can be used in the methods and compositions described herein to generate breaks both sides of a target position. Double-strand or paired single-strand breaks may be generated on both sides of a target position to remove the nucleic acid sequence between the two cuts (e.g., the region between the two breaks in deleted). In certain embodiments, two gRNAs, e.g., independently, unimolecular (or chimeric) or modular gRNA, are configured to position a double-strand break on both sides of a target position. In other embodiments, three gRNAs, e.g., independently, unimolecular (or chimeric) or modular gRNA, are configured to position a double-strand break (i.e., one gRNA complexes with a Cas9 nuclease) and two single-strand breaks or paired single-strand breaks (i.e., two gRNAs complex with Cas9 nickases) on either side of the target position. In certain embodiments, four gRNAs, e.g., independently, unimolecular (or chimeric) or modular gRNA, are configured to generate two pairs of single-strand breaks (i.e., two pairs of two gRNAs complex with Cas9 nickases) on either side of the target position. The double-strand break(s) or the closer of the two single-strand nicks in a pair will ideally be within 0-500 bp of the target position (e.g., no more than 450, 400, 350, 300, 250, 200, 150, 100, 50, or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20, or 10 bp).

Targeted Knockdown

Unlike CRISPR/Cas-mediated gene knockout, which permanently eliminates expression by mutating the gene at the DNA level, CRISPR/Cas knockdown allows for temporary reduction of gene expression through the use of artificial transcription factors. Mutating key residues in both DNA cleavage domains of the Cas9 molecule (e.g., the D10A and H840A mutations) results in the generation of a catalytically inactive Cas9 (referred to herein as "eiCas9", which is also known as dead Cas9 or dCas9) molecule. An eiCas9 complexes with a gRNA and localizes to the DNA sequence specified by that gRNA's targeting domain, however, it does not cleave the target DNA. Fusion of the eiCas9 to an effector domain, e.g., a transcription repression domain, enables recruitment of the effector to any DNA site specified by the gRNA. Although an eiCas9 itself can block transcription when recruited to early regions in the coding sequence, more robust repression can be achieved by fusing a transcriptional repression domain (for example KRAB, SID or ERD) to the eiCas9, referred to herein as a "Cas9-repressor", and recruiting the transcriptional repression domain to the target knockdown position, e.g., within 1000 bp of sequence 3' of the start codon or within 500 bp of a promoter region 5' of the start codon of a gene. It is likely that targeting DNAse I hypersensitive sites (DHSs) of the promoter may yield more efficient gene repression or activation because these regions are more likely to be accessible to the eiCas9 and are also more likely to harbor sites for endogenous transcription factors. Especially for gene repression, it is contemplated herein that blocking the binding site of an endogenous transcription factor would aid in downregulating gene expression. In certain embodiments, one or more eiCas9 molecules may be used to block binding of one or more endogenous transcription factors. In some embodiments, an eiCas9 molecule can be fused to a chromatin modifying protein. Altering chromatin status can result in decreased expression of the target gene. One or more eiCas9 molecules fused to one or more chromatin modifying proteins may be used to alter chromatin status.

In one embodiment, a gRNA molecule can be targeted to a known transcription response elements (e.g., promoters, enhancers, etc.), a known upstream activating sequences (UAS), and/or sequences of unknown or known function that are suspected of being able to control expression of the target DNA.

CRISPR/Cas-mediated gene knockdown can be used to reduce expression of an unwanted allele or transcript. Contemplated herein are scenarios wherein permanent destruction of the gene is not ideal. In these scenarios, site-specific repression may be used to temporarily reduce or eliminate expression. It is also contemplated herein that the off-target effects of a Cas9-repressor may be less severe than those of a Cas9-nuclease as a nuclease can cleave any DNA sequence and cause mutations whereas a Cas9-repressor may only have an effect if it targets the promoter region of an actively transcribed gene. However, while nuclease-mediated knockout is permanent, repression may only persist as long as the Cas9-repressor is present in the cells. Once the repressor is no longer present, it is likely that endogenous transcription factors and gene regulatory elements would restore expression to its natural state.

Single-Strand Annealing

Single-strand annealing (SSA) is another DNA repair process that repairs a double-strand break between two repeat sequences present in a target nucleic acid. Repeat sequences utilized by the SSA pathway are generally greater than 30 nucleotides in length. Resection at the break ends occurs to reveal repeat sequences on both strands of the target nucleic acid. After resection, single-strand overhangs containing the repeat sequences are coated with RPA protein to prevent the repeats sequences from inappropriate annealing, e.g., to themselves. RAD52 binds to and each of the repeat sequences on the overhangs and aligns the sequences to enable the annealing of the complementary repeat sequences. After annealing, the single-strand flaps of the overhangs are cleaved. New DNA synthesis fills in any gaps, and ligation restores the DNA duplex. As a result of the processing, the DNA sequence between the two repeats is deleted. The length of the deletion can depend on many factors including the location of the two repeats utilized, and the pathway or processivity of the resection.

In contrast to HDR pathways, SSA does not require a template nucleic acid to alter or correct a target nucleic acid sequence. Instead, the complementary repeat sequence is utilized.

Other DNA Repair Pathways

SSBR (Single-Strand Break Repair)

Single-stranded breaks (SSB) in the genome are repaired by the SSBR pathway, which is a distinct mechanism from the DSB repair mechanisms discussed above. The SSBR pathway has four major stages: SSB detection, DNA end processing, DNA gap filling, and DNA ligation. A more detailed explanation is given in Caldecott 2008, and a summary is given here.

In the first stage, when a SSB forms, PARP1 and/or PARP2 recognize the break and recruit repair machinery. The binding and activity of PARP1 at DNA breaks is transient and it seems to accelerate SSBr by promoting the focal accumulation or stability of SSBr protein complexes at the lesion. Arguably the most important of these SSBr proteins is XRCC1, which functions as a molecular scaffold that interacts with, stabilizes, and stimulates multiple enzymatic components of the SSBr process including the protein responsible for cleaning the DNA 3' and 5' ends. For instance, XRCC1 interacts with several proteins (DNA polymerase beta, PNK, and three nucleases, APE1, APTX, and APLF) that promote end processing. APE1 has endonuclease activity. APLF exhibits endonuclease and 3' to 5' exonuclease activities. APTX has endonuclease and 3' to 5' exonuclease activity.

This end processing is an important stage of SSBR since the 3'- and/or 5'-termini of most, if not all, SSBs are damaged. End processing generally involves restoring a damaged 3'-end to a hydroxylated state and and/or a damaged 5' end to a phosphate moiety, so that the ends become ligation-competent. Enzymes that can process damaged 3' termini include PNKP, APE1, and TDP1. Enzymes that can process damaged 5' termini include PNKP, DNA polymerase beta, and APTX. LIG3 (DNA ligase III) can also participate in end processing. Once the ends are cleaned, gap filling can occur.

At the DNA gap filling stage, the proteins typically present are PARP1, DNA polymerase beta, XRCC1, FEN1 (flap endonuclease 1), DNA polymerase delta/epsilon, PCNA, and LIG1. There are two ways of gap filling, the short patch repair and the long patch repair. Short patch repair involves the insertion of a single nucleotide that is missing. At some SSBs, "gap filling" might continue displacing two or more nucleotides (displacement of up to 12 bases have been reported). FEN1 is an endonuclease that removes the displaced 5'-residues. Multiple DNA polymerases, including Polβ, are involved in the repair of SSBs, with the choice of DNA polymerase influenced by the source and type of SSB.

In the fourth stage, a DNA ligase such as LIG1 (Ligase I) or LIG3 (Ligase III) catalyzes joining of the ends. Short patch repair uses Ligase III and long patch repair uses Ligase I.

Sometimes, SSBR is replication-coupled. This pathway can involve one or more of CtIP, MRN, ERCC1, and FEN1. Additional factors that may promote SSBR include: aPARP, PARP1, PARP2, PARG, XRCC1, DNA polymerase β, DNA polymerase delta, DNA polymerase epsilon, PCNA, LIG1, PNK, PNKP, APE1, APTX, APLF, TDP1, LIG3, FEN1, CtIP, MRN, and ERCC1.

MMR (Mismatch Repair)

Cells contain three excision repair pathways: MMR, BER, and NER. The excision repair pathways have a common feature in that they typically recognize a lesion on one strand of the DNA, then exo/endonucleases remove the lesion and leave a 1-30 nucleotide gap that is sub-sequentially filled in by DNA polymerase and finally sealed with ligase. A more complete picture is given in Li 2008, and a summary is provided here.

Mismatch repair (MMR) operates on mispaired DNA bases.

The MSH2/6 or MSH2/3 complexes both have ATPase activity that plays an important role in mismatch recognition and the initiation of repair. MSH2/6 preferentially recognizes base-base mismatches and identifies mispairs of 1 or 2 nucleotides, while MSH2/3 preferentially recognizes larger ID mispairs.

hMLH1 heterodimerizes with hPMS2 to form hMutLα which possesses an ATPase activity and is important for multiple steps of MMR. It possesses a PCNA/replication factor C (RFC)-dependent endonuclease activity which plays an important role in 3' nick-directed MMR involving EXO1 (EXO1 is a participant in both HR and MMR). It regulates termination of mismatch-provoked excision. Ligase I is the relevant ligase for this pathway. Additional factors that may promote MMR include: EXO1, MSH2, MSH3, MSH6, MLH1, PMS2, MLH3, DNA Pol delta, RPA, HMGB1, RFC, and DNA ligase I.

Base Excision Repair (BER)

The base excision repair (BER) pathway is active throughout the cell cycle; it is responsible primarily for removing small, non-helix-distorting base lesions from the genome. In contrast, the related Nucleotide Excision Repair pathway (discussed in the next section) repairs bulky helix-distorting lesions. A more detailed explanation is given in Caldecott 2008, and a summary is given here.

Upon DNA base damage, base excision repair (BER) is initiated and the process can be simplified into five major steps: (a) removal of the damaged DNA base; (b) incision of the subsequent a basic site; (c) clean-up of the DNA ends; (d) insertion of the desired nucleotide into the repair gap; and (e) ligation of the remaining nick in the DNA backbone. These last steps are similar to the SSBR.

In the first step, a damage-specific DNA glycosylase excises the damaged base through cleavage of the N-glycosidic bond linking the base to the sugar phosphate backbone. Then AP endonuclease-1 (APE1) or bifunctional DNA glycosylases with an associated lyase activity incises the phosphodiester backbone to create a DNA single-strand break (SSB). The third step of BER involves cleaning-up of the DNA ends. The fourth step in BER is conducted by Pol β that adds a new complementary nucleotide into the repair gap and in the final step XRCC1/Ligase III seals the remaining nick in the DNA backbone. This completes the short-patch BER pathway in which the majority (~80%) of damaged DNA bases are repaired. However, if the 5'-ends in step 3 are resistant to end processing activity, following one nucleotide insertion by Pol β there is then a polymerase switch to the replicative DNA polymerases, Pol δ/ε, which then add ~2-8 more nucleotides into the DNA repair gap. This creates a 5'-flap structure, which is recognized and excised by flap endonuclease-1 (FEN-1) in association with the processivity factor proliferating cell nuclear antigen (PCNA). DNA ligase I then seals the remaining nick in the DNA backbone and completes long-patch BER. Additional factors that may promote the BER pathway include: DNA glycosylase, APE1, Polβ, Pol delta, Pol epsilon, XRCC1, Ligase III, FEN-1, PCNA, RECQL4, WRN, MYH, PNKP, and APTX.

Nucleotide Excision Repair (NER)

Nucleotide excision repair (NER) is an important excision mechanism that removes bulky helix-distorting lesions from DNA. Additional details about NER are given in Marteijn et al. 2014, and a summary is given here. NER a broad pathway encompassing two smaller pathways: global genomic NER (GG-NER) and transcription coupled repair NER (TC-NER). GG-NER and TC-NER use different factors for recognizing DNA damage. However, they utilize the same machinery for lesion incision, repair, and ligation.

Once damage is recognized, the cell removes a short single-stranded DNA segment that contains the lesion. Endonucleases XPF/ERCC1 and XPG (encoded by ERCC5) remove the lesion by cutting the damaged strand on either side of the lesion, resulting in a single-strand gap of 22-30 nucleotides. Next, the cell performs DNA gap filling synthesis and ligation. Involved in this process are: PCNA, RFC, DNA Pol δ, DNA Pol ε or DNA Pol κ, and DNA ligase I or XRCC1/Ligase III. Replicating cells tend to use DNA pol ε and DNA ligase I, while non-replicating cells tend to use DNA Pol δ, DNA Pol κ, and the XRCC1/Ligase III complex to perform the ligation step.

NER can involve the following factors: XPA-G, POLH, XPF, ERCC1, XPA-G, and LIG1. Transcription-coupled NER (TC-NER) can involve the following factors: CSA, CSB, XPB, XPD, XPG, ERCC1, and TTDA. Additional factors that may promote the NER repair pathway include XPA-G, POLH, XPF, ERCC1, XPA-G, LIG1, CSA, CSB, XPA, XPB, XPC, XPD, XPF, XPG, TTDA, UVSSA, USP7, CETN2, RAD23B, UV-DDB, CAK subcomplex, RPA, and PCNA.

Interstrand Crosslink (ICL)

A dedicated pathway called the ICL repair pathway repairs interstrand crosslinks. Interstrand crosslinks, or covalent crosslinks between bases in different DNA strand, can occur during replication or transcription. ICL repair involves the coordination of multiple repair processes, in particular, nucleolytic activity, translesion synthesis (TLS), and HDR. Nucleases are recruited to excise the ICL on either side of the crosslinked bases, while TLS and HDR are coordinated to repair the cut strands. ICL repair can involve the following factors: endonucleases, e.g., XPF and RAD51C, endonucleases such as RAD51, translesion polymerases, e.g., DNA polymerase zeta and Rev1, and the Fanconi anemia (FA) proteins, e.g., FancJ.

Other Pathways

Several other DNA repair pathways exist in mammals.

Translesion synthesis (TLS) is a pathway for repairing a single stranded break left after a defective replication event and involves translesion polymerases, e.g., DNA pol ζ and Rev1.

Error-free postreplication repair (PRR) is another pathway for repairing a single stranded break left after a defective replication event.

Examples of gRNAs in Genome Editing Methods gRNA molecules as described herein can be used with Cas9 molecules, or Cas9 fusion molecules, that generate a double-strand break or a single-strand break to alter the sequence of a target nucleic acid, e.g., a target position or target genetic signature. gRNA molecules useful in these methods are described below.

In certain embodiments, the gRNA, e.g., a chimeric gRNA, is configured such that it comprises one or more of the following properties:

a) it can position, e.g., when targeting a Cas9 molecule, or Cas9 fusion molecule, that makes double-strand breaks, a double-strand break (i) within 50, 100, 150, 200, 250, 300, 350, 400, 450, or 500 nucleotides of a target position, or (ii) sufficiently close that the target position is within the region of end resection;

b) it has a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and (c)(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring S. pyogenes or S. aureus, tail and proximal domain, or a sequence that differs by no more than 1, 2, 3, 4, 5, 6, 7, 8, 9, or 10 nucleotides therefrom;

(c)(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring S. pyogenes or S. aureus gRNA, or a sequence that differs by no more than 1, 2, 3, 4, 5, 6, 7, 8, 9, or 10 nucleotides therefrom;

(c)(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring S. pyogenes or S. aureus gRNA, or a sequence that differs by no more than 1, 2, 3, 4, 5, 6, 7, 8, 9, or 10 nucleotides therefrom;

(c)(iv) the tail domain is at least 10, 15, 20, 25, 30, 35 or 40 nucleotides in length, e.g., it comprises at least 10, 15, 20, 25, 30, 35 or 40 nucleotides from a naturally occurring S. pyogenes or S. aureus tail domain, or a sequence that differs by no more than 1, 2, 3, 4, 5, 6, 7, 8, 9, or 10 nucleotides therefrom; or (c)(v) the tail domain comprises 15, 20, 25, 30, 35, 40 nucleotides or all of the corresponding portions of a naturally occurring tail domain, e.g., a naturally occurring S. pyogenes or S. aureus tail domain.

In certain embodiments, the gRNA is configured such that it comprises properties a and b(i); a and b(ii); a and b(iii); a and b(iv); a and b(v); a and b(vi); a and b(vii); a and b(viii); a and b(ix); a and b(x); a and b(xi); a and c; a, b, and c; a(i), b(i), and c(i); a(i), b(i), and c(ii); a(i), b(ii), and c(i); a(i), b(ii), and c(ii); a(i), b(iii), and c(i); a(i), b(iii), and c(ii); a(i), b(iv), and c(i); a(i), b(iv), and c(ii); a(i), b(v), and c(i); a(i), b(v), and c(ii); a(i), b(vi), and c(i); a(i), b(vi), and c(ii); a(i), b(vii), and c(i); a(i), b(vii), and c(ii); a(i), b(viii), and c(i); a(i), b(viii), and c(ii); a(i), b(ix), and c(i); a(i), b(ix), and c(ii); a(i), b(x), and c(i); a(i), b(x), and c(ii); a(i), b(xi), or c(i); a(i), b(xi), and c(ii).

In certain embodiments, the gRNA, e.g., a chimeric gRNA, is configured such that it comprises one or more of the following properties:

(a) one or both of the gRNAs can position, e.g., when targeting a Cas9 molecule, or Cas9 fusion molecule, that makes single-strand breaks, a single-strand break within (i) 50, 100, 150, 200, 250, 300, 350, 400, 450, or 500 nucleotides of a target position, or (ii) sufficiently close that the target position is within the region of end resection;

(b) one or both have a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and (c)(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring S. pyogenes or S. aureus tail and proximal domain, or a sequence that differs by no more than 1, 2, 3, 4, 5, 6, 7, 8, 9, or 10 nucleotides therefrom;

(c)(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring S. pyogenes, or S. aureus gRNA, or a sequence that differs by no more than 1, 2, 3, 4, 5, 6, 7, 8, 9, or 10 nucleotides therefrom;

(c)(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring S. pyogenes or S. aureus gRNA, or a sequence that differs by no more than 1, 2, 3, 4, 5, 6, 7, 8, 9, or 10 nucleotides therefrom;

(c)(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes*, or *S. aureus* tail domain, or a sequence that differs by no more than 1, 2, 3, 4, 5, 6, 7, 8, 9, or 10 nucleotides therefrom; or (c)(v) the tail domain comprises 15, 20, 25, 30, 35, 40 nucleotides or all of the corresponding portions of a naturally occurring tail domain, e.g., a naturally occurring *S. pyogenes* or *S. aureus* tail domain.

In certain embodiments, the gRNA is configured such that it comprises properties: a and b(i); a and b(ii); a and b(iii); a and b(iv); a and b(v); a and b(vi); a and b(vii); a and b(viii); a and b(ix); a and b(x); a and b(xi); a and c; a, b, and c; a(i), b(i), and c(i); a(i), b(i), and c(ii); a(i), b(ii), and c(i); a(i), b(ii), and c(ii); a(i), b(iii), and c(i); a(i), b(iii), and c(ii); a(i), b(iv), and c(i); a(i), b(iv), and c(ii); a(i), b(v), and c(i); a(i), b(v), and c(ii); a(i), b(vi), and c(i); a(i), b(vi), and c(ii); a(i), b(vii), and c(i); a(i), b(vii), and c(ii); a(i), b(viii), and c(i); a(i), b(viii), and c(ii); a(i), b(ix), and c(i); a(i), b(ix), and c(ii); a(i), b(x), and c(i); a(i), b(x), and c(ii); a(i), b(xi), and c(i); or a(i), b(xi), and c(ii).

In certain embodiments, the gRNA is used with a Cas9 nickase molecule having HNH activity, e.g., a Cas9 molecule, or a Cas9 fusion molecule, having the RuvC activity inactivated, e.g., a Cas9 molecule having a mutation at D10, e.g., the D10A mutation.

In one embodiment, the gRNA is used with a Cas9 nickase molecule having RuvC activity, e.g., a Cas9 molecule, or a Cas9 fusion molecule, having the HNH activity inactivated, e.g., a Cas9 molecule having a mutation at 840, e.g., the H840A.

In one embodiment, the gRNAs are used with a Cas9 nickase molecule having RuvC activity, e.g., a Cas9 molecule, or a Cas9 fusion molecule, having the HNH activity inactivated, e.g., a Cas9 molecule having a mutation at N863, e.g., the N863A mutation.

In embodiment, a pair of gRNAs, e.g., a pair of chimeric gRNAs, comprising a first and a second gRNA, is configured such that they comprises one or more of the following properties:

a) one or both of the gRNA molecules can position, e.g., when targeting a Cas9 molecule, or a Cas9 fusion molecule, that makes single-strand breaks, a single-strand break within (i) 50, 100, 150, 200, 250, 300, 350, 400, 450, or 500 nucleotides of a target position, or (ii) sufficiently close that the target position is within the region of end resection;

b) one or both have a targeting domain of at least 16 nucleotides, e.g., a targeting domain of (i) 16, (ii) 17, (iii) 18, (iv) 19, (v) 20, (vi) 21, (vii) 22, (viii) 23, (ix) 24, (x) 25, or (xi) 26 nucleotides;

(c)(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes* or *S. aureus* tail and proximal domain, or a sequence that differs by no more than 1, 2, 3, 4, 5, 6, 7, 8, 9, or 10 nucleotides therefrom;

(c)(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes* or *S. aureus* gRNA, or a sequence that differs by no more than 1, 2, 3, 4, 5, 6, 7, 8, 9, or 10 nucleotides therefrom;

(c)(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes* or *S. aureus* gRNA, or a sequence that differs by no more than 1, 2, 3, 4, 5, 6, 7, 8, 9, or 10 nucleotides therefrom;

(c)(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes* or *S. aureus* tail domain; or, or a sequence that differs by no more than 1, 2, 3, 4, 5, 6, 7, 8, 9, or 10 nucleotides therefrom; or (c)(v) the tail domain comprises 15, 20, 25, 30, 35, or 40 nucleotides or all of the corresponding portions of a naturally occurring tail domain, e.g., a naturally occurring *S. pyogenes* or *S. aureus* tail domain;

(d) the gRNAs are configured such that, when hybridized to target nucleic acid, they are separated by 0-50, 0-100, 0-200, at least 10, at least 20, at least 30 or at least 50 nucleotides;

(e) the breaks made by the first gRNA and second gRNA are on different strands; and (f) the PAMs are facing outwards.

In certain embodiments, one or both of the gRNAs is configured such that it comprises properties a and b(i); a and b(ii); a and b(iii); a and b(iv); a and b(v); a and b(vi); a and b(vii); a and b(viii); a and b(ix); a and b(x); a and b(xi); a and c; a, b, and c; a(i), b(i), and c(i); a(i), b(i), and c(ii); a(i), b(i), c, and d; a(i), b(i), c, and e; a(i), b(i), c, d, and e; a(i), b(ii), and c(i); a(i), b(ii), and c(ii); a(i), b(ii), c, and d; a(i), b(ii), c, and e; a(i), b(ii), c, d, and e; a(i), b(iii), and c(i); a(i), b(iii), and c(ii); a(i), b(iii), c, and d; a(i), b(iii), c, and e; a(i), b(iii), c, d, and e; a(i), b(iv), and c(i); a(i), b(iv), and c(ii); a(i), b(iv), c, and d; a(i), b(iv), c, and e; a(i), b(iv), c, d, and e; a(i), b(v), and c(i); a(i), b(v), and c(ii); a(i), b(v), c, and d; a(i), b(v), c, and e; a(i), b(v), c, d, and e; a(i), b(vi), and c(i); a(i), b(vi), and c(ii); a(i), b(vi), c, and d; a(i), b(vi), c, and e; a(i), b(vi), c, d, and e; a(i), b(vii), and c(i); a(i), b(vii), and c(ii); a(i), b(vii), c, and d; a(i), b(vii), c, and e; a(i), b(vii), c, d, and e; a(i), b(viii), and c(i); a(i), b(viii), and c(ii); a(i), b(viii), c, and d; a(i), b(viii), c, and e; a(i), b(viii), c, d, and e; a(i), b(ix), and c(i); a(i), b(ix), and c(ii); a(i), b(ix), c, and d; a(i), b(ix), c, and e; a(i), b(ix), c, d, and e; a(i), b(x), and c(i); a(i), b(x), and c(ii); a(i), b(x), c, and d; a(i), b(x), c, and e; a(i), b(x), c, d, and e; a(i), b(xi), and c(i); a(i), b(xi), and c(ii); a(i), b(xi), c, and d; a(i), b(xi), c, and e; or a(i), b(xi), c, d, and e.

In certain embodiments, the gRNAs are used with a Cas9 nickase molecule having HNH activity, e.g., a Cas9 molecule, or a Cas9 fusion molecule, having the RuvC activity inactivated, e.g., a Cas9 molecule having a mutation at D10, e.g., the D10A mutation.

In certain embodiments, the gRNAs are used with a Cas9 nickase molecule having RuvC activity, e.g., a Cas9 molecule, or a Cas9 fusion molecule, having the HNH activity inactivated, e.g., a Cas9 molecule having a mutation at H840, e.g., the H840A mutation.

In certain embodiments, the gRNAs are used with a Cas9 nickase molecule having RuvC activity, e.g., a Cas9 molecule, or a Cas9 fusion molecule, having the HNH activity inactivated, e.g., a Cas9 molecule having a mutation at N863, e.g., the N863A mutation.

VI. Target Cells

Cas9 fusion molecules and gRNA molecules, e.g., a Cas9 (fusion) molecule/gRNA molecule complex, can be used to manipulate a cell, e.g., to edit a target nucleic acid, in a wide variety of cells. Additional details on types of cells that can be manipulated may be found in the section entitled "VIIA. TARGETS: CELLS" of PCT Application WO 2015/048577, the entire contents of which are expressly incorporated herein by reference.

In certain embodiments, a cell is manipulated by editing (e.g., introducing a mutation in) a target gene as described herein. In one embodiment, a cell, or a population of cells, is manipulated by editing one or more non-coding sequences, e.g., an alteration in an intron or in a 5' or 3' non-translated or non-transcribed region. In one embodiment, a cell, or a population of cells, is manipulated by editing the sequence of a control element, e.g., a promoter, enhancer, or a cis-acting or trans-acting control element. In one embodiment, a cell, or a population of cells, is manipulated by editing one or more coding sequences, e.g., an alteration in an exon. In some embodiments, a cell, or a population of cells, is manipulated in vitro. In other embodiments, a cell, or a population of cells, is manipulated ex vivo. In some embodiments, a cell, or a population of cells, is manipulated in vivo. In some embodiments, the expression of one or more target genes (e.g., one or more target genes described herein) is modulated, e.g., in vivo. In other embodiments, the expression of one or more target genes (e.g., one or more target genes described herein) is modulated, e.g., ex vivo. In other embodiments, the expression of one or more target genes (e.g., one or more target genes described herein) is modulated, e.g., in vitro.

In one embodiment, a cell, or a population of cells, is manipulated by editing (e.g., inducing a mutation in) the target gene, e.g., as described herein. In one embodiment, the expression of the target gene is modulated, e.g., in vivo. In another embodiment, the expression of the target gene is modulated, e.g., ex vivo.

The Cas9 (or Cas9 fusion molecule) and gRNA molecules described herein can be delivered to a target cell. In certain embodiments, the target cell is an erythroid cell, e.g., an erythroblast. In certain embodiments, erythroid cells are preferentially targeted, e.g., at least about 90%, 95%, 96%, 97%, 98%, 99%, or 100% of the targeted cells are erythroid cells. For example, in the case of in vivo delivery, erythroid cells are preferentially targeted, and if cells are treated ex vivo and returned to the subject, erythroid cells are preferentially modified. In certain embodiments, the target cell is a circulating blood cell, e.g., a reticulocyte, megakaryocyte erythroid progenitor (MEP) cell, myeloid progenitor cell (CMP/GMP), lymphoid progenitor (LP) cell, hematopoietic stem/progenitor cell (HSC), or endothelial cell (EC). In certain embodiments, the target cell is a bone marrow cell (e.g., a reticulocyte, an erythroid cell (e.g., erythroblast), an MEP cell, myeloid progenitor cell (CMP/GMP), LP cell, erythroid progenitor (EP) cell, HSC, multipotent progenitor (MPP) cell, endothelial cell (EC), hemogenic endothelial (HE) cell, or mesenchymal stem cell). In certain embodiments, the target cell is a myeloid progenitor cell (e.g., a common myeloid progenitor (CMP) cell or granulocyte macrophage progenitor (GMP) cell). In certain embodiments, the target cell is a lymphoid progenitor cell, e.g., a common lymphoid progenitor (CLP) cell. In certain embodiments, the target cell is an erythroid progenitor cell (e.g., an MEP cell). In certain embodiments, the target cell is a hematopoietic stem/progenitor cell (e.g., a long term HSC (LT-HSC), short term HSC (ST-HSC), MPP cell, or lineage restricted progenitor (LRP) cell). In certain embodiments, the target cell is a $CD34^+$ cell, $CD34^+CD90^+$ cell, $CD34^+CD38^-$ cell, $CD34^+CD90^+CD49f^+CD38^-CD45RA^-$ cell, $CD105^+$ cell, $CD31^+$, or $CD133^+$ cell, or a $CD34^+CD90^+CD133^+$ cell. In certain embodiments, the target cell is an umbilical cord blood $CD34^+$HSPC, umbilical cord venous endothelial cell, umbilical cord arterial endothelial cell, amniotic fluid $CD34^+$ cell, amniotic fluid endothelial cell, placental endothelial cell, or placental hematopoietic $CD34^+$ cell. In certain embodiments, the target cell is a mobilized peripheral blood hematopoietic $CD34^+$ cell (after the patient is treated with a mobilization agent, e.g., G-CSF or Plerixafor). In certain embodiments, the target cell is a peripheral blood endothelial cell.

In certain embodiments, a target cell is manipulated ex vivo by editing (e.g., inducing a mutation in) the target gene and/or modulating the expression of the target gene, then the target cell is administered to the subject. Sources of target cells for ex vivo manipulation may include, for example, the subject's blood, cord blood, or marrow. Other sources of target cells for ex vivo manipulation may include, for example, heterologous donor blood, cord blood, or bone marrow.

In certain embodiments, an erythrocyte is removed from a subject, manipulated ex vivo as described above, and the erythrocyte is returned to the subject. In other embodiments, a hematopoietic stem cell is removed from a subject, manipulated ex vivo as described above, and the hematopoietic stem cell is returned to the subject. In certain embodiments, an erythroid progenitor cell is removed from a subject, manipulated ex vivo as described above, and the erythroid progenitor cell is returned to the subject. In certain embodiments, an myeloid progenitor cell is removed from a subject, manipulated ex vivo as described above, and the myeloid progenitor cell is returned to the subject. In certain embodiments, a hematopoietic stem/progenitor cell (HSC) is removed from a subject, manipulated ex vivo as described above, and returned to the subject. In certain embodiments, a $CD34^+$HSC is removed from a subject, manipulated ex vivo as described above, and returned to the subject.

In certain embodiments wherein modified HSCs generated ex vivo are administered to a subject without myeloblative pre-conditioning. In other embodiments, the modified HSCs are administered after mild myeloblative conditioning such that, followed engraftment, some of the hematopoietic cells are derived from the modified HSCs. In still other embodiments, the modified HSCs are administered after full myeloblation such that, following engraftment, 100% of the hematopoietic cells are derived from the modified HSCs.

A suitable cell can also include a stem cell such as, by way of example, an embryonic stem cell, induced pluripotent stem cell, hematopoietic stem cell, or hemogenic endothelial (HE) cell (precursor to both hematopoietic stem cells and endothelial cells). In certain embodiments, the cell is an induced pluripotent stem (iPS) cell or a cell derived from an iPS cell, e.g., an iPS cell generated from the subject, modified using methods disclosed herein and differentiated into a clinically relevant cell such as e.g., an erythrocyte. In one embodiment, AAV is used to transduce the target cells, e.g., the target cells described herein.

Cells produced by the methods described herein may be used immediately. Alternatively, the cells may be frozen (e.g., in liquid nitrogen) and stored for later use. The cells will usually be frozen in 10% dimethylsulfoxide (DMSO), 50% serum, 40% buffered medium, or some other such solution as is commonly used in the art to preserve cells at such freezing temperature and thawed in such a manner as commonly known in the art for thawing frozen cultured cells. Cells may also be thermostabilized for prolonged storage at 4° C.

Delivery, Formulations and Routes of Administration

The components, e.g., a Cas9 fusion molecule and at least one gRNA molecule (e.g., a Cas9 fusion molecule/gRNA molecule complex), can be delivered, formulated, or administered, in a variety of forms, see, e.g., Tables 5-6. In certain embodiments, the sequence(s) encoding the two or more (e.g., 2, 3, 4, or more) different gRNA molecules are present on the same nucleic acid molecule, e.g., an AAV vector. When a gRNA component is delivered encoded in DNA, the DNA will typically include a control region, e.g., comprising a promoter, to effect expression. In one embodiment, the promoter is a constitutive promoter. In another embodiment, the promoter is a tissue specific promoter. Useful promoters for gRNAs include T7, H1, EF-1a, U6, U1, and tRNA promoters. Promoters with similar or dissimilar strengths can be selected to tune the expression of components. Sequences encoding the Cas9 molecule of a Cas9 fusion molecule can comprise a nuclear localization signal (NLS), e.g., an SV40 NLS. In one embodiment, the sequence encoding the Cas9 molecule of a Cas9 fusion molecule comprises at least two nuclear localization signals. In one embodiment a promoter for the Cas9 molecule of a Cas9 fusion molecule or a gRNA molecule can be, independently, inducible, tissue specific, or cell specific.

Table 5 provides examples of how the components can be formulated, delivered, or administered.

TABLE 5

| Cas9 Fusion Molecule(s) | gRNA Molecule(s) | Optional Donor Template Nucleic Acid | Comments |
| --- | --- | --- | --- |
| Protein | DNA | DNA | In this embodiment, a Cas9 fusion molecule, typically an eaCas9 fusion molecule, is provided as a protein, covalently or non-covalently lined to the template nucleic acid, and a gRNA molecule is transcribed from DNA. |
| Protein | RNA | DNA | In this embodiment, a Cas9 fusion molecule, typically an eaCas9 fusion molecule, is provided as a protein, covalently or non-covalently lined to the template nucleic acid, and a gRNA molecule is provided as transcribed or synthesized RNA |

Table 6 summarizes various delivery methods for the components of a Cas system, e.g., the Cas9 molecule component and the gRNA molecule component, as described herein.

TABLE 6

| Delivery Vector/Mode | | Delivery into Non-Dividing Cells | Duration of Expression | Genome Integration | Type of Molecule Delivered |
| --- | --- | --- | --- | --- | --- |
| Physical (e.g., electroporation, particle gun, calcium phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

DNA-Based Delivery of One or More gRNA Molecules

Nucleic acids encoding gRNA molecules can be administered to subjects or delivered into cells by art-known methods or as described herein. For example, gRNA-encoding DNA can be delivered by, e.g., vectors (e.g., viral or non-viral vectors), non-vector based methods (e.g., using naked DNA or DNA complexes), or a combination thereof.

Nucleic acids encoding gRNA molecules can be conjugated to molecules (e.g., N-acetylgalactosamine) promoting uptake by the target cells (e.g., erythrocytes, HSCs).

In some embodiments, the gRNA-encoding DNA is delivered by a vector (e.g., viral vector/virus or plasmid).

Vectors can comprise a sequence that encodes a gRNA molecule. One or more regulatory/control elements, e.g., promoters, enhancers, introns, polyadenylation signals, Kozak consensus sequences, internal ribosome entry sites (IRES), can be included in the vectors. In some embodiments, the promoter is recognized by RNA polymerase II (e.g., a CMV promoter). In other embodiments, the promoter is recognized by RNA polymerase III (e.g., a U6 promoter). In some embodiments, the promoter is a regulated promoter (e.g., inducible promoter). In other embodiment, the promoter is a constitutive promoter. In some embodiments, the promoter is a tissue specific promoter. In other embodiments, the promoter is a viral promoter. In some embodiments, the promoter is a non-viral promoter.

In some embodiments, the vector is a viral vector (e.g., for generation of recombinant viruses). In some embodiments, the virus is a DNA virus (e.g., dsDNA or ssDNA virus). In other embodiments, the virus is an RNA virus (e.g., an ssRNA virus). In some embodiments, the virus infects dividing cells. In other embodiments, the virus infects non-dividing cells. Exemplary viral vectors/viruses include, e.g., retroviruses, lentiviruses, adenovirus, adeno-associated virus (AAV), vaccinia viruses, poxviruses, and herpes simplex viruses.

In some embodiments, the virus infects both dividing and non-dividing cells. In some embodiments, the virus can integrate into the host genome. In some embodiments, the virus is engineered to have reduced immunity, e.g., in human. In some embodiments, the virus is replication-competent. In other embodiments, the virus is replication-defective, e.g., having one or more coding regions for the genes necessary for additional rounds of virion replication and/or packaging replaced with other genes or deleted. In some embodiments, the virus causes transient expression of the gRNA molecule. In other embodiments, the virus causes long-lasting, e.g., at least 1 week, 2 weeks, 1 month, 2 months, 3 months, 6 months, 9 months, 1 year, 2 years, or permanent expression, of the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In one embodiment, the viral vector recognizes a specific cell type or tissue. For example, the viral vector can be pseudotyped with a different/alternative viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

In some embodiments, the gRNA-encoding nucleic acid sequence is delivered by a recombinant retrovirus. In some embodiments, the retrovirus (e.g., Moloney murine leukemia virus) comprises a reverse transcriptase, e.g., that allows integration into the host genome. In some embodiments, the retrovirus is replication-competent. In other embodiments, the retrovirus is replication-defective, e.g., having one of more coding regions for the genes necessary for additional rounds of virion replication and packaging replaced with other genes, or deleted.

In one embodiment, the gRNA-encoding nucleic acid sequence is delivered by a recombinant lentivirus. For example, the lentivirus is replication-defective, e.g., does not comprise one or more genes required for viral replication.

In some embodiments, the gRNA-encoding nucleic acid sequence is delivered by a recombinant adenovirus. In some embodiments, the adenovirus is engineered to have reduced immunity in human.

In some embodiments, the gRNA-encoding nucleic acid sequence is delivered by a recombinant AAV. In some embodiments, the AAV does not incorporate its genome into that of a host cell, e.g., a target cell as describe herein. In some embodiments, the AAV can incorporate its genome into that of a host cell. In some embodiments, the AAV is a self-complementary adeno-associated virus (scAAV), e.g., a scAAV that packages both strands which anneal together to form double stranded DNA.

In one embodiment, an AAV capsid that can be used in the methods described herein is a capsid sequence from serotype AAV1, AAV2, AAV3, AAV4, AAV5, AAV6, AAV7, AAV8, AAV9, AAV.rh8, AAV.rh10, AAV.rh32/33, AAV.rh43, AAV.rh64R1, or AAV7m8.

In one embodiment, the gRNA-encoding DNA is delivered in a re-engineered AAV capsid, e.g., with 50% or greater, e.g., 60% or greater, 70% or greater, 80% or greater, 90% or greater, or 95% or greater, sequence homology with a capsid sequence from serotypes AAV1, AAV2, AAV3, AAV4, AAV5, AAV6, AAV7, AAV8, AAV9, AAV.rh8, AAV.rh10, AAV.rh32/33, AAV.rh43, or AAV.rh64R1.

In one embodiment, the gRNA-encoding DNA is delivered by a chimeric AAV capsid. Exemplary chimeric AAV capsids include, but are not limited to, AAV9i1, AAV2i8, AAV-DJ, AAV2G9, AAV2i8G9, or AAV8G9.

In one embodiment, the AAV is a self-complementary adeno-associated virus (scAAV), e.g., a scAAV that packages both strands which anneal together to form double stranded DNA.

In some embodiments, the gRNA-encoding DNA is delivered by a hybrid virus, e.g., a hybrid of one or more of the viruses described herein. In one embodiment, the hybrid virus is hybrid of an AAV (e.g., of any AAV serotype), with a Bocavirus, B19 virus, porcine AAV, goose AAV, feline AAV, canine AAV, or MVM.

A packaging cell is used to form a virus particle that is capable of infecting a target cell. Exemplary packaging cells include 293 cells, which can package adenovirus, and ψ2 or PA317 cells, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable). For example, an AAV vector used in gene therapy typically only possesses inverted terminal repeat (ITR) sequences from the AAV genome which are required for packaging and gene expression in the host or target cell. The missing viral functions can be supplied in trans by the packaging cell line and/or plasmid containing E2A, E4, and VA genes from adenovirus, and plasmid encoding Rep and Cap genes from AAV, as described in "Triple Transfection Protocol." Henceforth, the viral DNA is packaged in a cell line, which contains a helper plasmid encoding the other AAV genes, namely rep and cap, but lacking ITR sequences. In certain embodiments, the viral DNA is packaged in a producer cell line, which contains E1A and/or E1B genes from adenovirus. The cell line is also infected with adenovirus as a helper. The helper virus (e.g., adenovirus or HSV) or helper plasmid promotes replication of the AAV vector and expression of AAV genes from the helper plasmid with ITRs. The helper plasmid is not packaged in significant amounts due to a lack of ITR sequences. Contamination with adenovirus can be reduced by, e.g., heat treatment to which adenovirus is more sensitive than AAV.

In certain embodiments, the viral vector is capable of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, single chain antibody, or growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In certain embodiments, the viral vector achieves cell type specific expression. For example, a tissue-specific promoter can be constructed to restrict expression of the transgene (gRNA) to only the target cell. The specificity of the vector can also be mediated by microRNA-dependent control of transgene expression. In one embodiment, the viral vector has increased efficiency of fusion of the viral vector and a target cell membrane. For example, a fusion protein such as fusion-competent hemagglutin (HA) can be incorporated to increase viral uptake into cells. In one embodiment, the viral vector has the ability of nuclear localization. For example, a virus that requires the breakdown of the nuclear envelope (during cell division) and therefore will not infect a non-diving cell can be altered to incorporate a nuclear localization peptide in the matrix protein of the virus thereby enabling the transduction of non-proliferating cells.

In some embodiments, the gRNA-encoding DNA is delivered by a non-vector based method (e.g., using naked DNA or DNA complexes). For example, the DNA can be delivered, e.g., by organically modified silica or silicate (Ormosil), electroporation, transient cell compression or squeezing (see, e.g., Lee 2012), gene gun, sonoporation, magnetofection, lipid-mediated transfection, dendrimers, inorganic nanoparticles, calcium phosphates, or a combination thereof.

In one embodiment, delivery via electroporation comprises mixing the cells with the gRNA-encoding DNA in a cartridge, chamber or cuvette and applying one or more electrical impulses of defined duration and amplitude. In one embodiment, delivery via electroporation is performed using a system in which cells are mixed with the gRNA-encoding DNA in a vessel connected to a device (e.g., a pump) which feeds the mixture into a cartridge, chamber or cuvette wherein one or more electrical impulses of defined duration and amplitude are applied, after which the cells are delivered to a second vessel.

In some embodiments, the gRNA-encoding DNA is delivered by a combination of a vector and a non-vector based method. For example, virosomes combine liposomes with an inactivated virus (e.g., HIV or influenza virus), which can result in more efficient gene transfer, e.g., in respiratory epithelial cells than either viral or liposomal methods alone.

As described above, a nucleic acid may comprise a sequence encoding a gRNA molecule comprising a targeting domain that is complementary with a desired target domain. In one embodiment, the nucleic acid molecule is an AAV vector. Exemplary AAV vectors that may be used in any of the described compositions and methods include an AAV2 vector, a modified AAV2 vector, an AAV3 vector, a modified AAV3 vector, an AAV6 vector, a modified AAV6 vector, an AAV8 vector and an AAV9 vector. In yet another embodiment, the nucleic acid may further comprise a sequence that encodes a second, third and/or fourth gRNA molecule as described herein. Each of the sequence encoding a gRNA molecule comprising a targeting domain that is complementary with a desired target domain and the sequence that encodes a second, third and/or fourth gRNA molecule may be present on the same nucleic acid molecule, e.g., the same vector, e.g., the same viral vector, e.g., the same adeno-associated virus (AAV) vector. In one embodiment, the nucleic acid molecule is an AAV vector.

In another embodiment, the sequence encoding a gRNA molecule comprising a targeting domain that is complementary with a desired target domain and the sequence that encodes a second, third and/or fourth gRNA molecule are on different vectors. For example, the sequence encoding a gRNA molecule comprising a targeting domain that is complementary with a desired target domain may be present on a first nucleic acid molecule, e.g., a first vector, e.g., a first viral vector, e.g., a first AAV vector; and the sequence that encodes a second, third and/or fourth gRNA molecule may be present on a second nucleic acid molecule, e.g., a second vector, e.g., a second vector, e.g., a second AAV vector. In one embodiment, the first and second nucleic acid molecules are AAV vectors.

In another embodiment, when a third and/or fourth gRNA molecule are present, each of the sequence encoding a gRNA molecule comprising a targeting domain that is complementary with a desired target domain and the sequence that encodes a second, third and/or fourth gRNA molecule may be present on the same nucleic acid molecule, e.g., the same vector, e.g., the same viral vector, e.g., an AAV vector. In one embodiment, the nucleic acid molecule is an AAV vector. In an alternate embodiment, each of the sequence encoding a gRNA molecule comprising a targeting domain that is complementary with a desired target domain and the sequence that encodes a second, third and/or fourth gRNA molecule may be present on the different nucleic acid molecules, e.g., different vectors, e.g., the different viral vectors, e.g., different AAV vectors. In further embodiments, each of the sequence encoding a gRNA molecule comprising a targeting domain that is complementary with a desired target domain and the sequence that encodes a second, third and/or fourth gRNA molecule may be present on more than one nucleic acid molecule, but fewer than five nucleic acid molecules, e.g., AAV vectors.

The nucleic acids described herein may comprise a promoter operably linked to the sequence that encodes the gRNA molecule of the sequence encoding a gRNA molecule comprising a targeting domain that is complementary with a desired target domain, e.g., a promoter described herein. The nucleic acid may further comprise a second promoter operably linked to the sequence that encodes the second, third and/or fourth gRNA molecule, e.g., a promoter described herein. The promoter and second promoter differ from one another. In one embodiment, the promoter and second promoter are the same.

In certain embodiments, the delivery vehicle is a non-viral vector, and in certain of these embodiments the non-viral vector is an inorganic nanoparticle. Exemplary inorganic nanoparticles include, e.g., magnetic nanoparticles (e.g., $Fe_3MnO_2$) or silica. The outer surface of the nanoparticle can be conjugated with a positively charged polymer (e.g., polyethylenimine, polylysine, polyserine) which allows for attachment (e.g., conjugation or entrapment) of payload. In one embodiment, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids for gene transfer are shown below in Table 7.

TABLE 7

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |

TABLE 7-continued

Lipids Used for Gene Transfer

| Lipid | Abbreviation | Feature |
|---|---|---|
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamide | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

Exemplary polymers for gene transfer are shown below in Table 8.

TABLE 8

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In one embodiment, the vehicle has targeting modifications to increase target cell update of nanoparticles and liposomes, e.g., cell specific antigens, monoclonal antibodies, single chain antibodies, aptamers, polymers, sugars (e.g., N-acetylgalactosamine (GalNAc)), and cell penetrating peptides. In one embodiment, the vehicle uses fusogenic and endosome-destabilizing peptides/polymers. In one embodiment, the vehicle undergoes acid-triggered conformational changes (e.g., to accelerate endosomal escape of the cargo). In one embodiment, a stimuli-cleavable polymer is used, e.g., for release in a cellular compartment. For example, disulfide-based cationic polymers that are cleaved in the reducing cellular environment can be used.

In one embodiment, the delivery vehicle is a biological non-viral delivery vehicle. In one embodiment, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In one embodiment, the vehicle is a genetically modified bacteriophage (e.g., engineered phages having large packaging capacity, less immunogenic, containing mammalian plasmid maintenance sequences and having incorporated targeting ligands). In one embodiment, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In one embodiment, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes-subject (i.e., patient) derived membrane-bound nanovesicle (30-100 nm) of endocytic origin (e.g., can be produced from various cell types and can therefore be taken up by cells without the need of for targeting ligands).

In one embodiment, one or more nucleic acid molecules (e.g., DNA molecules) other than the components of a Cas system, e.g., the Cas9 fusion molecule component and/or the gRNA molecule component described herein, are delivered. In one embodiment, the nucleic acid molecule is delivered at the same time as one or more of the gRNA molecule(s) are delivered. In one embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the gRNA molecule(s) are delivered. In one embodiment, the nucleic acid molecule is delivered by a different means than one or more of the gRNA molecule(s) are delivered. The nucleic acid molecule can be delivered by any of the delivery methods described herein. For example, the nucleic acid molecule can be delivered by a viral vector, e.g., an integration-deficient lentivirus, and the gRNA molecule component can be delivered by electroporation, e.g., such that the toxicity caused by nucleic acids (e.g., DNAs) can be reduced. In one embodiment, the nucleic acid molecule encodes a therapeutic protein, e.g., a protein described herein. In one embodiment, the nucleic acid molecule encodes an RNA molecule, e.g., an RNA molecule described herein.

Delivery of RNA Encoding a gRNA Molecule

RNA encoding gRNA molecules can be delivered into cells, e.g., target cells described herein, by art-known methods or as described herein. For example, gRNA-encoding RNA can be delivered, e.g., by microinjection, electroporation, transient cell compression or squeezing (see, e.g., Lee 2012), lipid-mediated transfection, peptide-mediated delivery, or a combination thereof. gRNA-encoding RNA can be conjugated to molecules promoting uptake by the target cells (e.g., target cells described herein).

In one embodiment, delivery via electroporation comprises mixing the cells with the RNA encoding gRNA molecules in a cartridge, chamber or cuvette and applying one or more electrical impulses of defined duration and amplitude. In one embodiment, delivery via electroporation is performed using a system in which cells are mixed with the RNA encoding gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel. gRNA-encoding RNA can be conjugated to molecules to promote uptake by the target cells (e.g., target cells described herein).

Delivery of Cas9 Polypeptides and Cas9 Fusion Molecules

Cas9 molecules and Cas9 fusion molecules can be delivered into cells by art-known methods or as described herein. For example, protein molecules can be delivered, e.g., by microinjection, electroporation, transient cell compression or squeezing (see, e.g., Lee 2012), lipid-mediated transfection, peptide-mediated delivery, or a combination thereof. Delivery can be accompanied by DNA encoding a gRNA or by a gRNA. Cas9 proteins and Cas9 fusion molecules can be conjugated to molecules promoting uptake by the target cells (e.g., target cells described herein).

In one embodiment, delivery via electroporation comprises mixing the cells with the Cas9 fusion molecules and/or gRNA molecules in a cartridge, chamber or cuvette and applying one or more electrical impulses of defined duration and amplitude. In one embodiment, delivery via electroporation is performed using a system in which cells are mixed with the Cas9 fusion molecules and/or gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel. gRNA-encoding RNA can be conjugated to molecules to promote uptake by the target cells (e.g., target cells described herein).

Route of Administration

Systemic modes of administration include oral and parenteral routes. Parenteral routes include, by way of example, intravenous, intramarrow, intrarterial, intramuscular, intradermal, subcutaneous, intranasal, inhalation, and intraperitoneal routes. Components administered systemically may be modified or formulated to target, e.g., HSCs, hematopoetic stem/progenitor cells, or erythroid progenitors or precursor cells.

Local modes of administration include, by way of example, intramarrow injection into the trabecular bone or intrafemoral injection into the marrow space, and infusion into the portal vein. In one embodiment, significantly smaller amounts of the components (compared with systemic approaches) may exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration may be provided as a periodic bolus (e.g., intravenously) or as continuous infusion from an internal reservoir or from an external reservoir (for example, from an intravenous bag or implantable pump). Components may be administered locally, for example, by continuous release from a sustained release drug delivery device.

In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used for injection. Typically the microspheres are composed of a polymer of lactic acid and glycolic acid, which are structured to form hollow spheres. The spheres can be approximately 15-30 microns in diameter and can be loaded with components described herein.

Bi-Modal or Differential Delivery of Components

Separate delivery of the components of a Cas system, e.g., the Cas9 fusion molecule component and the gRNA molecule component, and more particularly, delivery of the components by differing modes, can enhance performance, e.g., by improving tissue specificity and safety.

In one embodiment, the Cas9 fusion molecule and the gRNA molecule are delivered by different modes, or as sometimes referred to herein as differential modes. Different or differential modes, as used herein, refer modes of delivery that confer different pharmacodynamic or pharmacokinetic properties on the subject component molecule, e.g., a Cas9 fusion molecule, gRNA molecule, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components, e.g., a Cas9 fusion molecule and a gRNA molecule, can be delivered by modes that differ in terms of resulting half-life or persistent of the delivered component the body, or in a particular compartment, tissue or organ. In one embodiment, a gRNA molecule can be delivered by such modes. The Cas9 fusion molecule component can be delivered by a mode which results in less persistence or less exposure to the body or a particular compartment or tissue or organ.

More generally, in one embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In one embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA molecule, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a Cas9 fusion molecule, is delivered in a transient manner, for example as protein, ensuring that the full Cas9 molecule/gRNA molecule complex is only present and active for a short period of time.

Furthermore, the components can be delivered in different molecular form or with different delivery vectors that complement one another to enhance safety and tissue specificity.

Use of differential delivery modes can enhance performance, safety and/or efficacy, e.g., the likelihood of an eventual off-target modification can be reduced. Delivery of immunogenic components, e.g., Cas9 fusion molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in one embodiment, a first component, e.g., a gRNA molecule is delivered by a first delivery mode that results in a first spatial, e.g., tissue, distribution. A second component, e.g., a Cas9 fusion molecule is delivered by a second delivery mode that results in a second spatial, e.g., tissue, distribution. In one embodiment, the first mode comprises a first element selected from a liposome, nanoparticle, e.g., polymeric nanoparticle, and a nucleic acid, e.g., viral vector. The second mode comprises a second element selected from the group. In one embodiment, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the Cas9 fusion molecule is delivered in a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule and the Cas9 fusion molecule are packaged in separated delivery vehicles with distinct but overlapping tissue tropism, the fully functional complex is only be formed in the tissue that is targeted by both vectors.

Disclosed herein are methods of altering a cell, e.g., altering the structure, e.g., altering the sequence, of a target nucleic acid of a cell, comprising contacting said cell with: (a) a gRNA molecule that targets the target gene, e.g., a gRNA molecule as described herein; (b) a Cas9 fusion molecule, e.g., a Cas9 fusion molecule as described herein; and optionally, (c) a second, third and/or fourth gRNA that targets the target gene, e.g., a gRNA molecule; as described herein. In one embodiment, the method comprises contacting said cell with (a) and (b). In one embodiment, the method comprises contacting said cell with (a), (b), and (c). The targeting domain of the gRNA molecule of (a) and optionally (c) may be selected from a targeting domain sequence described herein.

In one embodiment, the method comprises contacting a cell from a subject suffering from or likely to develop a disease. The cell may be from a subject having a mutation at a target position in a target gene. In one embodiment, the cell being contacted in the disclosed method is an erythroid cell. The contacting may be performed ex vivo and the contacted cell may be returned to the subject's body after the contacting step. In another embodiment, the contacting step may be performed in vivo. In one embodiment, the method of altering a cell as described herein comprises acquiring knowledge of the sequence at a target position in said cell, prior to the contacting step. Acquiring knowledge of the sequence at a target position in the cell may be by sequencing the target gene, or a portion of the target gene. In one embodiment, the contacting step of the method comprises contacting the cell with a nucleic acid, e.g., a vector, e.g., an AAV vector, that expresses at least one of (a), (b), and (c). In one embodiment, the contacting step of the method comprises contacting the cell with a nucleic acid, e.g., a vector, e.g., an AAV vector, that expresses each of (a), (b), and (c). In another embodiment, the contacting step of the method comprises delivering to the cell a Cas9 fusion molecule of (b) and a nucleic acid which encodes a gRNA molecule (a) and optionally, a second gRNA molecule (c)(i) (and further optionally, a third gRNA molecule (c)(iv) and/or fourth gRNA molecule (c)(iii).

In one embodiment, contacting comprises contacting the cell with a nucleic acid, e.g., a vector, e.g., an AAV vector, e.g., an AAV2 vector, a modified AAV2 vector, an AAV3 vector, a modified AAV3 vector, an AAV6 vector, a modified AAV6 vector, an AAV8 vector or an AAV9 vector.

In one embodiment, contacting comprises delivering to the cell a Cas9 fusion molecule of (b), as a protein, and a nucleic acid which encodes (a) and optionally a second, third and/or fourth gRNA molecule of (c).

In one embodiment, contacting comprises delivering to the cell a Cas9 fusion molecule of (b), as a protein, said gRNA molecule of (a), as an RNA, and optionally said second, third and/or fourth gRNA molecule of (c), as an RNA.

When the method comprises correcting the mutation at a target position by HDR, a Cas9 fusion molecule of (b), at least one gRNA molecule, e.g., a gRNA molecule of (a) are included in the contacting step. In one embodiment, a cell of the subject is contacted ex vivo with (a), (b), and optionally (c)(i), further optionally (c)(ii), and still further optionally (c)(iii). In another embodiment, said cell is returned to the subject's body. In one embodiment, a cell of the subject is contacted is in vivo with (a), (b), and optionally (c)(i), further optionally (c)(ii), and still further optionally (c)(iii). In one embodiment, the cell of the subject is contacted in vivo by intravenous delivery of (a), (b), and optionally (c)(i), further optionally (c)(ii), and still further optionally (c)(iii). In one embodiment, the cell of the subject is contacted in vivo by intramuscular delivery of (a), (b), and optionally (c)(i), further optionally (c)(ii), and still further optionally (c)(iii). In one embodiment, the cell of the subject is contacted in vivo by subcutaneous delivery of (a), (b), and optionally (c)(i), further optionally (c)(ii), and still further optionally (c)(iii). In one embodiment, the cell of the subject is contacted in vivo by intra-bone marrow (IBM) delivery of (a), (b), and optionally (c)(i), further optionally (c)(ii), and still further optionally (c)(iii).

In one embodiment, contacting comprises contacting the subject with a nucleic acid, e.g., a vector, e.g., an AAV vector, described herein, e.g., a nucleic acid that encodes at least one of (a), (b), and optionally (c)(i), further optionally (c)(ii), and still further optionally (c)(iii).

In one embodiment, contacting comprises delivering to said subject said Cas9 fusion molecule of (b), as a protein, and a nucleic acid which encodes (a), and optionally (c)(i), further optionally (c)(ii), and still further optionally (c)(iii).

In one embodiment, contacting comprises delivering to the subject the Cas9 fusion molecule of (b), as a protein, the gRNA molecule of (a), as an RNA, and optionally the second, third and/or fourth gRNA molecule of (c), as an RNA.

In one embodiment, a cell of the subject is contacted ex vivo with (a), (b) and optionally (c)(i), further optionally (c)(ii), and still further optionally (c)(iii). In one embodiment, said cell is returned to the subject's body.

In one embodiment, a cell of the subject is contacted is in vivo with (a), (b) and optionally (c)(i), further optionally (c)(ii), and still further optionally (c)(iii). In one embodiment, the cell of the subject is contacted in vivo by intravenous delivery of (a), (b) and optionally (c)(i), further optionally (c)(ii), and still further optionally (c)(iii). In one embodiment, the cell of the subject is contacted in vivo by intramuscular delivery of (a), (b) and optionally (c)(i), further optionally (c)(ii), and still further optionally (c)(iii). In one embodiment, the cell of the subject is contacted in vivo by subcutaneous delivery of (a), (b) and optionally (c)(i), further optionally (c)(ii), and still further optionally (c)(iii). In one embodiment, the cell of the subject is contacted in vivo by intra-bone marrow (IBM) delivery of (a), (b) and optionally (c)(i), further optionally (c)(ii), and still further optionally (c)(iii).

In one embodiment, contacting comprises contacting the subject with a nucleic acid, e.g., a vector, e.g., an AAV vector, described herein, e.g., a nucleic acid that encodes at least one of (a), (b), and optionally (c)(i), further optionally (c)(ii), and still further optionally (c)(iii).

In one embodiment, contacting comprises delivering to said subject said Cas9 fusion molecule of (b), as a protein, and a nucleic acid which encodes (a) and optionally (c)(i), further optionally (c)(ii), and still further optionally (c)(iii).

In one embodiment, contacting comprises delivering to the subject the Cas9 fusion molecule of (b), as a protein, the gRNA molecule of (a), as an RNA, and optionally the second, third and/or fourth gRNA molecule of (c), as an RNA.

In one embodiment, disclosed herein are kits comprising compositions of the invention and instructions for use.

Ex Vivo Delivery

In some embodiments, components described in Table 5 are introduced into cells which are then introduced into the subject. Methods of introducing the components can include, e.g., any of the delivery methods described in Table 6.

Modified Nucleosides, Nucleotides, and Nucleic Acids

Modified nucleosides and modified nucleotides can be present in nucleic acids, e.g., particularly gRNA molecule, but also other forms of RNA, e.g., mRNA, RNAi, or siRNA. As described herein, "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:

(i) alteration, e.g., replacement, of one or both of the non-linking phosphate oxygens and/or of one or more of the linking phosphate oxygens in the phosphodiester backbone linkage;

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring nucleobase;

(v) replacement or modification of the ribose-phosphate backbone;

(vi) modification of the 3' end or 5' end of the oligonucleotide, e.g., removal, modification or replacement of a terminal phosphate group or conjugation of a moiety; and (vii) modification of the sugar.

The modifications listed above can be combined to provide modified nucleosides and nucleotides that can have two, three, four, or more modifications. For example, a modified nucleoside or nucleotide can have a modified sugar and a modified nucleobase. In one embodiment, every base of a gRNA is modified, e.g., all bases have a modified phosphate group, e.g., all are phosphorothioate groups. In one embodiment, all, or substantially all, of the phosphate groups of a unimolecular (or chimeric) or modular gRNA molecule are replaced with phosphorothioate groups.

In one embodiment, modified nucleotides, e.g., nucleotides having modifications as described herein, can be incorporated into a nucleic acid, e.g., a "modified nucleic acid." In one embodiment, the modified nucleic acids comprise one, two, three or more modified nucleotides. In one embodiment, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are a modified nucleotides.

Unmodified nucleic acids can be prone to degradation by, e.g., cellular nucleases. For example, nucleases can hydrolyze nucleic acid phosphodiester bonds. Accordingly, in one aspect the modified nucleic acids described herein can contain one or more modified nucleosides or nucleotides, e.g., to introduce stability toward nucleases.

In one embodiment, the modified nucleosides, modified nucleotides, and modified nucleic acids described herein can exhibit a reduced innate immune response when introduced into a population of cells, both in vivo and ex vivo. The term "innate immune response" includes a cellular response to exogenous nucleic acids, including single stranded nucleic acids, generally of viral or bacterial origin, which involves the induction of cytokine expression and release, particularly the interferons, and cell death. In one embodiment, the modified nucleosides, modified nucleotides, and modified nucleic acids described herein can disrupt binding of a major groove interacting partner with the nucleic acid. In one embodiment, the modified nucleosides, modified nucleotides, and modified nucleic acids described herein can exhibit a reduced innate immune response when introduced into a population of cells, both in vivo and ex vivo, and also disrupt binding of a major groove interacting partner with the nucleic acid.

miRNA Binding Sites microRNAs (or miRNAs) are naturally occurring cellular 19-25 nucleotide long noncoding RNAs. They bind to nucleic acid molecules having an appropriate miRNA binding site, e.g., in the 3' UTR of an mRNA, and down-regulate gene expression. While not wishing to be bound by theory it is believed that this down regulation occurs either by reducing nucleic acid molecule stability or by inhibiting translation. An RNA species disclosed herein, e.g., an mRNA encoding Cas9 can comprise an miRNA binding site, e.g., in its 3'UTR. The miRNA binding site can be selected to promote down regulation of expression is a selected cell type. By way of example, the incorporation of a binding site for miR-122, a microRNA abundant in liver, can inhibit the expression of the gene of interest in the liver.

Examples

The following Examples are merely illustrative and are not intended to limit the scope or content of the invention in any way.

Example 1: Constructing Single- and Multi-Cysteine Variant Cas9 Proteins

To generate single- and multi-cysteine variant Cas9 proteins, established molecular biology techniques and recombinant DNA procedures known to the ordinarily skilled artisan are used. A nucleotide sequence encoding the protein sequence of *Streptococcus pyogenes* Cas9 (SpCas9) and *Staphylococcus aureus* Cas9 (SaCas9) are modified using site-directed mutagenesis based, in part, on the published crystal structures of SpCas9 and SaCas9, as described in, e.g., in Anders et al., 2014 Nature 513(7519): 569-73; Nishimau et al. Cell, 162(5): 1113-26, to produce single- and multi-cysteine variant Cas9 proteins. For example, using site-directed mutagenesis, the protein sequence of SpCas9 is first mutated to replace native cysteine residues at positions 80 and 574 with serine (i.e., C80S and C574S). Similarly, using site-directed mutagenesis, the protein sequence of SaCas9 is first mutated to replace native cysteine residues at positions 237, 534 and 946 with serine (i.e., C237S, C534 and C946S). It is known that these conservative point mutations do not abolish Cas9 activity; see, e.g., Nishimau et al. Cell, 162(5): 1113-26. Site-directed mutagenesis is then performed to generate single- and multi-cysteine variant Cas9 proteins. Exemplary cysteine variant Cas9 proteins are provided below:

| Plasmid | Mutation(s) | Species | Description |
|---------|-------------|---------|-------------|
| pJZ001 | C80S C574S | Pyogenes | SpCas9 no cys variant |
| pJZ002 | C80S | Pyogenes | SpCas9 cys variant |
| pJZ003 | C80S C574S D147C | Pyogenes | SpCas9 cys variant |

-continued

| Plasmid | Mutation(s) | Species | Description |
|---|---|---|---|
| pJZ004 | C80S_C574S S204C | Pyogenes | SpCas9 cys variant |
| pJZ005 | C80S C574S Q228C | Pyogenes | SpCas9 cys variant |
| pJZ006 | C80S_C574S N235C | Pyogenes | SpCas9 cys variant |
| pJZ007 | C80S_C574S D257C | Pyogenes | SpCas9 cys variant |
| pJZ008 | C80S_C574S D284C | Pyogenes | SpCas9 cys variant |
| pJZ009 | C80S C574S T313C | Pyogenes | SpCas9 cys variant |
| pJZ010 | C80S C574S D326C | Pyogenes | SpCas9 cys variant |
| pJZ011 | C80S C574S D384C | Pyogenes | SpCas9 cys variant |
| pJZ012 | C80S C574S D428C | Pyogenes | SpCas9 cys variant |
| pJZ013 | C80S_C574S N504C | Pyogenes | SpCas9 cys variant |
| pJZ014 | C80S C574S R535C | Pyogenes | SpCas9 cys variant |
| pJZ015 | C80S C574S L551C | Pyogenes | SpCas9 cys variant |
| pJZ016 | C80S C574S N556C | Pyogenes | SpCas9 cys variant |
| pJZ017 | C80S C574S K558C | Pyogenes | SpCas9 cys variant |
| pJZ018 | C80S C574S E566C | Pyogenes | SpCas9 cys variant |
| pJZ019 | C80S_C574S D567C | Pyogenes | SpCas9 cys variant |
| pJZ020 | C80S C574S T605C | Pyogenes | SpCas9 cys variant |
| pJZ021 | C80S C574S T638C | Pyogenes | SpCas9 cys variant |
| pJZ022 | C80S C574S A640C | Pyogenes | SpCas9 cys variant |
| pJZ023 | C80S C574S Q674C | Pyogenes | SpCas9 cys variant |
| pJZ024 | C80S C574S E945C | Pyogenes | SpCas9 cys variant |
| pJZ025 | C80S C574S N946C | Pyogenes | SpCas9 cys variant |
| pJZ026 | C80S C574S L1004C | Pyogenes | SpCas9 cys variant |
| pJZ027 | C80S C574S T1065C | Pyogenes | SpCas9 cys variant |
| pJZ028 | C80S C574S K1076C | Pyogenes | SpCas9 cys variant |
| pJZ029 | C80S C574S D1117C | Pyogenes | SpCas9 cys variant |
| pJZ030 | C80S C574S S1154C | Pyogenes | SpCas9 cys variant |
| pJZ031 | C80S C574S D1328C | Pyogenes | SpCas9 cys variant |
| pJZ037 | C237S C534S C946A | Aureus | SaCas9 no cys variant |
| pJZ038 | D147C D384C N556C A640C E945C | Pyogenes | SpCas9 multi-cys variant |
| pJZ039 | Q192C S431C E745C D795C D849C | Aureus | SaCas9 multi-cys variant |
| pJZ040 | C237S C534S C946A Q192C | Aureus | SaCas9 cys variant |
| pJZ041 | C237S C534S C946A S431C | Aureus | SaCas9 cys variant |
| pJZ042 | C237S C534S C946A E745C | Aureus | SaCas9 cys variant |
| pJZ043 | C237S C534S C946A D795C | Aureus | SaCas9 cys variant |
| pJZ044 | C237S C534S C946A D849C | Aureus | SaCas9 cys variant |

For expression in bacteria, cultured cells, or animal tissues, the nucleotide sequence encoding the single- and multi-cysteine variant Cas9 proteins is operably linked to one or more transcriptional control elements, e.g., promoter and/or enhancer elements, which enable expression in the relevant bacteria, cultured cells, or animal tissue. The single- and multi-cysteine variant Cas9 proteins can be purified from the bacteria, cultured cells, or animal tissue using established biochemical techniques. To generate mRNA encoding the single- and multi-cysteine variant Cas9 proteins, the nucleotide sequence encoding the single- and multi-cysteine variant Cas9 proteins is operably linked to a promoter, e.g., a bacteriophage promoter, e.g., a T7 RNA polymerase promoter enabling in vitro transcription of mRNA encoding the single- and multi-cysteine variant Cas9 proteins.

The single- and multi-cysteine variant Cas9 proteins allow for site-specific bioconjugation to other molecular species, as described further herein.

Example 2: Generation of Cas9 Fusion Molecules by Covalent Attachment of Single- and Multi-Cysteine Variant Cas9 Proteins to Exogenous Donor Template Sequence Using 5'-Maleimide-Modified Exogenous Donor Template Sequence To generate Cas9 fusion molecules, the single- and multi-cysteine variant Cas9 proteins described in Example 1 are covalently attached to template nucleic acid using a 5'-maleimide-modified exogenous donor template sequence (FIG. 1). Generally, the template nucleic acid is prepared such that the 5'-end of the template nucleic acid is modified to include maleimide modification at its 5'-end. The maleimide modification may have a one, or two or more carbon spacer arm between the 5'-end of the template nucleic acid and the maleimide modification for purposes of reducing steric interactions between the maleimide modification and the template nucleic acid. The 5'-maleimide-modified template nucleic acid is then incubated in the presence of a single- and/or multi-cysteine variant Cas9 protein molecule described in Example 1, at 4° C. overnight or at room temperature for 4 hours in buffer containing TCEP (tris(2-carboxyethyl)phosphine) to keep free cysteines reduced and prevent disulfide bonds from forming, according to standard procedures known to the ordinarily skilled artisan, to covalently attach the 5'-maleimide-modified template nucleic acid to at least one thiol group (e.g., a surface exposed thiol group) from the single- and/or multi-cysteine variant Cas9 protein molecule described in Example 1, to generate a Cas9 fusion molecule (FIG. 1).

Figure 2:
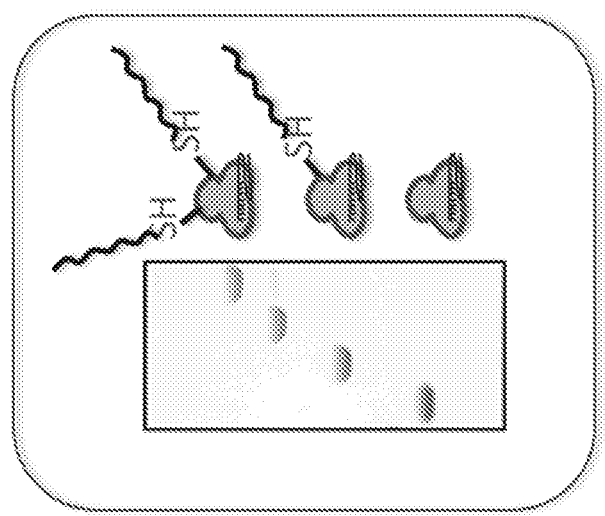
FIG. 2 depicts the results of an electrophoretic mobility shift assay of the products from reacting a 5'-maleimidemodified template nucleic acid with a cysteine-variant Cas9 protein molecule as described in Example 1. The data indicate the generation of Cas9 fusion molecules containing at least one covalently attached template nucleic acid.
Figure 3:
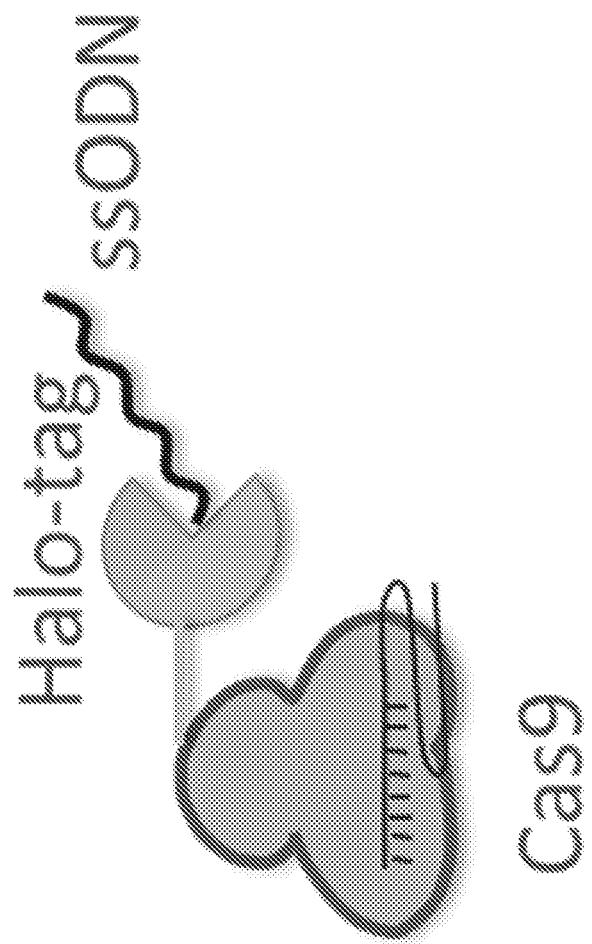
FIG. 3 depicts a Cas9 fusion molecule formed by covalent conjugation of a Cas9-HaloTag protein molecule to a template nucleic acid. The single stranded oligoDNA (ssDNA) is covalently attached to the HaloTag component of the Cas9-HaloTag protein molecule.

To test the efficiency of the Cas9 fusion molecule prepared as described in this Example, the reaction products are analyzed using an electrophoretic mobility shift assay using standard procedures known to the ordinary skilled artisan. Results provided in FIG. 2 indicate the generation of Cas9 fusion molecule as described in this Example.

Example 3: Generation of Cas9 Fusion Molecules by Covalent Attachment of a Cas9 Protein to Template Nucleic Acid Via HyNic-4FB Conjugation To generate Cas9 fusion molecules, a HyNic-modified Cas9 protein is covalently attached to a 5'-4-Formylbenzamide (4FB)-modified template nucleic acid. The template nucleic acid is prepared such that the 5'-end of the template nucleic acid is modified to include a 5'-4-formylbenzamide (4FB) moiety at its 5'-end (TriLink BioTechnologies). The chemistry that couples the Cas9 protein to the 4FB-modified template nucleic acid takes advantage of free primary amine groups that are present naturally (or are present as a consequence of site-directed mutagenesis) on the protein surface. Specifically, a Cas9 protein is incubated in the presence of succinimidyl-6-hydrazino-nicotinamide (S-HyNic) (Solulink), which reacts with at least one primary amine on the Cas9 protein to form a 6-hydrazino-nicotinamide (HyNic)-modified Cas9 molecule. The 6-hydrazino-nicotinamide (HyNic)-modified Cas9 protein molecule is then incubated with the 5'-(4FB)-modified template nucleic acid to generate Cas9 fusion molecules. Assays to test the efficiency of the Cas9 fusion molecule prepared as described in this Example can be performed by analyzing the reaction products via an electrophoretic mobility shift assay using standard procedures known to the ordinary skilled artisan.

Example 4: Generation of Cas9 Fusion Molecules by Reaction of a Cas9-HaloTag Protein Molecule with Haloalkane-Modified Template Nucleic Acid To generate Cas9 fusion molecules, a Cas9-HaloTag protein molecule is created by expressing a nucleic acid construct encoding a HaloTag, optionally fused to a nucleic acid sequence encoding a linker sequence, fused either to the N-terminus or C-terminus of a nucleic acid sequence encoding a Cas9 protein molecule. The nucleic acid construct encoding a HaloTag, is a variant nucleic acid sequence that encodes for a mutant HaloTag comprising a H272F mutation. The HaloTag variant protein (i.e., the H272F HaloTag protein) facilitates the formation of a covalent bond between the HaloTag variant and a haloalkane-modified nucleic acid, e.g., a bromoalkane-modified template nucleic acid.

Generally, for expression in bacteria, cultured cells, or animal tissues, the nucleotide sequence encoding the Cas9 protein fusion (i.e., a Cas9 protein molecule fused to a HaloTag variant) is operably linked to one or more transcriptional control elements, e.g., promoter and/or enhancer elements, which enable expression in the relevant bacteria, cultured cells, or animal tissue. The Cas9 protein fusion can be purified from the bacteria, cultured cells, or animal tissue using established biochemical techniques. Exemplary Cas9 protein fusions (i.e., a Cas9 protein molecule fused to a HaloTag variant) are provided below:

TABLE 9

| Cas9 protein fusion | Linker sequence (AA) | Abbreviation |
| --- | --- | --- |
| HaloTag-XTEN linker-Cas9 | SGSETPGTSESATPES | HXC |
| HaloTag-GGS9 linker-Cas9 | GGSGGSGGSGGSGGSGGSGGSGGSGGS | HGC |
| Cas9-XTEN linker-HaloTag | SGSETPGTSESATPES | CXH |
| Cas9-GGS9 linker-HaloTag | GGSGGSGGSGGSGGSGGSGGSGGSGGS | CGH |

The effect of covalent attachment of the template sequence to Cas9 on the frequency of gene correction (HDR) was examined. Generally, the Cas9 protein fusion molecules of Table 9 were prepared as follows.

Cloning: The Cas9 gene and the HaloTag gene were generated by gene synthesis and cloned into a bacterial expression vector (using standard molecular cloning techniques) with one of the linker sequences provided in Table 9 (i.e., the XTEN or the GGS9 linker) in the arrangements set forth in Table 9. This resulted in 4 unique nucleic acid sequences for expressing the Cas9 protein fusion molecules of Table 9. All four constructs comprise an N-terminal His-tag, with sequence $His_6$, and a nuclear localization signal (NLS), with sequence PKKKRKV. In alternative embodiments, the $His_6$-tag and the NLS can be cloned to the C-terminus of the Cas9 protein fusion molecules. In alternative embodiments, the Cas9 gene sequence from either S. Pyogenes (spcas9) or from S. aureus (sacas9) may also be used.

Figures 4A, 4B:
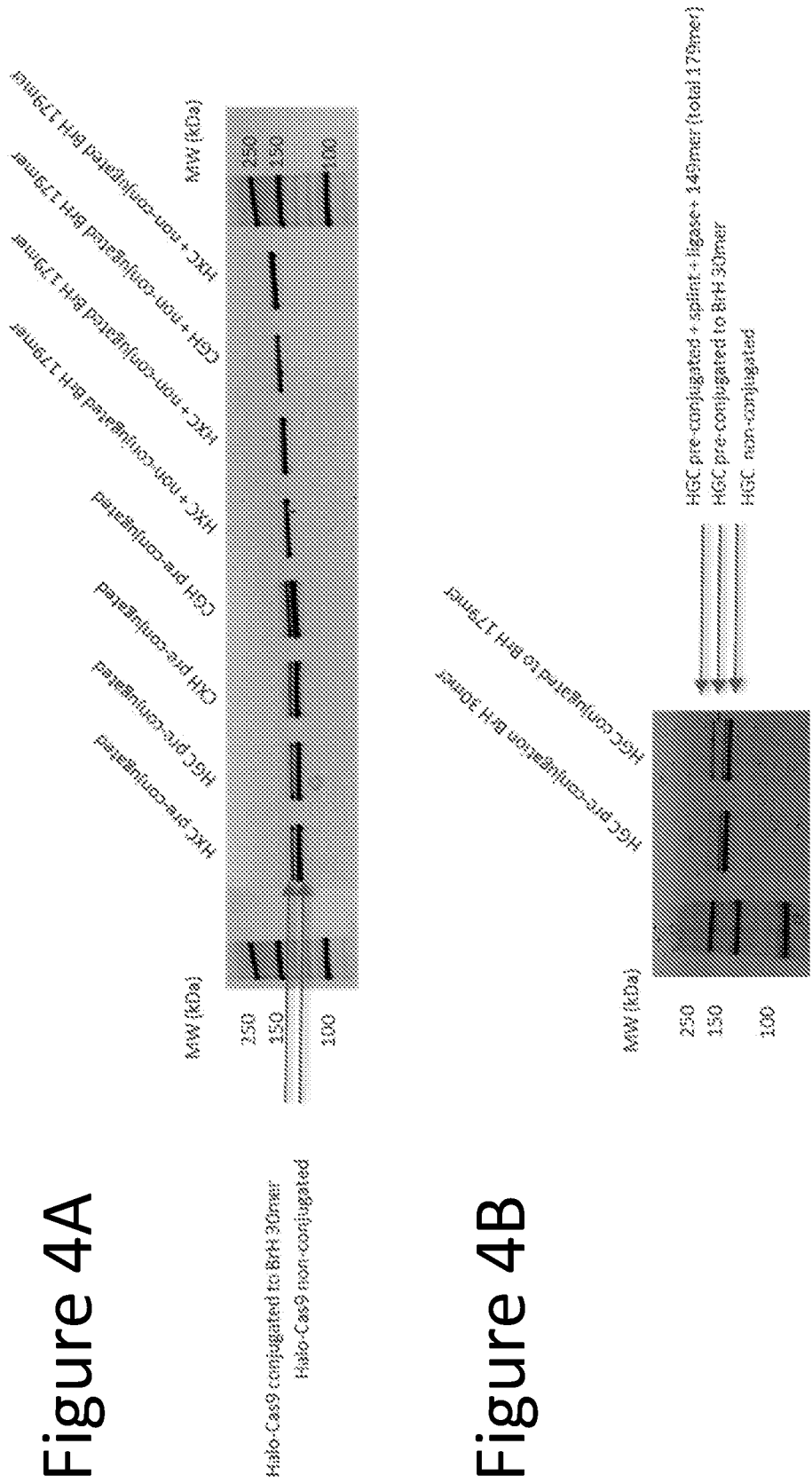
FIG. 4A depicts results of the pre-conjugation and pre-annealed methods for conjugating a Cas9-HaloTag protein fusion to template sequence using standard PAGE analysis for various Cas9 protein fusions provided in Table 9.
FIG. 4B depicts results of the pre-conjugation and pre-annealed methods for conjugating a Cas9-HaloTag protein fusion to template sequence using standard PAGE analysis for the HGC Cas9 protein fusion provided in Table 9.

Pre-Conjugation of Template Sequence to a Cas9-HaloTag Protein Fusion:

Cas9-HaloTag protein fusions (i.e., HXC, HGC, CXH, and CGH, see Table 9) were each incubated with a bromohexyl (BrH)-labeled 30 nucleotide (30 mer) nucleic acid sequence for 1 hour at 37° C., to form a Cas9-HaloTag protein fusion that is conjugated to the 30 nucleotide nucleic acid sequence (FIGS. 4A and 4B). A 149 nucleotide nucleic acid sequence (149 mer) was subsequently annealed to the nucleic acid portion of the Cas9-HaloTag protein fusion that is conjugated to the 30 nucleotide nucleic acid sequence by incubating the 149 mer with the Cas9-HaloTag protein fusion that is conjugated to the 30 nucleotide nucleic acid sequence in the presence of a DNA splint, followed by addition of a T4 DNA ligase, incubating the reaction at room temperature for 1 hour (FIG. 4). The reaction resulted in a Cas9-HaloTag fusion molecule covalently attached to a 179 nucleotide template sequence (FIG. 4). A CC8 guide molecule was subsequently added to the reaction mixture, which was then allowed to incubate for 15 minutes prior to nucleofecting into U2OS cells, according to standard procedures known to one of skill in the art. Four days after nucleofection, genomic DNA was extracted and a target sequence locus was amplified and analyzed by next-generation sequencing and scored for % HDR (see FIG. 5).

Conjugation of Pre-Annealed Template Sequence to a Cas9-HaloTag Protein Fusion:

The 149 mer was pre-annealed to a DNA splint. The BrH-labeled 30 mer was subsequently ligated to the pre-annealed 149mer-DNA splint complex using T4 DNA ligase. The ligation reaction was performed at room temperature for 1 hour, resulting in a full length template sequence of 179 nucleotides (i.e., 179 mer). The 179 mer was added to a reaction with a Cas9-HaloTag protein fusion (i.e., HXC, HGC, CXH, or CGH) and incubated for 1 hour at 37° C., resulting in a Cas9-HaloTag fusion molecule covalently attached to a 179 nucleotide template sequence (FIG. 4). The CC8 guide was then added to this mixture and incubated for 15 minutes prior to nucleofecting into U2OS cells, according to standard procedures known to one of skill in the art. Four days after nucleofection, genomic DNA was extracted and a target sequence locus was amplified and analyzed by next-generation sequencing and scored for % HDR (FIG. 5).

Results:

HDR efficiency can be assayed using a standard nuclofection assay in U2OS cells by comparing the results using the Cas9 fusion molecules (i.e., Cas9-HaloTag protein fusion-template nucleic acid conjugates) in comparison the Cas9-HaloTag protein fusion without a conjugated template nucleic acid. The results in FIG. 5 demonstrate that the Cas9 fusion molecules (i.e., Cas9-HaloTag protein fusion-template nucleic acid conjugates) increased the HDR efficiency compared to reactions performed with unconjugated template nucleic acid. Specifically, the results demonstrated a higher rate of HDR as detected by sequencing when the cells were nucleofected with the Cas9 fusion molecule HGC using the pre-conjugation method for conjugating the template nucleic acid to the Cas9-HaloTag protein fusion. Thus, the recruitment of the template nucleic acid to the Cas9 via covalent attachment resulted in a 4% increase in HDR gene correction (FIG. 5). The results also demonstrated that the conjugation method using a pre-annealed full length 179 mer does not yield significant conjugation products to the Halo-Cas9 protein fusions tested. Successful conjugation was only observed via the "pre-conjugation" method, by first conjugating the BrH-labeled 30 mer to the Halo-Cas9 protein fusion (FIG. 4A) followed by subsequent splint ligation using T4 DNA ligase and the 149 mer.

Example 5: Generation of Cas9 Fusion Molecules by Covalent Attachment of Single- and Multi-Cysteine Variant Cas9 Proteins to Template Nucleic Acid Using Acrydite-Modified Template Nucleic Acid To generate Cas9 fusion molecules, the single- and multi-cysteine variant Cas9 proteins described in Example 1 are covalently attached to template nucleic acid using an acrydite-modified template nucleic acid. The template nucleic acid is prepared such that the 5'-end of the template nucleic acid is modified to include an acrydite moiety at its 5'-end. The template nucleic acid may also be synthesized such that the 3'-end of the template nucleic acid is modified to include an acrydite moiety either at its 3'-end. The template nucleic acid may also be synthesized such that an internal nucleic acid residue of the template nucleic acid is modified to include an acrydite moiety either at an internal nucleic acid residue. The acrydite-modified template nucleic acid is then incubated in the presence of a single- and/or multi-cysteine variant Cas9 protein described in Example 1, according to standard procedures known to the ordinarily skilled artisan, to covalently attach the acrydite-modified template nucleic acid to at least one thiol group (e.g., a surface exposed thiol group) from the single- and/or multi-cysteine variant Cas9 protein described in Example 1, to generate Cas9 fusion molecules (FIG. 6). Assays to test the efficiency of the Cas9 fusion molecule prepared as described in this Example can be performed by analyzing the reaction products via an electrophoretic mobility shift assay using standard procedures known to the ordinary skilled artisan.

Figure 7:
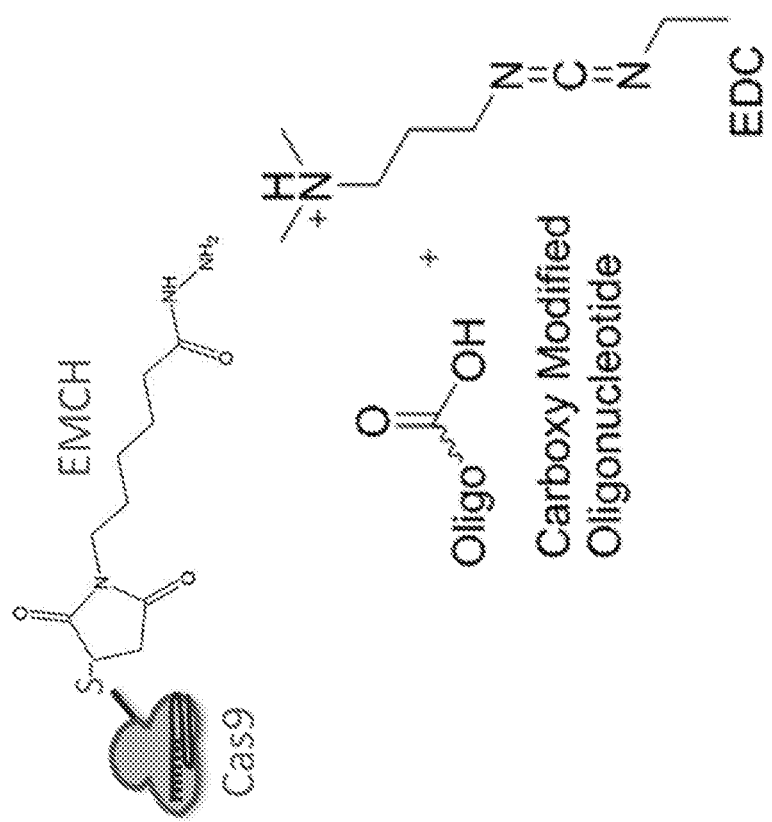
FIG. 7 depicts a scheme generating a Cas9 fusion molecule by covalent conjugation of a N-[ε-Maleimidocaproic acid] hydrazide (EMCH)-modified Cas9 protein molecule with a 1-ethyl-3-(3-dimethylaminopropyl) carbodiimide (EDC)-modified template nucleic acid.

Example 6: Generation of Cas9 Fusion Molecules by Covalent Attachment of a Cas9 Protein Molecule to Template Nucleic Acid Via EMCH and EDC Coupling Agents To generate Cas9 fusion molecules, a N-[ε-Maleimidocaproic acid] hydrazide (EMCH)-modified Cas9 protein molecule is covalently attached to a 1-ethyl-3-(3-dimethylaminopropyl) carbodiimide (EDC)-modified template nucleic acid. The template nucleic acid is prepared such that the 5'-end of the template nucleic acid is modified to include a carboxyl moiety (i.e., —COOH), therefore resulting in a carboxy-modified template nucleic acid. Alternatively, the template nucleic acid may be modified such that the template nucleic acid includes a carboxyl moiety (i.e., —COOH) at its 3'-end or at an internal nucleic acid residue. The carboxy-modified template nucleic acid is then incubated with 1-ethyl-3-(3-dimethylaminopropyl) carbodiimide (EDC), according to standard procedures known to the ordinarily skilled artisan, to covalently attach EDC to the carboxy-modified template nucleic acid (FIG. 7), thereby forming a 1-ethyl-3-(3-dimethylaminopropyl) carbodiimide (EDC)-modified template nucleic acid.

The N-[ε-Maleimidocaproic acid] hydrazide (EMCH)-modified Cas9 protein molecule is prepared as described herein. The chemistry that couples the Cas9 protein molecule to EMCH takes advantage of a surface-exposed thiol group on the Cas9 protein molecule (e.g., a cysteine residue) which is capable of forming a covalent bond with EMCH. The Cas9 protein molecule may be a wild-type Cas9 protein molecule. Alternatively, the Cas9 protein molecule may be a single- or multi-cysteine variant Cas9 protein molecule as described in Example 1. Specifically, the Cas9 protein molecule is incubated in the presence of EMCH, according to standard procedures known to the ordinarily skilled artisan, to form a N-[ε-Maleimidocaproic acid] hydrazide (EMCH)-modified Cas9 protein molecule.

The chemistry that couples the N-[ε-Maleimidocaproic acid] hydrazide (EMCH)-modified Cas9 protein molecule to the 1-ethyl-3-(3-dimethylaminopropyl) carbodiimide (EDC)-modified exogenous donor template sequence takes advantage of the primary amine group of the N-[ε-Maleimidocaproic acid] hydrazide (EMCH) modified Cas9 protein molecule that can form a covalent bond with the 1-ethyl-3-(3-dimethylaminopropyl) carbodiimide (EDC)-modified template nucleic acid. Specifically, a N-[ε-Maleimidocaproic acid] hydrazide (EMCH)-modified Cas9 protein molecule is incubated with the 1-ethyl-3-(3-dimethylaminopropyl) carbodiimide (EDC)-modified template nucleic acid, according to standard procedures known to the ordinarily skilled artisan, to generate a Cas9 fusion molecule (see also, *Immunogenicity and protective efficacy of Bacillus anthracis poly-gamma-D-glutamic acid capsule covalently coupled to a protein carrier using a novel triazine-based conjugation strategy*. Joyce J, Cook J, Chabot D, Hepler R, Shoop W, Xu Q, Stambaugh T, Aste-Amezaga M, Wang S, Indrawati L, Bruner M, Friedlander A, Keller P, Caulfield M J Biol Chem 2006; (281):8 4831-4843). Assays to test the efficiency of the Cas9 fusion molecule prepared as described in this Example can be performed by analyzing the reaction products via an electrophoretic mobility shift assay using standard procedures known to the ordinary skilled artisan.

Example 7: Generation of Cas9 Fusion Molecules Via Non-Covalent Coupling Agents

To generate Cas9 fusion molecules, a Cas9 protein molecule, covalently linked to biotin, and a template nucleic acid, covalently linked to biotin, are non-covalently attached via the interaction of the biotin moiety of the Cas9 protein molecule and the biotin moiety of the template nucleic acid each to a unique single monomer of tetrameric streptavidin. Using standard procedures known to the ordinarily skilled artisan, a Cas9 protein molecule is covalently attached to biotin via a polypeptide linker. The polypeptide linker may be one of the linkers disclosed herein (e.g., an XTEN linker, a GGC3 linker, a GGS6 linker, or a GGS9 linker). Generally, the polypeptide linker is sufficiently long to allow the Cas9 protein molecule to interact with the template nucleic acid without steric interference. The template nucleic acid, which is also covalently linked to a biotin molecule, is incubated with the Cas9-Biotin protein molecule in the presence of streptavidin, according to standard procedures known to the ordinarily skilled artisan, thereby forming a Cas9 fusion molecule (FIG. 8). Assays to test the efficiency of the Cas9 fusion molecule prepared as described in this Example can be performed by analyzing the reaction products via an electrophoretic mobility shift assay using standard procedures known to the ordinary skilled artisan.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

Anders et al. *Nature* 513(7519):569-573 (2014)
Bae et al. *Bioinformatics* 30(10):1473-1475 (2014)
Caldecott *Nat. Rev. Genet.* 9(8):619-631 (2008)
Cong et al. *Science* 399(6121):819-823 (2013)
Chylinski et al. *RNA Biol.* 10(5):726-737 (2013)
Deveau et al. *J. Bacteriol.* 190(4): 1390-1400 (2008)
Esvelt et al. *Nature* 472(7344): 499-503 (2011)
Friedland et al. *Genome Biol.* 16:257 (2015)
Fu et al. *Nat. Biotechnol.* 32:279-284 (2014)
Haft et al. *PLoS Computational Biology* 1(6): e60 (2005)
Heigwer et al. *Nat. Methods* 11(2):122-3 (2014)
Horvath et al. *Science* 327(5962): 167-170 (2010)
Hsu et al. *Nat. Biotechnol.* 31(9): 827-32 (2013)
Jinek et al. *Science* 337(6096):816-821 (2012)
Jinek et al. *Science* 343(6176):1247997 (2014)
Kleinstiver et al. *Nat. Biotechnol.* 33(12):1293-8 (2015)
Lee et al. *Nano Lett.* 12(12):6322-6327 (2012)
Li *Cell. Res.* 18(1):85-98 (2008)
Makarova et al. *Nature Review Microbiology* 9:467-477 (2011)
Mali et al. *Science* 399(6121): 823-826 (2013)
Marteijn et al. *Nat. Rev. Mol. Cell. Biol.* 15(7):465-481 (2014)
Mayle et al. *Science* 349: 742-47 (2015)
Neelsen and Lopes *Nat. Rev. Mol. Cell. Biol.* 16: 207-20 (2015)
Nishimasu et al. *Cell* 156(5):935-949 (2014)
Ran et al. *Cell* 154(6): 1380-1389 (2013)
Saleh-Gohari et al. *Mol. Cell. Biol.* 25: 7158-69 (2005)
Schlacher et al. *Cancer Cell* 22: 106-16 (2012)
Sternberg et al. *Nature* 507(7490):62-67 (2014)
Wang et al. *Cell* 153(4):910-918 (2013)
Xiao A. et al. *Bioinformatics* 30 (8):1180-1182 (2014)
Zellweger et al. *J. Cell. Biol.* 205: 563-79 (2015)
Zhou et al., *Nucleic Acids Res.* 42(3):e19 (2014)

What is claimed is:

1. An enzymatically active Cas9 (eaCas9) fusion molecule comprising an eaCas9 molecule covalently linked to a template nucleic acid by a polypeptide linker.

2. The eaCas9 fusion molecule of claim 1, wherein
   i) the eaCas9 molecule comprises at least one surface exposed cysteine residue;
   ii) the eaCas9 molecule comprises succinimidyl-6-hydrazino-nicotinamide (S-HyNic); or
   iii) the eaCas9 molecule comprises a tag linked to the eaCas9 molecule.

3. The eaCas9 fusion molecule of claim 1 wherein template nucleic acid comprises a double stranded nucleic acid or a single stranded nucleic acid.

4. The eaCas9 fusion molecule of claim 1, wherein the eaCas9 molecule is a wild-type Cas9 molecule, a Cas9 nickase molecule, a split Cas9 molecule, or an inducible Cas9 molecule.

5. A gene editing system, comprising
   at least one enzymatically active Cas9 (eaCas9) fusion molecule comprising an eaCas9 molecule covalently linked to a template nucleic acid by a polypeptide linker, and
   at least one gRNA molecule.

6. The gene editing system of claim 5,
   i) wherein the at least one gRNA molecule and the eaCas9 fusion molecule are designed to associate with a target nucleic acid and generate a double strand break on the target nucleic acid, wherein the double strand break is repaired by at least one DNA repair pathway, thereby producing a modified target nucleic acid; or
   ii) wherein the eaCas9 molecule is a Cas9 nickase molecule.

7. A pharmaceutical composition comprising the gene editing system of claim 5.

8. The eaCas9 fusion molecule of claim 1, wherein
   i) the polypeptide linker is between 3 and 100 amino acids in length; or
   ii) the polypeptide linker comprises an amino acid sequence selected from the group consisting of SEQ ID NO: 206-214.

9. The eaCas9 fusion molecule of claim 2, wherein the eaCas9 molecule comprises a tag linked to the eaCas9 molecule; and
   the template nucleic acid comprises a haloalkane; and
   the tag comprises a HaloTag molecule,
   wherein the HaloTag molecule is linked to the haloalkane-containing template nucleic acid using an $SN_2$ reaction.

10. A gene editing system, comprising
    (i) a first eaCas9 fusion molecule, wherein the first eaCas9 fusion molecule comprises a first Cas9 nickase molecule covalently linked to a template nucleic acid by a polypeptide linker;
    a first gRNA molecule;
    a second eaCas9 fusion molecule, wherein the second eaCas9 fusion molecule comprises a second Cas9 nickase molecule covalently linked to the template nucleic acid by a polypeptide linker; and
    a second gRNA molecule; or
    (ii) a first eaCas9 fusion molecule, wherein the first eaCas9 fusion molecule comprises a first Cas9 nickase molecule covalently linked to a first template nucleic acid by a polypeptide linker;
    a first gRNA molecule;
    a second eaCas9 fusion molecule, wherein the second eaCas9 fusion molecule comprises a second Cas9 nickase molecule covalently linked to a second template nucleic acid by a polypeptide linker; and a second gRNA molecule.

11. A method of modifying a target nucleic acid in a cell, the method comprising:
    contacting the cell with a gRNA molecule and the eaCas9 fusion molecule of claim 1;
    wherein the gRNA molecule and the eaCas9 fusion molecule associate with the target nucleic acid and generate a double strand break in the target nucleic acid; and
    wherein the double strand break is repaired by gene correction using the template nucleic acid of the eaCas9 fusion molecule.

12. A method of modifying a target nucleic acid in a cell, the method comprising:
    contacting the cell with a first gRNA molecule; a first eaCas9 molecule; a second gRNA molecule; and a second eaCas9 molecule;
    wherein at least one of the first and second eaCas9 molecule is covalently linked to a template nucleic acid by a polypeptide linker,
    wherein the first gRNA molecule and the first eaCas9 molecule associate with the target nucleic acid and generate a first single strand cleavage event on a first strand of the target nucleic acid;
    wherein the second gRNA molecule and the second eaCas9 molecule associate with the target nucleic acid and generate a second single strand cleavage event on a second strand of the target nucleic acid, thereby forming a double strand break having a first overhang and a second overhang; and wherein the first overhang and the second overhang in the target nucleic acid are repaired by gene correction using the template nucleic acid.

13. The method of claim 12, wherein the first eaCas9 molecule is covalently linked to the template nucleic acid by a polypeptide linker.

14. The method of claim 12, wherein both the first eaCas9 molecule and the second eaCas9 molecule are covalently linked to the template nucleic acid by a polypeptide linker.

* * * * *